(12) United States Patent
Martinsson et al.

(10) Patent No.: US 9,718,809 B2
(45) Date of Patent: Aug. 1, 2017

(54) BISARYLSULFONAMIDES USEFUL IN THE TREATMENT OF INFLAMMATION AND CANCER

(71) Applicant: Kancera AB, Solna (SE)

(72) Inventors: Jessica Martinsson, Sollentuna (SE); Katarina Faernegardh, Ekeroe (SE); Mattias Joensson, Knivsta (SE); Rune Ringom, Uppsala (SE)

(73) Assignee: Kancera AB, Solna (SE)

( * ) Notice: Subject to any disclaimer, the term of this patent is extended or adjusted under 35 U.S.C. 154(b) by 0 days.

(21) Appl. No.: 14/367,643

(22) PCT Filed: Dec. 21, 2012

(86) PCT No.: PCT/EP2012/076836
§ 371 (c)(1),
(2) Date: Jun. 20, 2014

(87) PCT Pub. No.: WO2013/093095
PCT Pub. Date: Jun. 27, 2013

(65) Prior Publication Data
US 2015/0025068 A1 Jan. 22, 2015

Related U.S. Application Data

(60) Provisional application No. 61/579,360, filed on Dec. 22, 2011.

(30) Foreign Application Priority Data

Dec. 22, 2011 (EP) .................................... 11195456
Dec. 28, 2011 (EP) .................................... 11195962

(51) Int. Cl.
| | | |
|---|---|---|
| C07C 311/21 | (2006.01) |
| C07D 409/14 | (2006.01) |
| C07D 215/12 | (2006.01) |
| C07D 333/22 | (2006.01) |
| C07D 333/34 | (2006.01) |
| C07D 333/62 | (2006.01) |
| C07D 409/04 | (2006.01) |
| C07D 277/26 | (2006.01) |
| C07D 295/096 | (2006.01) |
| C07D 295/192 | (2006.01) |
| C07D 213/34 | (2006.01) |
| C07D 307/79 | (2006.01) |
| C07D 213/71 | (2006.01) |
| C07D 213/74 | (2006.01) |
| C07D 231/38 | (2006.01) |
| C07D 405/04 | (2006.01) |
| C07D 409/12 | (2006.01) |
| C07D 261/14 | (2006.01) |
| C07D 285/15 | (2006.01) |
| C07D 295/088 | (2006.01) |
| C07D 307/64 | (2006.01) |
| C07D 307/82 | (2006.01) |

(52) U.S. Cl.
CPC .......... *C07D 409/14* (2013.01); *C07C 311/21* (2013.01); *C07D 213/34* (2013.01); *C07D 213/71* (2013.01); *C07D 213/74* (2013.01); *C07D 215/12* (2013.01); *C07D 231/38* (2013.01); *C07D 261/14* (2013.01); *C07D 277/26* (2013.01); *C07D 285/15* (2013.01); *C07D 295/088* (2013.01); *C07D 295/096* (2013.01); *C07D 295/192* (2013.01); *C07D 307/64* (2013.01); *C07D 307/79* (2013.01); *C07D 307/82* (2013.01); *C07D 333/22* (2013.01); *C07D 333/34* (2013.01); *C07D 333/62* (2013.01); *C07D 405/04* (2013.01); *C07D 409/04* (2013.01); *C07D 409/12* (2013.01); *C07C 2101/16* (2013.01)

(58) Field of Classification Search
CPC ........................... C07C 311/15; C07C 311/21
See application file for complete search history.

(56) References Cited

FOREIGN PATENT DOCUMENTS

| WO | WO2008114022 | * | 9/2008 |
| WO | WO2012/092442 | * | 7/2012 |
| WO | WO2012/151448 | * | 11/2012 |

OTHER PUBLICATIONS

CAS Reg No. 1175090-98-8 and 1175091-00-5, entered into STN Aug. 24, 2009.*
Golulb, 1999, Science, vol. 286, p. 531-537.*
Voskoglou-Nomikos, 2003, Clinical Caner Research, vol. 9, p. 4227-4239.*
Cancer Prevention Overview, retrieved Nov. 14, 2012, http://www.cancer.gov/cancertopics/pdq/prevention/overview/patient.*
Targeted Cancer Therapies, retrieved Dec. 8, 2015, http://www.cancer.gov/about-cancer/treatment/types/targeted.therapies/targeted-therapies-fact-sheet.*
Ando et al., "Interleukin 6 Enhances Glycolysis through Expression of the Glycolytic Enzymes Hexokinase 2 and 6-Phosphofructo-2-kinase/Fructose-2,6-bisphosphatase-3", J Nippon Med School, vol. 77, No. 2, 2010, pp. 97-105.

(Continued)

*Primary Examiner* — Rebecca Anderson
*Assistant Examiner* — Karen Cheng
(74) *Attorney, Agent, or Firm* — Renner, Otto, Boisselle & Sklar, LLP

(57) ABSTRACT

A compound of formula (I), useful for the treatment of cancer, inflammation and inflammatory disorders, and a pharmaceutical composition containing the compound.

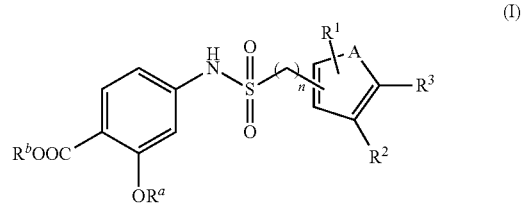

(I)

21 Claims, 4 Drawing Sheets

(56) References Cited

OTHER PUBLICATIONS

Bache et al., "Detection and Specific Targeting of Hypoxic Regions within Solid Tumors: Current Preclinical and Clinical Strategies", Current Medicinal Chemistry, vol. 15, No. 4, 2008, pp. 322-338.
Bobarykina et al., "Hypoxic regulation of PFKFB-3 and PFKFB-4 gene expression in gastric and pancreatic cancer cell lines and expression of PFKFB genes in gastric cancers", Acta Biochimica Polonica, vol. 53, No. 4, 2006, pp. 789-799.
Brown, "The Hypoxic Cell: A Target for Selective Cancer Therapy—Eighteenth Bruce F. Cain Memorial Award Lecture1", Cancer Research, vol. 59, Dec. 1, 1999, pp. 5863-5870.
Bruni et al., "An Endpoint Enzymatic Assay for Fructose 2,6-Bisphosphate Performed in 96-Well Plates1", Analytical Biochemistry, vol. 178, 1989, pp. 324-326.
Chesney et al., "An inducible gene product for 6-phosphofructo-2-kinase with an AU-rich instability element: Role in tumor cell glycolysis and the Warburg effect", Proc. Natl. Acad. Sci, USA, vol. 96, Mar. 1999, pp. 3047-3052.
Clem et al., "Small-molecule inhibition of 6-phosphofructo-2-kinase activity suppresses glycolytic flux and tumor growth", Mol Cancer Ther 2008, vol. 7, No. 1, Jan. 2008, pp. 110-120.
Del Rey et al., "The Transcriptional Response of Normal and Rheumatoid Arthritis Synovial Fibroblasts to Hypoxia", Arthritis & Rheumatism, vol. 62, No. 12, Dec. 2010, pp. 3584-3594.
Graham et al., "Topically Active Carbonic Anhydrase Inhibitors. 3. Benzofuran- and Indole-2-sulfonamides", Journal of Medicinal Chemistry, vol. 33, No. 2, 1990, pp. 749-754.
Hirata et al., "Inhibition of tumor Cell Growth by a Specific 6-Phosphofructo-2-kinase Inhibitor, N-Bromoacetylethanolamine Phosphate, and Its Analogues", Biosci. Biotechnol. Biochem., vol. 64, No. 10, 2000, pp. 2047-2052.
Huang et al., "New Ammonia Equivalents for the Pd-Catalyzed Amination of Aryl Halides", Organic Letters, vol. 3, No. 21, 2001, pp. 3417-3419.
Jiang et al., "Environmentally friendly synthesis of biaryls: Suzuki reaction of aryl bromides in water at low catalyst loadings", Tetrahedron Letters, vol. 47, 2006, pp. 197-200.
Kim et al., "A Direct Substrate—Substrate Interaction Found in the Kinase Domain of the Bifunctional Enzyme, 6-Phosphofructo-2-kinase/Fructose-2,6-bisphosphatase", J. Mol. Biol., vol. 370, 2007, pp. 14-26.
Liu et al., "Hypoxia increases tumor cell sensitivity to glycolytic inhibitors: a strategy for solid tumor therapy (Model C)", Biochemical Pharmacology, vol. 64, 2002, pp. 1745-1751.
Liu et al., "Hypersensitization of Tumor Cells to Glycolytic Inhibitors", Biochemistry, vol. 40, No. 18, 2001, pp. 5542-5547.
Minchenko et al., "Overexpression of 6-phosphofructo-2-kinase/fructose-2,6-bisphosphatase-4 in the human breast and colon malignant tumors", Biochimie, vol. 87, 2005, pp. 1005-1010.
Minchenko et al., "Hypoxia induces transcription of 6-phosphofructo-2-kinase/fructose-2,6-biphosphatase-4 gene via hypoxia-inducible factor-1a activation", FEBS Letters, vol. 576, 2004, pp. 14-20.
Okar et al., "PFK-2/FBPase-2: maker and breaker of the essential biofactor fructose-2,6-bisphosphate", TRENDS in Biochemical Sciences, vol. 26, No. 1, Jan. 2001, pp. 30.
Pan et al., "Metabolic Targeting as an Anticancer Strategy: Dawn of a New Era?", Science STKE, vol. 381, Apr. 12, 2007, pp. 1-4.
Pilkis et al., "6-Phosphofructo-2-Kinase/Fructose-2,6-Bisphosphatase: A Metabolic Signaling Enzyme", Annual Reviews Biochem., vol. 64, 1995, pp. 799-835.
Ple et al., "Synthesis of Substituted Benzol(b)thiophenes by Acid-Catalyzed Cyclization of Thiophenylacetals and Ketones", J. Heterocyclic Chem, vol. 25, Jul.-Aug. 1988, pp. 1271-1272.
Ramanathan et al., "Perturbational profiling of a cell-line model of tumorigenesis by using metabolic measurements", PNAS, vol. 102, No. 17, Apr. 26, 2005, pp. 5992-5997.
Rider et al., "6-Phosphofructo-2-kinase/fructose-2,6-bisphosphatase: head-to-head with a bifunctional enzyme that controls glycolysis", Biochemical Journal, vol. 381, 2004, pp. 561-579.
Ros et al., "Functional Metabolic Screen Identifies 6-Phosphofructo-2-Kinase/Fructose-2,6-Biphosphatase 4 as an Important Regulator of Prostate Cancer Cell Survival", Cancer Discovery, Apr. 2002, pp. 329-343.
Sakakibara et al., "Hexose Phosphate Binding Sites of Fructose-6-phosphate,2-kinase:Fructose-2,6-bisphosphatase",The Journal of Biological Chemistry, vol. 259, No. 22, Nov. 25, 1984, pp. 14023-14028.
Seo et al., "Structure-Based Development of Small Molecule PFKFB3 Inhibitors: A Framework for Potential Cancer Therapeutic Agents Targeting the Warburg Effect", PLoS One, vol. 6, Issue 9, Sep. 2011, 12 pages.
Telang et al., "Ras transformation requires metabolic control by 6-phosphofructo-2-kinase", Oncogene, vol. 24, 2006, pp. 7225-7234.
Van Schaftingen et al., "A Kinetic Study of Pyrophosphate: Fructose-6-Phosphate Phosphotransferase from Potato Tubers", Eur. J. Biochem, vol. 192, Feb. 1982, pp. 191-195.
Vander Heiden et al., "Understanding the Warburg Effect: The Metabolic Requirements of Cell Proliferation", Science, vol. 324, May 22, 2009, pp. 1029-1033.
Walenta et al., "Lactate: Mirror and Motor of Tumor Malignancy", Seminars in Radiation Oncology, vol. 14, No. 3, Jul. 2004, pp. 267-274.
Walenta et al., "Lactate in Solid Malignant Tumors: Potential Basis of a Metabolic Classification in Clinical Oncology", Current Medicinal Chemistry, vol. 11, No. 16, 2004, pp. 2195-2204.
Warburg, "On the Origin of Cancer Cells", Science, vol. 123, No. 3191, Feb. 24, 1956, pp. 309-314.
Xie et al., "Synthesis of benzofurans in ionic liquid by a PdCl2-catalyzed intramolecular Heck reaction", Tetrahedron Letters, vol. 45, 2004, pp. 6235-6237.
Xu et al., "Inhibition of Glycolysis in Cancer Cells: A Novel Strategy to Overcome Drug Resistance Associated with Mitochondrial Respiratory Defect and Hypoxia", Cancer Research, vol. 65, No. 2, Jan. 15, 2005, pp. 613-621.

\* cited by examiner

BISARYLSULFONAMIDES USEFUL IN THE TREATMENT OF INFLAMMATION AND CANCER

This application is a national phase of International Application No. PCT/EP2012/076836 filed Dec. 21, 2012 and published in the English language.

TECHNICAL FIELD

The present invention relates to novel sulfonamide derivatives, to pharmaceutical compositions comprising these derivatives, to processes for their preparation and to sulfonamide derivatives for use in a diagnostic method, profylaxis, or in therapy, e.g. for the treatment of inflammation and cancer.

BACKGROUND OF THE INVENTION

In the 1920s Otto Warburg first proposed non-oxidative metabolism of glucose as a unique feature of tumors (Warburg, (1930) Ueber den stoffwechsel der tumoren (London: Constable); Warburg, (1956) Science 123, 309-314). This hypothesis has since caused significant interest and although mechanistic links are still, almost 100 years later, under investigation. A high glucose flux of tumor is today exploited clinically, using PET imaging of $^{18}$F-2-deoxyglucose uptake as a diagnostic tool for solid tumors.

Lately, energy processing of cancer cells has been given new attention (e.g. Vander Heiden, et al., 2009, Science 324, 1029). The hypoxic microenvironment and consequential lactate accumulation resulting from altered tumor metabolism are reported predictive for both metastatic potential and therapy resistance, and thus survival of cancer patients (Brown, (1999) Cancer Res. 59, 5863-5870; Walenta& Mueller-Klieser, (2004) Semin. Radiat. Oncol. 14, 267-274; Walenta et al., (2004) Curr. Med. Chem. 11, 2195-2204). Targeting of hypoxic and/or acidotic tumor areas has therefore drawn attention as a complement to anti-proliferative treatments (see e.g. Pan &Mak, (2007) Sci. STKE 381, pe14; Bache et al., (2008) Curr. Med. Chem. 15, 322-338 for reviews).

Known inhibitors of glycolysis include among others 2-deoxyglucose and 2-bromo-puruvate targeting hexokinase (Liu et al., (2001) Biochemistry 40, 5542-5547; Liu et al. (2002) Biochem. Pharmacol. 64, 1745-1751; Xu et al., (2005) Cancer Res. 65, 613-621; Ramanathan et al., (2005) Proc. Natl. Acad. Sci. USA 102, 5992-5997). Fructose-2,6-bisphosphate ($F-2,6-P_2$) plays a regulatory role in glucose metabolism by relieving ATP inhibition of phosphofructokinase-1. The levels of $F-2,6-P_2$ are regulated by the bifunctional enzyme family 6-phosphofructo-2-kinase/fructose-2,6-bisphosphatase (PFKFB1-4).

Out of these four isozymes, mainly PFKFB3 and PFKFB4 are of particular interest for playing a role in cancer. Antisense treatment against PFKFB3 was shown to reduce tumor growth rate in vivo (Chesney et al., (1999) Proc. Natl. Acad. Sci. USA 96, 3047-3052). Similarly, a decreased anchorage independent growth was shown for siRNA treated fibroblasts (Telang et al., (2006) Oncogene 25, 7225-7234). A link between inflammation and enhanced glycolysis and a possible potential for PFKFB3 inhibitors to act as a anti-inflammatory agents was indicated by a report that the IL-6-STAT3 pathway may enhance glycolysis through the induction of PFKFB3 (Ando et al. J Nippon Med Sch (2010), 77, (2), 97-105). This possibility was further supported by a recent study using a small molecule; 3-(3-pyridinyl)-1-(4-pyridinyl)-2-propen-1-one (3PO), previously shown to reduce $F-2,6-P_2$ synthesis, glucose uptake and proliferation in transformed cells (see below). Telang et al. demonstrated that 3PO attenuates the activation of T cells in vitro and suppresses T cell dependent immunity in vivo, indicating that small molecule inhibitors of PFKFB3 may prove effective as T cell immunosuppressive agents (Telang et al., (2012) Journal of Translational Medicine 2012, 10:95). Moreover, hypoxia is a prominent feature in rheumatoid arthritis (RA) synovium and induces significant changes in the expression of PFKFB3 and PFKFB4 (Del Rey et al., (2010) Arthritis & Rheumatism 62, 3584-3594).

The PFKFB4 protein was reported to be strongly responsive to hypoxia (Minchenko et al., (2004) FEBS Lett. 576, 14-20); Minchenko et al., (2005), Biochemie 87, 1005-1010; Bobarykina et al., (2006), Acta Biochemica Polonica 3, 789-799). US2010/0267815 A1). Minchenko et al. demonstrated an increased expression of PFKFB4 mRNA in malignant breast and colon cancers, as compared to corresponding non-malignant tissue counterparts. Recently, Telang et al. showed decreased levels of $F-2,6-P_2$ and lactate as well as decreased tumor growth following siRNA silencing of PFKFB4 (Telang, S. et al, (2010). Further support for PFKFB4 as a potential target for the development of anti-neoplastic agents came from a functional metabolic screen that identified PFKFB4 as an important regulator in prostate cancer (Ros et al. (2012) Cancer Discov. 2(4):328-43).

Only a small number of specific inhibitors of the kinase activities of PFKFB3 and PFKFB4 have been identified. In one study, an alkylating inhibitor, N-bromoacetylethanolamine phosphate, was used as a tool to investigate the binding sites of the kinase and phosphatase domains of PFKFB3 and demonstrated to irreversibly inactivate PFK-2 (Sakakibara et al. (1984), J. Bio Chem 259, 14023-14028). The compound is a competitive inhibitor of PFK-2 with respect to F6P but a non-competitive inhibitor with respect to ATP. Analogues of this compound, N-(2-methoxyethyl)-bromoacetamide, N-(2-ethoxyethyl)-bromoacetamide and N-(3-methoxypropyl)-bromoacetamide, have demonstrated in vivo activity with increased survival rate of P388 transplant $BDF_1$ mice (Hirata et al. (2000) Biosci. Biotechnol. Biochem. 64, 2047-2052).

A crystal structure of the PFKFB3*ADP*phosphoenolpyruvate complex was described by Kim et al. (Kim et al. (2007), J. Mol. Biol. 370, 14-26). This paper also described the crystal structures of PFKFB3*AMPPCP*fructose-6 phosphate complex in which β,γ-methylene-adenosine 5'-triphosphate (AMPPCP) constituted a non-hydrolysable ATP-analogue. Recently, small molecule PFKFB3 inhibitors identified by virtual screening were described (Chrochet et al. (2011), Anal. Biochem. 418, 143-148; Seo et al., (2011), Plosone, 9, e24179 & Lee et al. (2012) US 2012/0302631). The identified PFKFB3 inhibitors were shown to reduce the levels of $F-2,6-P_2$, resulting in decreased tumor growth and increased cell death.

A drug-like compound was described (Clem et al. (2008) Mol. Cancer Ther. 7, 110-120; Chesney et al. (2008) WO 2008/156783) where 3-(3-pyridinyl)-1-(4-pyridinyl)-2-propen-1-one (3PO), by computational methods, was identified as a PFKFB3 inhibitor. Administration of 3PO reduced the intracellular concentration of $F-2,6-P_2$, glucose uptake, and growth of established tumors in vivo. Recently, substituted benzindoles were described as inhibitors of PFKFB3. The benzindoles were shown to inhibit proliferation in several cancer cell lines, inhibit glucose uptake as well as to reduce tumor growth in vivo in tumor models (Chand et al. (2011) WO2011/103557A1).

SUMMARY OF THE INVENTION

One object of the present invention is to provide compounds for use in a diagnostic method, prophylaxis and treatment of inflammation or cancer.

Another object of the present invention is to provide compounds for use in the inhibition of the metabolism of cancer cells and immune competent cells to modulate disease.

Another object of the present invention is to provide compounds for use in the inhibition of the glucose metabolism of cancer cells and immune competent cells to modulate disease.

One object of the present invention is to provide compounds affecting the $F-2,6-P_2$ levels in cells.

Thus, according to a first aspect, there is provided a compound according to formula (I)

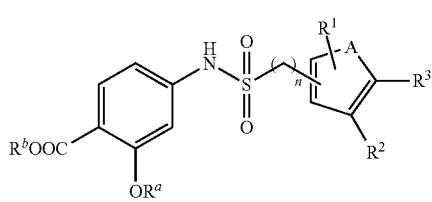

wherein
n is 0 or 1;
A is O, S, —CR$^4$=CR$^4$— or —CR$^4$=N—;
R$^1$ is selected from H; halogen; C1-C6 alkyl, optionally substituted with at least one halogen; and C1-C6 alkoxy, optionally substituted with at least one halogen;
R$^2$ and R$^3$ are each independently selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; heterocyclyloxy; carbocyclyl-C0-C3 alkyl; carbocyclyl-C2-C3 alkenyl; heterocyclyl-C0-C3 alkyl; and heterocyclyl-C2-C3 alkenyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one R$^5$;
or R$^2$ and R$^3$ form, together with the carbon atoms to which they are attached, a 5- or 6-membered carbocyclic or heterocyclic ring, which ring is optionally substituted with at least one R$^5$;
provided that R$^1$, R$^2$ and R$^3$ are not all hydrogen;
each R$^4$ is independently selected from H, halogen, monocyclic C3-C6 carbocyclyl and C1-C6 alkyl, wherein any alkyl is optionally substituted with at least one halogen;
each R$^5$ is independently selected from halogen; C1-C6 alkyl; C1-C6 alkoxy; phenoxy; amino; cyano; nitro; secondary or tertiary C1-C6 alkylamino; 5- or 6-membered cyclic amino, optionally containing at least one further heteroatom in the ring; C1-C6 alkylcarbonylamino; carbamoyl; secondary or tertiary C1-C6 alkylamido; 5- or 6-membered cyclic aminocarbonyl; C1-C6 alkoxycarbonylamino; hydroxy-C0-C6 alkyl; C1-C6-alkylthio; carboxy-C0-C6-alkyl; C1-C6 alkoxycarbonyl; C1-C6 alkylcarbonyl; C1-C6-alkylsulfonyl; and C1-C6 alkylsulfonylamino; wherein any alkyl is optionally substituted with at least one halogen;
R$^a$ is selected from H and C1-C6 alkylcarbonyl;
R$^b$ is selected from H, C1-C6 alkyl, C1-C6 alkyl substituted with at least one R$^6$; carbocyclyl-C0-C5 alkyl; and heterocyclyl-C0-C5 alkyl; wherein any carbocyclyl and heterocyclyl is 5- or 6-membered and is optionally substituted with at least one R$^7$ and optionally comprises at least one oxo group in the ring;
provided that R$^a$ and R$^b$ are not both H;
each R$^6$ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl) amino; (C1-C6 alkylcarbonyl)(C1-C6 alkyl)amino; carbamoyl; secondary or tertiary C1-C6 alkylamido wherein any alkyl is optionally substituted by OH or CONH$_2$; 5- or 6-membered carbocyclyl- or heterocyclylcarbamoyl; 5- or 6-membered cyclic aminocarbonyl, optionally containing at least one further heteroatom in the ring, and wherein the ring is optionally substituted with at least one C1-C6 alkyl; 5- or -6-membered carbocyclylamino or heterocyclylamino; and 5- or -6-membered carbocyclyloxy or heterocyclyloxy; wherein any alkyl is optionally substituted with at least one halogen and any 5- or 6-membered carbocyclyl or heterocyclyl is optionally substituted with at least one R$^8$;
each R$^7$ and R$^8$ is independently selected from C1-C6 alkyl; hydroxy-C0-C3 alkyl; C1-C6 alkoxy-C0-C3 alkyl; C1-C6 alkoxycarbonyl; carbocyclyl-C0-C4 alkyl; heterocyclyl-C0-C4 alkyl; C1-C6 alkylsulfinyl; amino; nitro; C1-C6 secondary or tertiary amino; halogen; carbamoyl; secondary or tertiary C1-C6 alkylamido-C0-C3 alkyl; C1-C6 alkylcarbonylamino; and 5- or 6-membered cyclic amino, optionally containing at least one further heteroatom in the ring and wherein the ring is optionally substituted with at least one C1-C6 alkyl; wherein any alkyl is optionally substituted with at least one halogen; wherein any carbocyclyl and heterocyclyl is 5- or 6-membered;
or a pharmaceutically acceptable salt thereof,
provided that the compound is not
5-(N-(3-hydroxy-4-(methoxycarbonyl)phenyl)sulfamoyl)-2-methoxybenzoic acid,
methyl 2-hydroxy-4-(4-propylphenylsulfonamido)benzoate,
methyl 4-(4-ethylphenylsulfonamido)-2-hydroxybenzoate,
methyl 4-(4-butylphenylsulfonamido)-2-hydroxybenzoate,
methyl 4-(3-bromophenylsulfonamido)-2-hydroxybenzoate,
methyl 4-(4-(tert-butyl)phenylsulfonamido)-2-hydroxybenzoate,
methyl 4-(3,5-dichlorophenylsulfonamido)-2-hydroxybenzoate,
methyl 2-hydroxy-4-(3-methylphenylsulfonamido)benzoate,
methyl 4-(3-fluorophenylsulfonamido)-2-hydroxybenzoate, ethyl 4-(4-acetamidophenylsulfonamido)-2-hydroxybenzoate,
methyl 4-(4-acetamidophenylsulfonamido)-2-hydroxybenzoate,
phenyl 2-hydroxy-4-(4-methylphenylsulfonamido)benzoate,
phenyl 4-(4-chlorophenylsulfonamido)-2-hydroxybenzoate,
methyl 2-hydroxy-4-(4-(4-oxo-1,4-dihydropyrazolo[1,5-a][1,3,5]triazin-8-yl)phenylsulfonamido)benzoate,
methyl 2-hydroxy-4-(4-methylphenylsulfonamido)benzoate,
2-acetoxy-4-(4-methylphenylsulfonamido)benzoic acid,
methyl 2-hydroxy-4-(3-(methylcarbamoyl)phenylsulfonamido)benzoate,
methyl 2-hydroxy-4-(3-(piperidine-1-carbonyl)phenylsulfonamido)benzoate,
methyl 4-(3-bromo-5-(trifluoromethyl)phenylsulfonamido)-2-hydroxybenzoate,
3-(N-(3-hydroxy-4-(methoxycarbonyl)phenyl)sulfamoyl)benzoic acid,
methyl 4-((3-bromophenyl)methylsulfonamido)-2-hydroxybenzoate, or
methyl 4-(4,5-dichlorothiophene-2-sulfonamido)-2-hydroxybenzoate.

In one embodiment, A is O, S, —CR$^4$═CR$^4$— or —CR$^4$═N—; and when A is —CR$^4$═CR$^4$— or —CR$^4$═N—, one of R$^2$ and R$^3$, e.g. R$^2$, is selected from carbocyclyl-C0-C3 alkyl; carbocyclyl-C2-C3 alkenyl; heterocyclyl-C0-C3 alkyl; and heterocyclyl-C2-C3 alkenyl; wherein any carbocyclyl or heterocyclyl is 5- or 6-membered monocyclyl or 9- or 10-membered bicyclyl; and any carbocyclyl or heterocyclyl is optionally substituted with at least one R$^5$; or R$^2$ and R$^3$ form, together with the carbon atoms to which they are attached, a 5- or 6-membered carbocyclic or heterocyclic ring, which ring is optionally substituted with at least one R$^5$.

In another embodiment, A is O, S, —CR$^4$═CR$^4$— or —CR$^4$═N—; and when A is O or S, R$^2$ and R$^3$ are each independently selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; wherein any alkyl is optionally substituted with at least one halogen.

In another embodiment, R$^3$ is selected from H; halogen; and C1-C6 alkyl, wherein any alkyl is optionally substituted with at least one halogen; or R$^2$ and R$^3$ form, together with the carbon atoms to which they are attached, a 5- or 6-membered carbocyclic or heterocyclic ring, which ring is optionally substituted with at least one R$^5$.

In another embodiment, R$^2$ is selected from H; halogen; C1-C6 alkyl; carbocyclyl-C0-C3 alkyl; carbocyclyl-C2-C3 alkenyl; heterocyclyl-C0-C3 alkyl; and heterocyclyl-C2-C3 alkenyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one R$^5$; or R$^2$ and R$^3$ form, together with the carbon atoms to which they are attached, a 5- or 6-membered carbocyclic or heterocyclic ring, which ring is optionally substituted with at least one R$^5$.

In another embodiment, R$^2$ is selected from carbocyclyl-C0-C3 alkyl; carbocyclyl-C2-C3 alkenyl; heterocyclyl-C0-C3 alkyl; and heterocyclyl-C2-C3 alkenyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one R$^5$; or R$^2$ and R$^3$ form, together with the carbon atoms to which they are attached, a 5- or 6-membered carbocyclic or heterocyclic ring, which ring is optionally substituted with at least one R$^5$.

The disclaimed compounds within the scope of formula (I) were found in a database search using the Internet search tool SciFinder. However, for most of these compounds, no particular use was found to be indicated; in particular, there was no indication that they had ever been used in therapy, with a few exceptions:

Therefore, another object of the invention is to provide a compound of formula (I) as defined herein above, for use in therapy, provided that the compound is not:
ethyl 4-(4-acetamidophenylsulfonamido)-2-hydroxybenzoate,
methyl 4-(4-acetamidophenylsulfonamido)-2-hydroxybenzoate,
phenyl 2-hydroxy-4-(4-methylphenylsulfonamido)benzoate, or
methyl 2-hydroxy-4-(4-(4-oxo-1,4-dihydropyrazolo[1,5-a][1,3,5]triazin-8-yl)phenylsulfonamido)benzoate.

Another object of the invention is to provide a compound of formula (I) as defined herein above, for use in the treatment of inflammation, inflammatory disorders or cancer, provided that the compound is not methyl 2-hydroxy-4-(4-(4-oxo-1,4-dihydropyrazolo[1,5-a][1,3,5]-triazin-8-yl)phenylsulfonamido)benzoate.

Furthermore, a pharmaceutical composition is provided, comprising a compound as defined herein, and optionally at least one pharmaceutically acceptable excipient.

Thus, the present invention provides a method of diagnosis, profylaxis and treatment of cancer and inflammation, by the modulation of F-2,6-P$_2$ levels, and a compound for use in such a method.

The compounds of the present invention may act as modulators of F-2,6-P$_2$ levels. In some embodiments, the compounds of the above formula can exhibit a F-2,6-P$_2$ level modulating activity corresponding to an IC$_{50}$ of from about 50 nM to about 25 µM; e.g., from about 100 nM to about 10 µM, from about 200 nM to about 5 µM, or from about 500 nM to about 1 µM or a lower concentration as tested in an conventional assay as will be described below.

While not wishing to be bound by theory, it is believed that the compounds described herein, by virtue of their F-2,6-P$_2$ level modulating activity, can be used, e.g., for the treatment or prevention of cancer and inflammation, and/or in treatment of disorders related to cancer and inflammation.

Of particular interest are tumors with elevated glucose uptake compared to normal nontumor tissues, identified by for example PET studies. These tumors include, but are not limited to breast cancer, lung cancer, prostate cancer, colorectal cancers, pancreatic cancers, haematological cancers and melanoma.

A further object of this invention relates to compounds of formula (I) for use as a medicament, especially for the treatment of cancer and inflammation.

In a further aspect the present invention relates to a method for the treatment or prophylaxis of a disease, disorder, or condition related to undesired level of F-2,6-P$_2$ (e.g., inflammatory disorder and cancer). The method includes administering to a subject (e.g., a subject in need thereof, e.g., a mammal; e.g., a human; e.g., a human having, identified as having, at risk of having, or identified as being at risk of having one or more of the diseases or disorders described herein) an effective amount of a compound of formula I or a pharmaceutically acceptable salt or prodrug thereof.

In one aspect, this invention relates to a method for the treatment or prophylaxis of cancer and inflammation, which includes administering to a subject (e.g., a subject in need of such treatment as described herein) an effective amount of a compound of formula I or a pharmaceutically acceptable salt or prodrug thereof.

In another aspect, this invention relates to a method for the treatment or prophylaxis (e.g., treatment) of cancer, which includes administering to a subject (e.g., a subject in need of such treatment as described herein) an effective amount of a compound of formula I or a pharmaceutically acceptable salt or prodrug thereof.

In some embodiments, the subject can be a subject in need of such treatment as described herein. Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject is a human.

In a further aspect, this invention relates to the use of a compound of formula I (e.g., as a medicament or) in the manufacture of a medicament containing a compound of formula I for a diagnostic method, treatment or prophylaxis (e.g., treatment) of a disease, disorder, or condition related to undesired levels of F-2,6-$P_2$ as described herein.

In one aspect, the invention relates to a compound (including a pharmaceutically acceptable salt thereof) of any of the formulae delineated herein (e.g., a compound having formula I, or subgenera thereof), including the specific compounds described herein); or a composition or formulation (e.g., a pharmaceutical composition or formulation) comprising a compound (including a pharmaceutically acceptable salt thereof) of any of the formulae delineated herein (e.g., a compound having formula I, or subgenera thereof), including the specific compounds described herein). In some embodiments, the composition or formulation can further include a pharmaceutically acceptable adjuvant, carrier or diluent. Any such compound can be used in the methods described herein.

DETAILED DESCRIPTION OF THE INVENTION

Figure 1:
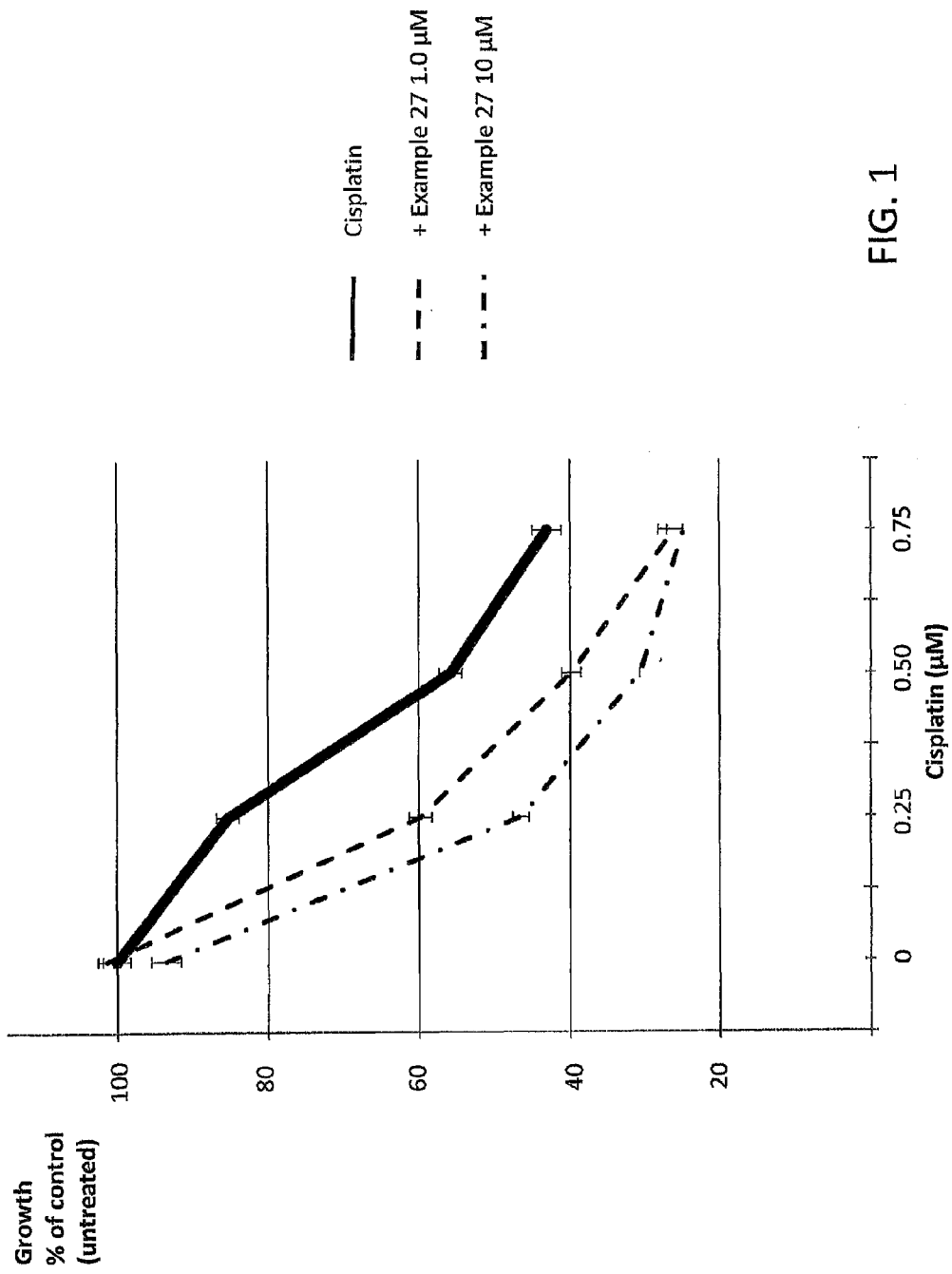
FIG. 1 is a chart representing the growth inhibitory effect of the compound of Example 27 in combination with cisplatin, on cell proliferation in the gastric tumor cell line NUGC-3 (72 h).

The following definitions shall apply throughout the specification and the appended claims.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"Diagnostic" as used herein includes a systematic/diagnostic method used to identify the presence of an entity where multiple alternatives are possible; either to help select the patients likely to benefit from the treatment, or to help define a combination of substances/therapies likely to be beneficial for a specific patient.

"An effective amount" refers to an amount of a compound that confers a therapeutic effect on the treated subject. The therapeutic effect may be objective (i.e., measurable by some test or marker) or subjective (i.e., subject gives an indication of or feels an effect).

Reference to compounds of "formula I" in embodiments herein also includes compounds of any of the formulae delineated herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

As used herein, the term "carbocyclyl" refers to a cyclic moiety containing only carbon atoms in the ring structure, while the term "heterocyclyl" refers to a cyclic moiety containing not only carbon atoms, but also at least one other atom in the ring structure, e.g. a nitrogen, sulphur or oxygen atom. For the purpose of the present invention and unless otherwise indicated or apparent from the context, the terms "carbocyclyl" and "heterocyclyl" should not be construed as encompassing cyclic moieties containing an oxo group in the ring, such as in e.g. cyclohexa-2,5-dienone, cyclohexanone or 3H-pyrrol-3-one.

As used herein with respect to any carbocyclyl or heterocyclyl, the term monocyclic refers to a cyclic moiety containing only one ring. The term bicyclic refers to a cyclic moiety containing two rings, fused to each other.

The term "oxo group" as used herein refers to a moiety of formula

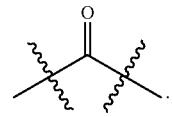 [SMILES: *C(*)=O]

A cyclic moiety containing an oxo group in the ring comprises at least one ring carbon atom which is the carbon atom of an oxo group.

Unless otherwise indicated or apparent from the context, any cyclyl, as referred to herein, may be carbocyclyl or heterocyclyl, saturated or unsaturated, and aromatic or non-aromatic. Thus, cyclohexyl, cyclohexenyl and phenyl are all examples of monocyclic C6 carbocyclyl.

The term "aromatic", as used herein, refers to an unsaturated cyclic (carbocyclic or heterocyclic) moiety that has an aromatic character, while the term "non-aromatic", as used herein, refers to a cyclic moiety, that may be unsaturated, but that does not have an aromatic character.

In a bicyclic ring system, as referred to herein, the two rings, fused to each other, may be both saturated or both unsaturated, e.g. both aromatic. The rings may also be of different degrees of saturation, and one ring may be aromatic whereas the other is non-aromatic. The rings also may comprise different numbers of atoms, e.g. one ring being 5-membered and the other one being 6-membered, forming together a 9-membered bicyclic ring.

In a bicyclic heterocyclyl (or heterocycle or heterocyclic moiety, etc.), as referred to herein, one or both of the rings may contain one or several, e.g. 1, 2, 3 or 4 heteroatoms. By heteroatom according to the invention is meant N, O and S.

An n-membered cyclic moiety as referred to herein contains n ring (or cyclic) atoms.

Examples of aromatic heterocyclic moieties according to the invention are pyrrolyl, pyrazolyl, imidazolyl, furyl, thienyl, oxadiazolyl, thiadiazolyl, thiazolyl, oxazolyl, triazolyl, tetrazolyl, isoxazolyl, isothiazolyl, pyridyl, pyrazinyl, pyrimidinyl, pyridazinyl, benzothiazolyl, benzoxadiazolyl, benzimidazolyl, indazolyl, benzothiadizolyl, benzofuryl, benzoxazolyl, benzothienyl, isoquinolinyl, naphthyridinyl, quinolinyl, phthalazinyl, quinazolinyl, quinolinyl, quinoxalinyl, cinnolinyl, pteridinyl, etc.

As used herein, and unless otherwise specified, the term "non-aromatic heterocycle" or "non-aromatic heterocyclyl" refers to a non-aromatic cyclic group or radical containing one or more heteroatom(s) preferably selected from N, O and S, such as a dihydropyrrolyl, dioxolanyl, dithiolanyl, imidazolidinyl, imidazolinyl, pyrrolidinyl, pyrazolidinyl, tetrahydrofuryl, thiolanyl, dihydropyranyl, dihydropyridyl, dioxanyl, dithianyl, morpholinyl, piperidyl, piperazinyl, pyranyl, tetrahydropyranyl, tetrahydropyridyl, tetrahydro-2H-thiopyranyl, and trithianyl etc.

Other examples of non-aromatic heterocycles are bicyclyl radicals, also including those containing one aromatic and one non-aromatic ring, e.g. indolinyl, chromanyl, thiochromanyl, dihydrobenzofuryl, 1,2,3,4-tetrahydroisoquinolyl, etc.

The term Cn refers to a radical or moiety containing n carbon atoms.

The term Cn-Cm, where m>n, refers to a radical or moiety containing n, n+1, n+2, . . . or m carbon atoms.

Thus, the term C1-C6 alkyl refers to an alkyl radical that may contain 1, 2, 3, 4, 5 or 6 carbon atoms.

The term C0 alkyl refers to a covalent bond. Thus, e.g. the term carbocyclyl-C0 alkyl refers to carbocyclyl.

An alkyl moiety according to the invention having from 1-6 C (i.e. a C1-C6 alkyl) may be branched or linear, e.g. selected from methyl, ethyl, n-propyl, i-propyl, n-butyl, i-butyl, sec-butyl, tert-butyl, n-pentyl, 2-methylbutyl, 2,2-dimethylpropyl, n-hexyl, 2-methylpentyl, 3-methylpentyl, 2,2-dimethylbutyl, and 2,3-dimethylbutyl.

Any C1-C6 alkyl according to the invention more particularly may be selected from C1-C5 alkyl, e.g. from C1-C4 alkyl, from C1-C3 alkyl, from C1-C2 alkyl, or from methyl.

An alkenyl moiety according to the invention is a straight or branched hydrocarbyl comprising at least one double bond between any two adjacent carbon atoms, e.g. a straight or branched hydrocarbyl comprising 1 double bond.

As used herein, and unless otherwise specified, the term "halogen" (or "halo") means fluorine (F), chlorine (Cl), bromine (Br) or iodine (I).

Any halogen according to the invention in particular may be selected from F, Cl, and Br, e.g. from F and Cl, or from F.

The term carbocyclyloxy refers to a radical of the type RO—, wherein R is a carbocyclyl moiety. Phenoxy is an example of a carbocyclyloxy radical.

The term phenoxy refers to the radical

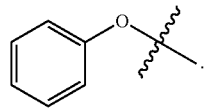 [SMILES: *Oc1ccccc1]

The term heterocyclyloxy refers to a radical of the type RO—, wherein R is a heterocyclyl moiety.

The term alkoxy refers to a radical of the type RO—, wherein R is an alkyl moiety.

The term C1-C6 alkoxy-C0-C3 alkyl refers to C1-C6 alkoxy (when C0-C3 alkyl is C0 alkyl) or to a C1-C3 alkyl radical substituted by a C1-C6 alkoxy.

The term alkoxycarbonyl refers to a radical of the type ROC(O)—, wherein R is an alkyl moiety.

The term carboxy refers to the radical HO(O)C—.

The term alkylthio refers to a radical of the type RS—, wherein R is an alkyl moiety.

The term amino refers to the radical $H_2N$—.

The term hydroxy refers to the radical HO—.

The term hydroxy-C0-C6 alkyl refers to a radical selected from hydroxy (viz. hydroxy-C0 alkyl) and a C1-C6 alkyl radical substituted with a hydroxy. The hydroxy may be attached at any carbon atom of the alkyl radical, and the alkyl radical may be branched or linear. For example, hydroxy-C1 alkyl is hydroxymethyl.

The term secondary or tertiary hydroxy-C1-C6 alkylamino refers to secondary or tertiary alkylamino wherein at least one alkyl is substituted by a hydroxy group.

The term hydroxy-C1-C6 alkoxy refers to a C1-C6 alkoxy wherein the alkyl moiety is substituted with a hydroxy group.

The term hydroxy-C1-C6 alkoxy-C1-C6 alkyl refers to a C1-C6 alkyl substituted with a hydroxy-C1-C6 alkoxy group.

The term cyano refers to the radical NC—.

The term benzyl refers to the radical

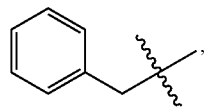 [SMILES: *Cc1ccccc1]

which radical may also be referred to as phenylmethyl.

By "alkyl substituted with at least one halogen" is meant an alkyl radical of the formula $C_nX_pH_{(2n+1-p)}$—, wherein $X_p$ refers to p independently selected halogen atoms, replacing p hydrogen atoms of the alkyl radical $C_nH_{2n+1}$— at the same or different carbon atoms. An example of an alkyl substituted with at least one halogen is trifluoromethyl. The alkyl substituted with at least one halogen may be a moiety forming a part of another radical, such as in trifluoromethoxy or difluoromethoxy.

The term trifluoromethyl refers to the radical $CF_3$—.

The term trifluoromethoxy refers to the radical $CF_3O$—.

The term difluoromethoxy refers to the radical $CHF_2O$—.

The term secondary alkylamino refers to a radical of the type RHN—, wherein R is an alkyl moiety.

The term tertiary alkylamino refers to a radical of the type RR'N—, wherein R and R' are each an independently selected alkyl moiety.

The term carbamoyl refers to the radical $NH_2C(O)$—.

The term secondary alkylamido refers to radical of the type RHNC(O)—, wherein R is an alkyl moiety.

The term tertiary alkylamido refers to a radical of the type RR'NC(O)—, wherein R and R' are each an independently selected alkyl moiety.

The term alkylcarbonylamino refers to a radical of the type RC(O)NH—, wherein R is an alkyl moiety.

The term alkoxylcarbonylamino refers to a radical of the type ROC(O)NH—, wherein R is an alkyl moiety.

The term (C1-C6 alkoxycarbonyl)(C1-C6 alkyl)amino refers to a radical of the type

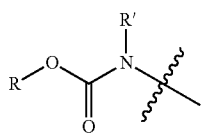

wherein R and R' are independently selected C1-C6 alkyl moieties.

The term (C1-C6 alkoxycarbonyl)(5- or 6-membered carbocyclyl or heterocyclyl)amino refers to a radical of the type

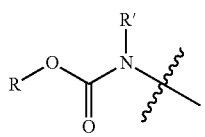

wherein R is a C1-C6 alkyl moiety and R' is a 5- or 6-membered carbocyclyl or heterocyclyl.

The term (C1-C6 alkoxycarbonyl)(phenyl)amino refers to a radical of the type

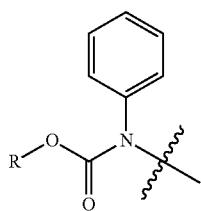

wherein R is a C1-C6 alkyl moiety.

The term benzoyl refers to the radical

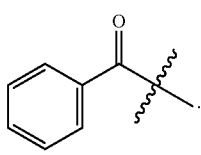 [SMILES: *C(=O)c1ccccc1]

The term carbocyclylcarbonylamino refers to a radical of the type RC(O)NH—, wherein R is a carbocyclic moiety, e.g. an aromatic carbocyclic moiety such as phenyl.

The term carbocyclylcarbonylamino-C0-C2 alkyl refers to a radical selected from carbocyclylcarbonylamino (viz. carbocyclylcarbonylamino-C0 alkyl), carbocyclylcarbonylaminomethyl (viz. carbocyclylcarbonylamino-C1 alkyl) or carbocyclylcarbonylaminoethyl (viz. carbocyclylcarbonylamino-C2 alkyl).

The term 5- or 6-membered carbocyclylamino refers to a radical of the type RNH—, wherein R is a carbocyclyl as defined herein above, and is 5- or 6-membered. An example is phenylamino, i.e. the radical

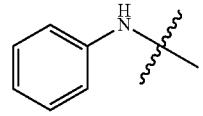

The term 5- or 6-membered or heterocyclylamino refers to a radical of the type RHN—, wherein R is a heterocyclyl as defined herein above, and is 5- or 6-membered. An example is pyridinylamino.

The term alkylcarbonyl refers to a radical of the type RC(O)—, wherein R is an alkyl moiety.

The term acetyl refers to an alkylcarbonyl radical of formula $CH_3C(O)$—.

The term cyclic amino refers to a radical of the type RR'N—, wherein R and R' together with the nitrogen atom to which they are attached form a nitrogen-containing cycle. An example of a cyclic amino is piperidin-1-yl.

The term cyclic amino optionally containing at least one further heteroatom in the ring refers to a radical of the type RR'N—, wherein R and R' together with the nitrogen atom to which they are attached form a nitrogen-containing cycle and wherein at least one of R and R' contains a heteroatom, e.g. O or N, that forms part of the ring. Examples of cyclic amino containing a further heteroatom in the ring are morpholino and piperazinyl. When the further heteroatom is nitrogen, this nitrogen may be substituted by C1-C6 alkyl, e.g. C1-C3 alkyl, e.g. methyl.

The term cyclic aminocarbonyl refers to a radical of the type RR'N—C(O)—, wherein RR'N— is a cyclic amino as defined herein above.

The term alkylsulfonyl refers to a radical of the type $RS(O)_2$—, wherein R is an alkyl moiety.

The term alkylsulfonylamino refers to a radical of the type $RS(O)_2NH$—, wherein R is an alkyl moiety.

The term nitro refers to the radical —$NO_2$.

The term carboxy-C0-C6 alkyl refers to a carboxy (i.e. carboxy-C0 alkyl) and a C1-C6 alkyl substituted with a carboxy.

The term C1-C6 alkylcarbonyloxy refers to a radical of the type

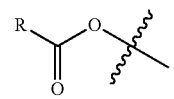

wherein R is C1-C6 alkyl.

The term C1-C6 alkoxycarbonyloxy refers to a radical of the type

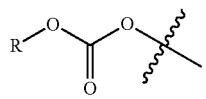

wherein R is C1-C6 alkyl.

The term (C1-C6 alkylcarbonyl)(C1-C6 alkyl)amino refers to a radical of the type

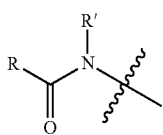

wherein R and R' are independently selected C1-C6 alkyl moieties.

The term C1-C6 alkoxycarbonylamino refers to a radical of the type

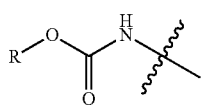

wherein R is C1-C6 alkyl.

The term phenylcarbamoyl refers to the radical

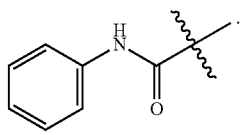 [SMILES: *C(=O)Nc1ccccc1]

The term C1-C6 alkylsulfinyl refers to the radical

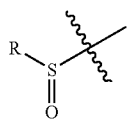

wherein R is C1-C6 alkyl.

According to one aspect, the present invention provides a compound of formula (I)

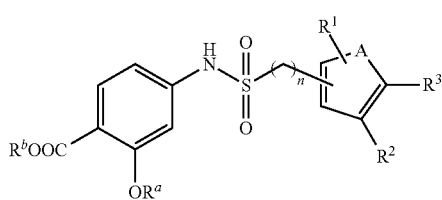

as defined herein above, or a pharmaceutically acceptable salt thereof.

In some embodiments, in a compound of formula (I), $R^1$, $R^2$, $R^3$, $R^a$ and n is as defined herein above, and
$R^b$ is selected from H, C1-C6 alkyl, C1-C6 alkyl substituted with at least one $R^6$; carbocyclyl-C0-C5 alkyl; and heterocyclyl-C0-C5 alkyl; wherein any carbocyclyl and heterocyclyl is 5- or 6-membered and is optionally substituted with at least one $R^7$ and optionally comprises at least one oxo group in the ring;

provided that $R^a$ and $R^b$ are not both H;

each $R^6$ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl) amino; (C1-C6 alkylcarbonyl)(C1-C6 alkyl)amino; carbamoyl; secondary or tertiary C1-C6 alkylamido wherein any alkyl is optionally substituted by OH or CONH2; 5- or 6-membered carbocyclyl- or heterocyclylcarbamoyl; and 5- or 6-membered cyclic aminocarbonyl, optionally containing at least one further heteroatom in the ring, and wherein the ring is optionally substituted with at least one C1-C6 alkyl; wherein any alkyl is optionally substituted with at least one halogen and any 5- or 6-membered carbocyclyl or heterocyclyl is optionally substituted with at least one $R^8$; and each $R^7$ and $R^8$ is independently selected from C1-C6 alkyl; hydroxy-C0-C3 alkyl; C1-C6 alkoxy; C1-C6 alkylsulfinyl; amino; nitro; C1-C6 secondary or tertiary amino; halogen; carbamoyl; secondary or tertiary C1-C6 alkylamido-C0-C3 alkyl; C1-C6 alkylcarbonylamino; and 5- or 6-membered cyclic amino, optionally containing at least one further heteroatom in the ring and wherein the ring is optionally substituted with at least one C1-C6 alkyl; wherein any alkyl is optionally substituted with at least one halogen.

In a compound of formula (I), the ring containing the moiety A ("the A-ring") is linked to the $R^aO$, $R^bOOC$— disubstituted phenyl ring through a sulfonamide moiety —NHS(O)$_2$(CH)n-. Depending on the point of attachment of the sulfonamide moiety to the A-ring, the compound of formula (I) may be represented by either formula (Ia) or (Ib):

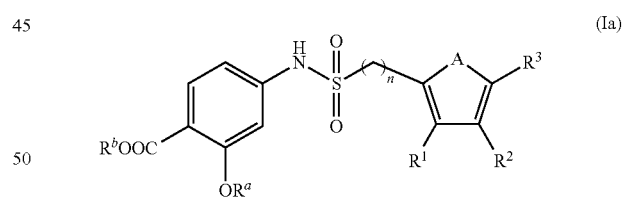

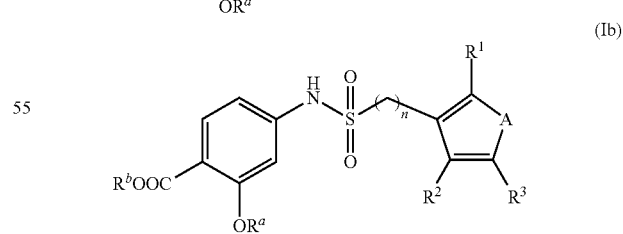

In some embodiments, the compound of formula (I) is a compound of formula (Ia).

In some other embodiments, the compound of formula (I) is a compound of formula (Ib).

In some embodiments, A is S and the compound of formula (I) may then be represented by formula (IA)

(IA)

In some embodiments, the compound of formula (IA) is represented by formula (IAa)

(IAa)

In some other embodiments, the compound formula (IA) is represented by formula (IAb)

(IAb)

In some embodiments, A is O and the compound of formula (I) may then be represented by formula (IB)

(IB)

In some embodiments, the compound of formula (IB) is represented by formula (IBa)

(IBa)

In some other embodiments, the compound of formula (IB) is represented by formula (IBb)

(IBb)

In some embodiments, in a compound of formula (I) as defined herein above, A is $CR^4$=$CR^4$ and the compound of formula (I) may then be represented by formula (IC)

(IC)

In some embodiments, the compound of formula (IC) is represented by formula (ICa)

(ICa)

In some other embodiments, the compound of formula (IC) is represented by formula (ICb)

(ICb)

In some embodiments, in a compound of formula (I) as defined herein above, A is N=$CR^4$ and the compound of formula (I) may then be represented by formula (ID)

(ID)

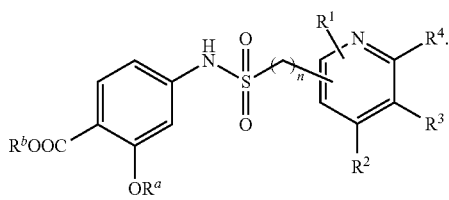

or by formula (IE)

(IE)

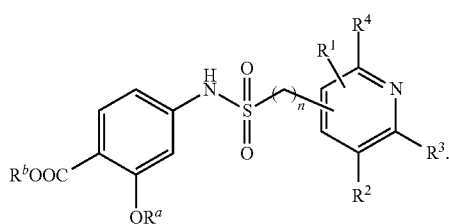

In some embodiments, the compound of formula (ID) is represented by formula (IDa)

(IDa)

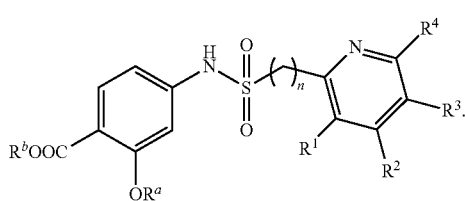

In some other embodiments, the compound of formula (ID) is represented by formula (IDb)

(IDb)

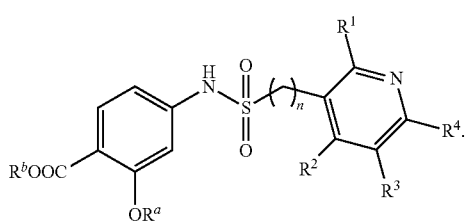

In some embodiments, the compound of formula (IE) is represented by formula (IEa)

(IEa)

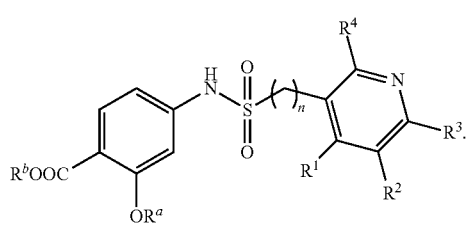

In some other embodiments, the compound of formula (IE) is represented by formula (IEb)

(IEb)

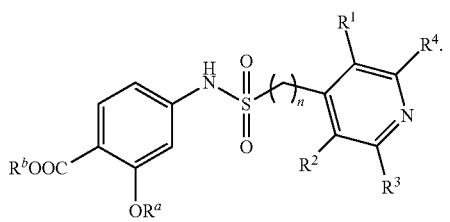

It should be understood that for the purpose of the present invention, unless otherwise specified or apparent from the context, any reference to a compound of formula (I) is meant to include a compound of any of the above formulas (Ia) or (Ib) or any of the embodiments of said formulas, as represented by formulas (IA), (IB), (IC), (ID) and (IE), or any of the embodiments thereof.

In some embodiments, the compound of formula (I) is a compound of formula (IA), (IB) or (IC). In some embodiments, the compound of formula (I) is a compound of formula (IA) or (IB), e.g. a compound of formula (IA). In still other embodiments, the compound of formula (I) is a compound of formula (IA) or (IC).

In some other embodiments, the compound of formula (I) is a compound of formula (IC), (ID) or (IE), e.g. a compound of formula (IC) or (IE), or a compound of formula (IC). In still other embodiments, the compound of formula (I) is a compound of formula (ID) or (IE), in particular a compound of formula (IE). For example, in some embodiments, the compound is a compound of formula (IDb) or (IEa), in particular a compound of formula (IEa). In some other embodiments, the compound is a compound of formula (IDa) or (IEa).

In some embodiments, the compound of formula (I) is a compound of formula (IAa), (IAb), (IBa), (IBb), (ICa), (ICb), (IDa) or (IEa). In some other embodiments, the compound of formula (I) is a compound of formula (IAa), (IAb), (IBa), (IBb), (ICa), (ICb), or (IEa). In some other embodiments, the compound of formula (I) is a compound of formula (IAa), (IBa), (ICa) or (IEa). In some other embodiments, the compound of formula (I) is a compound of formula (IAa), (IBa) or (ICa). In still other embodiments, the compound of formula (I) is a compound of formula (IAa) or (ICa).

In some other embodiments, the compound of formula (I) is a compound of formula (IAb) or (IBb).

In formula (I), the moiety C that links the ring containing the moiety A ("the A ring") to the disubstituted phenyl ring, may be a moiety —NHS(O)$_2$— (i.e. n is 0) or —NHS(O)$_2$CH$_2$— (i.e. n is 1). Preferably, n is 0, in which case formula (I) is represented as (I)

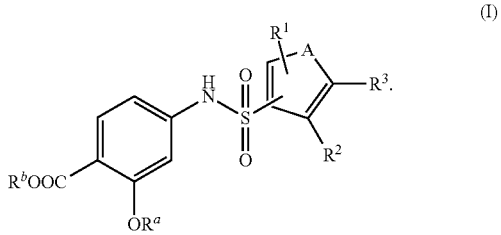

In some embodiments, n is 1, in which case formula (I) is represented as

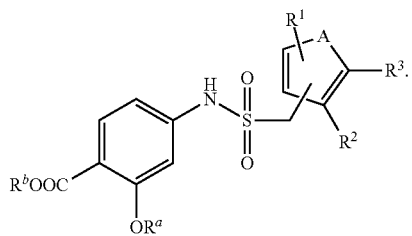

For example, in some embodiments of a compound of formula (IC), such as a compound of formula (ICa), n is 1.

In some embodiments of a compound of formula (I), n may be 1 only when the compound is a compound of formula (IC).

In some embodiments of a compound of formula (I), n may be 1 only when the compound is a compound of formula (ICa).

In a compound of formula (I), $R^1$ is selected from H; halogen, C1-C6 alkyl, e.g. C1-C3 alkyl, such as methyl, optionally substituted with at least one halogen; and C1-C6 alkoxy optionally substituted with at least one halogen, e.g. C1-C3 alkoxy optionally substituted with at least one halogen, e.g. methoxy or trifluoromethoxy.

In some embodiments, $R^1$ is selected from H, halogen and C1-C6 alkyl, e.g. C1-C3 alkyl, such as methyl, wherein the alkyl is optionally substituted with at least one halogen. For example, $R^1$ may be H, halogen, $CH_3$ or $CF_3$; e.g. H, Cl, Br, $CH_3$ and $CF_3$.

In some embodiments, $R^1$ is selected from H and C1-C6 alkyl, e.g. C1-C3 alkyl, such as methyl. For example, $R^1$ may be H or methyl, e.g. H.

In some embodiments, e.g. when A is S or O, in particular S, $R^1$ is selected from H and halogen.

In some embodiments, e.g. when A is S or O, in particular S, $R^1$ is selected from halogen and C1-C6 alkyl, optionally substituted with at least one halogen; such as halogen and C1-C3 alkyl, optionally substituted with at least one halogen; e.g. Cl, Br, $CH_3$, and $CF_3$; or Cl, Br, and $CH_3$.

In some embodiments, e.g. when A is —$CR^4$=$CR^4$— or —$CR^4$=N—, $R^1$ is selected from H, F, Cl, $CH_3$ and $CF_3$; e.g. $R^1$ is H.

In some embodiments, $R^1$ is C1-C6 alkyl. For example, in some embodiments of a compound of formula (IA) or (IB), e.g. formula (IAa) or formula (IBa), $R^1$ is C1-C6 alkyl; and $R^2$ and $R^3$ form, together with the carbon atoms to which they are attached, a 5- or 6-membered carbocyclic or heterocyclic ring, e.g. a benzene ring, which ring is optionally substituted with at least one $R^5$.

In a compound of formula (I), $R^2$ and $R^3$ are each independently selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; heterocyclyloxy; carbocyclyl-C0-C3 alkyl; carbocyclyl-C2-C3 alkenyl; heterocyclyl-C0-C3 alkyl; and heterocyclyl-C2-C3 alkenyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbamoyl; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; C1-C6 alkoxycarbonyl; cyano; carbocyclyloxy; heterocyclyloxy; carbocyclyl-C0-C3 alkyl; carbocyclyl-C2-C3 alkenyl; heterocyclyl-C0-C3 alkyl; and heterocyclyl-C2-C3 alkenyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

For example, $R^2$ and $R^3$ may each be independently selected from H; halogen, such as F, Cl, and Br, in particular F and Cl; C1-C6 alkyl, such as C1-C4 alkyl, or C1-C3 alkyl, in particular methyl; C1-C6 alkoxy, such as C1-C4 alkoxy, or C1-C3 alkoxy, e.g. methyl; carbamoyl; secondary or tertiary C1-C6 alkylamido, e.g. secondary or tertiary C1-C4 alkylamido, such as secondary or tertiary C1-C3 alkylamido, e.g. methylamido or dimethylamido; carbocyclylcarbonylamino-C0-C2 alkyl, e.g. carbocyclylcarbonylamino-C0-C1 alkyl, or carbocyclylcarbonylamino; 5- or 6-membered cyclic aminocarbonyl optionally containing a further heteroatom in the ring, e.g 5- or 6-membered cyclic aminocarbonyl optionally containing an oxygen atom in the ring; C1-C6 alkylcarbonylamino, e.g. C1-C4 alkylcarbonylamino, or C1-C3 alkylcarbonylamino, such as acetamido; C1-C6 alkylsulfonyl, such as C1-C4 alkylsulfonyl, or C1-C3 alkylsulfonyl, e.g. methylsulfonyl; hydroxy-C0-C6 alkyl, such as hydroxy-C0-C4 alkyl, or hydroxy-C0-C3 alkyl, e.g. hydroxy-C0-C1 alkyl, e.g. hydroxy; C1-C6 alkylcarbonyl, such as C1-C4 alkylcarbonyl, or C1-C3 alkylcarbonyl, e.g. acetyl; carboxy; C1-C6 alkoxycarbonyl, such as C1-C4 alkoxycarbonyl, or C1-C3 alkoxycarbonyl, e.g. methoxycarbonyl; cyano; carbocyclyloxy, such as phenyloxy; heterocyclyloxy; carbocyclyl-C0-C3 alkyl, such as carbocyclyl-C0-C2 alkyl, or carbocyclyl-C0-C1 alkyl, e.g. phenyl or benzyl; carbocyclyl-C2-C3 alkenyl; heterocyclyl-C0-C3 alkyl, such as heterocyclyl-C0-C2 alkyl, or heterocyclyl-C0-C1 alkyl, e.g. heterocyclyl; and heterocyclyl-C2-C3 alkenyl; wherein any alkyl is optionally substituted with at least one halogen, e.g. 1, 2 or 3 halogens; any carbocyclyl or heterocyclyl is 5- or 6-membered monocyclyl, e.g. phenyl or 5- or 6-membered aromatic or non-aromatic heterocyclyl; or 9- or 10-membered bicyclyl, e.g. naphthyl or 9- or 10-membered aromatic or non-aromatic heterocyclyl; and any carbocyclyl or heterocyclyl is optionally substituted with at least one $R^5$, e.g. 1-5 $R^5$, or 1-4 $R^5$, such as 1, 2 or 3 $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; heterocyclyloxy; carbocyclyl-C0-C3 alkyl; and heterocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbamoyl; secondary or tertiary C1-C6 alkylamido; carbocyclylcarbonylamino-C0-C1 alkyl; 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; carbocyclyl; and heterocyclyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbocyclylcarbonylamino-C0-C2 alkyl; C1-C6 alkylcarbonylamino; hydroxy-C0-C6 alkyl, C1-C6 alkylcarbonyl; C1-C6 alkoxycarbonyl; cyano; carbocyclyloxy; heterocyclyloxy; carbocyclyl-C0-C3 alkyl; and heterocyclyl-C0-C3 alkyl, wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbocyclylcarbonylamino-C0-C1 alkyl; alkylcarbonylamino; hydroxy-C0-C6 alkyl, C1-C6 alkylcarbonyl; C1-C6 alkoxycarbonyl; cyano; carbocyclyloxy; heterocyclyloxy; and carbocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; heterocyclyloxy; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; carbamoyl; secondary or tertiary C1-C6 alkylamido; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; wherein any alkyl is optionally substituted with at least one halogen; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are each independently selected from H; halogen; C1-C6 alkyl; C1-C6 alkoxy; hydroxy-C0-C6 alkyl, C1-C6 alkylcarbonyl; C1-C6 alkoxycarbonyl; cyano; carbocyclyloxy; and carbocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are independently selected from H, halogen, C1-C6 alkyl, C1-C6 alkoxy, carbocyclyl-C0-C3 alkyl, heterocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, $R^2$ and $R^3$ are independently selected from H, halogen, C1-C6 alkyl, C1-C6 alkoxy, wherein any alkyl is optionally substituted with at least one halogen; or $R^2$ and $R^3$ form, together with the carbon atoms to which they are attached, a 5- or 6-membered carbocyclic or heterocyclic ring, which ring is optionally substituted with at least one $R^5$.

In some other embodiments, one of $R^2$ and $R^3$, e.g. $R^2$, is selected from carbocyclyl-C0-C3 alkyl; carbocyclyl-C2-C3 alkenyl; heterocyclyl-C0-C3 alkyl; and heterocyclyl-C2-C3 alkenyl; wherein any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, the compound of formula (I) is a compound of formula (IA) or (IB), in particular a compound of formula (IA), e.g. a compound of formula (IAa) and one of $R^2$ and $R^3$, e.g. $R^2$, is selected from carbocyclyl-C0-C3 alkyl; carbocyclyl-C2-C3 alkenyl; heterocyclyl-C0-C3 alkyl; and heterocyclyl-C2-C3 alkenyl; wherein any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some other embodiments, the compound of formula (I) is a compound of formula (IC), (ID) or (IE), in particular a compound of formula (IC), e.g. a compound of formula (IC) and one of $R^2$ and $R^3$, e.g. $R^2$, is selected from carbocyclyl-C0-C3 alkyl; carbocyclyl-C2-C3 alkenyl; heterocyclyl-C0-C3 alkyl; and heterocyclyl-C2-C3 alkenyl; wherein any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some other embodiments, $R^2$ and $R^3$ are independently selected from H, halogen, and C1-C6 alkyl, wherein any alkyl is optionally substituted with at least one halogen; or $R^2$ and $R^3$ form, together with the carbon atoms to which they are attached, a 5- or 6-membered carbocyclic or heterocyclic ring, which ring is optionally substituted with at least one $R^5$.

In still some other embodiments, $R^2$ and $R^3$ are independently selected from H and halogen; or $R^2$ and $R^3$ form, together with the carbon atoms to which they are attached, a 5- or 6-membered carbocyclic or heterocyclic ring, which ring is optionally substituted with at least one $R^5$.

With respect to $R^2$ and $R^3$, in any of the above embodiments, any halogen e.g. may be selected from F, Cl and Br, or F and Cl; and any C1-C6 alkyl e.g. may be selected from C1-C4 alkyl, or C1-C3 alkyl, e.g. methyl; any C0-C3 alkyl e.g. may be selected from C0-C2 alkyl, or C0-C1 alkyl, such as C0 alkyl (i.e. a direct bond).

It should be understood that for the purpose of the present invention, and unless otherwise indicated or apparent from the context, any alkyl that is optionally substituted with at least one halogen may optionally be part of a radical, i.e. an alkoxy or alkylcarbonyl. Thus, $R^2$ and $R^3$ may be e.g. a halogenated alkyl, a halogenated alkoxy or a halogenated alkylcarbonyl etc. The number of halogen atoms attached to any one alkyl may be e.g. 1, 2 or 3 and may be independently selected from e.g. F and Cl. For example, any alkyl may be substituted by 1, 2 or 3 halogens that are all fluoro, such as in trifluoromethyl, trifluoromethoxy or difluoromethoxy.

It also should be understood that for the purpose of the present invention, and unless otherwise indicated or apparent from the context, the reference to "any carbocyclyl or heterocyclyl" as being 5- or 6-membered monocyclyl or 9- or 10-membered bicyclyl also includes the carbocyclyl and heterocycyl, respectively, when present as a moiety of a radical such as e.g. carbocyclyloxy or carbocyclyl-C2-C3 alkenyl.

In some embodiments, when either $R^2$ or $R^3$ is carbocyclyl or heterocyclyl optionally substituted by at least one $R^5$, or a radical comprising a carbocyclyl or heterocyclyl moiety optionally substituted by at least one $R^5$, such carbocyclyl is aromatic and/or any heterocyclyl is heteroaromatic. For example, any carbocyclyl may be selected from phenyl and naphthyl, and any heterocyclyl may be selected from 5-10-membered heterocyclyl comprising one or several heteroatoms selected from N, O and S 1, 2, 3 or 4 heteroatoms selected from N, O and S, such as dihydrobenzofuryl, piperidinyl, pyridinyl, benzofuryl, thiazolyl, quinolinyl, or thienyl. In some embodiments, any carbocyclyl is an aryl and any heterocyclyl is a heteroaryl.

In some embodiments, when either $R^2$ or $R^3$ is bicyclic 9- or 10-membered carbocyclyl or heterocyclyl, optionally substituted with at least one $R^5$, said bicyclic carbocyclyl or heterocyclyl comprises at least one aromatic ring, e.g. at least one phenyl ring, fused to another ring which may be aromatic or non-aromatic. For example, this other ring may be phenyl or a heterocyclic, non-aromatic or aromatic 5- or 6-membered ring, e.g. comprising 1-3 heteroatoms, e.g. 1 or 2 heteroatoms selected from N, O and S, e.g. N and 0.

In some embodiments, either $R^2$ or $R^3$ is phenyl substituted with at least one $R^5$, e.g. from 1 to 4 $R^5$; or from 1 to 4 $R^5$; e.g. or 1, 2 or 3 $R^5$, in particular 1 or 2 $R^5$.

In some embodiments, either $R^2$ or $R^3$ is selected from phenyl, 2-hydroxyphenyl, 2-(hydroxymethyl)phenyl, 2-nitrophenyl, 2-hydroxy-5-fluorophenyl, 3-fluorophenyl, 3-chlorophenyl, 3-aminophenyl, 3-ethoxyphenyl, 3-(isopropoxycarbonyl)phenyl, 3-acetylphenyl, 3-carbamoylphenyl, 3-acetamidophenyl, 3-cyanophenyl, 3-(methylsulfonyl)phenyl, 4-trifluoromethylphenyl, 4-methoxyphenyl, 4-trifluoromethoxyphenyl, 4-(methylsulfonamido)phenyl, 4-carbamoylphenyl, 4-(dimethylamino)phenyl, 4-(methylthio)phenyl, 4-(dimethylcarbamoyl)phenyl, 2-fluoro-3-methoxyphenyl, 2,5-difluorophenyl, 5-chloro-2-methoxyphenyl, 3-fluoro-4-hydroxyphenyl, 3-fluoro-4-methoxyphenyl, 4-fluoro-3-methylphenyl, 3,5-difluorophenyl, 4-hydroxy-3,5-dimethylphenyl, 4-methoxy-3,5-dimethylphenyl, 2-methylthiazol-4-yl, 5-acetylthiophen-2-yl, pyridinyl, e.g. pyridin-4-yl, pyridin-3-yl, 1-piperidinyl, 6-methoxypyridin-3-yl, 6-hydroxypyridin-3-yl, 2,3-dihydrobenzofuran-5-yl, benzofuran-2-yl, and quinolin-6-yl.

In some embodiments, $R^2$ and $R^3$ are not both selected from a group that is cyclic (carbocyclic or heterocyclic) or comprises a cyclic moiety. Thus, in some embodiments, $R^2$ is a radical that is or comprises a cyclic moiety, and $R^3$ is not such a radical, while in some other embodiments, $R^3$ is a radical that is or comprises a cyclic moiety and $R^2$ is not such a radical.

For example, in some embodiments of a compound of formula (ICa), $R^2$ is a radical that is or comprises a cyclic moiety and $R^3$ is not such a radical. Likewise, in some embodiments of a compound of formula (IAa), $R^2$ is a radical that is or comprises a cyclic moiety and $R^3$ is not such a radical.

In some embodiments of a compound of formula (ICa), $R^3$ is not (an optionally substituted) phenyl. For example, in some embodiments of a compound of formula (ICa), when $R^1$, $R^2$, and each $R^4$ are hydrogen, $R^3$ is not (an optionally substituted) phenyl. In some other embodiments of a compound of formula (ICa), when $R^1$, $R^2$, and each $R^4$ are hydrogen and n is 0, $R^3$ is not an optionally substituted phenyl. In some embodiments, when the compound is a compound of formula (IC), the A-ring is not monosubstituted in para-position with respect to the sulfonamide moiety. In some other embodiments, when the compound is a compound of formula (IC), and n is 0, the A-ring is not monosubstituted in para-position with respect to the sulfonamide moiety.

In some embodiments, e.g. in a compound of formula (ICa), $R^2$ is as defined herein above, and $R^3$ is selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; heterocyclyloxy; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments, e.g. in a compound of formula (ICa), $R^2$ is as defined herein above, and $R^3$ is selected from H, halogen, C1-C6 alkyl, and carbocyclyl-C0-C3 alkyl; wherein any alkyl is optionally substituted with at least one halogen; any carbocyclyl is 5- or 6-membered monocyclyl or 9- or 10-membered bicyclyl; and any carbocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some particular embodiments, e.g. in a compound of formula (ICa), $R^2$ is as defined herein above, and $R^3$ is selected from H, halogen, and C1-C6 alkyl, wherein any alkyl is optionally substituted with at least one halogen; or $R^2$ and $R^3$ form, together with the carbon atoms to which they are attached, a 5- or 6-membered carbocyclic or heterocyclic ring, which ring is optionally substituted with at least one $R^5$.

In some embodiments, e.g. in a compound of formula (ICa), $R^2$ is as defined herein above, and $R^3$ is selected from H and halogen.

In some embodiments, e.g. in a compound of formula (ICa), $R^2$ is as defined herein above, and $R^3$ is H.

In some embodiments, e.g. in a compound of formula (ICa), $R^3$ is as defined herein above, and $R^2$ is selected from carbocyclyloxy, heterocyclyloxy, carbocyclyl-C0-C3 alkyl, carbocyclyl-C2-C3 alkenyl, heterocyclyl-C0-C3 alkyl, and heterocyclyl-C2-C3 alkenyl; in particular from carbocyclyl-C0-C3 alkyl and heterocyclyl-C0-C3 alkyl; e.g. from carbocyclyl alkyl and heterocyclyl; wherein any carbocyclyl or heterocyclyl is 5- or 6-membered monocyclyl or 9- or 10-membered bicyclyl; and any carbocyclyl or heterocyclyl is optionally substituted with at least one $R^5$. In these embodiments, $R^3$ e.g. may be selected from $R^3$ is selected from H, halogen, C1-C6 alkyl, C1-C6 alkoxy, carbamoyl, secondary or tertiary C1-C6 alkylamido, C1-C6 alkylcarbonylamino, C1-C6 alkylsulfonyl, hydroxy-C0-C6 alkyl, C1-C6 alkylcarbonyl, carboxy, C1-C6 alkoxycarbonyl, and cyano; or from H, halogen, and C1-C6 alkyl; from H and halogen, or from H and C1-C6 alkyl.

In some embodiments of compound of formula (IA) or (IB), in particular formula (IA), $R^2$ is as defined herein above, and $R^3$ is selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; carbocyclyloxy; heterocyclyloxy; carbocyclyl-C0-C3 alkyl; carbocyclyl-C2-C3 alkenyl; heterocyclyl-C0-C3 alkyl; and heterocyclyl-C2-C3 alkenyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments of a compound of formula (IA) or (IB), in particular formula (IA), $R^2$ is as defined herein above, and $R^3$ is selected from H; halogen; C1-C6 alkyl; C1-C6 alkoxy; carbamoyl; secondary or tertiary C1-C6 alkylamido; carbocyclylcarbonylamino-C0-C2 alkyl; 5- or 6-membered cyclic aminocarbonyl optionally containing a further heteroatom in the ring; C1-C6 alkylcarbonylamino; C1-C6 alkylsulfonyl; hydroxy-C0-C6 alkyl, C1-C6 alkylcarbonyl; carboxy; C1-C6 alkoxycarbonyl; cyano; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In some embodiments of a compound of formula (IA) or (IB), in particular formula (IA), $R^2$ is as defined herein above, and $R^3$ is selected from H, halogen, C1-C6 alkyl, carbocyclylcarbonylamino-C0-C2 alkyl, and carbocyclyl-C0-C3 alkyl; wherein any alkyl is optionally substituted with at least one halogen; any carbocyclyl is 5- or 6-membered monocyclyl or 9- or 10-membered bicyclyl; and any carbocyclyl is optionally substituted with at least one $R^5$; or $R^2$ and $R^3$ form, together with the carbon atoms to which they are attached, a 5- or 6-membered carbocyclic or heterocyclic ring, which ring is optionally substituted with at least one $R^5$.

In still other embodiments of a compound of formula (IA) or (IB), in particular formula (IA), $R^2$ is as defined herein above, and $R^3$ is selected from H, halogen, and C1-C6 alkyl, wherein any alkyl is optionally substituted with at least one halogen; or $R^2$ and $R^3$ form, together with the carbon atoms to which they are attached, a 5- or 6-membered carbocyclic or heterocyclic ring, which ring is optionally substituted with at least one $R^5$.

In still other embodiments of a compound of formula (IA) or (IB), in particular formula (IA), $R^2$ is as defined herein above, and $R^3$ is selected from H and halogen. For example, both $R^2$ and $R^3$ may be selected from H and halogen.

$R^2$ and $R^3$ preferably should not both be H. In some embodiments, $R^2$ is as defined herein above, but $R^2$ is not H.

In some embodiments, $R^2$ and $R^3$ are as defined herein above, but $R^2$ and $R^3$ do not form, together with the carbon atoms to which they are attached, a 5- or 6-membered carbocyclic or heterocyclic ring.

In some other embodiments, $R^2$ and $R^3$, together with the carbon atoms to which they are attached, form a 5- or 6-membered carbocyclic or heterocyclic ring, which ring is optionally substituted with at least one $R^5$. For example, $R^2$ and $R^3$ together with the carbon atoms to which they are attached may form a 5- or 6-membered carbocyclic or heterocyclic aromatic ring. For example, in some embodiments, the ring formed by $R^2$ and $R^3$ is a carbocyclic aromatic ring, e.g. a benzene ring. In some other embodiments, the ring formed by $R^2$ and $R^3$ is a 5- or 6-membered heterocyclic, aromatic or non-aromatic ring containing 1-4, e.g. 1, 2 or 3 heteroatoms selected from N, O and S, such as a thiadiazole, e.g. a 1,2,5-thiadiazole, an oxadiazole, e.g. a 1,2,5-oxadiazole, or a tetrahydrofuran ring.

In some embodiments, when $R^2$ and $R^3$, together with the carbon atoms to which they are attached, form a 6-membered heterocyclic ring, said ring is not pyridine.

In some embodiments, when $R^2$ and $R^3$, together with the carbon atoms to which they are attached, form a 5- or 6-membered carbocyclic or heterocyclic ring, which ring is optionally substituted with at least one $R^5$, said ring is a phenyl ring or a 5-membered heterocyclic ring.

In some embodiments, when $R^2$ and $R^3$, together with the carbon atoms to which they are attached, form a 5- or 6-membered carbocyclic or heterocyclic ring, the compound of formula (I) is a compound of formula (IA) or (IB).

In some other embodiments, when $R^2$ and $R^3$, together with the carbon atoms to which they are attached, form a 5- or 6-membered carbocyclic or heterocyclic ring, the compound of formula (I) is a compound of formula (IC), in particular a compound of formula (ICb).

When the compound of formula (I) is a compound of formula (IC), (ID) or (IE), it comprises either one or two groups $R^4$, independently selected from H; halogen, e.g. F, Cl and Br; monocyclic C3-C6 carbocyclyl, e.g. phenyl; and C1-C6 alkyl, such as C1-C4 alkyl, or C1-C3 alkyl, e.g. methyl; wherein any alkyl is optionally substituted with at least one halogen, e.g. 1, 2 or 3 halogen, such as 1, 2, or 3 F. In some embodiments, each $R^4$ is selected from H, halogen, and C1-C6 alkyl, wherein any alkyl is optionally substituted with at least one halogen. In some embodiments, each $R^4$ is selected from H and halogen. In still other embodiments, each $R^4$ is selected from H and C1-C6 alkyl. In some embodiments, each $R^4$ is selected from H, F, Cl, Br, $CH_3$ and $CF_3$. In some embodiments, each $R^4$ is H.

When $R^2$ and/or $R^3$ is a cyclic moiety or $R^2$ and $R^3$, together with the carbon atoms to which they are attached form a cyclic moiety, such cyclic moiety may optionally be substituted with at least one $R^5$, e.g. 1-5 $R^5$, or 1-4 $R^5$, in particular 1, 2 or 3 $R^5$. Each $R^5$ is independently selected from halogen, e.g. F and Cl; C1-C6 alkyl, e.g. C1-C4 alkyl, such as methyl, ethyl, n-propyl, isopropyl and n-butyl; C1-C6 alkoxy, e.g. C1-C4 alkoxy, such as methoxy, ethoxy, n-propoxy, isopropoxy and n-butoxy; phenoxy; amino; cyano; nitro; secondary or tertiary C1-C6 alkylamino, e.g. secondary or tertiary C1-C4 alkylamino, such as dimethylamino; 5- or 6-membered cyclic amino, optionally containing at least one further heteroatom in the ring; C1-C6 alkylcarbonylamino, such as C1-C4 alkylcarbonylamino, e.g. acetylamido; carbamoyl; secondary or tertiary C1-C6 alkylamido, such as secondary or tertiary C1-C4 alkylamido, e.g. dimethylcarbamoyl and diisopropylcarbamoyl; 5- or 6-membered cyclic aminocarbonyl; C1-C6 alkoxycarbonylamino, such as C1-C4 alkoxycarbonylamino; hydroxy-C0-C6 alkyl e.g. hydroxy-C0-C4 alkyl, such as hydroxy and hydroxymethyl; C1-C6-alkylthio such as C1-C4 alkylthio, e.g. methylthio; carboxy-C0-C6-alkyl, e.g. carboxy-C0-C4 alkyl, such as carboxy; C1-C6 alkoxycarbonyl, such as C1-C4 alkoxycarbonyl, e.g. methoxycarbonyl and isopropoxycarbonyl; C1-C6 alkylcarbonyl such as C1-C4 alkylcarbonyl, e.g. acetyl; C1-C6 alkylsulfonyl, such as C1-C4 alkylsulfonyl, e.g. methylsulfonyl; and C1-C6 alkylsulfonylamino, such as C1-C4 alkylsulfonylamino, e.g. methylsulfonamido; wherein any alkyl is optionally substituted with at least one halogen; such as in trifluoromethyl or trifluoromethoxy.

In some embodiments, when A is $CR^4=CR^4$ and n is 0, neither $R^2$ nor $R^3$ is selected from 4-hydroxypyrazolo[1,5-a]-1,3,5-triazin-8-yl and 2,4-dihydroxypyrazolo[1,5-a]-1,3,5-triazin-8-yl.

In some embodiments, each $R^5$ is independently selected from halogen; C1-C6 alkyl; C1-C6 alkoxy; phenoxy; amino; cyano; nitro; secondary or tertiary C1-C6 alkylamino; 5- or 6-membered cyclic amino, optionally containing at least one further heteroatom in the ring; C1-C6 alkylcarbonylamino; carbamoyl; 5- or 6-membered cyclic aminocarbonyl; C1-C6 alkoxycarbonylamino; hydroxy-C0-C6 alkyl; C1-C6-alkylthio; C1-C6 alkoxycarbonyl; C1-C6 alkylcarbonyl; C1-C6-alkylsulfonyl; and C1-C6 alkylsulfonylamino; wherein any alkyl is optionally substituted with at least one halogen.

In some embodiments, each $R^5$ is independently selected from halogen, e.g. F and Cl; C1-C6 alkyl, e.g. C1-C4 alkyl, such as methyl, ethyl, n-propyl, isopropyl and n-butyl; C1-C6 alkoxy, e.g. C1-C4 alkoxy, such as methoxy, ethoxy, n-propoxy, isopropoxy and n-butoxy; amino; cyano; nitro; secondary or tertiary C1-C6 alkylamino, e.g. secondary or tertiary C1-C4 alkylamino, such as dimethylamino; C1-C6 alkylcarbonylamino, such as C1-C4 alkylcarbonylamino, e.g. acetylamido; carbamoyl; secondary or tertiary C1-C6 alkylamido, such as secondary or tertiary C1-C4 alkylamido, e.g. dimethylcarbamoyl and diisopropylcarbamoyl; hydroxy-C0-C6 alkyl e.g. hydroxy-C0-C4 alkyl, such as hydroxy and hydroxymethyl; C1-C6-alkylthio such as C1-C4 alkylthio, e.g. methylthio; C1-C6 alkoxycarbonyl, such as C1-C4 alkoxycarbonyl, e.g. methoxycarbonyl and isopropoxycarbonyl; C1-C6 alkylcarbonyl such as C1-C4 alkylcarbonyl, e.g. acetyl; C1-C6 alkylsulfonyl, such as C1-C4 alkylsulfonyl, e.g. methylsulfonyl; and C1-C6 alkylsulfonylamino, such as C1-C4 alkylsulfonylamino, e.g methylsulfonamido; wherein any alkyl is optionally substituted with at least one halogen; such as in trifluoromethyl or trifluoromethoxy.

In some embodiments, each $R^5$ is independently selected from halogen, e.g. F and Cl; C1-C6 alkyl, e.g. C1-C4 alkyl, such as methyl and isopropyl; C1-C6 alkoxy, e.g. C1-C4 alkoxy, such as methoxy, ethoxy, and isopropoxy; amino; cyano; nitro; secondary or tertiary C1-C6 alkylamino, e.g. secondary or tertiary C1-C4 alkylamino, such as dimethylamino; C1-C6 alkylcarbonylamino, such as C1-C4 alkylcarbonylamino, e.g. acetylamido; carbamoyl; secondary or tertiary C1-C6 alkylamido, such as secondary or tertiary C1-C4 alkylamido, e.g. dimethylcarbamoyl; hydroxy-C0-C6 alkyl e.g. hydroxy-C0-C4 alkyl, such as hydroxy and hydroxymethyl; C1-C6-alkylthio such as C1-C4 alkylthio, e.g. methylthio; C1-C6 alkoxycarbonyl, such as C1-C4 alkoxycarbonyl, e.g. isopropoxycarbonyl; C1-C6 alkylcarbonyl such as C1-C4 alkylcarbonyl, e.g. acetyl; C1-C6 alkylsulfonyl, such as C1-C4 alkylsulfonyl, e.g. methylsulfonyl; and C1-C6 alkylsulfonylamino, such as C1-C4 alkylsulfonylamino, e.g methylsulfonamido; wherein any alkyl is optionally substituted with at least one halogen; such as in trifluoromethyl or trifluoromethoxy.

In some embodiments, each $R^5$ is selected from hydroxy, C1-C6 alkoxy and halogen, e.g. hydroxy, C1-C3 alkoxy and halogen, such as hydroxy, methoxy and F, in particular hydroxy and F. For example, $R^2$ or $R^3$, in particular $R^2$, is phenyl substituted by 1 or 2, in particular 2, of said moeities, e.g. 2 moieties selected from OH and halogen, in particular OH and F. In some embodiments, $R^2$ or $R^3$, in particular $R^2$, is phenyl substituted by any such $R^5$ in 2- and 5-position, e.g. $R^2$ or $R^3$, in particular $R^2$, is 5-fluoro-2-hydroxyphenyl or 2,5-difluorophenyl, in particular 5-fluoro-2-hydroxyphenyl.

The moiety $R^a$ is selected from H and C1-C6 alkylcarbonyl. In some embodiments, $R^a$ is selected from H and C1-C4 alkylcarbonyl. In some other embodiments, $R^a$ is selected from H and C1-C3 alkylcarbonyl, e.g from H and acetyl. In some embodiments, $R^a$ is H. In these embodiments, $R^b$ is not H.

In some embodiments, $R^a$ is C1-C6 alkylcarbonyl, e.g. C1-C4 alkylcarbonyl, or C1-C3 alkylcarbonyl, e.g. acetyl. In these embodiments, $R^b$ may be H or different from H, e.g. $R^b$ is different from H.

$R^b$ is selected from H, C1-C6 alkyl, C1-C6 alkyl substituted with at least one $R^6$; carbocyclyl-C0-C5 alkyl; and heterocyclyl-C0-C5 alkyl; wherein any carbocyclyl and heterocyclyl is 5- or 6-membered and is optionally substituted with at least one $R^7$ and optionally comprises at least one oxo group in the ring.

When $R^b$ is an alkyl substituted by at least one $R^6$, said alkyl may be substituted by e.g. 1, 2 or 3 $R^6$, e.g. 1 $R^6$.

When $R^b$ is 5- or 6-membered carbocyclyl-C0-C5 alkyl or heterocyclyl-C0-C5 alkyl comprising at least one oxo group in the ring, it e.g. may be heterocyclyl C0-C5 alkyl comprising at least one oxo group in the ring, e.g. heterocyclyl-C0-C5 alkyl comprising one oxo group in the ring. In some embodiments, $R^b$ may comprise 1 or 2 oxo groups in the ring, or 1 oxo group in the ring. For example, the ring may be 2-oxo-1,3-dioxolyl. In some embodiments, $R^b$ does not comprise any oxo group in the ring.

In some embodiments, $R^b$ is selected from C1-C6 alkyl, C1-C6 alkyl substituted with at least one $R^6$; carbocyclyl-C0-C5 alkyl; and heterocyclyl-C0-C5 alkyl; wherein any carbocyclyl and heterocyclyl is 5- or 6-membered and is optionally substituted with at least one $R^7$ and optionally comprises at least one oxo group in the ring.

In some embodiments, $R^b$ is selected from H and C1-C6 alkyl optionally substituted with at least one $R^6$, e.g. C1-C6 alkyl optionally substituted with at least one $R^6$.

When $R^b$ is C1-C6 alkyl or C1-C6 alkyl substituted with at least one $R^6$, said C1-C6 alkyl e.g. may be C1-C4 alkyl, such as methyl, ethyl, n-propyl, isopropyl or n-butyl, e.g. C1-C3 alkyl, such as methyl or ethyl, e.g. methyl.

In some embodiments, when $R^b$ is C1-C6 alkyl, it is unsubstituted, e.g. in some embodiments, $R^b$ is C1-C6 alkyl, or C1-C4 alkyl, or C1-C3 alkyl, such as methyl.

In some embodiments, $R^b$ is selected from carbocyclyl-C0-C5 alkyl, e.g. phenyl-C0-C5 alkyl; heterocyclyl-C0-C5 alkyl, e.g. tetrahydrofuryl-C0-C5 alkyl, pyrrolyl-C0-C5 alkyl or imidazolyl-C0-C5 alkyl; C1-C6 alkyl; and C1-C6 alkyl substituted with at least one $R^6$, e.g. 1 or 2 $R^6$, e.g. one $R^6$, wherein each $R^6$ is independently selected from C1-C6 alkoxy, e.g. C1-C3 alkoxy; and 5- or 6-membered cyclic amino optionally containing at least one further heteroatom in the ring and wherein the ring is optionally substituted with at least one, e.g. 1 or 2, e.g. 1, substituent selected from C1-C6 alkyl, e.g. at least one C1-C3 alkyl.

In some embodiments, $R^b$ is selected from carbocyclyl-C0-C5 alkyl, e.g. phenyl-C0-C5 alkyl; heterocyclyl-C0-C5 alkyl, e.g. tetrahydrofuryl-C0-C5 alkyl, pyrrolyl-C0-C5 alkyl, imidazolyl-C0-C5 alkyl, pyrrolidinyl-C0-C5 alkyl, piperidinyl-C0-C5 alkyl; C1-C6 alkyl; and C1-C6 alkyl substituted with at least one $R^6$, e.g. 1 or 2 $R^6$, e.g. one $R^6$, wherein each $R^6$ is independently selected from C1-C6 alkoxy, e.g. C1-C3 alkoxy; and 5- or 6-membered cyclic amino optionally containing at least one further heteroatom in the ring and wherein the ring is optionally substituted with at least one, e.g. 1 or 2, e.g. 1, substituent selected from C1-C6 alkyl, e.g. at least one C1-C3 alkyl.

When $R^b$ is carbocyclyl-C0-C5 alkyl, optionally substituted with at least one $R^7$ and optionally comprising at least one oxo group in the ring, it e.g. may be carbocyclyl-C0-C4 alkyl, carbocyclyl-C0-C3 alkyl, carbocyclyl-C0-C2 alkyl, or carbocyclyl-C0-C1 alkyl substituted with at least one $R^7$ and optionally comprising at least one oxo group in the ring, wherein the carbocyclyl e.g. may be phenyl.

In some embodiments, when $R^b$ is carbocyclyl-C0-C5 alkyl, optionally substituted with at least one $R^7$, $R^b$ is phenyl-C0-C5 alkyl, phenyl-C0-C4 alkyl, phenyl-C0-C3 alkyl, or phenyl-C0-C2 alkyl, e.g. benzyl or phenyl, wherein the phenyl ring is optionally substituted with at least one $R^7$.

In some embodiments, $R^b$ is phenyl, optionally substituted with at least one $R^7$. In some other embodiments, $R^b$ is benzyl, optionally substituted with at least one $R^7$.

When $R^b$ is heterocyclyl-C0-C5 alkyl, optionally substituted with at least one $R^7$ and optionally comprising at least one oxo group in the ring, it e.g. may be heterocyclyl-C0-C4 alkyl, heterocyclyl-C0-C3 alkyl, heterocyclyl-C0-C2 alkyl, or heterocyclyl-C0-C1 alkyl optionally substituted with at least one $R^7$ and optionally comprising at least one oxo group in the ring. In this case, the heterocyclyl e.g. may contain 1-4 heteroatoms, selected from N, O and S, e.g. N and O. For example, the heterocyclyl may be tetrahydrofuryl, pyrrolyl, imidazolyl, or dioxolyl, optionally comprising an oxo group in the ring, such as in 2-oxo-1,3-dioxolyl. In other embodiments, the heterocyclyl is selected from tetrahydrofuryl, pyrrolyl and imidazolyl. In other embodiments, the heterocyclyl is selected from tetrahydrofuryl, pyrrolyl, imidazolyl, e.g imidazol-1-yl, pyrrolidinyl and piperidinyl. In one particular embodiment, the heterocyclyl is selected from pyrrolyl and imidazolyl. In another particular embodiment, the heterocyclyl is tetrahydrofuryl In some embodiments, $R^b$ is 2-nitro-1H-imidazol-5-yl-C0-C3 alkyl or 2-(methylsulfinyl)-1H-imidazol-5-yl)-C0-C3 alkyl, e.g. (2-nitro-1H-imidazol-5-yl)methyl or 2-(methylsulfinyl)-1H-imidazol-5-yl)methyl. In some embodiments, the 1H-imidazol-5-yl is substituted by a group $R^7$ in 1-position, e.g. a group $R^7$ selected from C1-C6 alkyl, such as a C1-C3 alkyl, e.g. methyl. For example, $R^b$ may be 1-methyl-2-nitro-1H-imidazol-5-yl-C0-C3 alkyl, e.g. 1-methyl-2-nitro-1H-imidazol-5-ylmethyl.

In some embodiments, $R^b$ is 1H-imidazolyl. In other embodiments, $R^b$ is 1H-imidazol-5-yl.

In some embodiments, when $R^b$ is carbocyclyl-C0-C5 alkyl or heterocyclyl-C0-C5 alkyl, optionally substituted with at least one $R^7$, said cyclyl does not contain any oxo group in the ring.

In some embodiments, $R^b$ is selected from H, carbocyclyl-C0-C5 alkyl; and heterocyclyl-C0-C5 alkyl; wherein any carbocyclyl and heterocyclyl is optionally substituted with at least one $R^7$ and optionally comprises at least one oxo group in the ring.

In some other embodiments, $R^b$ is selected from H, and carbocyclyl-C0-C5 alkyl; wherein any carbocyclyl is optionally substituted with at least one $R^7$ and optionally comprises at least one oxo group in the ring. In other embodiments, $R^b$ is carbocyclyl-C0-C5 alkyl; wherein any carbocyclyl is optionally substituted with at least one $R^7$ and optionally comprises at least one oxo group in the ring In some embodiments, $R^b$ is selected from H and heterocyclyl-C0-C5 alkyl; wherein any carbocyclyl is optionally substituted with at least one $R^7$ and optionally comprises at least one oxo group in the ring, e.g. $R^b$ is heterocyclyl-C0-C5 alkyl. In other embodiments, $R^b$ is heterocyclyl-C0-C5 alkyl, e.g. $R^b$ is heterocyclyl-C0-C5 alkyl.

In some embodiments, $R^b$ is selected from H; C1-C6 alkyl; C1-C6 alkyl substituted with at least one moiety $R^6$ selected from C1-C6 alkoxy, hydroxy, hydroxy-C1-C6 alkoxy, secondary or tertiary C1-C6 alkylamino, secondary or tertiary hydroxy-C1-C6 alkylamino, 5- or 6-membered cyclic amino optionally containing at least one further heteroatom in the ring and wherein the ring is optionally substituted with at least one C1-C6 alkyl, and carbamoyl;

phenyl-C0-C5 alkyl, wherein the phenyl is optionally substituted with at least one $R^7$, and 5- or 6-membered heterocyclyl-C0-C5 alkyl, wherein the heterocyclyl is optionally substituted with at least one $R^7$ and optionally contains an oxo group in the ring.

In some embodiments, $R^b$ is selected from H; C1-C6 alkyl; C1-C6 alkyl substituted with at least one moiety $R^6$ selected from C1-C6 alkoxy, hydroxy, hydroxy-C1-C6 alkoxy, C1-C6 alkoxycarbonylamino, secondary or tertiary C1-C6 alkylamino, secondary or tertiary hydroxy-C1-C6 alkylamino, 5- or 6-membered cyclic amino optionally containing at least one further heteroatom in the ring and wherein the ring is optionally substituted with at least one C1-C6 alkyl, and carbamoyl; phenyl-C0-C5 alkyl, wherein the phenyl is optionally substituted with at least one $R^7$; 5- or 6-membered heterocyclyl-C0-C5 alkyl; 5- or -6-membered carbocyclylamino; 5- or -6-membered heterocyclylamino; 5- or -6-membered carbocyclyloxy; and 5- or -6-membered heterocyclyloxy; wherein any carbocyclyl or heterocyclyl is optionally substituted with at least one $R^7$ and optionally contains an oxo group in the ring.

For example, $R^b$ may be selected from H, methyl, ethyl, n-propyl, isopropyl, n-butyl, n-pentyl, n-hexyl, 2-hydroxyetyl, 2-methoxyethyl, 2-ethoxyethyl, 3-hydroxypropyl, 2-(2-hydroxyethoxy)ethyl, tetrahydrofuran-3-yl, (tetrahydrofuran-3-yl)methyl, 3-dimethylaminopropyl, 4-dimethylaminobutyl, 2-amino-2-oxoethyl, 3-morpholinopropyl, 3-(4-methylpiperazin-1-yl)propyl, (5-methyl-2-oxo-1,3-dioxol-4-yl)methyl, 2-[bis(2-hydroxyethyl)amino]ethyl, 3-(1H-pyrrol-1-yl)propyl, 3-(1H-imidazol-1-yl)propyl, 2-(1H-pyrrol-1-yl)ethyl, phenyl, and benzyl.

For example, $R^b$ may be selected from H, methyl, ethyl, n-propyl, isopropyl, n-butyl, n-pentyl, n-hexyl, 2-hydroxyetyl, 2-methoxyethyl, 2-ethoxyethyl, 3-hydroxypropyl, 2-(2-hydroxyethoxy)ethyl, tetrahydrofuran-3-yl, (tetrahydrofuran-3-yl)methyl, 3-dimethylaminopropyl, 4-dimethylaminobutyl, 2-amino-2-oxoethyl, 3-(tert-butoxycarbonyl)amino)propyl, 3-morpholinopropyl, 4-morpholinobutyl, 1-methyl-3-morpholinopropyl, 3-(2,6-dimethylmorpholino)propyl, 3-(4-methylpiperazin-1-yl)propyl, 1-methylpiperidin-4-yl, 1-methylpyrrolidin-3-yl, 2-methoxy-1-methylethyl, 1-(methoxymethyl)propyl, 2-ethoxy-1-(ethoxymethyl)ethyl, 2-methoxybutyl, 2-methoxy-1-(methoxymethyl)ethyl, (5-methyl-2-oxo-1,3-dioxol-4-yl)methyl, 2-[bis(2-hydroxyethyl)amino]ethyl, 3-(1H-pyrrol-1-yl)propyl, 3-(1H-imidazol-1-yl)propyl, 2-(1H-pyrrol-1-yl)ethyl, (1-methyl-2-nitro-1H-imidazol-5-yl)methyl, 1-benzylpyrrolidin-3-yl, 1-(tert-butoxycarbonyl)pyrrolidin-3-yl, 2-[(6-chloropyridin-3-yl)oxy]ethyl, 2-[3-(methoxymethyl)phenoxy]ethyl, 2-(3-carbamoylphenoxy)ethyl, 3-(pyridin-3-ylamino)propyl, 3-[(1-methyl-1H-pyrazol-5-yl)amino]propyl, 3-[(5-methylisoxazol-3-yl)amino]propyl, 2-phenoxyethyl, phenyl, and benzyl.

More particularly, $R^b$ may be selected from methyl, ethyl, n-propyl, isopropyl, n-butyl, n-pentyl, n-hexyl, 2-methoxyethyl, 2-ethoxyethyl, tetrahydrofuran-3-yl, (tetrahydrofuran-3-yl)methyl, 3-morpholinopropyl, 3-(4-methylpiperazin-1-yl)propyl, 3-(1H-pyrrol-1-yl)propyl, 3-(1H-imidazol-1-yl)propyl, 2-(1H-pyrrol-1-yl)ethyl, phenyl, and benzyl.

More particularly, $R^b$ may be selected from methyl, ethyl, n-propyl, isopropyl, n-butyl, n-pentyl, n-hexyl, 2-hydroxyetyl, 2-methoxyethyl, 2-ethoxyethyl, 3-hydroxypropyl, tetrahydrofuran-3-yl, (tetrahydrofuran-3-yl)methyl, 3-(tert-butoxycarbonyl)amino)propyl, 3-morpholinopropyl, 4-morpholinobutyl, 1-methyl-3-morpholinopropyl, 3-(2,6-dimethylmorpholino)propyl, 3-(4-methylpiperazin-1-yl)propyl, 1-methylpiperidin-4-yl, 1-methylpyrrolidin-3-yl, 2-methoxy-1-methylethyl, 1-(methoxymethyl)propyl, 2-ethoxy-1-(ethoxymethyl)ethyl, 2-methoxybutyl, 2-methoxy-1-(methoxymethyl)ethyl, 3-(1H-pyrrol-1-yl)propyl, 3-(1H-imidazol-1-yl)propyl, 2-(1H-pyrrol-1-yl)ethyl, (1-methyl-2-nitro-1H-imidazol-5-yl)methyl, 1-benzylpyrrolidin-3-yl, 1-(tert-butoxycarbonyl)pyrrolidin-3-yl, 2-[(6-chloropyridin-3-yl)oxy]ethyl, 2-[3-(methoxymethyl)phenoxy]ethyl, 2-(3-carbamoylphenoxy)ethyl, 3-(pyridin-3-ylamino)propyl, 3-[(1-methyl-1H-pyrazol-5-yl)amino]propyl, 3-[(5-methylisoxazol-3-yl)amino]propyl, 2-phenoxyethyl, phenyl, and benzyl.

In some embodiments, $R^b$ is selected from H, C1-C6 alkyl and C1-C6 alkyl substituted with C1-C6 alkoxy, e.g. H, C1-C6 alkyl and C1-C6 alkyl substituted with C1-C4 alkoxy, or with C1-C3 alkoxy, such as methoxy or ethoxy. For example, $R^b$ may be selected from H, C1-C6 alkyl, such as C1-C4 alkyl, or C1-C3 alkyl, in particular methyl; and C1-C6 alkyl, such as C1-C4 alkyl, or C1-C3 alkyl, in particular ethyl, substituted with C1-C6 alkoxy, e.g. with C1-C4 alkoxy, or with C1-C3 alkoxy, e.g. methoxy or ethoxy.

In some embodiments, $R^b$ is selected from C1-C6 alkyl and C1-C6 alkyl substituted with C1-C6 alkoxy, e.g. H, C1-C6 alkyl and C1-C6 alkyl substituted with C1-C4 alkoxy, or with C1-C3 alkoxy, such as methoxy or ethoxy. For example, $R^b$ may be selected from H, C1-C6 alkyl, such as C1-C4 alkyl, or C1-C3 alkyl, in particular methyl; and C1-C6 alkyl, such as C1-C4 alkyl, or C1-C3 alkyl, in particular ethyl, substituted with C1-C6 alkoxy, e.g. with C1-C4 alkoxy, or with C1-C3 alkoxy, e.g. methoxy or ethoxy.

In some embodiments, $R^b$ is selected from H and C1-C6 alkyl substituted with C1-C6 alkoxy; e.g. H and C1-C6 alkyl substituted with C1-C4 alkoxy or with C1-C3 alkoxy, such as methoxy or ethoxy. For example, $R^b$ may be selected from H and C1-C6 alkyl, such as C1-C4 alkyl, or C1-C3 alkyl, e.g. ethyl, substituted with C1-C6 alkoxy, e.g. with C1-C4 alkoxy, or with C1-C3 alkoxy, e.g. methoxy or ethoxy. In these embodiments, the alkyl moiety may be substituted either by one or by several alkoxy moieties, e.g. 1 or 2 alkoxy moieties. Thus, $R^b$ e.g. may be selected from C2-C5 alkyl, e.g. C2-C4 alkyl, substituted by 1 or 2 methoxy or ethoxy groups, such as in 2-methoxyethyl, 1-methoxypropan-2-yl, 1-methoxybutan-2-yl, 2-methoxybutyl, 1,3-dimethoxypropan-2-yl, 1,3-diethoxypropan-2-yl, etc.

In some embodiments, $R^b$ is selected from H and C1-C6 alkyl substituted with hydroxy. For example, $R^b$ may be selected from H and C1-C6 alkyl, e.g. C2-C6 alkyl, such as C2-C5 alkyl, or C2-C4 alkyl, e.g. ethyl or propyl, substituted with one or several hydroxy groups, e.g. 1 or 2 hydroxy groups, in particular 1 hydroxy group. In some embodiments, $R^b$ is hydroxy-C1-C6 alkyl, such as hydroxy-C2-C6 alkyl, or hydroxy-C2-C5 alkyl, e.g. hydroxy-C2-C4 alkyl, such as hydroxyethyl or hydroxypropyl.

In some embodiments, $R^b$ is as defined herein above, but is not H.

For example, $R^b$ may be selected from, C1-C6 alkyl and C1-C6 alkyl substituted with C1-C6 alkoxy, e.g. C1-C6 alkyl and C1-C6 alkyl substituted with C1-C4 alkoxy, or with C1-C3 alkoxy, such as methoxy or ethoxy. In particular, Rb may be selected from C1-C6 alkyl, such as C1-C4 alkyl, or C1-C3 alkyl, in particular methyl; and C1-C6 alkyl, such as C1-C4 alkyl, or C1-C3 alkyl, in particular ethyl, substituted with C1-C6 alkoxy, e.g. with C1-C4 alkoxy, or with C1-C3 alkoxy, e.g. methoxy or ethoxy.

In a compound of formula (I), each $R^6$ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl)amino; (C1-C6 alkylcarbonyl)(C1-C6 alkyl)amino; carbamoyl; secondary or tertiary C1-C6 alkylamido wherein any alkyl is optionally substituted by OH or $CONH_2$; 5- or 6-membered carbocyclyl- or heterocyclylcarbamoyl; 5- or 6-membered cyclic aminocarbonyl, optionally containing at least one further heteroatom in the ring, and wherein the ring is optionally substituted with at least one C1-C6 alkyl; 5- or -6-membered carbocyclylamino or heterocyclylamino; and 5- or 6-membered carbocyclyloxy or heterocyclyloxy; wherein any alkyl is optionally substituted with at least one halogen and any 5- or 6-membered carbocyclyl or heterocyclyl is optionally substituted with at least one $R^8$.

In some embodiments, each $R^6$ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl)amino; (C1-C6 alkylcarbonyl)(C1-C6 alkyl)amino; carbamoyl; secondary or tertiary C1-C6 alkylamido wherein any alkyl is optionally substituted by OH or $CONH_2$; 5- or 6-membered carbocyclyl- or heterocyclylcarbamoyl; and 5- or 6-membered cyclic aminocarbonyl, optionally containing at least one further heteroatom in the ring, and wherein the ring is optionally substituted with at least one C1-C6 alkyl; wherein any alkyl is optionally substituted with at least one halogen and any 5- or 6-membered carbocyclyl or heterocyclyl is optionally substituted with at least one $R^8$.

In some embodiments, each $R^6$ is independently selected from hydroxy; C1-C6 alkoxy; hydroxy-C1-C6 alkoxy; C1-C6 alkylcarbonyloxy; C1-C6 alkoxycarbonyloxy; benzoyl wherein the phenyl is optionally substituted with at least one $R^8$; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(phenyl)amino wherein the phenyl is optionally substituted with at least one $R^8$; (C1-C6 alkylcarbonyl)(C1-C6 alkyl)amino; carbamoyl; secondary or tertiary C1-C6 alkylamido wherein any alkyl is optionally substituted by OH or $CONH_2$; phenylcarbamoyl wherein the phenyl is optionally substituted with at least one $R^8$; and 5- or 6-membered cyclic aminocarbonyl, optionally containing at least one further heteroatom in the ring, and wherein the ring is optionally substituted with at least one C1-C6 alkyl; wherein any alkyl is optionally substituted with at least one halogen.

In some embodiments, each $R^6$ is independently selected from carbamoyl, amino, secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; hydroxy; C1-C6 alkoxy; hydroxy-C1-C6 alkoxy, C1-C6 alkoxycarbonylamino, (C1-C6 alkoxycarbonyl)(C1-C6 alkyl)amino, and C1-C6 alkoxycarbonyloxy.

In some other embodiments, each $R^6$ is independently selected from hydroxy; C1-C6 alkoxy; hydroxy-C1-C6 alkoxy; carbamoyl, secondary or tertiary C1-C6 alkylamino; secondary or tertiary hydroxy-C1-C6 alkylamino; and 5- or 6-membered cyclic amino optionally containing at least one further heteroatom in the ring and wherein the ring is optionally substituted with at least one C1-C6 alkyl.

In some embodiments, each $R^6$ is hydroxy.

In some other embodiments, each $R^6$ is independently selected from C1-C6 alkoxy, e.g. C1-C3 alkoxy; and 5- or 6-membered cyclic amino optionally containing at least one further heteroatom in the ring and wherein the ring is optionally substituted with at least one, e.g. 1 or 2, e.g. 1, substituent selected from C1-C6 alkyl, e.g. at least one C1-C3 alkyl. Examples of such cyclic amino groups are morpholinyl and piperazinyl.

In some other embodiments, each $R^6$ is selected from C1-C6 alkylcarbonyloxy, 5- or 6-membered carbocyclylcarbonyl or heterocyclylcarbonyl; C1-C6 alkylcarbonylamino; C1-C6 alkoxy; C1-C6 alkoxycarbonylamino; (C1-C6 alkoxycarbonyl)(C1-C6 alkyl)amino; C1-C6 alkoxycarbonyloxy; and 5- or 6-membered cyclic amino optionally containing at least one further heteroatom in the ring and wherein the ring is optionally substituted with at least one C1-C6 alkyl.

In one embodiment, each $R^6$ is independently selected from hydroxy; C1-C6 alkoxy; 5- or 6-membered cyclic amino optionally containing at least one further heteroatom in the ring and wherein the ring is optionally substituted with at least one C1-C6 alkyl.

In another embodiment, each $R^6$ is independently selected from hydroxy; C1-C6 alkoxy; 5- or 6-membered cyclic amino optionally containing at least one further heteroatom in the ring and wherein the ring is optionally substituted with at least one C1-C6 alkyl; C1-C6 alkoxycarbonylamino; 5- or -6-membered carbocyclylamino or heterocyclylamino; and 5- or 6-membered carbocyclyloxy or heterocyclyloxy.

In some embodiments, the 5- or 6-membered cyclic amino is morpholinyl, preferably attached to $R^b$ by a bond to the nitrogen atom of the morpholinyl ring. For example, $R^6$ is morpholinyl, preferably attached by the nitrogen atom of the morpholinyl ring, to a C1-C5 alkyl, e.g. a C2-C5 alkyl, or a C3-C5 alkyl, in particular a C3-C4 alkyl; e.g. $R^b$ is morpholino-3-propyl or morpholino-4-butyl.

In some other embodiments, each $R^6$ is independently selected from C1-C6 alkylcarbonylamino; (C1-C6 alkylcarbonyl)(C1-C6 alkyl)amino; secondary or tertiary C1-C6 alkylamido wherein any alkyl is optionally substituted by OH or $CONH_2$; 5- or 6-membered carbocyclyl- or heterocyclylcarbamoyl; and 5- or 6-membered cyclic aminocarbonyl.

In some embodiments, each $R^6$ is independently selected from C1-C6 alkoxy, e.g. C1-C4 alkoxy, or C1-C3 alkoxy, such as methoxy or ethoxy.

Each $R^7$ and $R^8$ is independently selected from C1-C6 alkyl; hydroxy-C0-C3 alkyl; C1-C6 alkoxy-C0-C3 alkyl; C1-C6 alkoxycarbonyl; carbocyclyl-C0-C4 alkyl; heterocyclyl-C0-C4 alkyl; C1-C6 alkylsulfinyl; amino; nitro; C1-C6 secondary or tertiary amino; halogen; carbamoyl; secondary or tertiary C1-C6 alkylamido-C0-C3 alkyl; C1-C6 alkylcarbonylamino; and 5- or 6-membered cyclic amino, optionally containing at least one further heteroatom in the ring and wherein the ring is optionally substituted with at least one C1-C6 alkyl; wherein any alkyl is optionally substituted with at least one halogen; wherein any carbocyclyl and heterocyclyl is 5- or 6-membered.

In some embodiments, each $R^7$ and $R^8$ is independently selected from C1-C6 alkyl, such as C1-C4 alkyl, or C1-C3 alkyl, e.g. methyl; hydroxy-C0-C3 alkyl, such as hydroxy C0-C2 alkyl, e.g. hydroxy or hydroxymethyl; C1-C6 alkoxy, such as C1-C4 alkoxy, or C1-C3 alkoxy, e.g. methoxy; C1-C6 alkylsulfinyl, e.g. C1-C4 alkylsufinyl, such as methylsulfinyl; amino; nitro; C1-C6 secondary or tertiary amino, such as C1-C4 secondary or tertiary amino, or C1-C3 secondary or tertiary amino, e.g. methylamino or dimethylamino; halogen, such as F or Cl, e.g. F; carbamoyl; secondary or tertiary C1-C6 alkylamido-C0-C3 alkyl, such as secondary or tertiary C1-C4 alkylamido-C0-C3 alkyl, or C1-C3 alkylamido-C0-C3 alkyl, wherein the C0-C3 alkyl moiety e.g. may be a C0-C1 moiety, or C0 (i.e. a direct bond); C1-C6 alkylcarbonylamino; such as C1-C4 alkylcarbonylamino, or C1-C3 alkylcarbonylamino; e.g. acetamido; and 5- or 6-membered cyclic amino, optionally containing at least one further heteroatom in the ring and wherein the ring is optionally substituted with at least one C1-C6 alkyl, such as piperidinyl or morpholinyl optionally substituted with at least one C1-C6 alkyl; wherein any alkyl is optionally substituted by at least one halogen.

When $R^7$ or $R^8$ is a 5- or 6-membered cyclic amino, optionally containing at least one further heteroatom in the ring, it e.g. may contain one further heteroatom in the ring. When the cyclic amino is substituted with at least one C1-C6 alkyl it e.g. may be substituted with 1, 2 or 3 C1-C6 alkyl, e.g. one C1-C6 alkyl, whereby any C1-C6 alkyl may be e.g. e.g. a C1-C3 alkyl, such as methyl.

In some embodiments, any $R^7$ and $R^8$ is independently selected from C1-C6 alkyl, such as C1-C4 alkyl, or C1-C3 alkyl, e.g. methyl; hydroxy-C0-C3 alkyl, such as hydroxy C0-C2 alkyl, e.g. hydroxy or hydroxymethyl; C1-C6 alkoxy, such as C1-C4 alkoxy, or C1-C3 alkoxy, e.g. methoxy; halogen, such as F or Cl, e.g. F; amino, and C1-C6 secondary or tertiary amino, such as C1-C4 secondary or tertiary amino, or C1-C3 secondary or tertiary amino, e.g. methylamino or dimethylamino.

In some embodiments, any $R^7$ and $R^8$ is independently selected from C1-C6 alkyl, such as C1-C4 alkyl, or C1-C3 alkyl, e.g. methyl; hydroxy-C0-C3 alkyl, such as hydroxy C0-C2 alkyl, e.g. hydroxy or hydroxymethyl; C1-C6 alkoxy, such as C1-C4 alkoxy, or C1-C3 alkoxy, e.g. methoxy; and halogen, such as F or Cl, e.g. F.

In some embodiments, any $R^7$ and $R^8$ is independently is selected from halogen and C1-C6 alkyl, such as C1-C4 alkyl, or C1-C3 alkyl, e.g. methyl.

In some embodiments, any $R^7$ and $R^8$ is independently is selected from C1-C6 alkyl, such as C1-C4 alkyl, or C1-C3 alkyl, e.g. methyl.

In some embodiments, $R^7$ is absent. In some other embodiments, $R^8$ is absent. In still other embodiments, both $R^7$ and $R^8$ are absent.

In one embodiment, a compound is provided, selected from the compounds according to Examples 1-4, 7-21, 24-26, 28-29, 31-35, 37-137, 140-144, 146-232, or from pharmaceutically acceptable salts thereof.

In one embodiment, a compound is provided, selected from the compounds according to Examples 1-4, 7-21, 24-26, 28-29, 31-35, 38-49, 52-92, 94-111, 113-134, 136-137, 140, 142-143, 149-150, 152-232, or from pharmaceutically acceptable salts thereof.

In one embodiment, a compound is provided for use in therapy, selected from any of the above-mentioned compounds, as well as from compounds according to Examples 5, 6, 22, 23, 27, 30, 36, 138, 139 and 145, or from pharmaceutically acceptable salts thereof.

In one embodiment, a compound is provided for use in therapy, selected from any of the above-mentioned compounds, as well as from compounds according to Examples 5, 6, 22, 23, 27, 30 and 36, or from pharmaceutically acceptable salts thereof.

Depending on the process conditions the end products of formula (I) are obtained either in neutral or salt form. Both the free base and the free acid, as well as the salts of these end products are within the scope of the invention. Acid addition salts of the inventive compounds may in a manner known per se be transformed into the free base using basic agents such as alkali or by ion exchange. The free base obtained may also form salts with organic or inorganic acids. Alkali addition salts of the inventive compounds may in a manner known per se be transformed into the free acid by using acidic agents such as acid or by ion exchange. The free acid obtained may also form salts with organic or inorganic bases.

In the preparation of acid or base addition salts, preferably such acids or bases are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, trifluoroacetic acid, propionic acid, succinic acid, fumaric acid, glycolic acid, lactic acid, malic acid, tartaric acid, citric acid, ascorbic acid, maleic acid, hydroxymaleic acid, pyruvic acid, benzoic acid, gluconic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

Throughout the specification and the appended claims, a given chemical formula or name shall also encompass all salts, hydrates, solvates, N-oxides and prodrug forms thereof. Further, a given chemical formula or name shall encompass all stereoisomeric forms thereof. Stepreoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometric isomers, which can be present in their pure cis or trans forms or as mixtures of those.

The term "prodrug forms" means a pharmacologically acceptable derivative, such as an ester or an amide, which derivative is biotransformed in the body to form the active drug. Reference is made to Goodman and Gilman's, The Pharmacological basis of Therapeutics, 8$^{th}$ ed., McGraw-Hill, Int. Ed. 1992, "Biotransformation of Drugs", p. 13-15.

Pharmaceutical formulations are usually prepared by mixing the active substance, i.e. a compound of the invention, or a pharmaceutically acceptable salt thereof, with conventional pharmaceutical excipients. The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

For clinical use, the compounds of the invention are formulated into pharmaceutical formulations for oral, rectal, parenteral, intravenous or other mode of administration. These pharmaceutical preparations are a further object of the invention.

Usually the amount of active compounds is between 0.1-95% by weight of the preparation, preferably between 0.2-20% by weight in preparations for parenteral use and preferably between 1 and 50% by weight in preparations for oral administration.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral, intravenous, nasal or pulmonal administration may also be chosen.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral, e.g. intravenous, administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The compounds of the present invention may also be used or administered in combination with one or more additional therapeutically active agents, e.g. drugs useful in a diagnostic method, profylaxis or treatment of inflammation and inflammatory diseases or cancer. The components may be in the same formulation or in separate formulations for administration simultaneously or sequentially. Examples of combination therapies are, but not limited to;

anti cancer therapy (such as gemcitabine, cisplatin, oxaliplatin, epirubicin, methotrexate, 5-FU, capecitabine, docetaxel, vincristine, irinotecan, doxorubicin, velcade), or anti inflammatory therapy, e.g. with steroids (such as methotrexate, corticosteroids) or non-steroidal anti-inflammatory drugs/NSAIDs (such as aspirin, ibuprofen, naproxen).

Accordingly, in a further aspect of the invention, there is provided a combination product comprising:
(A) a compound of the invention, as defined herein; and
(B) another therapeutic agent, e.g. one that is useful in the treatment of, inflammation, inflammatory diseases, or cancer; whereby (A) and (B) is formulated in admixture with a pharmaceutically acceptable excipient.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent, and a pharmaceutically acceptable excipient, e.g. an adjuvant, diluent or carrier; and
(2) a kit of parts comprising, as components:
(a) a pharmaceutical formulation including a compound of the invention, as defined herein, in admixture with a pharmaceutically acceptable excipient, e.g. an adjuvant, diluent or carrier; and
(b) a pharmaceutical formulation including another therapeutic agent in admixture with a pharmaceutically acceptable excipient, e.g. an adjuvant, diluent or carrier, which components (a) and (b) are each provided in a form that is suitable for administration in conjunction with the other.

The compounds of the present invention may also be used or administered in combination with other treatment such as irradiation for the treatment of cancer.

Furthermore, a pharmaceutical composition is provided, comprising a compound of formula (I) as defined herein, and optionally at least one pharmaceutically acceptable excipient.

Another object of the present invention relates to modulation of F-2,6-$P_2$ levels with the compounds of formula (I).

Thus, in one aspect, a compound as defined herein is provided for use in a diagnostic method treatment or profylaxis of a disorder related to or mediated the F-2,6-$P_2$ levels.

In one aspect, a compound as defined herein is provided, for use in a diagnostic method, treatment or profylaxis of cancer, inflammation or an inflammatory disorder.

The use of a compound as defined herein in the manufacturing of a medicament for a diagnostic method, treatment or profylaxis of cancer, inflammation or an inflammatory disorder also is provided.

Finally, one object of the invention is to provide a method for the profylaxis or treatment of cancer, inflammation or an inflammatory disorder in a mammal in need of such treatment by administering to said mammal a compound as defined herein.

The invention will now be further illustrated by the following non-limiting Examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. The necessary starting materials for preparing the compounds of formula I are either known or may be prepared, by a person skilled in the art, in analogy with the preparation of known compounds. All references and publications cited herein are hereby incorporated by reference in their entirety.

The compounds of the invention may be prepared according to known methods for those skilled in the art. Other reaction schemes, as well as a variety of different solvents, temperatures and other reaction conditions, could be readily devised by those skilled in the art.

Substituted benzothiophenes were synthesized according to Scheme 1 as described by Plé et al. (Plé et al., (1988) J. Heterocyclic Chem. 25, 1271-1272). Alkylation of substituted thiophenols with chloroacetone, followed by PPA-mediated cyclization of the ketones gave 5-substituted 3-methylbenzothiophenes.

Scheme 1

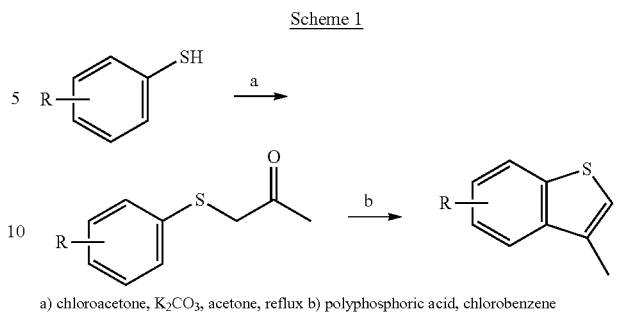

a) chloroacetone, $K_2CO_3$, acetone, reflux b) polyphosphoric acid, chlorobenzene Substituted benzofuranes were synthesized from the corresponding phenols in three steps according to Scheme 2 (Xie et al., (2004) Tetrahedron Lett. 45, 6235-6237). Iodination of the phenols with N-iodosuccinimide followed by allylation with allylbromide gave 1-allyloxy-2-iodo-benzenes as intermediates, which were transformed to the substituted benzofuranes by palladium mediated Heck couplings.

Scheme 2

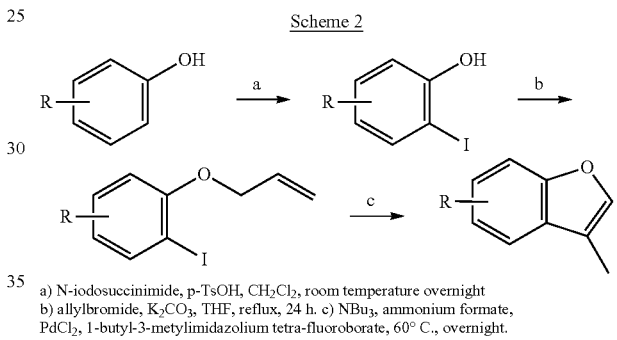

a) N-iodosuccinimide, p-TsOH, $CH_2Cl_2$, room temperature overnight
b) allylbromide, $K_2CO_3$, THF, reflux, 24 h. c) $NBu_3$, ammonium formate, $PdCl_2$, 1-butyl-3-metylimidazolium tetra-fluoroborate, 60° C., overnight.

The preparation of some sulfonyl chlorides was performed by a two step procedure wherein the sulfonylation using $SO_3$/dioxane complex or $H_2SO_4/Ac_2O$ (Graham et al., (1990) J. Med. Chem. 33, 749-754) was followed by chlorination with $POCl_3$ or $POCl_3/PCl_5$. Alternatively, the sulfonylation was done using chlorosulfonic acid (Scheme 3). Regarding the handling and use of $SO_3$/dioxane-complex see Paquette, *Encyclopedia of Reagents for Organic Synthesis* and references therein.

Scheme 3

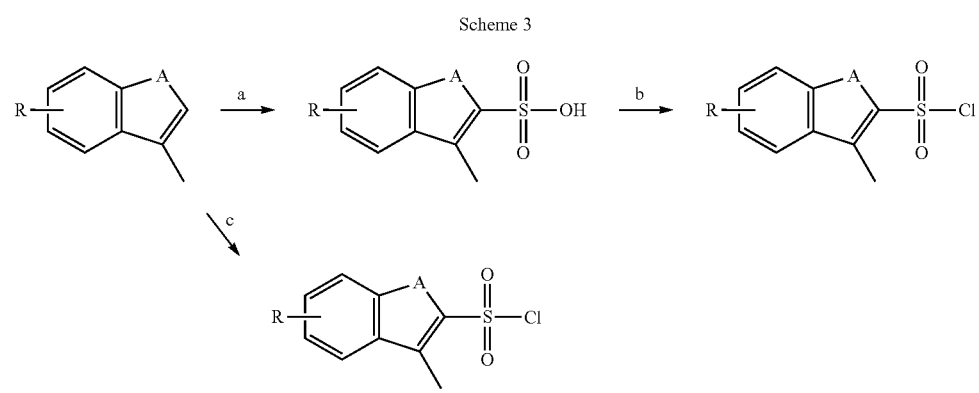

a) $SO_3$/dioxane complex, 1,2-dichloroethane, room temperature or $H_2SO_4/AC_2O$, EtOAc, room temperature b) $POCl_3$, $CH_2Cl_2$, 60° C. or $POCl_3/PCl_5/CH_2Cl_2$, room temperature c) chlorosulfonic acid, $CH_2Cl_2$ or $CHCl_3$, -20° C. to room temperature, followed by 35-50° C. A=O or S.

Sulfonyl chlorides of aryl-substituted thiophenes were prepared via palladium-mediated Suzuki couplings followed by sulfonylations using chlorosulfonic acid (Scheme 4).

Scheme 4

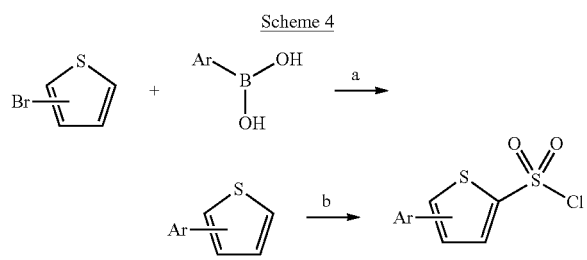

a) DIPEA, Pd(dppf)Cl$_2$:CH$_2$Cl$_2$, aqueous dioxane, 80° C. overnight b) chlorosulfonic acid, CHCl$_3$, 0° C.

The sulfonamides were, for example, synthesized from sulfonyl chlorides and methyl 4-aminosalicylate according to any of the methods illustrated in Scheme 5, wherein A corresponds to S, O, —CR$^4$═CR$^4$— or —CR$^4$═N— according to the Formula (I).

Scheme 5

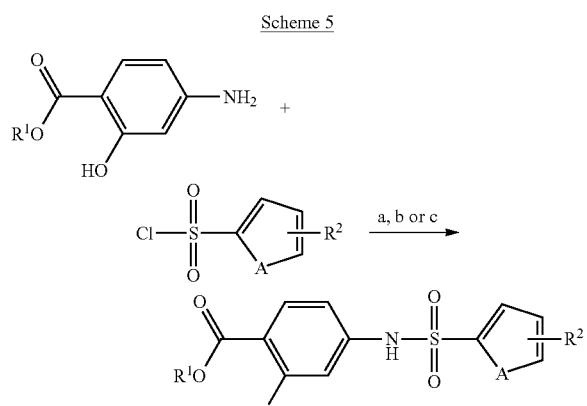

a) pyridine, CH$_2$Cl$_2$, 60° C. b) aqueous dioxane, room temperature c) pyridine, MeCN, temperature ranging from room temperature to 80° C.

For some of examples described below, the intermediate acids were obtained by alkaline hydrolysis of the methyl esters (Scheme 6).

Scheme 6

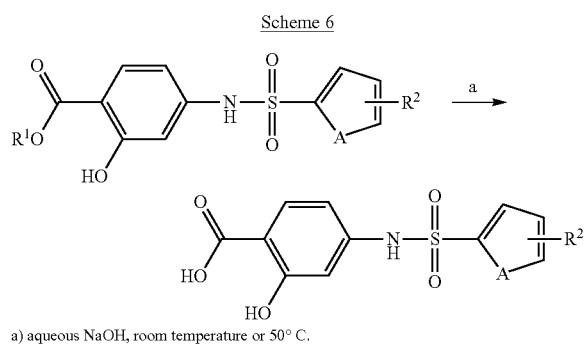

a) aqueous NaOH, room temperature or 50° C.

For some of the examples described below, the desired ester or amide functionalities were introduced by reacting the corresponding acids with a coupling reagent (1,1'-carbonyldiimidazole) followed by addition of the appropriate alcohol or amine. Alternatively, the desired ester was obtained by esterification using conc. H$_2$SO$_4$ and excess of the alcohol, or via formation of the intermediate acid chloride which was reacted with the appropriate alcohol (Scheme 7).

Scheme 7

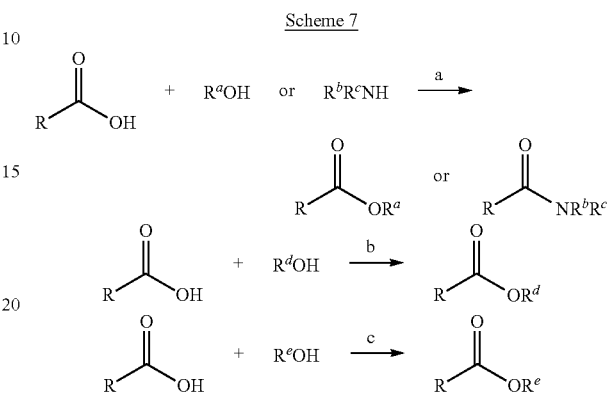

a) 1,1'-carbonyldiimidazole, pyridine, MeCN, room temperature or 55-65° C. b) H$_2$SO$_4$, excess alcohol, 60-80° C. c) SOCl$_2$, MeCN, room temperature.

For some esters containing a basic moiety within the ester group an intermediate alkyl halide was prepared, which was subsequently reacted with an appropriate amine (Scheme 8). For amines with low nucleophilicity, the latter reaction was carried out in the presence of potassium iodide.

Scheme 8

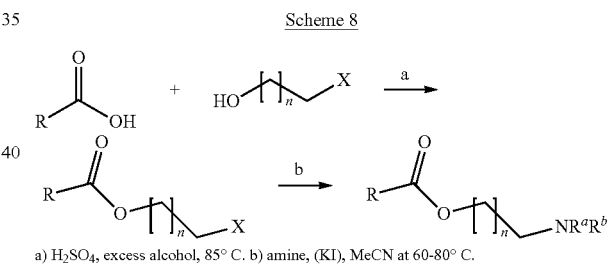

a) H$_2$SO$_4$, excess alcohol, 85° C. b) amine, (KI), MeCN at 60-80° C.

The biaryl compounds (wherein A=S, —CR$^4$═CR$^4$— or —CR$^4$═N—) were prepared by Suzuki couplings at 80° C. according to a modified procedure based on the method described by Jiang et al. (Jiang et al., (2006) Tetrahedron Lett. 47, 197-200) (Scheme 9, step d). The same synthetic procedures should be applicable for biaryl compounds with A=O.

Scheme 9

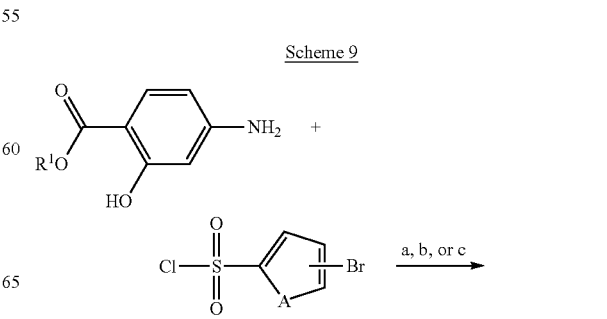

-continued

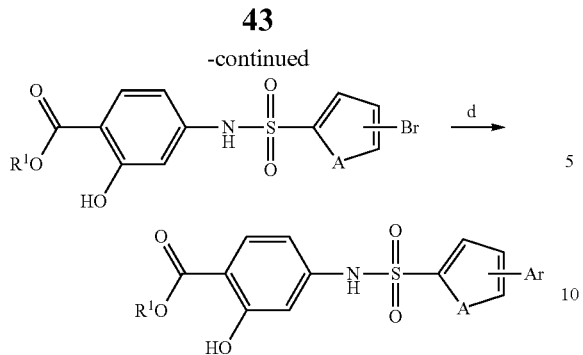

a) pyridine, CH₂Cl₂, 60° C. b) aqueous dioxane, room temperature c) pyridine, MeCN, temperature ranging from room temperature to 80° C. d) aryl boronic acid, DIPEA or K₂CO₃, Pd(dppf)Cl₂:CH₂Cl₂, aqueous dioxane, 80° C. overnight or 145° C., 900 s using microwave reactor. A═S, ─CR⁴═CR⁴─ or ─CR⁴═N─.

Amine substituted benzothiophene analogues were synthesized from the corresponding bromides following the procedures described by Harris et. al (Harris et al., (2001) Org. Lett 3, 21, 3417-3419) (Scheme 10).

Scheme 10

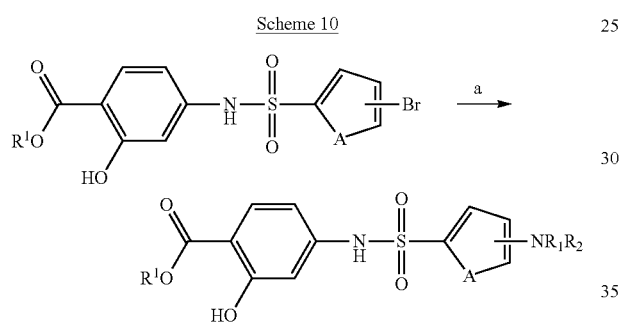

a) amine, Pd₂(dba)₃, 2′-(dicyclohexylphosphino)-N,N-dimethyl [1,1′-biphenyl]-2-amine, LiHMDS, THF, 100° C. in a microwave reactor.

Different esters were prepared by nucleophilic substitution of the carboxylic acids using alkyl halides as the electrophiles (Scheme 11).

Scheme 11

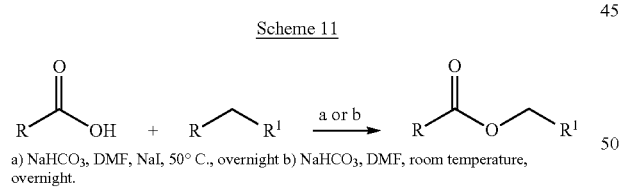

a) NaHCO₃, DMF, NaI, 50° C., overnight b) NaHCO₃, DMF, room temperature, overnight.

Examples described herein, containing acetylated phenols, were synthesized in 3-5 steps according to Schemes 12 and 13.

Scheme 12

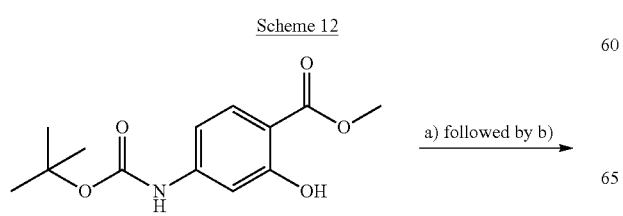

a) Ac₂O, pyridine, MeCN, 70° C., 2 weeks b) TFA/CH₂Cl₂, room temperature, overnight c) ArSO₂Cl, pyridine, MeCN, room temperature.

Scheme 13

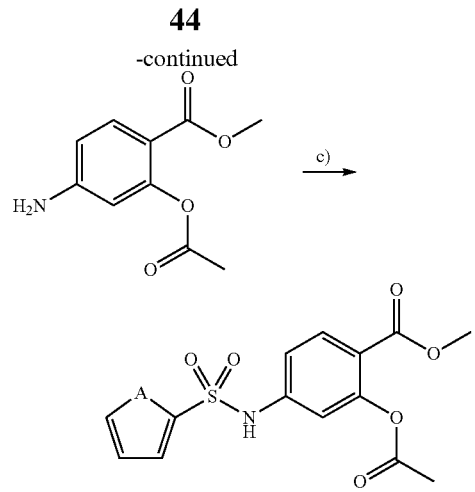

a) 1,1′-carbonyldiimidazole, benzyl alcohol, pyridine, MeCN, 50° C., overnight b) acetyl chloride, DIPEA, MeCN, overnight c) TFA/CH₂Cl₂, room temperature, overnight d) ArSO₂Cl, pyridine, MeCN, 50° C., 2 h e) Pd/C, H₂, 2 h.

Some of the starting materials used for synthesis of aryloxy- and heteroaryloxy substituted esters were prepared according to the methods described by Nilsson et. al (2002) U.S. Pat. No. 6,465,467 and Nilsson et. al. (2000) WO 2000076984.

EXAMPLES

NMR spectra were recorded on a Varian Inova 500 instrument equipped with a triple resonance probe, a Varian Inova 600 equipped with a triple resonance cold probe or a triple resonance probe, or a Bruker DRX400 equipped with a QNP probe. All spectra were recorded using the residual solvent proton resonance or tetramethylsilane (TMS) as internal standard. Analytical HPLC was carried out on an Agilent Series 1100 system using either an ACE C8 (3 μm, 3.0×50 mm) column with 0.1% TFA in MilliQ water/MeCN as mobile phase (acidic system) or an XTerra (3.5 μm 3.0×50 mm) column with 10 mM pH10 NH$_4$HCO$_3$/MeCN as mobile phase (basic system). Electrospray mass spectrometry (ES-MS) was performed using an Agilent 1100 Series Liquid Chromatograph/Mass Selective Detector (MSD) to obtain the pseudo molecular [M+H]$^+$ ion of the target molecules. Preparative HPLC was performed on a Gilson 306 or Gilson 333 HPLC system using either an ACE C8 (5 μm, 21×50 mm) column with 0.1% TFA in MilliQ H$_2$O/MeCN as mobile phase (acidic system), an XTerra Prep MS C18 (5 μm, 19×50 mm) column with 50 mM pH10 NH$_4$HCO$_3$/MeCN as mobile phase (basic system 1), a GeminiNX Prep MS C18 (5 μm, 21×50 mm) column with 50 mM pH10 NH$_4$HCO$_3$/MeCN (basic system 2) or an ACE C8 (5 μm 21×50 mm) column with 50 mM NH$_4$OAc in water/MeCN (neutral system). Fractions were collected based on the UV-signal at 220 or 254 nm. Preparative flash chromatography was performed on Merck silica gel 60 (230-400 mesh) or YMC gel 120 Å S-150 μm. Accurate masses were measured using an Agilent MSD-TOF connected to an Agilent 1100 HPLC system. During the analyses the calibration was checked by two masses and automatically corrected when needed. Spectra were acquired in positive electrospray mode. The acquired mass range was m/z 100-1100. Profile detection of the mass peaks was used. Microwave reactions were performed with a Personal Chemistry Smith Creator using 0.5-2 mL or 2-5 mL Smith Process Vials fitted with aluminum caps and septa. The compounds were named using the software ACD Labs 6.0 or 10.0.

Intermediate 1

4-{[(4-Bromo-5-chlorothiophen-2-yl)sulfonyl]amino}-2-hydroxybenzoic acid

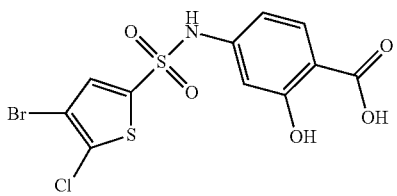 [SMILES: O=C(O)c1ccc(NS(=O)(=O)c2cc(Br)c(Cl)s2)cc1O]

A mixture of 4-aminosalicylic acid (0.57 g, 3.7 mmol) and 3-bromo-2-chlorothiophene-5-sulfonyl chloride (1.0 g, 3.4 mmol) in aqueous dioxane (50 mL dioxane, 50 mL water) was stirred at room temperature for 3 days. EtOAc (100 mL) was added. The organic phase was washed with 1 M HCl (3×50 mL), water and brine and then dried with MgSO$_4$, filtered and concentrated. The brown residue was crystallized from water/MeOH at 50° C. The precipitate was collected by filtration and dried in vacuum giving the title compound as a light brown solid (0.64 g, 43%). $^1$H NMR (500 MHz, DMSO-d$_6$) δ ppm 6.71 (d, J=2.20 Hz, 1H) 6.75 (dd, J=8.55, 2.20 Hz, 1H) 7.72 (d, J=8.55 Hz, 1H) 7.80 (s, 1H) 11.26 (br. s., 1H) 11.39 (br. s., 1H). MS (ESI+) m/z 412 [M+H]$^+$.

Intermediate 2

4-({[5-Chloro-4-(2,3-dihydro-1-benzofuran-5-yl)thiophen-2-yl]sulfonyl}amino)-2-hydroxybenzoic acid

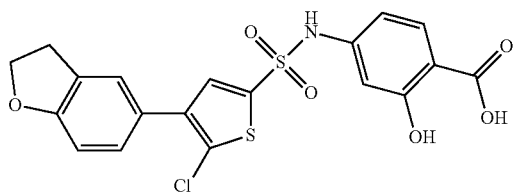 [SMILES: O=C(O)c1ccc(NS(=O)(=O)c2cc(-c3ccc4c(c3)CCO4)c(Cl)s2)cc1O]

A mixture of 4-{[(4-bromo-5-chlorothiophen-2-yl)sulfonyl]amino}-2-hydroxybenzoic acid (Intermediate 1) (150 mg, 0.36 mmol), 2,3-dihydrobenzofuran-5-boronic acid (65 mg, 0.40 mmol), DIPEA (140 mg, 1.1 mmol) and Pd(dppf)Cl$_2$.CH$_2$Cl$_2$ (15 mg, 0.018 mmol) in aqueous dioxane (5 mL dioxane, 1 mL water) was heated at 80° C. under N$_2$ atmosphere overnight. CH$_2$Cl$_2$ (50 mL) followed by 1 M Na$_2$CO$_3$ (10 mL) were added to the reaction mixture. The aqueous phase was washed with CH$_2$Cl$_2$ (2×50 mL) and then acidified with conc. H$_3$PO$_4$. EtOAc (100 mL) was added. The organic phase was washed with 1 M HCl (2×50 mL), water and brine, and dried with MgSO$_4$, filtered and concentrated. The crude product was purified by preparative HPLC (acidic system). The title compound was obtained as a white solid (50 mg, 31%). $^1$H NMR (500 MHz, CD$_3$OD) δ ppm 3.24 (t, J=8.67 Hz, 2H) 4.58 (t, J=8.67 Hz, 2H) 6.72 (dd, J=8.55, 2.20 Hz, 1H) 6.76-6.81 (m, 2H) 7.22 (dd, J=8.18, 2.08 Hz, 1H) 7.33 (d, J=1.46 Hz, 1H) 7.54 (s, 1H) 7.78 (d, J=8.79 Hz, 1H). MS (ESI+) m/z 452 [M+H]$^+$.

Intermediate 3

Methyl 4-{[(4-bromo-5-chloro-2-thienyl)sulfonyl]amino}-2-hydroxybenzoate

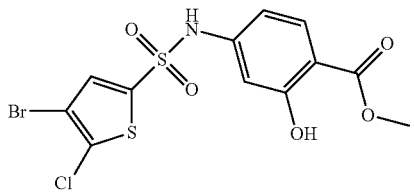

A reaction mixture with methyl 4-amino-salicylate (330 mg, 2.0 mmol), 2-chloro-3-bromothiophene-5-sulfonyl chloride (590 mg, 2.0 mmol) and pyridine (1.58 g, 20 mmol) in MeCN (100 mL) was heated at 60° C. for 3 days. After removal of the solvent under reduced pressure, EtOAc (100 mL) followed by 1 M HCl (100 mL) were added.

The organic phase was washed with 1 M HCl (3×100 mL), water and brine, then dried over MgSO$_4$, filtered and concentrated. The residue was stirred in refluxing MeOH (50 mL). After cooling overnight the white impurity was removed by filtration. The mother-liquid was concentrated to dryness giving a solid, which was recrystallized from toluene/heptane. The title compound was obtained as a white solid (300 mg, 35%). $^1$H NMR (500 MHz, CDCl$_3$) δ ppm 3.95 (s, 3H) 6.69 (dd, J=8.67, 2.32 Hz, 1H) 6.74 (d, J=2.44 Hz, 1H) 6.91 (br. s., 1H) 7.46 (s, 1H) 7.80 (d, J=8.79 Hz, 1H) 10.93 (s, 1H). MS (ESI+) m/z 426 [M+H]$^+$.

Intermediate 4

General Procedure 1

Methyl 4-{[(3-bromophenyl)sulfonyl]amino}-2-hydroxybenzoate

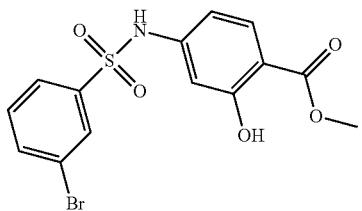 [SMILES: COC(=O)c1ccc(NS(=O)(=O)c2cccc(Br)c2)cc1O]

A reaction mixture with methyl 4-amino-salicylate (1.3 g, 7.8 mmol), 3-bromobenzenesulfonyl chloride (2.0 g, 7.8 mmol) and pyridine (1.2 g, 15 mmol) in MeCN (100 mL) was stirred at 80° C. overnight. After removal of the solvent under reduced pressure, toluene (100 mL) followed by 1 M HCl (100 mL) were added. The organic phase was washed with 1 M HCl (3×100 mL), water and brine, then dried over MgSO$_4$, filtered and concentrated to a light brown oil. The crude product was recrystallized from MeOH/water giving the title compound as white solid (2.4 g, 79%). $^1$H NMR (500 MHz, CDCl$_3$) δ ppm 3.92 (s, 3H) 6.64 (dd, J=8.55, 2.20 Hz, 1H) 6.68 (d, J=2.20 Hz, 1H) 7.01 (s, 1H) 7.37 (t, J=7.93 Hz, 1H) 7.67-7.72 (m, 1H) 7.74 (d, J=8.79 Hz, 1H) 7.78-7.84 (m, 1H) 8.04 (t, J=1.83 Hz, 1H) 10.87 (s, 1H). MS (ESI+) m/z 386 [M+H]$^+$.

Intermediate 5

Methyl 4-({[3-bromo-5-(trifluoromethyl)phenyl]sulfonyl}amino)-2-hydroxybenzoate

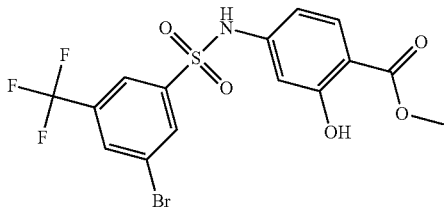 [SMILES: COC(=O)c1ccc(NS(=O)(=O)c2cc(Br)cc(C(F)(F)F)c2)cc1O]

A reaction mixture with methyl 4-amino-salicylate (170 mg, 1.0 mmol), 3-bromo-5-trifluoromethylbenzenesulphonyl chloride (320 mg, 1.0 mmol) and pyridine (156 mg, 2.0 mmol) in MeCN (50 mL) was heated at 70° C. overnight. After removal of the solvent under reduced pressure, EtOAc (100 mL) followed by 1 M K$_2$CO$_3$ (50 mL) were added. The organic phase was washed with 1 M K$_2$CO$_3$, 1 M HCl, water and brine, then dried over MgSO$_4$, filtered and concentrated. The residue was recrystallized from refluxing MeOH/water. The title compound was obtained as a white solid (280 mg, 61%). $^1$H NMR (500 MHz, CDCl$_3$) δ ppm 3.93 (s, 3H) 6.63-6.69 (m, 2H) 6.92 (s, 1H) 7.74-7.82 (m, 1H) 7.96 (s, 1H) 8.04 (s, 1H) 8.18 (s, 1H) 10.90 (s, 1H). MS (ESI+) m/z 454 [M+H]$^+$.

Intermediate 6

4-{[(2,5-Dichlorothiophen-3-yl)sulfonyl]amino}-2-hydroxybenzoic acid

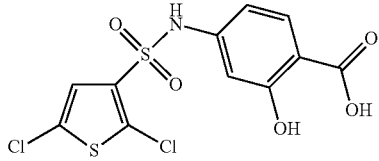 [SMILES: O=C(O)c1ccc(NS(=O)(=O)c2cc(Cl)sc2Cl)cc1O]

A mixture of 4-amino salicylic acid (1.16 g, 7.6 mmol) and 2,5-dichlorothiophene-3-sulfonyl chloride (0.95 g, 3.8 mmol) in aqueous dioxane (95 mL dioxane, 5 mL water) was stirred at room temperature for 2 weeks. The pH of the reaction mixture was adjusted to 10 by addition of 1 M Na$_2$CO$_3$, and then EtOAc (200 mL) followed by water (100 mL) were added. The aqueous phase was washed with EtOAc (2×100 mL) and then the pH was adjusted to 3 by addition of concentrated phosphoric acid. EtOAc (200 mL) was added and the organic phase was washed with 1 M HCl (3×100 mL) and brine, and then dried over MgSO$_4$, filtered and concentrated. The brown residue was crystallized from water/MeOH at 60° C. The precipitate was collected by filtration and dried in vacuum giving the title compound as a light brown solid (0.58 g, 42%). $^1$H NMR (500 MHz, CD$_3$OD) δ ppm 6.67 (dd, J=8.61, 2.26 Hz, 1H) 6.70 (d, J=2.26 Hz, 1H) 7.26 (s, 1H) 7.74 (d, J=8.61 Hz, 1H). MS (ESI+) m/z 368 [M+H]$^+$.

Intermediate 7

4-{[(4,5-Dichlorothiophen-2-yl)sulfonyl]amino}-2-hydroxybenzoic acid

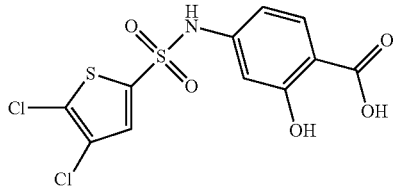 [SMILES: O=C(O)c1ccc(NS(=O)(=O)c2cc(Cl)c(Cl)s2)cc1O]

The intermediate methyl ester was prepared from methyl 4-amino-salicylate (0.84 g, 5 mmol) and 2,3-dichlorothiophene-5-sulfonyl chloride (1.38 g, 5.5 mmol) according to the General Procedure 1, described in Intermediate 4, using toluene for the extractive workup. The residue was recrystallized from refluxing toluene/heptane, giving the intermediate methyl 4-{[(4,5-dichlorothiophen-2-yl)sulfonyl]amino}-2-hydroxybenzoate as a white solid (0.97 g). A second crop of 0.6 g was collected from the mother liquid giving a total yield of 82% (1.57 g) of the methyl 4-{[(4,5-dichlorothiophen-2-yl)sulfonyl]amino}-2-hydroxybenzoate. $^1$H NMR (500 MHz, CDCl$_3$) δ ppm 3.94 (s, 3H) 6.68

(dd, J=8.67, 2.32 Hz, 1H) 6.73 (d, J=2.32 Hz, 1H) 6.83 (br. s., 1H) 7.42 (s, 1H) 7.79 (d, J=8.67 Hz, 1H) 10.92 (s, 1H). MS (ESI+) m/z 382 [M+H]$^+$.

The methyl 4-{[(4,5-dichlorothiophen-2-yl)sulfonyl]-amino}-2-hydroxybenzoate (0.6 g, 1.6 mmol) was dissolved in 1 M NaOH (10 mL) and stirred at 60° C. for 2 h. The aqueous reaction mixture was washed with CH$_2$Cl$_2$ (2×50 mL) and then acidified with phosphoric acid giving a white precipitate. EtOAc (100 mL) was added. The organic phase was washed with 1 M HCl (2×50 mL), water and brine and then dried over MgSO$_4$, filtered and concentrated. The residue was refluxed in water/MeOH. After cooling, the title compound was collected by filtration (white solid, 0.43 g, 1.2 mmol, 75%). $^1$H NMR (500 MHz, CD$_3$OD) δ ppm 6.70 (dd, J=8.55, 2.20 Hz, 1H) 6.75 (d, J=1.95 Hz, 1H) 7.52 (s, 1H) 7.78 (d, J=8.55 Hz, 1H). MS (ESI+) m/z 368 [M+H]$^+$.

Intermediate 8

Methyl 4-{[(5-bromo-6-chloropyridin-3-yl)sulfonyl]amino}-2-hydroxybenzoate

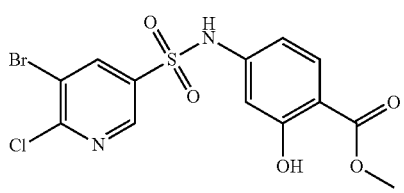 [SMILES: COC(=O)c1ccc(NS(=O)(=O)c2cnc(Cl)c(Br)c2)cc1O]

The product was prepared from methyl 4-amino-salicylate (401 mg, 2.4 mmol) and 3-bromo-2-chloropyridine-5-sulfonyl chloride (698 mg, 2.4 mmol) according to the General Procedure 1, described in Intermediate 4, using toluene for the extractive workup. The solid collected after recrystallization was refluxed in EtOAc/heptane. After cooling, a white impurity was removed by filtration. The mother liquid was concentrated to dryness giving the title compound as an off-white solid (449 mg, 44%). $^1$H NMR (600 MHz, DMSO-d$_6$) δ ppm 3.83 (s, 3H) 6.72 (d, J=2.20 Hz, 1H) 6.74 (dd, J=8.60, 2.20 Hz, 1H) 7.69 (d, J=8.60 Hz, 1H) 8.55 (d, J=2.20 Hz, 1H) 8.80 (d, J=2.20 Hz, 1H) 10.59 (s, 1H) 11.15 (br. s., 1H). MS (ESI+) m/z 421 [M+H]$^+$.

Intermediate 9

General Procedure 2

4-{[(5-Bromothiophen-2-yl)sulfonyl]amino}-2-hydroxybenzoic acid

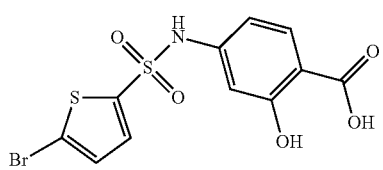 [SMILES: O=C(O)c1ccc(NS(=O)(=O)c2ccc(Br)s2)cc1O]

A mixture of 4-aminosalicylic acid (1.16 g, 7.6 mmol) and 5-bromothiophene-2-sulfonyl chloride (1.0 g, 3.8 mmol) in aqueous dioxane (95 mL dioxane, 5 mL water) was stirred at room temperature for 7 weeks. EtOAc (100 mL) was added. The organic phase was washed with 1 M HCl (3×50 mL), water and brine and then dried over MgSO$_4$, filtered and concentrated. The brown residue was crystallized from water/MeOH at 60° C. The precipitate was collected by filtration and dried in vacuum giving the title compound as a light brown solid (0.64 g, 45%). $^1$H NMR (500 MHz, DMSO-d$_6$) δ ppm 6.70 (d, J=1.95 Hz, 1H) 6.72 (dd, J=8.55, 2.20 Hz, 1H) 7.33 (d, J=4.15 Hz, 1H) 7.52 (d, J=4.15 Hz, 1H) 7.70 (d, J=8.79 Hz, 1H) 11.11 (s, 1H). MS (ESI+) m/z 378 [M+H]$^+$.

Intermediate 10

General Procedure 3

4-{[(3-Bromobenzyl)sulfonyl]amino}-2-hydroxybenzoic acid

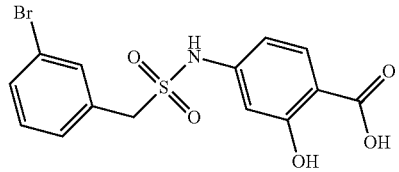 [SMILES: O=C(O)c1ccc(NS(=O)(=O)Cc2cccc(Br)c2)cc1O]

A mixture of methyl 4-aminosalicylate (67 mg, 0.400 mmol), 3-bromobenzylsulfonyl chloride (108 mg, 0.400 mmol) and pyridine (31 mg, 0.400 mmol) in MeCN (2 mL) was stirred at room temperature overnight. The solvent was removed and the residue was dissolved in 5 M NaOH (1 mL, 5.0 mmol) and then heated at 60° C. for 30 minutes. The reaction mixture was acidified with conc. H$_3$PO$_4$ and extracted with EtOAc (2×3 mL). The combined organic phases were washed with brine, dried over MgSO$_4$, filtered and concentrated. The residue was stirred in aqueous MeOH (1 mL MeOH, 5 mL water) at 60° C. After cooling to room temperature, the solid was collected by filtration and dried in vacuum. The title compound was obtained as a white solid (24 mg, 17%). $^1$H NMR (500 MHz, CD$_3$OD) δ ppm 4.50 (s, 2H) 6.65 (dd, J=8.55, 2.20 Hz, 1H) 6.73 (d, J=2.20 Hz, 1H) 7.22-7.26 (m, 2H) 7.44 (br. s., 1H) 7.47-7.52 (m, 1H) 7.77 (d, J=8.55 Hz, 1H). MS (ESI+) m/z 386 [M+H]$^+$.

Intermediate 11

4-{[(4-Bromobenzyl)sulfonyl]amino}-2-hydroxybenzoic acid

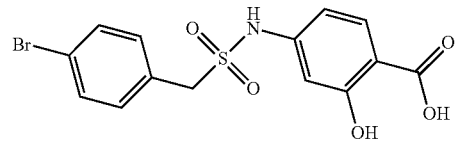 [SMILES: O=C(O)c1ccc(NS(=O)(=O)Cc2ccc(Br)cc2)cc1O]

The product was prepared from methyl 4-aminosalicylate (67 mg, 0.400 mmol) and 4-bromobenzylsulfonyl chloride (108 mg, 0.400 mmol) according to the General Procedure 3, described in Intermediate 10. The title compound was obtained as a white solid (69 mg, 51%). $^1$H NMR (500 MHz, CD$_3$OD) δ 4.47 (s, 2H) 6.64 (dd, J=8.79, 2.20 Hz, 1H) 6.72

(d, J=2.20 Hz, 1H) 7.15-7.22 (m, 2H) 7.45-7.53 (m, 2H) 7.77 (d, J=8.55 Hz, 1H). MS (ESI+) m/z 386 [M+H].

Intermediate 12

4-{[(3-Bromophenyl)sulfonyl]amino}-2-hydroxybenzoic acid

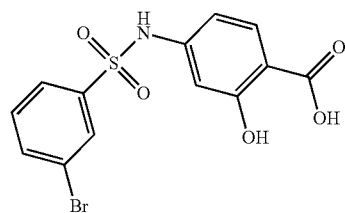 [SMILES: O=C(O)c1ccc(NS(=O)(=O)c2cccc(Br)c2)cc1O]

The product was prepared from 4-aminosalicylic acid (0.57 g, 3.7 mmol) and 3-bromobenzenesulfonyl chloride (0.87 g, 3.4 mmol) according to the General Procedure 2, described in Intermediate 9, using a modified reaction time (room temperature overnight). The title compound was obtained as a light brown solid (0.41 g, 32%). $^1$H NMR (500 MHz, DMSO-$d_6$) δ ppm 6.64 (d, J=2.20 Hz, 1H) 6.69 (dd, J=8.67, 2.08 Hz, 1H) 7.56 (t, J=8.06 Hz, 1H) 7.66 (d, J=8.55 Hz, 1H) 7.81-7.84 (m, 1H) 7.86-7.91 (m, 1H) 7.96 (t, J=1.71 Hz, 1H) 10.94 (s, 1H) 11.36 (br. s., 1H). MS (ESI+) m/z 372 [M+H]$^+$.

Intermediate 13

3-(2-Chloro-5-{[3-hydroxy-4-(methoxycarbonyl)phenyl]sulfamoyl}thiophen-3-yl)benzoic acid

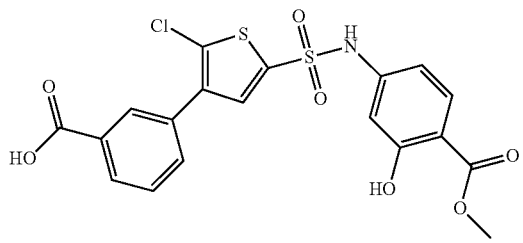 [SMILES: COC(=O)c1ccc(NS(=O)(=O)c2cc(-c3cccc(C(=O)O)c3)c(Cl)s2)cc1O]

A reaction mixture containing methyl 4-{[(4-bromo-5-chloro-2-thienyl)sulfonyl]amino}-2-hydroxybenzoate (Intermediate 3) (128 mg, 0.30 mmol), 3-carboxyphenylboronic acid (50 mg, 0.30 mmol), DIPEA (155 mg, 1.2 mmol) and Pd(dppf)Cl$_2$.CH$_2$Cl$_2$ (3 mg, 0.003 mmol) in aqueous dioxane (4 mL dioxane, 0.4 mL water) was heated at 80° C. under N$_2$ atmosphere overnight. EtOAc (5 mL) and 0.5 M Na$_2$CO$_3$ (5 mL) were added to the reaction mixture. The aqueous phase was washed with EtOAc (2×5 mL) and then acidified to pH 3 by addition of conc. H$_3$PO$_4$. EtOAc (5 mL) was added. The organic phase was washed with 1 M H$_3$PO$_4$ (2×5 mL) and brine, and then dried with MgSO$_4$, filtered and concentrated giving the title compound in 80% purity (85 mg). An analytical sample of the crude product (14 mg) was purified by preparative HPLC (acidic system) to give the title compound in 100% purity (5.3 mg, 38%). $^1$H NMR (600 MHz, CD$_3$OD) δ ppm 3.91 (s, 3H) 6.76 (dd, J=8.70, 2.20 Hz, 1H) 6.82 (dd, J=2.20, 0.30 Hz, 1H) 7.57 (td, J=7.78, 0.50 Hz, 1H) 7.68 (s, 1H) 7.73 (ddd, J=7.78, 1.88, 1.18 Hz, 1H) 7.79 (dd, J=8.70, 0.30 Hz, 1H) 8.06 (ddd, J=7.78, 1.65, 1.18 Hz, 1H) 8.14 (ddd, J=1.88, 1.65, 0.50 Hz, 1H). MS (ESI+) m/z 468 [M+H]$^+$.

Intermediate 14

Methyl 4-[(tert-butoxycarbonyl)amino]-2-hydroxybenzoate

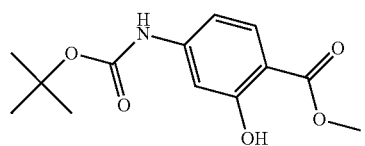 [SMILES: COC(=O)c1ccc(NC(=O)OC(C)(C)C)cc1O]

Methyl 4-amino-2-hydroxybenzenecarboxylate (3.0 g, 17.9 mmol) and BOC-anhydride (3.9 g, 17.9 mmol) were mixed neat and stirred at 70° C. for 2 days. The reaction was diluted with toluene and washed with water, 1 M H$_2$SO$_4$ and brine. The organic phase was dried over MgSO$_4$, filtered and concentrated. The brown oily residue was recrystallized from heptane/toluene. The title compound was obtained in 45% yield (2.13 g). $^1$H NMR (600 MHz, CD$_3$OD) δ ppm 1.52 (s, 9H) 3.90 (s, 3H) 6.90 (dd, J=8.79, 2.20 Hz, 1H) 7.14 (d, J=2.20 Hz, 1H) 7.70 (d, J=8.79 Hz, 1H). MS (ESI+) m/z 268 [M+H]$^+$.

Intermediate 15

3-({[3-Hydroxy-4-(methoxycarbonyl)phenyl]amino}sulfonyl)benzoic acid

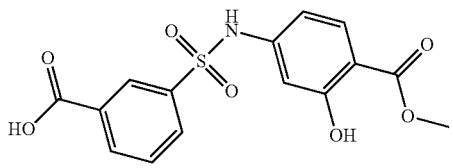 [SMILES: COC(=O)c1ccc(NS(=O)(=O)c2cccc(C(=O)O)c2)cc1O]

A mixture of 3-(chlorosulfonyl)benzoic acid (0.50 g, 2.3 mmol) and methyl 4-amino-salicylate (0.38 g, 2.3 mmol) was stirred at 60° C. for 3 days. The reaction was concentrated under reduced pressure. EtOAc and 0.5 M Na$_2$CO$_3$ were added. The aqueous phase was washed with EtOAc and then acidified with 1 M H$_3$PO$_4$ until pH ~3. EtOAc (100 mL) was added. The organic phase was washed with 1 M H$_3$PO$_4$ and brine, dried over MgSO$_4$, filtered and concentrated to a light brown oil. The product was purified by flash chromatography (silica, 50% hexane in EtOAc+1% acetic acid). The title compound was obtained in 22% yield (180 mg). $^1$H NMR (600 MHz, CD$_3$OD) δ ppm 3.88 (s, 3H) 6.68 (dd, J=8.70, 2.23 Hz, 1H) 6.71 (dd, J=2.23, 0.31 Hz, 1H) 7.64 (td, J=7.86, 0.55 Hz, 1H) 7.69 (dd, J=8.70, 0.31 Hz, 1H) 8.05 (ddd, J=7.86, 1.96, 1.15 Hz, 1H) 8.21 (ddd, J=7.86, 1.67, 1.15 Hz, 1H) 8.48 (ddd, J=1.96, 1.67, 0.55 Hz, 1H) MS (ESI+) m/z 352 [M+H]$^+$.

Intermediate 16

4-{[(5'-Fluoro-2'-hydroxybiphenyl-3-yl)sulfonyl]amino}-2-hydroxybenzoic acid

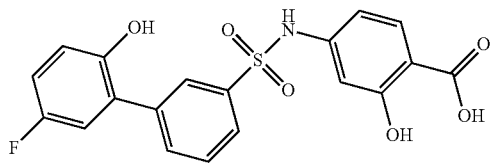 [SMILES: O=C(O)c1ccc(NS(=O)(=O)c2cccc(-c3cc(F)ccc3O)c2)cc1O]

A mixture of methyl 4-{[(3-bromophenyl)sulfonyl]amino}-2-hydroxybenzoate (Intermediate 4) (1.05 g, 2.7 mmol), 5-fluoro-2-hydroxyphenylboronic acid (0.47 g, 3.0 mmol), DIPEA (1.05 g, 8.1 mmol) and Pd(dppf)Cl$_2$·CH$_2$Cl$_2$ (44 mg, 54 µmol) in aqueous dioxane (30 mL dioxane, 5 mL water) was heated at 80° C. under N$_2$ atmosphere overnight. Water and EtOAc were added. The organic phase was washed with 1 M HCl and brine, dried over MgSO$_4$, filtered and concentrated. To the residue was added 1 M NaOH (20 mL). The reaction was stirred at room temperature for 3 h. A spoonful of charcoal was added. The mixture was stirred for 1 h and filtered through a pad of celite. The mother liquid was washed twice with CH$_2$Cl$_2$ and acidified with conc. H$_3$PO$_4$. EtOAc was added. The organic phase was washed with 1 M HCl and brine, dried over MgSO$_4$, filtered and concentrated. The residue was recrystallized from water/MeOH. The title compound was obtained as a white solid (0.77 g, 70%). $^1$H NMR (600 MHz, CD$_3$OD) δ ppm 6.68 (dd, J=8.85, 2.14 Hz, 1H) 6.72 (d, J=1.83 Hz, 1H) 6.86-6.90 (m, 1H) 6.92-6.99 (m, 2H) 7.56 (t, J=7.78 Hz, 1H) 7.70 (d, J=8.54 Hz, 1H) 7.78-7.82 (m, 2H) 7.81 (d, J=1.83 Hz, 1H) 8.11 (t, J=1.68 Hz, 1H). MS (ESI+) m/z 404 [M+H]$^+$.

Intermediate 17

4-({[4-(1,3-Benzodioxol-5-yl)-5-chloro-2-thienyl]sulfonyl}amino)-2-hydroxybenzoic acid

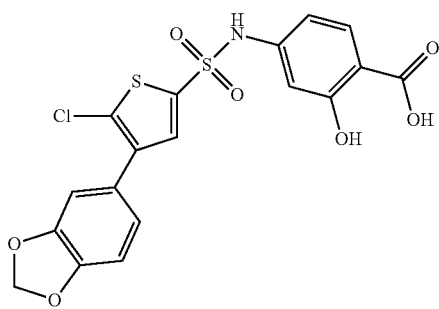 [SMILES: O=C(O)c1ccc(NS(=O)(=O)c2cc(-c3ccc4c(c3)OCO4)c(Cl)s2)cc1O]

A mixture of methyl 4-({[4-(1,3-benzodioxol-5-yl)-5-chloro-2-thienyl]sulfonyl}amino)-2-hydroxybenzoate (Example 158) (62 mg, 0.13 mmol) in 2 ml of 1 M NaOH was stirred at 60° C. for 6 h. Water and Et$_2$O was added. The aqueous phase was separated and acidified with conc. H$_3$PO$_4$. EtOAc was added. The organic phase was washed with 1 M H$_3$PO$_4$ and brine, dried over MgSO$_4$, filtered and concentrated. The title compound was obtained in 85% yield (52 mg). $^1$H NMR (600 MHz, CD$_3$OD) δ ppm 5.99 (s, 2H) 6.72 (dd, J=8.54, 2.14 Hz, 1H) 6.78 (d, J=2.14 Hz, 1H) 6.89 (d, J=8.24 Hz, 1H) 6.93-6.97 (m, 1H) 6.98 (d, J=1.53 Hz, 1H) 7.56 (s, 1H) 7.78 (d, J=8.54 Hz, 1H). MS (ESI+) m/z 454 [M+H]$^+$.

Intermediate 18

2-Hydroxy-4-{[(2,4,5-trichloro-3-thienyl)sulfonyl]amino}benzoic acid

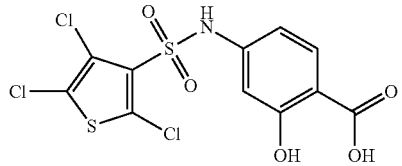 [SMILES: O=C(O)c1ccc(NS(=O)(=O)c2c(Cl)sc(Cl)c2Cl)cc1O]

Chlorosulfonic acid (285 µL, 4.3 mmol) was added to a solution of 2,3,5-trichlorothiophene (0.72 g, 3.8 mmol) in CH$_2$Cl$_2$. After 1 h of stirring at room temperature additional chlorosulfonic acid (1000 µL, 15.2 mmol) was added to the reaction mixture, which was then heated at reflux for 3 h followed by stirring at room temperature overnight. The reaction was quenched by slow addition of brine. The product was extracted with CH$_2$Cl$_2$. The organic phase was dried over MgSO$_4$. Removal of the solvents gave the 2,4,5-trichlorothiophene-3-sulfonyl chloride as a brown oil, which was used in the following step without further purification (0.90 g, 83% yield).

A mixture of methyl 4-aminosalicylate (263 mg, 1.57 mmol), the preformed 2,4,5-trichlorothiophene-3-sulfonyl chloride (450 mg, 1.57 mmol) and pyridine (0.25 g, 3.1 mmol) in MeCN (7 mL) was heated at 60° C. for 3 days. The solvent was evaporated, and the crude product was partitioned between water and CH$_2$Cl$_2$. The organic phase was washed with brine, dried (MgSO$_4$) and evaporated to yield a dark red sticky oil. The crude oil was dissolved in toluene and washed with 1 M HCl followed by brine. Evaporation gave crude oily crystals which were recrystallized from MeOH/water to yield methyl 2-hydroxy-4-{[(2,4,5-trichloro-3-thienyl)sulfonyl]amino}benzoate (257 mg, 39%) as light brown crystals. MS (ESI+) m/z 416 [M+H]$^+$.

Methyl 2-hydroxy-4-{[(2,4,5-trichloro-3-thienyl)sulfonyl]amino}benzoate (0.26 g, 0.62 mmol) was dissolved in 1 M NaOH (4 mL). The reaction was stirred at 60° C. overnight. A few mL of water were added and the reaction mixture was washed with Et$_2$O. The pH was adjusted to approximately 2 by addition of 1 M HCl. The formed precipitate was filtered off and dried. The filtrate was extracted with EtOAc and evaporated. The two lots were pooled to yield the title compound in 85% yield (0.21 g). MS (ESI+) m/z 402 [M+H]$^+$.

Intermediate 19

4-{[(2',5'-Difluorobiphenyl-3-yl)sulfonyl]amino}-2-hydroxybenzoic acid

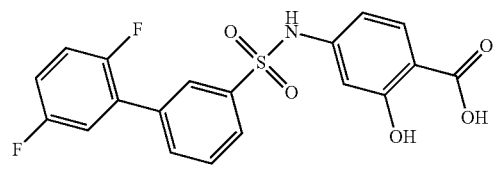 [SMILES: O=C(O)c1ccc(NS(=O)(=O)c2cccc(-c3cc(F)ccc3F)c2)cc1O]

A mixture of methyl 4-{[(3-bromophenyl)sulfonyl] amino}-2-hydroxybenzoate (Intermediate 4) (0.74 g, 2.0 mmol), 2,5-difluorophenylboronic acid (0.34 g, 2.2 mmol), DIPEA (1.1 g, 8.8 mmol) and Pd(dppf)Cl$_2$.CH$_2$Cl$_2$ (66 mg, 81 μmol) in aqueous dioxane (20 mL dioxane, 3 mL water) was heated at 80° C. under N$_2$ atmosphere overnight. Water and EtOAc were added. The organic phase was washed with 1 M H$_3$PO$_4$, sat. NaHCO$_3$ and brine, dried over MgSO$_4$, filtered and concentrated. To the residue was added 1 M NaOH (20 mL). The reaction was stirred at room temperature for 3 h. A spoonful of charcoal was added. The mixture was stirred for 1 h and filtered through a pad of celite. The mother liquid was washed twice with CH$_2$Cl$_2$ and acidified with conc. H$_3$PO$_4$. EtOAc was added. The organic phase was washed with 1 M H$_3$PO$_4$ and brine, dried over MgSO$_4$, filtered and concentrated. The residue was recrystallized from water/MeOH. The title compound was obtained as a white solid (0.54 g, 65%). $^1$H NMR (600 MHz, CD$_3$OD) δ ppm 6.66 (d, J=8.85 Hz, 1H) 6.71 (s, 1H) 7.09-7.30 (m, 3H) 7.64 (t, J=7.78 Hz, 1H) 7.70 (d, J=8.54 Hz, 1H) 7.78 (d, J=7.93 Hz, 1H) 7.89 (d, J=7.93 Hz, 1H) 8.02 (s, 1H). MS (ESI+) m/z 406 [M+H]$^+$.

Intermediate 20

4-({[3-(2,3-Dihydro-1-benzofuran-5-yl)phenyl] sulfonyl}amino)-2-hydroxybenzoic acid

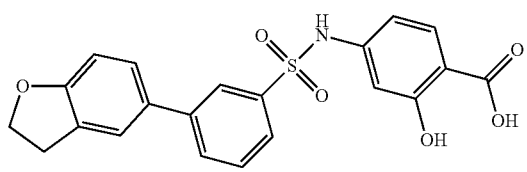 [SMILES: O=C(O)c1ccc(NS(=O)(=O)c2cccc(-c3ccc4c(c3)CCO4)c2)cc1O]

A mixture of methyl 4-{[(3-bromophenyl)sulfonyl] amino}-2-hydroxybenzoate (Intermediate 4) (0.74 g, 2.0 mmol), 2,3-dihydrobenzofuran-5-boronic acid (0.36 g, 2.2 mmol), DIPEA (1.1 g, 8.8 mmol) and Pd(dppf)Cl$_2$.CH$_2$Cl$_2$ (66 mg, 81 μmol) in aqueous dioxane (20 mL dioxane, 3 mL water) was heated at 80° C. under N$_2$ atmosphere overnight. Water and EtOAc were added. The organic phase was washed with 1 M H$_3$PO$_4$, sat. NaHCO$_3$ and brine, dried over MgSO$_4$, filtered and concentrated. To the residue was added 1 M NaOH (20 mL). The reaction was stirred at room temperature for 3 h. A spoonful of charcoal was added. The mixture was stirred for 1 h and filtered through a pad of celite. The mother liquid was washed twice with CH$_2$Cl$_2$ and acidified with conc. H$_3$PO$_4$. EtOAc was added. The organic phase was washed with 1 M H$_3$PO$_4$ and brine, dried over MgSO$_4$, filtered and concentrated. The residue was recrystallized from water/MeOH. The title compound was obtained as a white solid. $^1$H NMR (600 MHz, CD$_3$OD) δ ppm 3.26 (t, J=8.70 Hz, 2H) 4.59 (t, J=8.54 Hz, 2H) 6.66 (d, J=8.54 Hz, 1H) 6.73 (s, 1H) 6.80 (d, J=8.24 Hz, 1H) 7.31 (d, J=8.24 Hz, 1H) 7.39 (s, 1H) 7.54 (t, J=7.93 Hz, 1H) 7.70 (d, J=8.85 Hz, 1H) 7.73-7.80 (m, 2H) 7.95 (s, 1H). MS (ESI+) m/z 412 [M+H]$^+$.

Intermediate 21

4-{[(3,5-Dichlorophenyl)sulfonyl]amino}-2-hydroxybenzoic acid

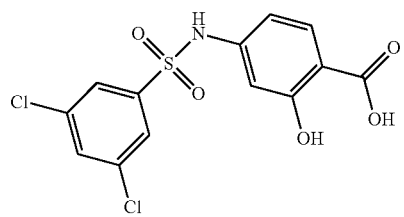 [SMILES: O=C(O)c1ccc(NS(=O)(=O)c2cc(Cl)cc(Cl)c2)cc1O]

A mixture of 3,5-dichlorobenzene-sulfonyl chloride (1.03 g, 4.2 mmol), methyl 4-amino-salicylate (0.65 g, 3.9 mmol) and pyridine (0.58 g, 7.3 mmol) was stirred in 50 mL of MeCN at 80° C. overnight. The solvent was removed under reduced pressure. Toluene and 1 M HCl was added. The organic phase was washed with 1 M HCl, water and brine, dried over MgSO$_4$, filtered and concentrated. The residue was dissolved in 20 mL of 1 M NaOH. The reaction mixture was stirred at 60° C. for 2 h. Water and CH$_2$Cl$_2$ was added. The aqueous phase was washed twice with CH$_2$Cl$_2$. The alkaline solution was acidified with orto-phosphoric acid to pH 2-3 giving lots of white precipitate. The precipitate was collected and washed with water. The title compound was obtained as a white solid (1.11 g, 78%). $^1$H NMR (600 MHz, CD$_3$OD) δ ppm 6.66 (dd, J=8.54, 2.14 Hz, 1H) 6.69 (d, J=2.14 Hz, 1H) 7.72 (t, J=1.83 Hz, 1H) 7.74 (d, J=8.54 Hz, 1H) 7.77 (d, J=1.83 Hz, 2H). MS (ESI+) m/z 362 [M+H]$^+$.

Intermediate 22

4-{[(4-Bromo-2,5-dichlorothiophen-3-yl)sulfonyl] amino}-2-hydroxybenzoic acid

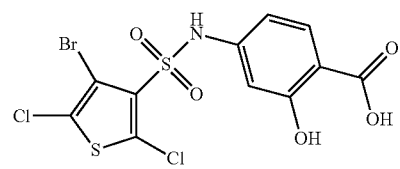 [SMILES: O=C(O)c1ccc(NS(=O)(=O)c2c(Cl)sc(Cl)c2Br)cc1O]

A mixture of 4-aminosalicylic acid (0.15 g, 1.0 mmol) and 4-bromo-2,5-dichlorothiophene-3-sulfonyl chloride (0.33 g, 1.0 mmol) in aqueous dioxane (19 mL dioxane, 1 mL water) was stirred at room temperature for 3 weeks. Water (100 mL) and EtOAc (100 mL) were added and the pH was adjusted to about 10 by addition of 1 M Na$_2$CO$_3$. The aqueous phase was washed with EtOAc (2×100 mL) and then the pH was adjusted to about 2 by addition of concentrated phosphoric acid. EtOAc (100 mL) was added and the organic phase was washed with 1 M HCl (2×50 mL) and brine, and then dried over MgSO$_4$, filtered and concentrated. The residue was crystallized from water/MeOH. The precipitate was collected by filtration and dried in vacuum giving the title compound as a light brown solid (60 mg, 13%). $^1$H NMR (500 MHz, CD$_3$OD) δ ppm 6.55-6.76 (m, 2H) 7.74 (d, J=8.55 Hz, 1H). MS (ESI+) m/z 446 [M+H]$^+$.

Intermediate 23

Methyl 4-{[(5-bromo-4-chloro-2-thienyl)sulfonyl]amino}-2-hydroxybenzoate

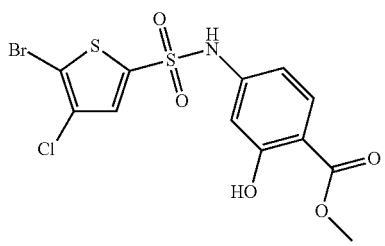 [SMILES: COC(=O)c1ccc(NS(=O)(=O)c2cc(Cl)c(Br)s2)cc1O]

Chlorosulfonic acid (0.65 g, 5.6 mmol) in CH₂Cl₂ (10 mL) was added to a cooled solution of 2-bromo-3-chlorothiophene (1.00 g, 5.1 mmol) in CH₂.Cl₂ (100 mL). After 20 minutes of stirring, additional chlorosulfonic acid (2.3 g, 20 mmol) was added to the reaction mixture, which was then heated at reflux overnight. The reaction was quenched by slow addition of water. The organic phase was washed with water and brine, dried over MgSO₄, filtered and concentrated. The intermediate 5-bromo-4-chlorothiophene-2-sulfonyl chloride was obtained as a light green solid which was used in the following step without further purification (1.2 g, 80%). ¹H NMR (600 MHz, CDCl₃) δ ppm 7.68 (s, 1H).

A reaction mixture with methyl 4-amino-salicylate (0.46 g, 2.8 mmol), 5-bromo-4-chlorothiophene-2-sulfonyl chloride (0.68 g, 2.3 mmol) and pyridine (0.36 g, 4.6 mmol) in MeCN (50 mL) was heated at 60° C. for 5 days. EtOAc and water was added. The organic phase was washed with 1 M H₃PO₄ and brine, dried over MgSO₄, filtered and concentrated. The residue was recrystallized from water/MeCN. The title compound was obtained in 61% yield (0.60 g). ¹H NMR (600 MHz, CDCl₃) δ ppm 3.95 (s, 3H) 6.69 (dd, J=8.70, 2.29 Hz, 1H) 6.74 (d, J=2.14 Hz, 1H) 6.83 (br. s., 1H) 7.41 (s, 1H) 7.80 (d, J=8.54 Hz, 1H) 10.93 (s, 1H). MS (ESI+) m/z 426 [M+H]⁺.

Intermediate 24

4-({[5-Chloro-4-(5-fluoro-2-hydroxyphenyl)-2-thienyl]sulfonyl}amino)-2-hydroxybenzoic acid

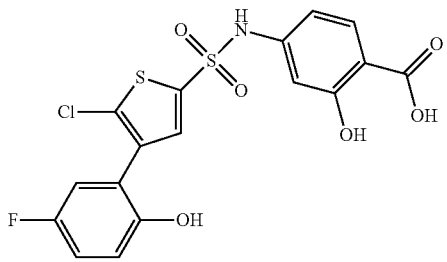 [SMILES: O=C(O)c1ccc(NS(=O)(=O)c2cc(-c3cc(F)ccc3O)c(Cl)s2)cc1O]

A reaction mixture containing methyl 4-({[5-chloro-4-(5-fluoro-2-hydroxyphenyl)-2-thienyl]sulfonyl}amino)-2-hydroxybenzoate (Example 157) (3.2 g, 7.1 mmol) in 30 mL of 1 M NaOH was stirred at room temperature for 3 days. Conc. H₃PO₄ was added until acidic followed by EtOAc.

The organic phase was washed with 1 M H₃PO₄ and brine, dried over MgSO₄, filtered and concentrated. The residue was recrystallized from water/MeOH. The title compound was obtained in 79% yield (2.5 g). ¹H NMR (600 MHz, CD₃OD) δ ppm 6.72 (dd, J=8.85, 2.14 Hz, 1H) 6.78 (d, J=2.14 Hz, 1H) 6.87 (dd, J=9.00, 4.73 Hz, 1H) 6.94-6.99 (m, 1H) 7.01 (dd, J=9.15, 3.05 Hz, 1H) 7.64 (s, 1H) 7.77 (d, J=8.54 Hz, 1H). MS (ESI+) m/z 444 [M+H]⁺.

Intermediate 25

3-Bromopropyl 4-{[(5'-fluoro-2'-hydroxybiphenyl-3-yl)sulfonyl]amino}-2-hydroxybenzoate

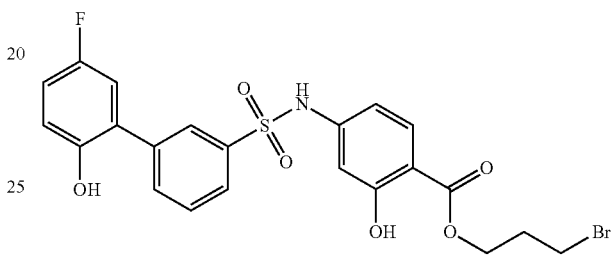

A mixture of 4-{[(5'-fluoro-2'-hydroxybiphenyl-3-yl)sulfonyl]amino}-2-hydroxybenzoic acid (Intermediate 16) (60 mg, 0.15 mmol), conc. H₂SO₄ (15 μL) and 3-bromopropan-1-ol (0.60 mL) was heated at 85° C. overnight. The reaction mixture was diluted with MeCN and purified by preparative HPLC (acidic system). The title compound was obtained in 62% yield (48 mg). MS (ESI+) m/z 524 [M+H]⁺.

Intermediate 26

3-Bromopropyl 4-({[5-chloro-4-(5-fluoro-2-hydroxyphenyl)-2-thienyl]sulfonyl}amino)-2-hydroxybenzoate

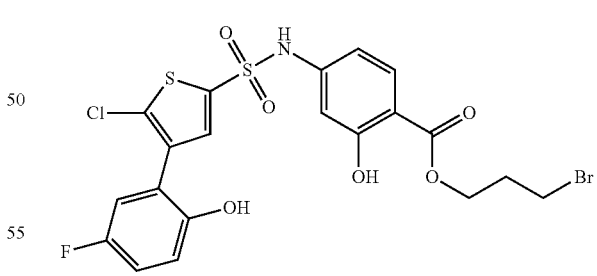

A mixture of 4-({[5-chloro-4-(5-fluoro-2-hydroxyphenyl)-2-thienyl]sulfonyl}amino)-2-hydroxybenzoic acid (Intermediate 24) (42 mg, 0.095 mmol), conc. H₂SO₄ (20 μL) and 3-bromopropan-ol (0.40 mL) was heated at 85° C. overnight. The reaction mixture was diluted with MeCN and purified by preparative HPLC (acidic system). The title product was obtained in 60% yield (32 mg). MS (ESI+) m/z 564 [M+H]⁺.

Intermediate 27

4-{[(5-Chloro-4-phenyl-2-thienyl)sulfonyl]amino}-2-hydroxybenzoic acid

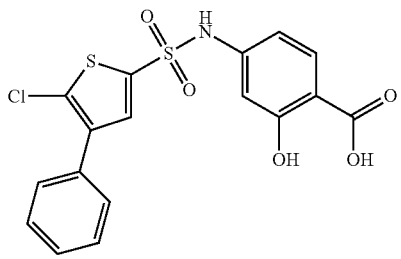 [SMILES: O=C(O)c1ccc(NS(=O)(=O)c2cc(-c3ccccc3)c(Cl)s2)cc1O]

A mixture of 4-{[(4-bromo-5-chlorothiophen-2-yl)sulfonyl]amino}-2-hydroxybenzoic acid (Intermediate 1) (0.70 g, 1.7 mmol), phenylboronic acid (0.31 g, 2.5 mmol), sodium carbonate (0.5 M (aq), 0.90 g) and Pd(dppf)Cl$_2$.CH$_2$Cl$_2$ (0.11 g, 0.14 mmol) in aqueous dioxane (35 mL dioxane, 3.5 ml water) was stirred at 80° C. overnight. The reaction mixture was concentrated. The residue was slurried in water and filtered. Conc. HCl was added to the filtrate until acidic. The precipitate was collected by filtration. The crude product was purified by preparative HPLC (acidic system). The title compound was obtained in 16% yield (0.11 g). $^1$H NMR (600 MHz, CD$_3$OD) δ ppm 6.73 (dd, J=8.54, 2.14 Hz, 1H) 6.79 (d, J=2.14 Hz, 1H) 7.37-7.41 (m, 1H) 7.42-7.46 (m, 2H) 7.47-7.50 (m, 2H) 7.61 (s, 1H) 7.78 (d, J=8.85 Hz, 1H). MS (ESI+) m/z 410 [M+H]$^+$.

Intermediate 28

4-({[5-Chloro-4-(3-fluorophenyl)-2-thienyl]sulfonyl}amino)-2-hydroxybenzoic acid

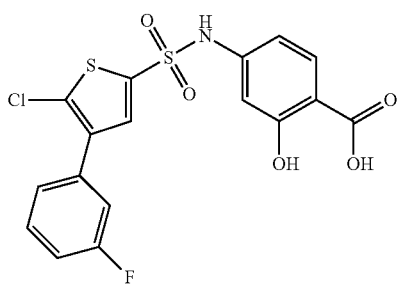 [SMILES: O=C(O)c1ccc(NS(=O)(=O)c2cc(-c3cccc(F)c3)c(Cl)s2)cc1O]

A mixture of 4-{[(4-bromo-5-chlorothiophen-2-yl)sulfonyl]amino}-2-hydroxybenzoic acid (Intermediate 1) (0.50 g, 1.2 mmol), 3-fluorophenylboronic acid (0.24 g, 1.7 mmol), sodium carbonate (0.5 M (aq), 0.64 g) and Pd(dppf)Cl$_2$.CH$_2$Cl$_2$ (0.079 g, 0.097 mmol) in aqueous dioxane (25 mL dioxane, 3 ml water) was stirred at 80° C. overnight. Conc. HCl was added until acidic. The reaction mixture was concentrated, redissolved in MeOH and filtered. The crude product was purified by preparative HPLC (acidic system). The title compound was obtained in 32% yield (0.17 g). $^1$H NMR (600 MHz, CD$_3$OD) δ ppm 6.73 (dd, J=8.54, 2.14 Hz, 1H) 6.79 (d, J=2.14 Hz, 1H) 7.15 (td, J=8.32, 1.98 Hz, 1H) 7.28 (dt, J=9.84, 2.10 Hz, 1H) 7.31 (d, J=7.93 Hz, 1H) 7.47 (td, J=8.09, 6.10 Hz, 1H) 7.64 (s, 1H) 7.78 (d, J=8.54 Hz, 1H). MS (ESI+) m/z 428 [M+H]$^+$.

Intermediate 29

4-({[5-Chloro-4-(2-fluoro-3-methoxyphenyl)-2-thienyl]sulfonyl}amino)-2-hydroxybenzoic acid

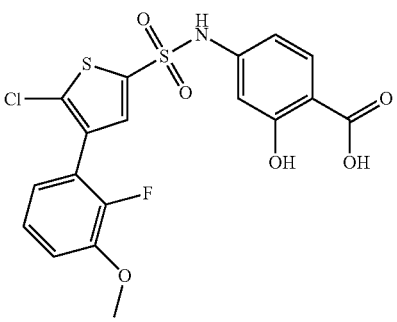 [SMILES: COc1cccc(-c2cc(S(=O)(=O)Nc3ccc(C(=O)O)c(O)c3)sc2Cl)c1F]

A mixture of 4-{[(4-bromo-5-chlorothiophen-2-yl)sulfonyl]amino}-2-hydroxybenzoic acid (Intermediate 1) (0.70 g, 1.7 mmol), 2-fluoro-3-methoxyphenylboronic acid (0.35 g, 2.1 mmol), sodium carbonate (0.5 M (aq), 0.90 g) and Pd(dppf)Cl$_2$.CH$_2$Cl$_2$ (0.11 g, 0.14 mmol) in aqueous dioxane (35 mL dioxane, 3.5 ml water) was stirred at 80° C. overnight. Water (50 mL) was added and the reaction mixture was filtered. The filtrate was acidified with conc. HCl. The precipitate was collected by filtration and washed with water. The solid was dissolved in MeOH and filtered through a plug of silica with 10% MeOH (aq) as eluent. The most pure fractions were evaporated and the residue filtered through a plug of silica using 5% MeOH in CH$_2$Cl$_2$ as eluent. The most pure fractions were evaporated and the residue recrystallized from CH$_2$Cl$_2$. The title compound was obtained in 29% yield (0.23 g). $^1$H NMR (600 MHz, CD$_3$OD) δ ppm 3.89 (s, 3H) 6.71 (dd, J=8.55, 2.14 Hz, 1H) 6.77 (d, J=2.14 Hz, 1H) 6.89-6.93 (m, 1H) 7.12-7.19 (m, 2H) 7.53 (d, J=1.22 Hz, 1H) 7.77 (d, J=8.54 Hz, 1H). MS (ESI+) m/z 458 [M+H]$^+$.

Example 1

Methyl 4-({[5-chloro-4-(3-fluoro-4-hydroxyphenyl)-2-thienyl]sulfonyl}amino)-2-hydroxybenzoate

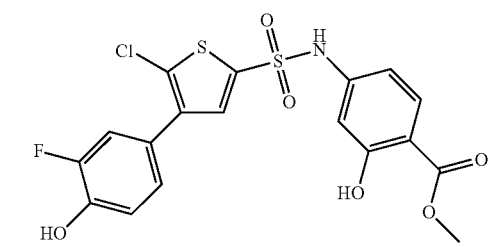 [SMILES: COC(=O)c1ccc(NS(=O)(=O)c2cc(-c3ccc(O)c(F)c3)c(Cl)s2)cc1O]

A solution of 4-{[(4-bromo-5-chlorothiophen-2-yl)sulfonyl]amino}-2-hydroxybenzoic acid (Intermediate 1) (40 mg, 0.097 mmol) in dioxane (2 mL) was added to a mixture of (3-fluoro-4-hydroxyphenyl)boronic acid (24 mg, 0.15 mmol), K$_2$CO$_3$ (40 mg, 0.29 mmol) and Pd(dppf)Cl$_2$·CH$_2$Cl$_2$ (8 mg, 0.0097 mmol). Water (0.5 mL) was added and the reaction mixture was heated for 900 s at 145° C. in a microwave reactor. The reaction mixture was diluted with EtOAc. The organic phase was washed with 1 M HCl, dried and concentrated to give the crude 4-({[5-chloro-4-(3-fluoro-4-hydroxyphenyl)thiophen-2-yl]sulfonyl}amino)-2-hydroxybenzoic acid.

H$_2$SO$_4$ (500 μL) was added to a solution of the crude 4-({[5-chloro-4-(3-fluoro-4-hydroxyphenyl)thiophen-2-yl]sulfonyl}amino)-2-hydroxybenzoic acid (43 mg, 0.096 mmol) in dry MeOH (20 mL). The mixture was refluxed for 24 h. The reaction mixture was diluted with EtOAc and the organic phase was washed with water, dried and concentrated. The crude product was purified by preparative HPLC (acidic system). The fractions were neutralized with aqueous NH$_4$OAc (sat) before evaporation. The residue was dissolved in EtOAc. The organic solution was washed with diluted HCl to remove the salts, dried and concentrated. The title compound was obtained in 24% yield (10.6 mg). $^1$H NMR (500 MHz, DMSO-d$_6$) δ ppm 3.83 (s, 3H) 6.74-6.81 (m, 2H) 7.03 (dd, J=9.09, 8.42 Hz, 1H) 7.22 (dd, J=8.42, 2.20 Hz, 1H) 7.40 (dd, J=12.27, 2.20 Hz, 1H) 7.71 (d, J=8.54 Hz, 1H) 7.78 (s, 1H) 10.26 (s, 1H) 10.60 (s, 1H) 11.21 (br. s., 1H). MS (ESI+) m/z 458 [M+H]$^+$.

Example 2

Methyl 4-({[5-chloro-4-(2,3-dihydro-1-benzofuran-5-yl)-2-thienyl]sulfonyl}amino)-2-hydroxybenzoate

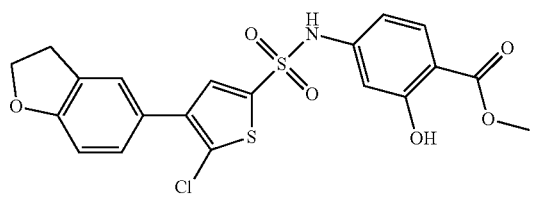 [SMILES: COC(=O)c1ccc(NS(=O)(=O)c2cc(-c3ccc4c(c3)CCO4)c(Cl)s2)cc1O]

H$_2$SO$_4$ (10 μL) was added to a solution of 4-({[5-chloro-4-(2,3-dihydro-1-benzofuran-5-yl)thiophen-2-yl]sulfonyl}amino)-2-hydroxybenzoic acid (Intermediate 2) (9.5 mg, 0.021 mmol) in MeOH (1 mL). The reaction mixture was heated at 60° C. for 2 days. After cooling to room temperature, the mixture was diluted using THF (250 μL) and water (100 μL). The crude product was purified by preparative HPLC (acidic system). The title compound was obtained as a white solid (7.1 mg, 73%). $^1$H NMR (500 MHz, CDCl$_3$) δ ppm 3.26 (t, J=8.79 Hz, 2H) 3.93 (s, 3H) 4.63 (t, J=8.79 Hz, 2H) 6.71 (dd, J=8.67, 2.32 Hz, 1H) 6.76 (d, J=2.20 Hz, 1H) 6.84 (d, J=8.30 Hz, 1H) 6.88 (s, 1H) 7.22 (dd, J=8.30, 1.95 Hz, 1H) 7.29-7.33 (m, 1H) 7.55 (s, 1H) 7.79 (d, J=8.79 Hz, 1H) 10.91 (s, 1H). MS (ESI+) m/z 466 [M+H]$^+$.

Example 3

Methyl 4-{[(4-bromo-2,5-dichloro-3-thienyl)sulfonyl]amino}-2-hydroxybenzoate

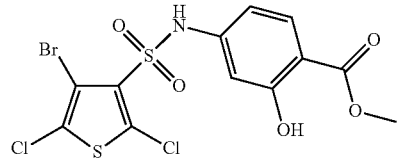

A reaction mixture with methyl 4-amino-salicylate (463 mg, 2.77 mmol), 4-bromo-2,5-dichlorothiophene-3-sulfonyl chloride (913 mg, 2.76 mmol) and pyridine (450 μL, 5.58 mmol) in MeCN (20 mL) was stirred at room temperature for 5 days. After removal of the solvent under reduced pressure, the residue was dissolved in EtOAc. The organic phase was washed with 2 M HCl twice, water twice and brine, and then dried over MgSO$_4$, filtered and concentrated. The crude product was recrystallized from MeOH (45 mL)/water (20 mL) giving the product as a white solid, which was purified further by refluxing in MeOH for 3 h. The white solid was collected, washed with MeOH and then with heptane. The title compound was obtained as a white solid (0.54 g, 42%). $^1$H NMR (500 MHz, DMSO-d$_6$) δ ppm 3.83 (s, 3H) 6.62-6.70 (m, 2H) 7.69 (d, J=8.55 Hz, 1H) 10.63 (s, 1H) 11.60 (br. s., 1H). MS (ESI+) m/z 460 [M+H]$^+$.

Example 4

Methyl 4-{[(4-bromo-5-chloro-2-thienyl)sulfonyl]amino}-2-hydroxybenzoate

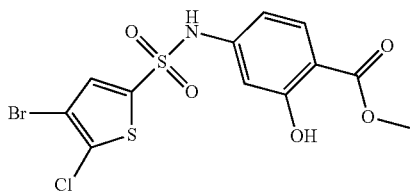

The product was prepared from methyl 4-amino-salicylate (330 mg, 2.0 mmol) and 2-chloro-3-bromothiophene-5-sulfonyl chloride (590 mg, 2.0 mmol) as described for Intermediate 3. The title compound was obtained as a white solid (300 mg, 35%). $^1$H NMR (500 MHz, CDCl$_3$) δ ppm 3.95 (s, 3H) 6.69 (dd, J=8.67, 2.32 Hz, 1H) 6.74 (d, J=2.44 Hz, 1H) 6.91 (br. s., 1H) 7.46 (s, 1H) 7.80 (d, J=8.79 Hz, 1H) 10.93 (s, 1H). MS (ESI+) m/z 426 [M+H]$^+$.

Example 5

Methyl 4-{[(3-bromophenyl)sulfonyl]amino}-2-hydroxybenzoate

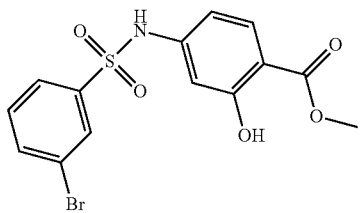 [SMILES: COC(=O)c1ccc(NS(=O)(=O)c2cccc(Br)c2)cc1O]

The product was prepared from methyl 4-amino-salicylate (1.3 g, 7.8 mmol) and 3-bromobenzenesulfonyl chloride (2.0 g, 7.8 mmol) as described for Intermediate 4. The title compound was obtained as a white solid (2.4 g, 79%). $^1$H NMR (500 MHz, CDCl$_3$) δ ppm 3.92 (s, 3H) 6.64 (dd, J=8.55, 2.20 Hz, 1H) 6.68 (d, J=2.20 Hz, 1H) 7.01 (s, 1H) 7.37 (t, J=7.93 Hz, 1H) 7.67-7.72 (m, 1H) 7.74 (d, J=8.79 Hz, 1H) 7.78-7.84 (m, 1H) 8.04 (t, J=1.83 Hz, 1H) 10.87 (s, 1H). MS (ESI+) m/z 386 [M+H]$^+$.

Example 6

Methyl 4-({[3-bromo-5-(trifluoromethyl)phenyl]sulfonyl}amino)-2-hydroxybenzoate

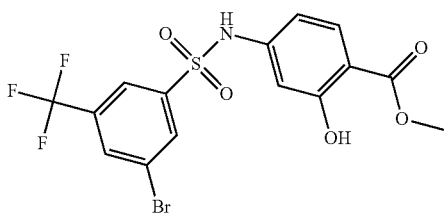 [SMILES: COC(=O)c1ccc(NS(=O)(=O)c2cc(Br)cc(C(F)(F)F)c2)cc1O]

The product was prepared from methyl 4-amino-salicylate (170 mg, 1.0 mmol) and 3-bromo-5-trifluoromethylbenzenesulphonyl chloride (320 mg, 1.0 mmol) as described for Intermediate 5. The title compound was obtained as a white solid (280 mg, 61%). $^1$H NMR (500 MHz, CDCl$_3$) δ ppm 3.93 (s, 3H) 6.63-6.69 (m, 2H) 6.92 (s, 1H) 7.74-7.82 (m, 1H) 7.96 (s, 1H) 8.04 (s, 1H) 8.18 (s, 1H) 10.90 (s, 1H). MS (ESI+) m/z 454 [M+H]$^+$.

Example 7

General Procedure 4

Methyl 4-{[(2-chloro-4-fluorophenyl)sulfonyl]amino}-2-hydroxybenzoate

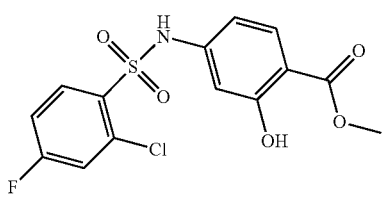 [SMILES: COC(=O)c1ccc(NS(=O)(=O)c2ccc(F)cc2Cl)cc1O]

A mixture of methyl 4-aminosalicylate (8.5 mg, 0.050 mmol), 2-chloro-4-fluorobenzenesulfonyl chloride (11.4 mg, 0.050 mmol) and pyridine (8 µL, 0.100 mmol) in MeCN (400 µL) was heated at 55° C. overnight. The reaction mixture was diluted with MeCN/MeOH/water. TFA (50 µL) was added and the crude product was purified by preparative HPLC (acidic system). The title compound was obtained in 48% yield (8.6 mg). $^1$H NMR (500 MHz, CDCl$_3$) δ ppm 3.89 (s, 3H) 6.61 (dd, J=8.67, 2.32 Hz, 1H) 6.68 (d, J=2.32 Hz, 1H) 7.10 (ddd, J=8.87, 7.45, 2.44 Hz, 1H) 7.20 (br. s., 1H) 7.23 (dd, J=8.06, 2.44 Hz, 1H) 7.69 (d, J=8.67 Hz, 1H) 8.15 (dd, J=8.87, 5.74 Hz, 1H) 10.83 (s, 1H). MS (ESI+) m/z 360 [M+H]$^+$.

Example 8

Methyl 4-{[(3-chloro-4-methylphenyl)sulfonyl]amino}-2-hydroxybenzoate

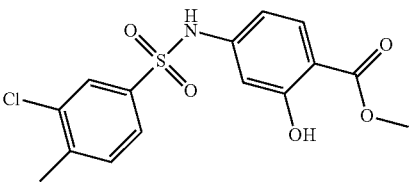 [SMILES: COC(=O)c1ccc(NS(=O)(=O)c2ccc(C)c(Cl)c2)cc1O]

Methyl 4-aminosalicylate (9.1 mg, 0.054 mmol) and 3-chloro-4-methylbenzenesulfonyl chloride (8.4 mg, 0.037 mmol) were allowed to react according to the General Procedure 4, described in Example 7 giving 15.3 mg of the title compound. $^1$H NMR (500 MHz, CDCl$_3$) δ ppm 2.41 (s, 3H) 3.91 (s, 3H) 6.61-6.66 (m, 2H) 6.84 (s, 1H) 7.33 (d, J=8.06 Hz, 1H) 7.64 (dd, J=8.06, 1.95 Hz, 1H) 7.72 (d, J=8.79 Hz, 1H) 7.85 (d, J=1.95 Hz, 1H) 10.85 (s, 1H). MS (ESI+) m/z 356 [M+H]$^+$.

Example 9

Methyl 4-[(1-benzofuran-2-ylsulfonyl)amino]-2-hydroxybenzoate

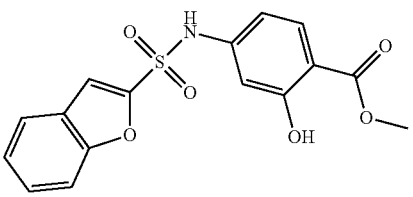 [SMILES: COC(=O)c1ccc(NS(=O)(=O)c2cc3ccccc3o2)cc1O]

The product was prepared from methyl 4-aminosalicylate (9.1 mg, 0.054 mmol) and 1-benzofuran-2-sulfonyl chloride (10.8 mg, 0.050 mmol) according to the General Procedure 4, described in Example 7. The title compound was obtained in 70% yield (12.1 mg). $^1$H NMR (500 MHz, CDCl$_3$) δ ppm 3.89 (s, 3H) 6.69 (dd, J=8.67, 2.32 Hz, 1H) 6.79 (d, J=2.32 Hz, 1H) 7.20 (br. s., 1H) 7.32 (ddd, J=7.90, 7.16, 1.04 Hz, 1H) 7.46 (ddd, J=8.37, 7.16, 1.29 Hz, 1H) 7.51 (s, 1H) 7.51-7.53 (m, 1H) 7.66 (ddd, J=7.90, 1.29, 0.70 Hz, 1H) 7.72 (d, J=8.67 Hz, 1H) 10.85 (s, 1H). MS (ESI+) m/z 348 [M+H]$^+$.

Example 10

Methyl 2-hydroxy-4-({[2-methyl-5-(trifluoromethyl)furan-3-yl]sulfonyl}amino)benzoate

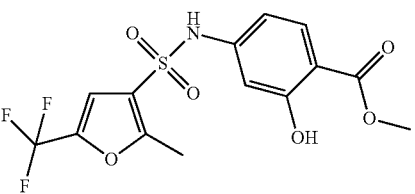 [SMILES: COC(=O)c1ccc(NS(=O)(=O)c2cc(C(F)(F)F)oc2C)cc1O]

The product was prepared from methyl 4-aminosalicylate (9.1 mg, 0.054 mmol) and 2-methyl-5-(trifluoromethyl)-3-furansulfonyl chloride (12.4 mg, 0.054 mmol) according to the General Procedure 4, described in Example 7. The title compound was obtained in 67% yield (12.8 mg). $^1$H NMR (500 MHz, CDCl$_3$) δ ppm 2.59 (s, 3H) 3.93 (s, 3H) 6.62 (dd, J=8.67, 2.20 Hz, 1H) 6.70 (d, J=2.20 Hz, 1H) 6.90-6.92 (m, 1H) 6.95 (br. s., 1H) 7.77 (d, J=8.67 Hz, 1H) 10.90 (s, 1H). MS (ESI+) m/z 380 [M+H]$^+$.

Example 11

Methyl 4-{[(3-chloro-2-methylphenyl)sulfonyl]amino}-2-hydroxybenzoate

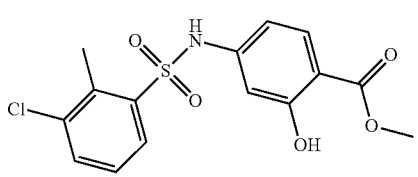 [SMILES: COC(=O)c1ccc(NS(=O)(=O)c2cccc(Cl)c2C)cc1O]

The product was prepared from methyl 4-aminosalicylate (9.1 mg, 0.054 mmol) and 3-chloro-2-methylbenzenesulfonyl chloride (11.8 mg, 0.052 mmol) according to the General Procedure 4, described in Example 7. The title compound was obtained in 70% yield (12.9 mg). $^1$H NMR (500 MHz, CDCl$_3$) δ ppm 2.73 (s, 3H) 3.90 (s, 3H) 6.54 (dd, J=8.67, 2.32 Hz, 1H) 6.60 (d, J=2.20 Hz, 1H) 7.08 (s, 1H) 7.28 (t, J=7.69 Hz, 1H) 7.59 (dd, J=8.06, 0.98 Hz, 1H) 7.70 (d, J=8.79 Hz, 1H) 8.02 (dd, J=8.06, 0.98 Hz, 1H) 10.85 (s, 1H). MS (ESI+) m/z 356 [M+H]$^+$.

Example 12

Methyl 4-{[(5-bromo-2-thienyl)sulfonyl]amino}-2-hydroxybenzoate

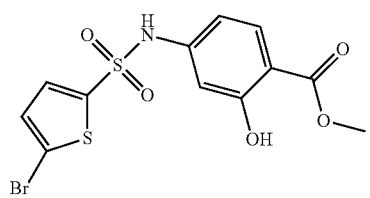 [SMILES: COC(=O)c1ccc(NS(=O)(=O)c2ccc(Br)s2)cc1O]

The product was prepared from methyl 4-aminosalicylate (9.1 mg, 0.054 mmol) and 5-bromothiophene-2-sulfonyl chloride (13.8 mg, 0.053 mmol) according to the General Procedure 4, described in Example 7. The title compound was obtained in 71% yield (14.7 mg). $^1$H NMR (500 MHz, CDCl$_3$) δ ppm 3.93 (s, 3H) 6.68 (dd, J=8.67, 2.32 Hz, 1H) 6.73 (d, J=2.20 Hz, 1H) 6.98 (s, 1H) 7.02 (d, J=4.15 Hz, 1H) 7.40 (d, J=4.15 Hz, 1H) 7.77 (d, J=8.55 Hz, 1H) 10.90 (s, 1H). MS (ESI+) m/z 392 [M+H]$^+$.

Example 13

Methyl 4-{[(5-chloro-2-thienyl)sulfonyl]amino}-2-hydroxybenzoate

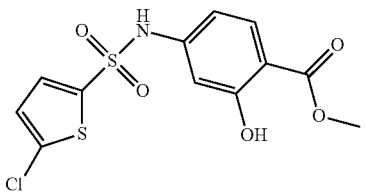 [SMILES: COC(=O)c1ccc(NS(=O)(=O)c2ccc(Cl)s2)cc1O]

The product was prepared from methyl 4-aminosalicylate (9.1 mg, 0.054 mmol) and 5-chlorothiophene-2-sulfonyl chloride (10.9 mg, 0.050 mmol) according to the General Procedure 4, described in Example 7. The title compound was obtained in 76% yield (13.2 mg). $^1$H NMR (500 MHz, CDCl$_3$) δ ppm 3.94 (s, 3H) 6.68 (dd, J=8.55, 2.20 Hz, 1H) 6.73 (d, J=2.20 Hz, 1H) 6.88 (br. S., 1H) 6.89 (d, J=4.15 Hz, 1H) 7.44 (d, J=4.15 Hz, 1H) 7.77 (d, J=8.55 Hz, 1H) 10.90 (s, 1H). MS (ESI+) m/z 348 [M+H]$^+$.

Example 14

Methyl 4-{[(5-bromo-6-chloropyridin-3-yl)sulfonyl]amino}-2-hydroxybenzoate

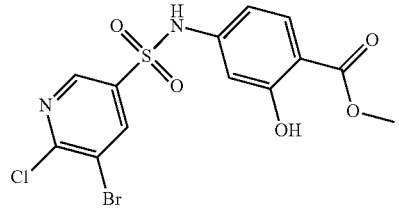 [SMILES: COC(=O)c1ccc(NS(=O)(=O)c2cnc(Cl)c(Br)c2)cc1O]

The product was prepared from methyl 4-aminosalicylate (9.1 mg, 0.054 mmol) and 5-bromo-6-chloropyridine-3-sulfonyl chloride (15.0 mg, 0.051 mmol) according to the General Procedure 4, described in Example 7. The title compound was obtained in 41% yield (8.9 mg). $^1$H NMR (500 MHz, CDCl$_3$) δ ppm 3.75 (s, 3H) 6.59 (dd, J=8.79, 2.20 Hz, 1H) 6.65 (d, J=2.20 Hz, 1H) 7.54 (d, J=8.79 Hz, 1H) 8.22 (d, J=2.20 Hz, 1H) 8.59 (d, J=2.20 Hz, 1H) 10.55 (s, 1H) 10.66 (s, 1H). MS (ESI+) m/z 421 [M+H]$^+$.

Example 15

Methyl 2-hydroxy-4-{[(5-isopropyl-3-methyl-1-benzothien-2-yl)sulfonyl]amino}benzoate The 5-isopropyl-3-methyl-1-benzothiophene-2-sulfonyl chloride was prepared according to the following multistep procedure. A mixture of 4-isopropyl-thiophenol (5.0 g, 32.8 mmol), chloroacetone (7.0 mL, 88 mmol) and $K_2CO_3$ (6.4 g, 46.3 mmol) in acetone (100 mL) was refluxed overnight. More $K_2CO_3$ (2 g, 14.5 mmol) and chloroacetone (3.5 mL, 43 mmol) were added and the reaction mixture was heated for another 5 h. The reaction mixture was filtered and the solvent was evaporated. The crude product was mixed with polyphosphoric acid (15 g) and chlorobenzene (100 mL) and the reaction mixture was heated at reflux for 5 hours (Plé et al., (1988) J. Heterocyclic Chem. 25, 1271-1272). The reaction mixture was diluted with $CH_2Cl_2$ and washed with water. The combined organic phases were dried and the solvent was evaporated. The crude product was purified on silica using heptane as eluent, giving 4.2 g of 5-isopropyl-3-methylbenzothiophene as a colorless oil (67% over two steps). $^1$H NMR (400 MHz, $CDCl_3$) δ ppm 1.37 (d, 6H) 2.47 (d, 3H) 3.02-3.16 (m, 1H) 7.08 (s, 1H) 7.27-7.30 (m, 1H) 7.58 (d, 1H) 7.80 (d, 1H).

A solution of sulfur trioxide (580 mg, 7.24 mmol) in 1,2-dichloroethane (10 mL) was cooled on ice and dioxane (610 μL, 7.15 mmol) in 1,2-dichloroethane (1 mL) was added dropwise. The resulting white mixture was stirred for 30 minutes at 0° C. A solution of 5-isopropyl-3-methylbenzothiophene (420 mg, 2.2 mmol) in 1,2-dichloroethane (4 mL) was added and the resulting dark purple mixture was stirred at room temperature for 1 h. The mixture was poured on ice and extracted with EtOAc. The acid crystallized spontaneously in the organic phase and 265 mg (44%) of 5-isopropyl-3-methylbenzothiophene-2-sulfonic acid was collected. $^1$H NMR (400 MHz, $CD_3OD$) δ ppm 1.32 (d, J=6.90 Hz, 6H) 2.64 (s, 3H) 3.05 (spt, J=6.90 Hz, 1H) 7.32 (ddd, J=8.34, 1.70, 0.44 Hz, 1H) 7.61 (dt, J=1.70, 0.70 Hz, 1H) 7.72 (dd, J=8.34, 0.70 Hz, 1H).

A mixture of 5-isopropyl-3-methylbenzothiophene-2-sulfonic acid (2.54 g, 9.4 mmol), $POCl_3$ (10 mL) and $PCl_5$ (4.0 g, 19.2 mmol) in $CH_2Cl_2$ (100 mL) was stirred at room temperature for 2 h. The reaction was quenched by addition of ice and water and stirred for 1 h. The organic phase was separated and dried. 1.74 g sulfonyl chloride was obtained as an oil after evaporation of the solvents. The crude product was purified on silica using $CH_2Cl_2$ as eluent giving 1.46 g (54%) of 5-isopropyl-3-methyl-1-benzothiophene-2-sulfonyl chloride.

The title compound was prepared from methyl 4-aminosalicylate (9.1 mg, 0.054 mmol) and 5-isopropyl-3-methyl-1-benzothiophene-2-sulfonyl chloride (15.4 mg, 0.053 mmol) according to the General Procedure 4, described in Example 7. The title compound was obtained in 70% yield (15.5 mg). $^1$H NMR (500 MHz, $CDCl_3$) δ ppm 1.30 (d, J=6.84 Hz, 6H) 2.64 (s, 3H) 3.03 (spt, J=6.84 Hz, 1H) 3.88 (s, 3H) 6.70 (dd, J=8.55, 2.20 Hz, 1H) 6.72 (dd, J=2.20, 0.46 Hz, 1H) 7.15 (s, 1H) 7.38 (dd, J=8.42, 1.73 Hz, 1H) 7.58 (dt, J=1.73, 0.65 Hz, 1H) 7.70 (dd, J=8.55, 0.46 Hz, 1H) 7.71 (dd, J=8.42, 0.65 Hz, 1H) 10.82 (s, 1H). MS (ESI+) m/z 420 $[M+H]^+$.

Example 16

Methyl 2-hydroxy-4-({[4-(trifluoromethyl)phenyl]sulfonyl}amino)benzoate

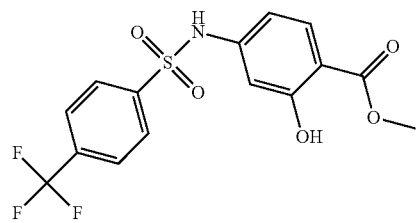 [SMILES: COC(=O)c1ccc(NS(=O)(=O)c2ccc(C(F)(F)F)cc2)cc1O]

The product was prepared from methyl 4-aminosalicylate (9.1 mg, 0.054 mmol) and 4-trifluoromethylbenzenesulfonyl chloride (12.5 mg, 0.051 mmol) according to the General Procedure 4, described in Example 7. The title compound was obtained in 65% yield (12.5 mg). $^1$H NMR (500 MHz, $CDCl_3$) δ ppm 3.91 (s, 3H) 6.62 (dd, J=8.67, 2.32 Hz, 1H) 6.69 (d, J=2.20 Hz, 1H) 6.98 (s, 1H) 7.72 (d, J=8.55 Hz, 1H) 7.75 (m, 2H) 8.00 (m, 2H) 10.87 (s, 1H). MS (ESI+) m/z 376 $[M+H]^+$.

Example 17

Methyl 4-{[(3-chloro-2-fluorophenyl)sulfonyl]amino}-2-hydroxybenzoate

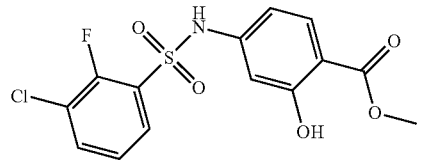

The product was prepared from methyl 4-aminosalicylate (9.1 mg, 0.054 mmol) and 3-chloro-2-fluorobenzenesulfonyl chloride (11.5 mg, 0.050 mmol) according to the General Procedure 4, described in Example 7. The title compound was obtained in 72% yield (13.0 mg). $^1$H NMR (500 MHz, $CDCl_3$) δ ppm 3.60 (s, 3H) 6.43 (dd, J=8.67, 2.08 Hz, 1H) 6.48 (d, J=2.20 Hz, 1H) 6.98 (td, J=8.06, 0.98 Hz, 1H) 7.35 (ddd, J=8.12, 6.53, 1.71 Hz, 1H) 7.36 (d, J=8.79 Hz, 1H) 7.59 (ddd, J=7.87, 6.29, 1.71 Hz, 1H) 10.48 (s, 1H) 10.69 (s, 1H). MS (ESI+) m/z 360 $[M+H]^+$.

Example 18

Methyl 4-{[(3-chlorophenyl)sulfonyl]amino}-2-hydroxybenzoate

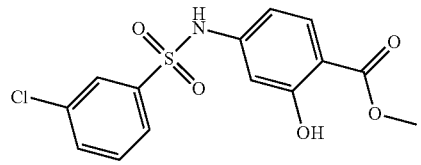 [SMILES: COC(=O)c1ccc(NS(=O)(=O)c2cccc(Cl)c2)cc1O]

The product was prepared from methyl 4-aminosalicylate (9.1 mg, 0.054 mmol) and 3-chlorobenzenesulfonyl chloride (11.7 mg, 0.055 mmol) according to the General Procedure 4, described in Example 7. The title compound was obtained in 75% yield (13.8 mg). $^1$H NMR (500 MHz, CDCl$_3$) δ ppm 3.91 (s, 3H) 6.63 (d, J=8.55, 2.20 Hz, 1H) 6.66 (d, J=2.20 Hz, 1H) 6.86 (s, 1H) 7.42 (t, J=7.93 Hz, 1H) 7.54 (ddd, J=8.06, 2.20, 0.98 Hz, 1H) 7.73 (d, J=8.55 Hz, 1H) 7.74 (ddd, J=7.90, 1.71, 0.98 Hz, 1H) 7.86 (t, J=1.95 Hz, 1H) 10.86 (s, 1H). MS (ESI+) m/z 342 [M+H]$^+$.

Example 19

Methyl 4-{[(2,5-dichlorophenyl)sulfonyl]amino}-2-hydroxybenzoate

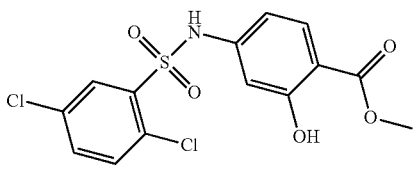 [SMILES: COC(=O)c1ccc(NS(=O)(=O)c2cc(Cl)ccc2Cl)cc1O]

The product was prepared from methyl 4-aminosalicylate (9.1 mg, 0.054 mmol) and 2,5-dichlorobenzenesulfonyl chloride (12.7 mg, 0.052 mmol) according to the General Procedure 4, described in Example 7. The title compound was obtained in 31% yield (6.0 mg). $^1$H NMR (500 MHz, CDCl$_3$) δ ppm 3.73 (s, 3H) 6.56 (dd, J=8.55, 2.20 Hz, 1H) 6.61 (d, J=2.20 Hz, 1H) 7.25 (d, J=8.55 Hz, 1H) 7.30 (dd, J=8.55, 2.44 Hz, 1H) 7.50 (d, J=8.79 Hz, 1H) 7.98 (d, J=2.44 Hz, 1H) 10.51 (s, 1H) 10.63 (s, 1H). MS (ESI+) m/z 376 [M+H]$^+$.

Example 20

Methyl 4-{[(5-chloro-2-fluorophenyl)sulfonyl]amino}-2-hydroxybenzoate

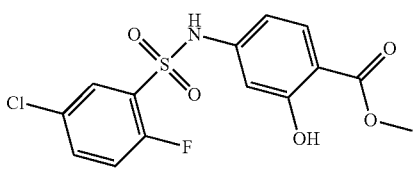 [SMILES: COC(=O)c1ccc(NS(=O)(=O)c2cc(Cl)ccc2F)cc1O]

The product was prepared from methyl 4-aminosalicylate (9.1 mg, 0.054 mmol) and 5-chloro-2-fluorobenzenesulfonyl chloride (16.6 mg, 0.072 mmol) according to the General Procedure 4, described in Example 7. The title compound was obtained in 68% yield (13.3 mg). $^1$H NMR (500 MHz, CDCl$_3$) δ ppm 3.90 (s, 3H) 6.66 (dd, J=8.55, 2.20 Hz, 1H) 6.68 (d, J=2.20 Hz, 1H) 6.99 (s, 1H) 7.13 (t, J=9.03 Hz, 1H) 7.51 (ddd, J=8.85, 4.33, 2.69 Hz, 1H) 7.72 (d, J=8.55 Hz, 1H) 7.90 (dd, J=6.10, 2.69 Hz, 1H) 10.85 (s, 1H). MS (ESI+) m/z 360 [M+H]$^+$.

Example 21

Methyl 4-{[(5-chloro-2,4-difluorophenyl)sulfonyl]amino}-2-hydroxybenzoate

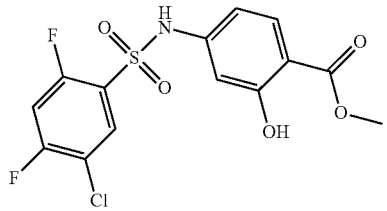 [SMILES: COC(=O)c1ccc(NS(=O)(=O)c2cc(Cl)c(F)cc2F)cc1O]

The product was prepared from methyl 4-aminosalicylate (9.1 mg, 0.054 mmol) and 5-chloro-2,4-difluorobenzenesulfonyl chloride (16.6 mg, 0.067 mmol) according to the General Procedure 4, described in Example 7. The title compound was obtained in 66% yield (13.5 mg). $^1$H NMR (500 MHz, CDCl$_3$) δ ppm 3.91 (s, 3H) 6.65 (dd, J=8.55, 2.20 Hz, 1H) 6.68 (d, J=2.20 Hz, 1H) 7.03 (dd, J=9.28, 8.30 Hz, 1H) 7.14 (s, 1H) 7.73 (d, J=8.79 Hz, 1H) 8.01 (t, J=7.57 Hz, 1H) 10.87 (s, 1H). MS (ESI+) m/z 378 [M+H]$^+$.

Example 22

Methyl 4-{[(3,5-dichlorophenyl)sulfonyl]amino}-2-hydroxybenzoate

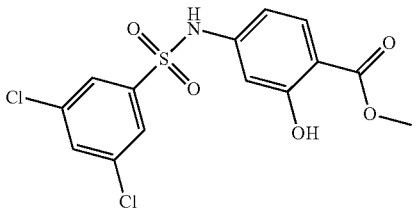 [SMILES: COC(=O)c1ccc(NS(=O)(=O)c2cc(Cl)cc(Cl)c2)cc1O]

The product was prepared from methyl 4-aminosalicylate (9.1 mg, 0.054 mmol) and 3,5-dichlorobenzenesulfonyl chloride (15.0 mg, 0.061 mmol) according to the General Procedure 4, described in Example 7. The title compound was obtained in 70% yield (14.2 mg). $^1$H NMR (500 MHz, CDCl$_3$) δ ppm 3.92 (s, 3H) 6.65 (d, J=8.55, 2.20 Hz, 1H) 6.66 (d, J=2.20 Hz, 1H) 7.02 (s, 1H) 7.54 (t, J=1.83 Hz, 1H) 7.73 (d, J=1.95 Hz, 2H) 7.76 (d, J=8.55 Hz, 1H) 10.88 (s, 1H). MS (ESI+) m/z 376 [M+H]$^+$.

Example 23

Methyl 4-{[(3-bromobenzyl)sulfonyl]amino}-2-hydroxybenzoate

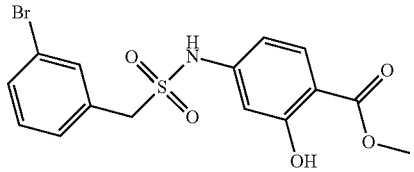 [SMILES: COC(=O)c1ccc(NS(=O)(=O)Cc2cccc(Br)c2)cc1O]

The product was prepared from methyl 4-aminosalicylate (8.5 mg, 0.050 mmol) and 3-bromobenzylsulfonyl chloride (13.5 mg, 0.050 mmol) according to the General Procedure 4, described in Example 7. The title compound was obtained in 45% yield (9.1 mg). $^1$H NMR (500 MHz, DMSO-$d_6$: CD$_3$OD 7:1) δ ppm 3.87 (s, 3H) 4.61 (s, 2H) 6.72 (dd, J=8.67, 2.20 Hz, 1H) 6.74 (d, J=2.20 Hz, 1H) 7.21-7.25 (m, 1H) 7.30 (td, J=7.69, 0.61 Hz, 1H) 7.44 (t, J=1.59 Hz, 1H) 7.51-7.55 (m, 1H) 7.72 (d, J=8.67 Hz, 1H). MS (ESI+) m/z 400 [M+H]$^+$.

Example 24

Methyl 4-{[(4-bromobenzyl)sulfonyl]amino}-2-hydroxybenzoate

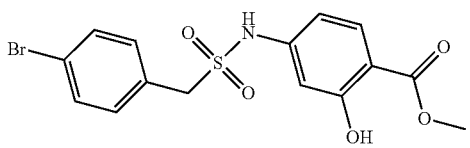 [SMILES: COC(=O)c1ccc(NS(=O)(=O)Cc2ccc(Br)cc2)cc1O]

The product was prepared from methyl 4-aminosalicylate (8.5 mg, 0.050 mmol) and 4-bromobenzylsulfonyl chloride (13.5 mg, 0.050 mmol) according to the General Procedure 4, described in Example 7. The title compound was obtained in 63% yield (12.7 mg). $^1$H NMR (500 MHz, DMSO-$d_6$: CD$_3$OD 7:1) δ ppm 3.87 (s, 3H) 4.58 (s, 2H) 6.71 (dd, J=8.55, 2.20 Hz, 1H) 6.73 (d, J=2.20 Hz, 1H) 7.16-7.20 (m, 2H) 7.51-7.56 (m, 2H) 7.72 (d, J=8.55 Hz, 1H). MS (ESI+) m/z 400 [M+H]$^+$.

Example 25

Methyl 4-{[(2,5-dichloro-3-thienyl)sulfonyl]amino}-2-hydroxybenzoate

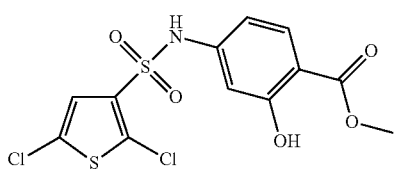 [SMILES: COC(=O)c1ccc(NS(=O)(=O)c2cc(Cl)sc2Cl)cc1O]

The product was prepared from methyl 4-aminosalicylate (12.0 mg, 0.072 mmol) and 2,5-dichlorothiophene-3-sulfonyl chloride (18.0 mg, 0.072 mmol) according to the General Procedure 4, described in Example 7. The title compound was obtained in 68% yield (18.7 mg). $^1$H NMR (500 MHz, DMSO-$d_6$:CD$_3$OD 6:1) δ ppm 3.84 (s, 3H) 6.70 (d, J=2.22 Hz, 1H) 6.72 (dd, J=8.60, 2.22 Hz, 1H) 7.39 (s, 1H) 7.70 (d, J=8.60 Hz, 1H). MS (ESI+) m/z 382 [M+H]$^+$.

Example 26

Methyl 2-hydroxy-4-{[(4-methyl-1-naphthyl)sulfonyl]amino}benzoate

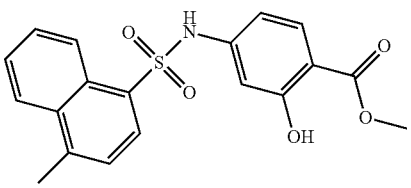 [SMILES: COC(=O)c1ccc(NS(=O)(=O)c2ccc(C)c3ccccc23)cc1O]

The product was prepared from methyl 4-aminosalicylate (12.0 mg, 0.072 mmol) and 4-methyl-1-naphthalenesulfonyl chloride (17.0 mg, 0.071 mmol) according to the General Procedure 4, described in Example 7. The title compound was obtained in 70% yield (18.4 mg). $^1$H NMR (500 MHz, DMSO-$d_6$:CD$_3$OD 6:1) δ ppm 2.70 (d, J=1.00 Hz, 3H) 3.77 (s, 3H) 6.59 (d, J=2.20 Hz, 1H) 6.61 (dd, J=8.67, 2.20 Hz, 1H) 7.52 (dq, J=7.57, 1.00 Hz, 1H) 7.55 (d, J=8.67 Hz, 1H) 7.68 (ddd, J=8.36, 6.84, 1.28 Hz, 1H) 7.74 (ddd, J=8.48, 6.84, 1.40 Hz, 1H) 8.15 (ddd, J=8.36, 1.40, 0.70 Hz, 1H) 8.21 (d, J=7.57 Hz, 1H) 8.70 (ddd, J=8.48, 1.28, 0.70 Hz, 1H). MS (ESI+) m/z 372 [M+H]$^+$.

Example 27

Methyl 4-{[(4,5-dichloro-2-thienyl)sulfonyl]amino}-2-hydroxybenzoate

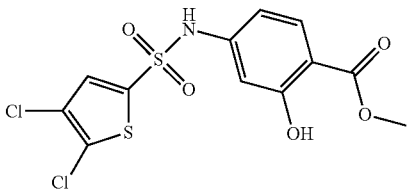 [SMILES: COC(=O)c1ccc(NS(=O)(=O)c2cc(Cl)c(Cl)s2)cc1O]

The product was prepared from methyl 4-aminosalicylate (12.0 mg, 0.072 mmol) and 2,3-dichlorothiophene-5-sulfonyl chloride (18.0 mg, 0.072 mmol) according to the General Procedure 4, described in Example 7. The title compound was obtained in 60% yield (16.3 mg). $^1$H NMR (500 MHz, DMSO-$d_6$:CD$_3$OD 6:1) δ ppm 3.84 (s, 3H) 6.75 (dd, J=2.20, 0.50 Hz, 1H) 6.77 (dd, J=8.55, 2.20 Hz, 1H) 7.73 (dd, J=8.55, 0.50 Hz, 1H) 7.77 (s, 1H). MS (ESI+) m/z 382 [M+H]$^+$.

Example 28

Methyl 2-hydroxy-4-[(1-naphthylsulfonyl)amino]benzoate

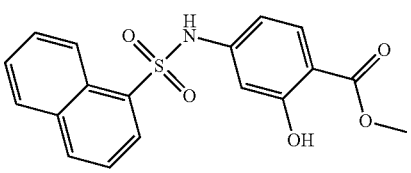 [SMILES: COC(=O)c1ccc(NS(=O)(=O)c2cccc3ccccc23)cc1O]

The product was prepared from methyl 4-aminosalicylate (8.5 mg, 0.050 mmol) and 1-naphthalenesulfonyl chloride (12.0 mg, 0.053 mmol) according to the General Procedure 4, described in Example 7. The title compound was obtained in 78% yield (13.9 mg). $^1$H NMR (500 MHz, CDCl$_3$) δ ppm 3.87 (s, 3H) 6.54 (dd, J=8.67, 2.20 Hz, 1H) 6.57 (d, J=2.20 Hz, 1H) 7.14 (br. s., 1H) 7.53 (dd, J=8.25, 7.42 Hz, 1H) 7.62 (ddd, J=8.19, 6.92, 1.12 Hz, 1H) 7.61 (d, J=8.67 Hz, 1H) 7.71 (ddd, J=8.65, 6.92, 1.35 Hz, 1H) 7.94 (dddd, J=8.19, 1.35, 0.62, 0.62 Hz, 1H) 8.05-8.09 (m, 1H) 8.34 (dd, J=7.42, 1.27 Hz, 1H) 8.65 (dddd, J=8.65, 1.12, 0.91, 0.62 Hz, 1H) 10.77 (s, 1H). MS (ESI+) m/z 358 [M+H]$^+$.

Example 29

Methyl 4-{[(4-bromo-2,5-difluorophenyl)sulfonyl]amino}-2-hydroxybenzoate

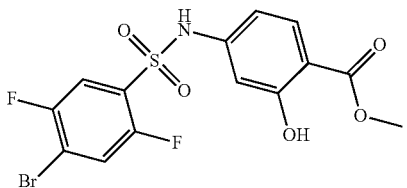 [SMILES: COC(=O)c1ccc(NS(=O)(=O)c2cc(F)c(Br)cc2F)cc1O]

The product was prepared from methyl 4-aminosalicylate (8.5 mg, 0.050 mmol) and 4-bromo-2,5-difluorobenzenesulphonyl chloride (16.1 mg, 0.055 mmol) according to the General Procedure 4, described in Example 7. The title compound was obtained in 70% yield (14.7 mg). $^1$H NMR (500 MHz, CDCl$_3$) δ ppm 3.91 (s, 3H) 6.65 (dd, J=8.67, 2.32 Hz, 1H) 6.69 (d, J=2.20 Hz, 1H) 7.18 (br. s., 1H) 7.43 (dd, J=8.79, 5.13 Hz, 1H) 7.68 (dd, J=7.02, 6.04 Hz, 1H) 7.73 (d, J=8.67 Hz, 1H) 10.86 (s, 1H). MS (ESI+) m/z 422 [M+H]$^+$.

Example 30

Methyl 2-hydroxy-4-{[(3-methylphenyl)sulfonyl]amino}benzoate

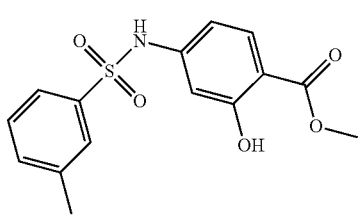 [SMILES: COC(=O)c1ccc(NS(=O)(=O)c2cccc(C)c2)cc1O]

The product was prepared from methyl 4-aminosalicylate (8.5 mg, 0.050 mmol) and 3-toluenesulfonyl chloride (9.5 mg, 0.050 mmol) according to the General Procedure 4, described in Example 7. The title compound was obtained in 88% yield (14.2 mg). $^1$H NMR (500 MHz, CDCl$_3$) δ ppm 2.39 (s, 3H) 3.90 (s, 3H) 6.62 (dd, J=8.67, 2.20 Hz, 1H) 6.64 (d, J=2.20 Hz, 1H) 6.79 (br. s., 1H) 7.34-7.39 (m, 2H) 7.64-7.70 (m, 2H) 7.69 (d, J=8.67 Hz, 1H) 10.83 (s, 1H). MS (ESI+) m/z 322 [M+H]$^+$.

Example 31

Methyl 4-({[3-(difluoromethoxy)phenyl]sulfonyl}amino)-2-hydroxybenzoate

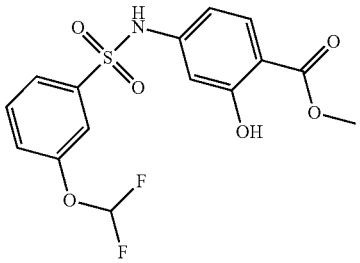 [SMILES: COC(=O)c1ccc(NS(=O)(=O)c2cccc(OC(F)F)c2)cc1O]

The product was prepared from methyl 4-aminosalicylate (8.5 mg, 0.050 mmol) and 3-(difluoromethoxy)benzenesulfonyl chloride (12.1 mg, 0.050 mmol) according to the General Procedure 4, described in Example 7. The title compound was obtained in 78% yield (14.6 mg). $^1$H NMR (500 MHz, CDCl$_3$) δ ppm 3.91 (s, 3H) 6.52 (t, J=72.63 Hz, 1H) 6.63 (dd, J=8.67, 2.32 Hz, 1H) 6.66 (d, J=2.32 Hz, 1H) 6.80 (br. s., 1H) 7.31-7.35 (m, 1H) 7.49 (dd, J=8.30, 7.89 Hz, 1H) 7.62 (dd, J=2.30, 1.78 Hz, 1H) 7.71 (ddd, J=7.89, 1.78, 0.97 Hz, 1H) 7.73 (d, J=8.67 Hz, 1H) 10.85 (s, 1H). MS (ESI+) m/z 374 [M+H]$^+$.

Example 32

Methyl 4-{[(3-chloro-4-fluorophenyl)sulfonyl]amino}-2-hydroxybenzoate

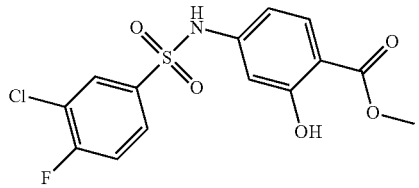 [SMILES: COC(=O)c1ccc(NS(=O)(=O)c2ccc(F)c(Cl)c2)cc1O]

The product was prepared from methyl 4-aminosalicylate (8.5 mg, 0.050 mmol) and 3-chloro-4-fluorobenzenesulfonyl chloride (11.4 mg, 0.050 mmol) according to the General Procedure 4, described in Example 7. The title compound was obtained in 82% yield (14.8 mg). $^1$H NMR (500 MHz, CDCl$_3$) δ ppm 3.91 (s, 3H) 6.62 (dd, J=8.61, 2.26 Hz, 1H) 6.67 (d, J=2.26 Hz, 1H) 6.91 (br. s., 1H) 7.24 (dd, J=8.72, 8.35 Hz, 1H) 7.74 (d, J=8.61 Hz, 1H) 7.76 (ddd, J=8.72, 4.31, 2.32 Hz, 1H) 7.95 (dd, J=6.59, 2.32 Hz, 1H) 10.87 (s, 1H). MS (ESI+) m/z 360 [M+H]$^+$.

Example 33

Methyl 4-{[(4-fluoro-1-naphthyl)sulfonyl]amino}-2-hydroxybenzoate

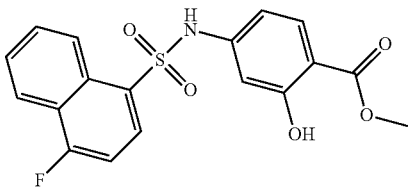 [SMILES: COC(=O)c1ccc(NS(=O)(=O)c2ccc(F)c3ccccc23)cc1O]

The product was prepared from methyl 4-aminosalicylate (8.5 mg, 0.050 mmol) and 4-fluoronaphthalene-1-sulfonyl chloride (12.3 mg, 0.050 mmol) according to the General Procedure 4, described in Example 7. The title compound was obtained in 77% yield (14.4 mg). $^1$H NMR (500 MHz, CDCl$_3$) δ ppm 3.86 (s, 3H) 6.51 (dd, J=8.67, 2.20 Hz, 1H) 6.55 (d, J=2.20 Hz, 1H) 7.14 (br. s., 1H) 7.18 (dd, J=9.40, 8.30 Hz, 1H) 7.61 (d, J=8.67 Hz, 1H) 7.68 (ddd, J=8.37, 6.93, 0.99 Hz, 1H) 7.77 (ddd, J=8.76, 6.93, 1.34 Hz, 1H) 8.19-8.23 (m, 1H) 8.32 (dd, J=8.30, 5.25 Hz, 1H) 8.62-8.66 (m, 1H) 10.77 (s, 1H). MS (ESI+) m/z 376 [M+H]$^+$.

Example 34

Methyl 4-{[(2,3-dichlorophenyl)sulfonyl]amino}-2-hydroxybenzoate

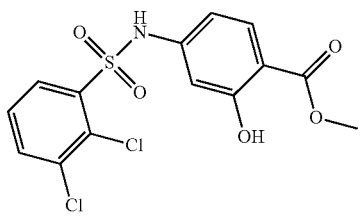 [SMILES: COC(=O)c1ccc(NS(=O)(=O)c2cccc(Cl)c2Cl)cc1O]

The product was prepared from methyl 4-aminosalicylate (8.5 mg, 0.050 mmol) and 2,3-dichlorobenzenesulfonyl chloride (12.4 mg, 0.050 mmol) according to the General Procedure 4, described in Example 7. The title compound was obtained in 66% yield (12.4 mg). $^1$H NMR (500 MHz, CDCl$_3$) δ ppm 3.89 (s, 3H) 6.61 (dd, J=8.67, 2.20 Hz, 1H) 6.70 (d, J=2.20 Hz, 1H) 7.26 (br. s., 1H) 7.35 (t, J=8.03 Hz, 1H) 7.66 (dd, J=8.03, 1.56 Hz, 1H) 7.69 (d, J=8.67 Hz, 1H) 8.08 (dd, J=8.03, 1.56 Hz, 1H) 10.83 (s, 1H). MS (ESI+) m/z 376 [M+H]$^+$.

Example 35

Methyl 4-[(biphenyl-4-ylsulfonyl)amino]-2-hydroxybenzoate

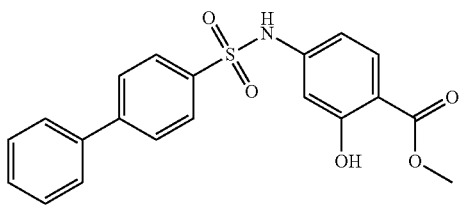 [SMILES: COC(=O)c1ccc(NS(=O)(=O)c2ccc(-c3ccccc3)cc2)cc1O]

The product was prepared from methyl 4-aminosalicylate (8.5 mg, 0.050 mmol) and biphenyl-4-sulfonyl chloride (12.9 mg, 0.051 mmol) according to the General Procedure 4, described in Example 7. The title compound was obtained in 56% yield (10.8 mg). $^1$H NMR (500 MHz, CDCl$_3$) δ ppm 3.90 (s, 3H) 6.65 (dd, J=8.67, 2.20 Hz, 1H) 6.70 (d, J=2.20 Hz, 1H) 6.94 (br. s., 1H) 7.38-7.43 (m, 1H) 7.43-7.48 (m, 2H) 7.54-7.58 (m, 2H) 7.66-7.70 (m, 2H) 7.71 (d, J=8.67 Hz, 1H) 7.92-7.95 (m, 2H) 10.85 (s, 1H). MS (ESI+) m/z 384 [M+H]$^+$.

Example 36

Methyl 4-{[(4-tert-butylphenyl)sulfonyl]amino}-2-hydroxybenzoate

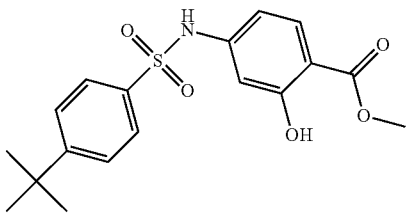 [SMILES: COC(=O)c1ccc(NS(=O)(=O)c2ccc(C(C)(C)C)cc2)cc1O]

The product was prepared from methyl 4-aminosalicylate (8.5 mg, 0.050 mmol) and 4-tert-butylbenzenesulfonyl chloride (12.5 mg, 0.053 mmol) according to the General Procedure 4, described in Example 7. The title compound was obtained in 96% yield (17.4 mg). $^1$H NMR (500 MHz, CDCl$_3$) δ ppm 1.31 (s, 9H) 3.90 (s, 3H) 6.64 (dd, J=8.67, 2.20 Hz, 1H) 6.66 (d, J=2.32 Hz, 1H) 6.87 (br. s., 1H) 7.46-7.51 (m, 2H) 7.70 (d, J=8.67 Hz, 1H) 7.78-7.81 (m, 2H) 10.84 (s, 1H). MS (ESI+) m/z 364 [M+H]$^+$.

Example 37

Methyl 4-[(2,1,3-benzothiadiazol-4-ylsulfonyl)amino]-2-hydroxybenzoate

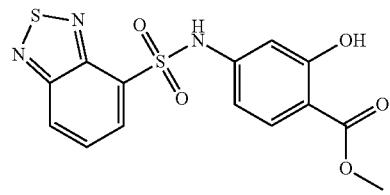 [SMILES: COC(=O)c1ccc(NS(=O)(=O)c2cccc3nsnc23)cc1O]

The product was prepared from methyl 4-aminosalicylate (8.3 mg, 0.050 mmol) and 2,1,3-benzothiadiazole-4-sulfonyl chloride (11.7 mg, 0.050 mmol) according to the General Procedure 4, described in Example 7. DMSO was added to the reaction mixture prior to the purification in order to dissolve precipitated material. The title compound was obtained in 27% yield (4.9 mg). $^1$H NMR (600 MHz, CD$_3$OD) δ ppm 3.83 (s, 3H) 6.65 (dd, J=8.75, 2.21 Hz, 1H) 6.70 (d, J=2.21 Hz, 1H) 7.58 (d, J=8.75 Hz, 1H) 7.79 (dd, J=8.85, 7.02 Hz, 1H) 8.27 (dd, J=8.85, 1.07 Hz, 1H) 8.38 (dd, J=7.02, 1.07 Hz, 1H). MS (ESI+) m/z 366 [M+H]$^+$.

Example 38

Methyl 2-hydroxy-4-{[(4-phenoxyphenyl)sulfonyl]amino}benzoate

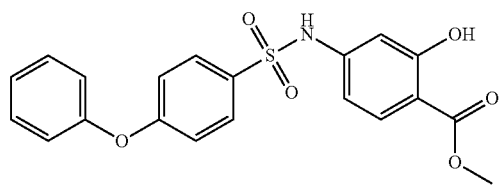 [SMILES: COC(=O)c1ccc(NS(=O)(=O)c2ccc(Oc3ccccc3)cc2)cc1O]

The product was prepared from methyl 4-aminosalicylate (8.3 mg, 0.050 mmol) and 4-phenoxybenzenesulfonyl chloride (13.4 mg, 0.050 mmol) according to the General Procedure 4, described in Example 7. The title compound was obtained in 78% yield (15.6 mg). $^1$H NMR (600 MHz, CD$_3$OD) δ ppm 3.89 (s, 3H) 6.66 (dd, J=8.70, 2.25 Hz, 1H) 6.70 (dd, J=2.25, 0.31 Hz, 1H) 6.99-7.03 (m, 2H) 7.04-7.07 (m, 2H) 7.20-7.24 (m, 1H) 7.38-7.44 (m, 2H) 7.68 (dd, J=8.70, 0.31 Hz, 1H) 7.81-7.85 (m, 2H). MS (ESI+) m/z 400 [M+H]$^+$.

Example 39

Methyl 2-hydroxy-4-[(naphthalen-2-ylsulfonyl)amino]benzoate

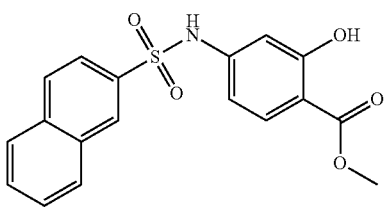 [SMILES: COC(=O)c1ccc(NS(=O)(=O)c2ccc3ccccc3c2)cc1O]

The product was prepared from methyl 4-aminosalicylate (8.3 mg, 0.050 mmol) and 2-naphthalenesulfonyl chloride (11.3 mg, 0.050 mmol) according to the General Procedure 4, described in Example 7. The title compound was obtained in 72% yield (12.8 mg). $^1$H NMR (600 MHz, CD$_3$OD) δ ppm 3.85 (s, 3H) 6.68 (dd, J=8.72, 2.21 Hz, 1H) 6.75 (dd, J=2.21, 0.31 Hz, 1H) 7.62 (ddd, J=8.09, 6.89, 1.37 Hz, 1H) 7.65 (dd, J=8.72, 0.31 Hz, 1H) 7.66 (ddd, J=8.09, 6.89, 1.40 Hz, 1H) 7.82 (dd, J=8.73, 1.93 Hz, 1H) 7.92-7.95 (m, 1H) 8.00 (d, J=8.73 Hz, 1H) 8.01-8.04 (m, 1H) 8.46-8.48 (m, 1H). MS (ESI+) m/z 358 [M+H]$^+$.

Example 40

Methyl 4-({[5-(dimethylamino)naphthalen-1-yl]sulfonyl}amino)-2-hydroxybenzoate trifluoroacetate

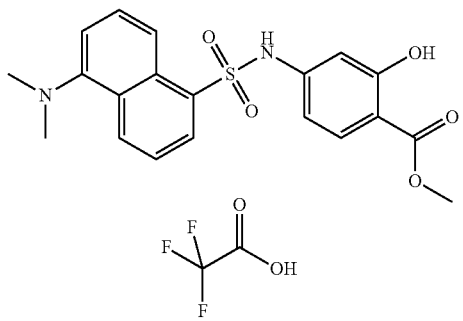

A mixture of methyl 4-aminosalicylate (8.3 mg, 0.050 mmol), 5-dimethylaminonaphthalene-1-sulfonyl chloride (13.5 mg, 0.050 mmol) and pyridine (8 μL, 0.100 mmol) in MeCN (400 μL) was heated at 60° C. for 5 h. Due to low solubility of the reagents, MeCN (400 μL) was added and the mixture was heated at 60° C. overnight. A second portion of 5-dimethylaminonaphthalene-1-sulfonyl chloride was added (13.6 mg, 0.05 mmol) and the mixture was heated at 60° C. for another 24 h. After 2 days, additional 5-dimethylaminonaphthalene-1-sulfonyl chloride (6.7 mg, 0.025 mmol) was added and the reaction mixture was heated at 60° C. overnight. The reaction mixture was filtered and the clear solution obtained was diluted with DMSO/MeOH/water. TFA (50 μL) was added and the crude product was purified by preparative HPLC (acidic system). The title compound was obtained in 42% yield (10.9 mg). $^1$H NMR (600 MHz, CD$_3$OD) δ ppm 2.95 (s, 6H) 3.84 (s, 3H) 6.57 (dd, J=8.77, 2.21 Hz, 1H) 6.61 (dd, J=2.21, 0.30 Hz, 1H) 7.40 (d, J=7.70 Hz, 1H) 7.58 (dd, J=8.77, 0.30 Hz, 1H) 7.62 (dd, J=8.54, 7.40 Hz, 1H) 7.66 (dd, J=8.54, 7.70 Hz, 1H) 8.36 (dd, J=7.40, 1.04 Hz, 1H) 8.48 (d, J=8.54 Hz, 1H) 8.53 (dt, J=8.54, 1.04 Hz, 1H). MS (ESI+) m/z 401 [M+H]$^+$.

Example 41

Methyl 2-hydroxy-4-{[(5-{[(phenylcarbonyl)amino]methyl}thiophen-2-yl)sulfonyl]amino}benzoate

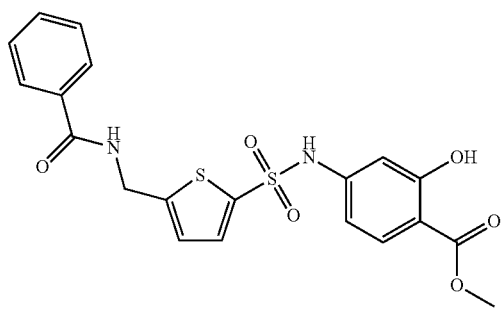 [SMILES: COC(=O)c1ccc(NS(=O)(=O)c2ccc(CNC(=O)c3ccccc3)s2)cc1O]

The product was prepared from methyl 4-aminosalicylate (8.3 mg, 0.050 mmol) and 5-[(benzoylamino)methyl]thiophene-2-sulfonyl chloride (16.3 mg, 0.052 mmol) according to the General Procedure 4, described in Example 7, with a modified reaction volume of 800 μL. The title compound was obtained in 61% yield (13.7 mg). $^1$H NMR (600 MHz, CD$_3$OD) δ ppm 3.89 (s, 3H) 4.69 (d, J=0.90 Hz, 2H) 6.69 (dd, J=8.71, 2.19 Hz, 1H) 6.74 (dd, J=2.19, 0.29 Hz, 1H) 7.01 (dt, J=3.83, 0.90 Hz, 1H) 7.44-7.48 (m, 2H) 7.50 (d, J=3.83 Hz, 1H) 7.53-7.57 (m, 1H) 7.69 (dd, J=8.71, 0.29 Hz, 1H) 7.77-7.82 (m, 2H). MS (ESI+) m/z 447 [M+H]$^+$.

Example 42

Methyl 4-{[(4-chlorophenyl)sulfonyl]amino}-2-hydroxybenzoate

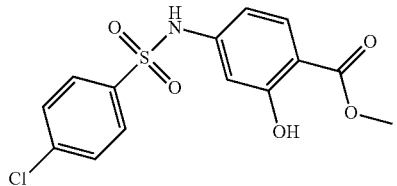 [SMILES: COC(=O)c1ccc(NS(=O)(=O)c2ccc(Cl)cc2)cc1O]

The product was prepared from methyl 4-aminosalicylate (8.5 mg, 0.050 mmol) and 4-chlorobenzenesulfonyl chloride (11.6 mg, 0.050 mmol) according to the General Procedure 4, described in Example 7. The title compound was obtained in 68% yield (11.6 mg). ¹H NMR (500 MHz, CDCl₃) δ ppm 3.91 (s, 3H) 6.61 (dd, J=8.67, 2.26 Hz, 1H) 6.66 (d, J=2.26 Hz, 1H) 6.86 (s, 1H) 7.43-7.47 (m, 2H) 7.71 (d, J=8.67 Hz, 1H) 7.78-7.82 (m, 2H) 10.86 (s, 1H). MS (ESI+) m/z 342 [M+H]⁺.

Example 43

Methyl 4-{[(2-chloro-6-methylphenyl)sulfonyl] amino}-2-hydroxybenzoate

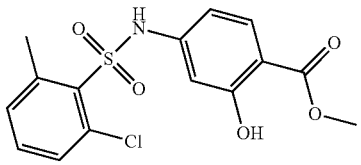 [SMILES: COC(=O)c1ccc(NS(=O)(=O)c2c(C)cccc2Cl)cc1O]

The product was prepared from methyl 4-aminosalicylate (8.5 mg, 0.050 mmol) and 2-chloro-6-methylbenzenesulfonyl chloride (11.3 mg, 0.050 mmol) according to the General Procedure 4, described in Example 7. The title compound was obtained in 30% yield (5.4 mg). ¹H NMR (500 MHz, CDCl₃) δ ppm 2.73 (s, 3H) 3.89 (s, 3H) 6.64 (dd, J=8.67, 2.20 Hz, 1H) 6.68 (d, J=2.20 Hz, 1H) 7.17-7.20 (m, 1H) 7.29 (t, J=7.81 Hz, 1H) 7.34-7.37 (m, 1H) 7.38 (br. s., 1H) 7.69 (d, J=8.67 Hz, 1H) 10.81 (s, 1H). MS (ESI+) m/z 356 [M+H]⁺.

Example 44

Methyl 2-hydroxy-4-({[3-(trifluoromethoxy)phenyl] sulfonyl}amino)benzoate

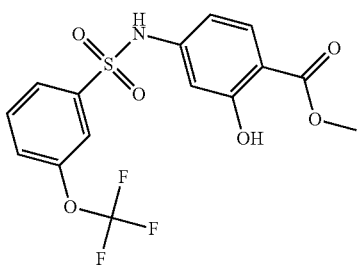 [SMILES: COC(=O)c1ccc(NS(=O)(=O)c2cccc(OC(F)(F)F)c2)cc1O]

The product was prepared from methyl 4-aminosalicylate (8.5 mg, 0.050 mmol) and 3-(trifluoromethoxy)benzenesulfonyl chloride (13.0 mg, 0.050 mmol) according to the General Procedure 4, described in Example 7. The title compound was obtained in 66% yield (12.9 mg). ¹H NMR (500 MHz, CDCl₃) δ ppm 3.91 (s, 3 H) 6.63 (dd, J=8.54, 2.20 Hz, 1 H) 6.65 (d, J=2.20 Hz, 1 H) 6.74 (br. s., 1 H) 7.40-7.44 (m, 1 H) 7.54 (dd, J=8.27, 7.92 Hz, 1 H) 7.71 (br. s., 1 H) 7.73 (d, J=8.54 Hz, 1 H) 7.80 (ddd, J=7.92, 1.71, 0.98 Hz, 1 H) 10.86 (s, 1 H). MS (ESI+) m/z 392 [M+H]⁺.

Example 45

Methyl 4-({[5-chloro-4-(2,5-difluorophenyl)-2-thienyl]sulfonyl}amino)-2-hydroxybenzoate

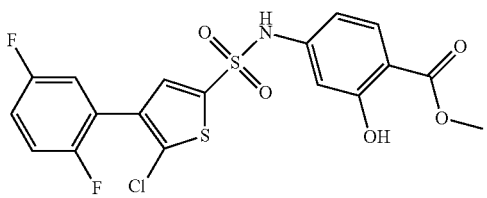 [SMILES: COC(=O)c1ccc(NS(=O)(=O)c2cc(-c3cc(F)ccc3F)c(Cl)s2)cc1O]

A solution of 3-bromo-2-chlorothiophene (2.43 g, 12.3 mmol), 2,5-difluorophenylboronic acid (2.91 g, 18.4 mmol), DIPEA (4.8 g, 37 mmol) and Pd(dppf)Cl₂.CH₂Cl₂ (300 mg, 0.37 mmol) was stirred in dioxane (100 mL) and water (10 mL) at 80° C. for two days. Toluene (100 mL) was added. The organic phase was washed with 1 M NaOH, 1 M HCl and brine, dried and concentrated to a brown oil. The brown oil was purified by distillation (twice) in a Kugelrohr apparatus at 120° C. and ~10 mbar resulting in 0.73 g (26%) of the intermediate 2-chloro-3-(2,5-difluorophenyl)thiophene. ¹H NMR (500 MHz, CDCl₃) δ ppm 7.01-7.23 (m, 5H).

A solution of 2-chloro-3-(2,5-difluorophenyl)thiophene (0.73 g, 3.2 mmol) in CH₂Cl₂ (100 mL) was cooled on ice. Chlorosulfonic acid (0.37 g, 3.2 mmol) in CH₂Cl₂ (50 mL) was added dropwise over 1 h. The reaction was refluxed overnight. The reaction mixture was cooled and washed with water (2×100 mL) and brine, dried over MgSO₄, filtered and concentrated to a dark brown oil. The oil was dissolved in heptane (50 mL) and stored in the fridge for 3 days. A black tar precipitated. The solution was decanted and concentrated to give the intermediate 5-chloro-4-(2,5-difluorophenyl) thiophene-2-sulfonyl chloride as a light brown oil (0.87 g, 21% over two steps). MS (ESI+) m/z 293 [M−Cl]⁺.

The title compound was prepared from methyl 4-aminosalicylate (8.5 mg, 0.050 mmol) and 5-chloro-4-(2,5-difluorophenyl)thiophene-2-sulfonyl chloride (16.5 mg, 0.050 mmol) according to the General Procedure 4, described in Example 7. The title compound was obtained in 47% yield (10.9 mg). ¹H NMR (500 MHz, CDCl₃) δ ppm 3.93 (s, 3 H) 6.71 (dd, J=8.67, 2.32 Hz, 1 H) 6.76 (d, J=2.32 Hz, 1 H) 6.95 (s, 1 H) 7.06-7.16 (m, 3 H) 7.58 (d, J=1.95 Hz, 1 H) 7.79 (d, J=8.67 Hz, 1 H) 10.91 (s, 1 H). MS (ESI+) m/z 460 [M+H]⁺.

Example 46

Methyl 2-hydroxy-4-({[3-(trifluoromethyl)phenyl] sulfonyl}amino)benzoate

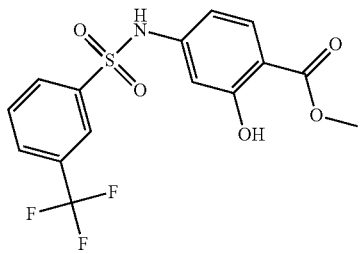 [SMILES: COC(=O)c1ccc(NS(=O)(=O)c2cccc(C(F)(F)F)c2)cc1O]

The product was prepared from methyl 4-aminosalicylate (8.5 mg, 0.050 mmol) and 3-trifluoromethylbenzenesulfochloride (12.2 mg, 0.050 mmol) according to the General Procedure 4, described in Example 7. The title compound was obtained in 76% yield (14.3 mg). ¹H NMR (500 MHz, CDCl₃) δ ppm 3.91 (s, 3 H) 6.64 (dd, J=8.54, 2.32 Hz, 1 H) 6.66 (d, J=2.32 Hz, 1 H) 6.94 (s, 1 H) 7.64 (t, J=7.87 Hz, 1 H) 7.73 (d, J=8.54 Hz, 1 H) 7.81-7.85 (m, 1 H) 8.02-8.06 (m, 1 H) 8.14 (s, 1 H) 10.86 (s, 1 H). MS (ESI+) m/z 376 [M+H]⁺.

Example 47

Methyl 4-{[(3-bromo-5-chlorothiophen-2-yl)sulfonyl]amino}-2-hydroxybenzoate

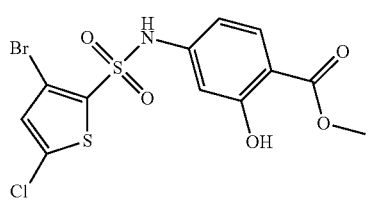 [SMILES: COC(=O)c1ccc(NS(=O)(=O)c2sc(Cl)cc2Br)cc1O]

The product was prepared from methyl 4-aminosalicylate (8.5 mg, 0.050 mmol) and 3-bromo-5-chlorothiophene-2-sulfonyl chloride (15.0 mg, 0.051 mmol) according to the General Procedure 4, described in Example 7. The title compound was obtained in 37% yield (8.0 mg). ¹H NMR (500 MHz, CDCl₃) δ ppm 3.92 (s, 3 H) 6.72 (dd, J=8.67, 2.20 Hz, 1 H) 6.75 (d, J=2.20 Hz, 1 H) 6.92 (s, 1 H) 7.35 (br. s., 1 H) 7.76 (d, J=8.67 Hz, 1 H) 10.88 (s, 1 H). MS (ESI+) m/z 426 [M+H]⁺.

Example 48

Methyl 4-{[(5-chloro-2-methyl-3-thienyl)sulfonyl]amino}-2-hydroxybenzoate

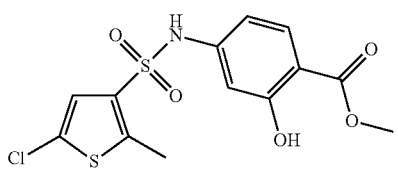

The product was prepared from methyl 4-aminosalicylate (8.5 mg, 0.050 mmol) and 5-chloro-2-methylthiophene-3-sulfonyl chloride (11.5 mg, 0.050 mmol) according to the General Procedure 4, described in Example 7. The title compound was obtained in 17% yield (3.0 mg). ¹H NMR (600 MHz, CDCl₃) δ ppm 2.58 (s, 3 H) 3.92 (s, 3 H) 6.61 (dd, J=8.60, 2.26 Hz, 1 H) 6.65 (d, J=2.26 Hz, 1 H) 6.81 (br. s., 1 H) 7.06 (s, 1 H) 7.75 (d, J=8.60 Hz, 1 H) 10.89 (s, 1 H). MS (ESI+) m/z 362 [M+H]⁺.

Example 49

Methyl 4-{[(5-bromo-2,4-difluorophenyl)sulfonyl]amino}-2-hydroxybenzoate

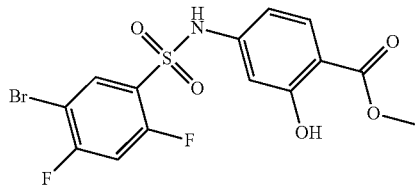 [SMILES: COC(=O)c1ccc(NS(=O)(=O)c2cc(Br)c(F)cc2F)cc1O]

The product was prepared from methyl 4-aminosalicylate (8.5 mg, 0.050 mmol) and 5-bromo-2,4-difluorobenzenesulfonyl chloride (14.5 mg, 0.050 mmol) according to the General Procedure 4, described in Example 7. The title compound was obtained in 66% yield (14.0 mg). ¹H NMR (600 MHz, CDCl₃) δ ppm 3.91 (s, 3 H) 6.65 (dd, J=8.60, 2.23 Hz, 1 H) 6.68 (d, J=2.23 Hz, 1 H) 7.00 (dd, J=9.52, 7.69 Hz, 1 H) 7.06 (br. s., 1 H) 7.73 (d, J=8.60 Hz, 1 H) 8.15 (t, J=7.32 Hz, 1 H) 10.87 (s, 1 H). MS (ESI+) m/z 422 [M+H]⁺.

Example 50

Methyl 4-{[(3-cyanophenyl)sulfonyl]amino}-2-hydroxybenzoate

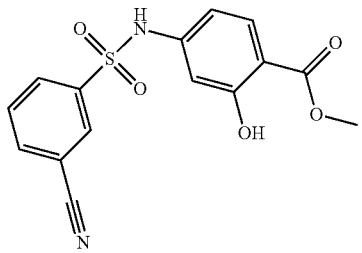 [SMILES: COC(=O)c1ccc(NS(=O)(=O)c2cccc(C#N)c2)cc1O]

The product was prepared from methyl 4-aminosalicylate (9.1 mg, 0.054 mmol) and 3-cyanobenzenesulfonyl chloride (10.4 mg, 0.052 mmol) according to the General Procedure 4, described in Example 7. The title compound was obtained in 64% yield (11.1 mg). ¹H NMR (500 MHz, CDCl₃) δ ppm 3.92 (s, 3 H) 6.64 (dd, J=8.35, 2.25 Hz, 1 H) 6.66 (dd, J=2.25, 0.60 Hz, 1 H) 7.06 (br. s., 1 H) 7.64 (ddd, J=8.04, 7.77, 0.55 Hz, 1 H) 7.74 (dd, J=8.35, 0.60 Hz, 1 H) 7.85 (ddd, J=7.77, 1.59, 1.16 Hz, 1 H) 8.08 (ddd, J=8.04, 1.89, 1.16 Hz, 1 H) 8.15 (ddd, J=1.89, 1.59, 0.55 Hz, 1 H) 10.88 (s, 1 H). MS (ESI+) m/z 333 [M+H]⁺.

Example 51

Methyl 2-hydroxy-4-({[3-(methylsulfonyl)phenyl]sulfonyl}amino)benzoate

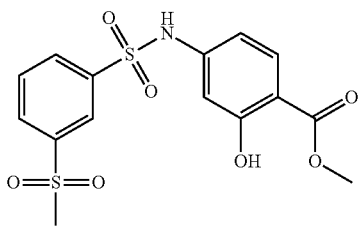 [SMILES: COC(=O)c1ccc(NS(=O)(=O)c2cccc(S(C)(=O)=O)c2)cc1O]

The product was prepared from methyl 4-aminosalicylate (8.4 mg, 0.050 mmol) and 3-methylsulphonyl)benzenesulphonyl chloride (12.8 mg, 0.050 mmol) according to the General Procedure 4, described in Example 7. The title compound was obtained in 62% yield (11.9 mg). $^1$H NMR (600 MHz, CD$_3$OD) δ ppm 3.13 (s, 3 H) 3.89 (s, 3 H) 6.69 (dd, J=8.70, 2.21 Hz, 1 H) 6.72 (dd, J=2.21, 0.42 Hz, 1 H) 7.71 (dd, J=8.70, 0.42 Hz, 1H) 7.81 (td, J=7.85, 0.55 Hz, 1H) 8.16 (ddd, J=7.85, 1.83, 1.07 Hz, 1 H) 8.18 (ddd, J=7.85, 1.83, 1.07 Hz, 1 H) 8.38 (td, J=1.83, 0.55 Hz, 1 H). MS (ESI+) m/z 386 [M+H]$^+$.

Example 52

Methyl 4-[(1-benzothien-3-ylsulfonyl)amino]-2-hydroxybenzoate

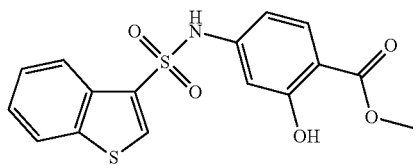 [SMILES: COC(=O)c1ccc(NS(=O)(=O)c2csc3ccccc23)cc1O]

A mixture of methyl 4-aminosalicylate (10 mg, 0.060 mmol), 1-benzothiophene-3-sulfonyl chloride (11.5 mg, 0.049 mmol) and pyridine (50 μL) in CH$_2$Cl$_2$ (1 mL) was heated in a sealed tube at 60° C. overnight. The solvent was evaporated, and the crude product was purified by preparative HPLC (acidic system). The title compound was obtained in 53% yield (11.6 mg). $^1$H NMR (500 MHz, CD$_3$OD) δ ppm 3.86 (s, 3 H) 6.64 (dd, J=8.79, 2.20 Hz, 1 H) 6.70 (d, J=2.20 Hz, 1 H) 7.46 (ddd, J=8.20, 7.10, 1.20 Hz, 1 H) 7.52 (ddd, J=8.10, 7.10, 1.20 Hz, 1 H) 7.63 (d, J=8.79 Hz, 1 H) 7.95 (ddd, J=8.10, 1.20, 0.75 Hz, 1 H) 8.25 (ddd, J=8.20, 1.20, 0.75 Hz, 1 H) 8.51 (s, 1 H). MS (ESI+) m/z 364 [M+H]$^+$.

Example 53

General Procedure 5

Methyl 4-{[(2,5-dichloro-4-methyl-3-thienyl)sulfonyl]amino}-2-hydroxybenzoate

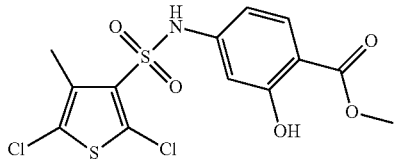 [SMILES: COC(=O)c1ccc(NS(=O)(=O)c2c(Cl)sc(Cl)c2C)cc1O]

Chlorosulfonic acid (52 μL, 0.77 mmol) was added to a solution of 2,5-dichloro-3-methylthiophene (125 mg, 0.75 mmol) in CH$_2$Cl$_2$. After 1 h of stirring at room temperature another portion of chlorosulfonic acid (52 μL, 0.77 mmol) was added. Complete conversion to the intermediate sulfonic acid was observed after stirring at room temperature overnight. Chlorosulfonic acid (100 μL, 1.55 mmol) was added to the reaction mixture, which was then heated at 50° C. for 3 h followed by stirring at room temperature for 3 days. The reaction was quenched by slow addition of water. The product was extracted with CH$_2$Cl$_2$. The organic phase was dried. Removal of the solvents gave the 2,5-dichloro-4-methylthiophene-3-sulfonyl chloride as a dark oil, which was used in the following step without further purification (119 mg).

A mixture of methyl 4-aminosalicylate (10 mg, 0.060 mmol), the preformed 2,5-dichloro-4-methylthiophene-3-sulfonyl chloride (13 mg, 0.049 mmol) and pyridine (50 μL) in CH$_2$Cl$_2$ (1 mL) was heated in a sealed tube at 50° C. overnight. The solvent was evaporated, and the crude product was purified by preparative HPLC (acidic system). The title compound was obtained in 18% yield (3.5 mg). $^1$H NMR (500 MHz, CD$_3$OD) δ ppm 2.37 (s, 3 H) 3.90 (s, 3 H) 6.63 (dd, J=8.67, 2.26 Hz, 1 H) 6.68 (d, J=2.26 Hz, 1 H) 7.72 (d, J=8.67 Hz, 1 H). MS (ESI+) m/z 396 [M+H]$^+$.

Example 54

Methyl 2-hydroxy-4-{[(2,4,5-trichloro-3-thienyl)sulfonyl]amino}benzoate

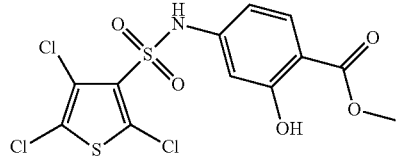

2,4,5-Trichlorothiophene-3-sulfonyl chloride was prepared from 2,3,5-trichlorothiophene (138 mg, 0.74 mmol) and chlorosulfonic acid (First step: 2×52 μL, 2×0.77 mmol; second step: 100 μL, 1.55 mmol) according the General Procedure 5, described in Example 53. 2,4,5-trichlorothiophene-3-sulfonyl chloride was obtained as a dark oil (165 mg).

The title compound was obtained by reacting the preformed 2,4,5-trichlorothiophene-3-sulfonyl chloride (14 mg, 0.049 mmol) with methyl 4-aminosalicylate (10 mg, 0.060 mmol) according to the General Procedure 5, described in Example 53. The title compound was obtained in 16% yield (3.2 mg). $^1$H NMR (500 MHz, CD$_3$OD) δ ppm 3.90 (s, 3 H) 6.66 (dd, J=8.67, 2.20 Hz, 1 H) 6.71 (d, J=2.20 Hz, 1 H) 7.72 (d, J=8.67 Hz, 1 H). MS (ESI+) m/z 416 [M+H]$^+$.

Example 55

General Procedure 6

Methyl 4-{[(3,5-dibromothiophen-2-yl)sulfonyl]amino}-2-hydroxybenzoate

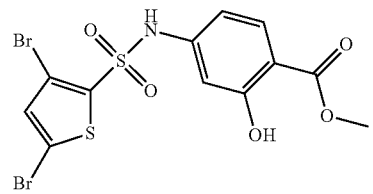 [SMILES: COC(=O)c1ccc(NS(=O)(=O)c2sc(Br)cc2Br)cc1O]

A solution of 2,4-dibromothiophene (24 mg, 0.100 mmol) in CH$_2$Cl$_2$ (1.5 mL) was cooled to −20° C. and a cold solution of chlorosulfonic acid (12 mg, 0.100 mmol) in CH$_2$Cl$_2$ (0.5 mL) was added. The reaction was allowed to reach room temperature over 2 h, after which more chlorosulfonic acid was added (35 mg, 0.300 mmol). The reaction mixture was stirred at 35° C. overnight and was then passed through a column loaded with hydromatrix (3 g) and water (1 mL). The column was eluted with CH$_2$Cl$_2$ (2 mL). The eluate was concentrated to dryness under vacuum to give 3,5-dibromothiophene-2-sulfonyl chloride, which was dissolved in MeCN (0.5 mL) together with methyl 4-aminosalicylate (16 mg, 0.100 mmol) and pyridine (15 mg, 0.200 mmol). The reaction mixture was allowed to react at 60° C. overnight. The crude product was diluted with water/MeCN. TFA (50 µL) was added and the product was purified by preparative HPLC (acidic system). The title compound was obtained in 37% yield (17.5 mg). $^1$H NMR (500 MHz, CDCl$_3$) δ ppm 3.92 (s, 3 H) 6.72 (dd, J=8.61, 2.20 Hz, 1 H) 6.75 (d, J=2.20 Hz, 1 H) 7.04 (s, 1 H) 7.32 (br. s., 1 H) 7.76 (d, J=8.61 Hz, 1 H) 10.88 (s, 1 H). MS (ESI+) m/z 470 [M+H]$^+$.

Example 56

Methyl 4-{[(5-chloro-4-methylthiophen-2-yl)sulfonyl]amino}-2-hydroxybenzoate

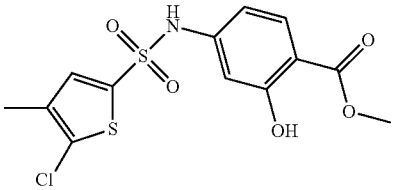

The intermediate 5-chloro-4-methylthiophene-2-sulfonyl chloride was prepared from 2-chloro-3-methylthiophene (13.5 mg, 0.20 mmol) and chlorosulfonic acid (47 mg, 0.40 mmol) according to the General Procedure 6, described in Example 55. The title compound was obtained by reacting the preformed 5-chloro-4-methylthiophene-2-sulfonyl chloride with methyl 4-aminosalicylate (16 mg, 0.100 mmol) and pyridine (15 mg, 0.200 mmol) according to the General Procedure 6. The title compound was obtained in 59% yield (21.4 mg). $^1$H NMR (500 MHz, CDCl$_3$) δ ppm 2.16 (d, J=0.40 Hz, 3 H) 3.92 (s, 3 H) 6.67 (dd, J=8.67, 2.20 Hz, 1 H) 6.72 (d, J=2.20 Hz, 1 H) 6.90 (br. s., 1 H) 7.34 (q, J=0.40 Hz, 1 H) 7.76 (d, J=8.67 Hz, 1 H) 10.89 (s, 1 H). MS (ESI+) m/z 362 [M+H]$^+$.

Example 57

Methyl 4-{[(3,4-dibromothiophen-2-yl)sulfonyl]amino}-2-hydroxybenzoate

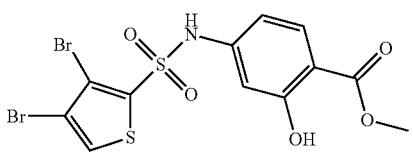 [SMILES: COC(=O)c1ccc(NS(=O)(=O)c2scc(Br)c2Br)cc1O]

The intermediate 3,4-dibromothiophene-2-sulfonyl chloride was prepared from 3,4-dibromothiophene (24 mg, 0.10 mmol) and chlorosulfonic acid (47 mg, 0.40 mmol) according to the General Procedure 6, described in Example 55. The title compound was obtained by reacting the preformed 3,4-dibromothiophene-2-sulfonyl chloride with methyl 4-aminosalicylate (16 mg, 0.100 mmol) and pyridine (15 mg, 0.200 mmol) according to the General Procedure 6. The title compound was obtained in 13% yield (5.9 mg). $^1$H NMR (500 MHz, CDCl$_3$:DMSO-d$_6$ 6:1) δ ppm 3.58 (s, 3 H) 6.45 (dd, J=8.67, 2.20 Hz, 1 H) 6.51 (d, J=2.20 Hz, 1 H) 7.36 (d, J=8.67 Hz, 1 H) 7.43 (s, 1 H) 10.47 (s, 1 H) 10.85 (s, 1 H). MS (ESI+) m/z 470 [M+H]$^+$.

Example 58

Methyl 4-{[(5-bromo-4-methylthiophen-2-yl)sulfonyl]amino}-2-hydroxybenzoate

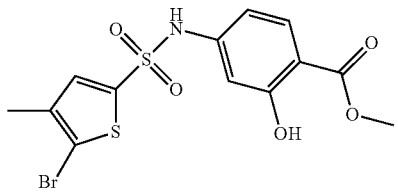

The intermediate 5-bromo-4-methylthiophene-2-sulfonyl chloride was prepared from 2-bromo-3-methylthiophene (17.5 mg, 0.10 mmol) and chlorosulfonic acid (47 mg, 0.40 mmol) according to the General Procedure 6, described in Example 55. The title compound was obtained by reacting the preformed 5-bromo-4-methylthiophene-2-sulfonyl chloride with methyl 4-aminosalicylate (16 mg, 0.100 mmol) and pyridine (15 mg, 0.200 mmol) according to the General Procedure 6. The title compound was obtained in 44% yield (17.9 mg). $^1$H NMR (500 MHz, CDCl$_3$) δ ppm 2.16 (d, J=0.43 Hz, 3 H) 3.92 (s, 3 H) 6.67 (dd, J=8.67, 2.20 Hz, 1 H) 6.72 (d, J=2.20 Hz, 1 H) 6.91 (br. s., 1 H) 7.32 (q, J=0.43 Hz, 1 H) 7.76 (d, J=8.67 Hz, 1 H) 10.89 (s, 1 H). MS (ESI+) m/z 406 [M+H]$^+$.

Example 59

General Procedure 7

2-Methoxyethyl 4-{[(2,5-dichloro-3-thienyl)sulfonyl]amino}-2-hydroxybenzoate

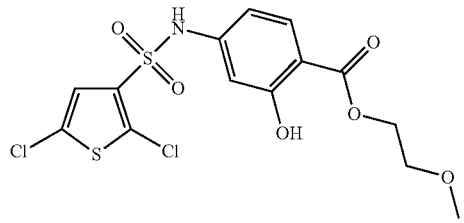 [SMILES: COCCOC(=O)c1ccc(NS(=O)(=O)c2cc(Cl)sc2Cl)cc1O]

A reaction mixture containing 4-{[(2,5-dichlorothiophen-3-yl)sulfonyl]amino}-2-hydroxybenzoic acid (18 mg, 0.050 mmol) (Intermediate 6), 1,1'-carbonyldiimidazole (16 mg, 0.100 mmol) and pyridine (8 mg, 0.100 mmol) in MeCN (0.5 mL) was stirred at room temperature for 45 min, and then 2-methoxyethanol (7.6 mg, 0.100 mmol) was added. The reaction mixture was stirred at room temperature overnight, then acidified with TFA and diluted with MeCN/MeOH/water. The crude product was purified by preparative HPLC (acidic system). The title compound was obtained in 66% yield (14 mg). $^1$H NMR (500 MHz, DMSO-$d_6$:CD$_3$OD 6:1) δ ppm 3.29 (s, 3 H) 3.61-3.65 (m, 2 H) 4.36-4.41 (m, 2 H) 6.70 (d, J=2.20 Hz, 1 H) 6.74 (dd, J=8.67, 2.20 Hz, 1 H) 7.40 (s, 1 H) 7.71 (d, J=8.67 Hz, 1 H). MS (ESI+) m/z 426 [M+H]$^+$.

Example 60

General Procedure 8

Ethyl 4-{[(4,5-dichloro-2-thienyl)sulfonyl]amino}-2-hydroxybenzoate

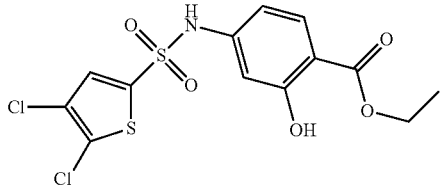 [SMILES: CCOC(=O)c1ccc(NS(=O)(=O)c2cc(Cl)c(Cl)s2)cc1O]

A reaction mixture containing 4-{[(4,5-dichlorothiophen-2-yl)sulfonyl]amino}-2-hydroxybenzoic acid (18 mg, 0.050 mmol) (Intermediate 7), 1,1'-carbonyldiimidazole (16 mg, 0.100 mmol) and pyridine (8 mg, 0.100 mmol) in MeCN (0.7 mL) was stirred at room temperature for 30 min, and then EtOH (50 μL, 0.858 mmol) was added. The reaction mixture was stirred at 55° C. for overnight, then acidified with TFA and diluted with MeCN/MeOH/water. The crude product was purified by preparative HPLC (acidic system). The title compound was obtained in 70% yield (13.9 mg). $^1$H NMR (500 MHz, CDCl$_3$) δ ppm 1.40 (t, J=7.14 Hz, 3 H) 4.39 (q, J=7.14 Hz, 2 H) 6.69 (dd, J=8.61, 2.26 Hz, 1 H) 6.74 (d, J=2.26 Hz, 1 H) 7.23 (br. s., 1 H) 7.41 (s, 1 H) 7.80 (d, J=8.61 Hz, 1 H) 11.01 (s, 1 H). MS (ESI+) m/z 396 [M+H]$^+$.

Example 61

2-(1H-Pyrrol-1-yl)ethyl 4-{[(4,5-dichlorothiophen-2-yl)sulfonyl]amino}-2-hydroxybenzoate

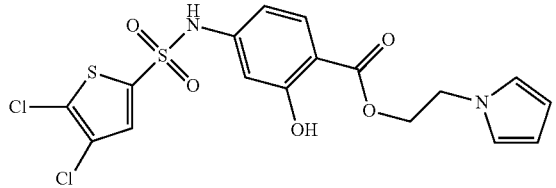 [SMILES: O=C(OCCn1cccc1)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18.4 mg, 0.050 mmol) (Intermediate 7), 1,1'-carbonyldiimidazole (32.5 mg, 0.200 mmol), pyridine (16 mg, 0.200 mmol) and 2-hydroxyethylpyrrole (22.4 mg, 0.200 mmol) according to the General Procedure 8, described in Example 60. The title compound was obtained in 60% yield (13.8 mg). $^1$H NMR (600 MHz, CD$_3$OD) δ ppm 4.28 (t, J=5.34 Hz, 2 H) 4.54 (t, J=5.34 Hz, 2 H) 6.05 (t, J=2.14 Hz, 2 H) 6.71 (dd, J=8.70, 2.20 Hz, 1 H) 6.74 (t, J=2.14 Hz, 2 H) 6.76 (d, J=2.20 Hz, 1 H) 7.52 (s, 1 H) 7.74 (d, J=8.70 Hz, 1 H). MS (ESI+) m/z 461 [M+H]$^+$.

Example 62

3-(1H-Pyrrol-1-yl)propyl 4-{[(4,5-dichlorothiophen-2-yl)sulfonyl]amino}-2-hydroxybenzoate

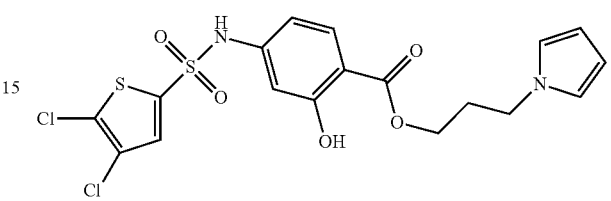

The product was prepared from 4-{[(4,5-dichlorothiophen-2-yl)sulfonyl]amino}-2-hydroxybenzoic acid (18.4 mg, 0.050 mmol) (Intermediate 7), 1,1'-carbonyldiimidazole (32.5 mg, 0.200 mmol), pyridine (16 mg, 0.200 mmol) and 1-(3-hydroxypropyl)pyrrole (25.7 mg, 0.205 mmol) according to the General Procedure 8, described in Example 60. The title compound was obtained in 66% yield (15.7 mg). $^1$H NMR (600 MHz, CD$_3$OD) δ ppm 2.16-2.24 (m, 2 H) 4.08 (t, J=6.64 Hz, 2 H) 4.26 (t, J=6.10 Hz, 2 H) 6.03 (t, J=2.14 Hz, 2 H) 6.69 (t, J=2.14 Hz, 2 H) 6.74 (dd, J=8.69, 2.21 Hz, 1 H) 6.77 (dd, J=2.21, 0.31 Hz, 1 H) 7.54 (s, 1 H) 7.77 (dd, J=8.70, 0.31 Hz, 1 H). MS (ESI+) m/z 475 [M+H]$^+$.

Example 63

3-Morpholin-4-ylpropyl 4-{[(4,5-dichlorothiophen-2-yl)sulfonyl]amino}-2-hydroxybenzoate trifluoroacetate

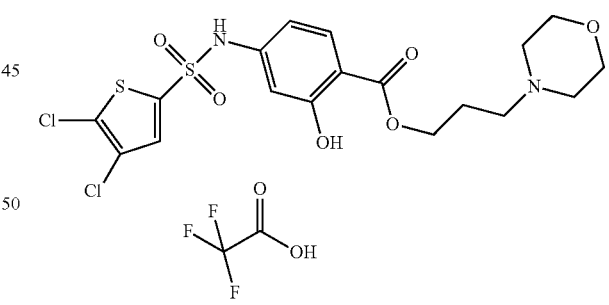

The product was prepared from 4-{[(4,5-dichlorothiophen-2-yl)sulfonyl]amino}-2-hydroxybenzoic acid (18.4 mg, 0.050 mmol) (Intermediate 7), 1,1'-carbonyldiimidazole (32.5 mg, 0.200 mmol), pyridine (16 mg, 0.200 mmol) and 4-(3-hydroxypropyl)morpholine (29.1 mg, 0.200 mmol) according to the General Procedure 8, described in Example 60. The title compound was obtained in 50% yield (15.3 mg). $^1$H NMR (600 MHz, CD$_3$OD) δ ppm 2.20-2.27 (m, 2 H) 3.32 (br. m., 2 H) 3.31-3.35 (m, 2 H) 3.47 (br. m., 2 H) 3.79 (br. m., 2 H) 4.04 (br. m., 2 H) 4.46 (t, J=6.03 Hz, 2 H) 6.76-6.79 (m, 2 H) 7.54 (s, 1 H) 7.82-7.85 (m, 1 H). MS (ESI+) m/z 495 [M+H]$^+$.

Example 64

3-(1H-Imidazol-1-yl)propyl 4-{[(4,5-dichlorothiophen-2-yl)sulfonyl]amino}-2-hydroxybenzoate trifluoroacetate

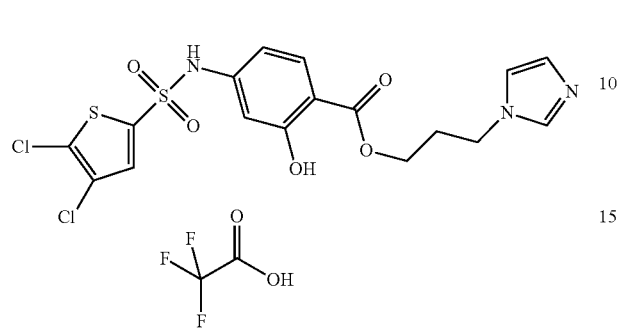

The product was prepared from 4-{[(4,5-dichlorothiophen-2-yl)sulfonyl]amino}-2-hydroxybenzoic acid (18.4 mg, 0.050 mmol) (Intermediate 7), 1,1'-carbonyldiimidazole (32.5 mg, 0.200 mmol), pyridine (16 mg, 0.200 mmol) and 3-(1H-imidazol-1-yl)propan-1-ol (25.9 mg, 0.205 mmol) according to the General Procedure 8, described in Example 60. The title compound was obtained in 68% yield (20.2 mg). $^1$H NMR (600 MHz, CD$_3$OD) δ ppm 2.36-2.43 (m, 2 H) 4.43 (t, J=5.85 Hz, 2 H) 4.44 (t, J=7.02 Hz, 2 H) 6.75-6.78 (m, 2 H) 7.55 (s, 1 H) 7.56 (t, J=1.64 Hz, 1 H) 7.72 (t, J=1.64 Hz, 1 H) 7.72-7.75 (m, 1 H) 8.99 (s, 1 H). MS (ESI+) m/z 476 [M+H]$^+$.

Example 65

3-(4-Methylpiperazin-1-yl)propyl 4-{[(4,5-dichlorothiophen-2-yl)sulfonyl]amino}-2-hydroxybenzoate trifluoroacetate

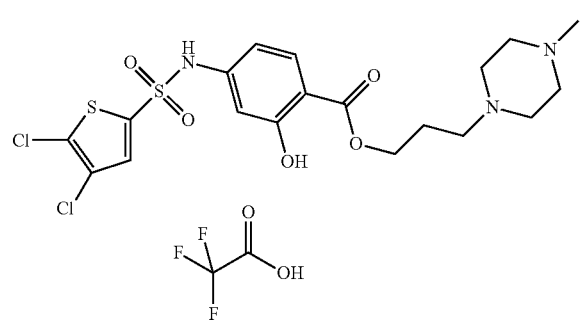 [SMILES: CN1CCN(CCCOC(=O)c2ccc(NS(=O)(=O)c3cc(Cl)c(Cl)s3)cc2O)CC1 ; O=C(O)C(F)(F)F]

The product was prepared from 4-{[(4,5-dichlorothiophen-2-yl)sulfonyl]amino}-2-hydroxybenzoic acid (18.4 mg, 0.050 mmol) (Intermediate 7), 1,1'-carbonyldiimidazole (32.5 mg, 0.200 mmol), pyridine (16 mg, 0.200 mmol) and 1-(3-hydroxypropyl)-4-methylpiperazine (32.6 mg, 0.206 mmol) according to the General Procedure 8, described in Example 60. The title compound was obtained in 47% yield (14.6 mg). $^1$H NMR (600 MHz, CD$_3$OD) δ ppm 1.99-2.06 (m, 2 H) 2.50-3.25 (br. m., 4 H) 2.74 (t, J=7.02 Hz, 2 H) 2.83 (s, 3 H) 3.21 (br. m., 4 H) 4.43 (t, J=6.33 Hz, 2 H) 6.76 (dd, J=8.54, 2.14 Hz, 1 H) 6.77 (dd, J=2.14, 0.31 Hz, 1 H) 7.54 (s, 1 H) 7.80 (dd, J=8.54, 0.31 Hz, 1 H). MS (ESI+) m/z 508 [M+H]$^+$.

Example 66

2-Ethoxyethyl 4-{[(2,5-dichloro-3-thienyl)sulfonyl]amino}-2-hydroxybenzoate

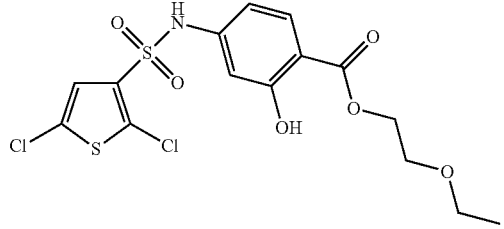 [SMILES: CCOCCOC(=O)c1ccc(NS(=O)(=O)c2cc(Cl)sc2Cl)cc1O]

The product was prepared from 4-{[(2,5-dichlorothiophen-3-yl)sulfonyl]amino}-2-hydroxybenzoic acid (18 mg, 0.50 mmol) (Intermediate 6) and 2-ethoxyethanol (8 mg, 0.105 mmol) according to the General Procedure 7, described in Example 59. The title compound was obtained in 15% yield (3.4 mg). $^1$H NMR (500 MHz, CDCl$_3$) δ ppm 1.23 (t, J=7.08 Hz, 3 H) 3.58 (q, J=7.00 Hz, 2 H) 3.73-3.78 (m, 2 H) 4.44-4.49 (m, 2 H) 6.67 (dd, J=8.55, 2.20 Hz, 1 H) 6.71 (d, J=2.20 Hz, 1 H) 7.17 (s, 1 H) 7.48 (s, 1 H) 7.81 (d, J=8.79 Hz, 1 H) 10.84 (s, 1 H). MS (ESI+) m/z 440 [M+H]$^+$.

Example 67

Tetrahydrofuran-3-yl 4-{[(2,5-dichloro-3-thienyl)sulfonyl]amino}-2-hydroxybenzoate

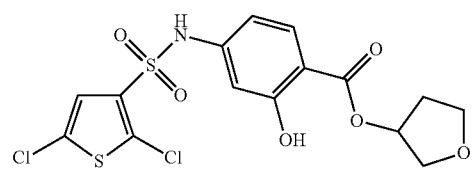 [SMILES: O=C(OC1CCOC1)c1ccc(NS(=O)(=O)c2cc(Cl)sc2Cl)cc1O]

The product was prepared from 4-{[(2,5-dichlorothiophen-3-yl)sulfonyl]amino}-2-hydroxybenzoic acid (18 mg, 0.50 mmol) (Intermediate 6) and 3-hydroxytetrahydrofuran (9 mg, 0.102 mmol) according to the General Procedure 7, described in Example 59. The title compound was obtained in 64% yield (14.0 mg). $^1$H NMR (500 MHz, DMSO-d$_6$) δ ppm 2.01-2.09 (m, 1 H) 2.17-2.26 (m, 1 H) 3.75 (td, J=8.30, 4.52 Hz, 1 H) 3.80-3.88 (m, 2 H) 3.86 (dd, J=10.50, 4.27 Hz, 1 H) 5.43-5.47 (m, 1 H) 6.69 (d, J=2.20 Hz, 1 H) 6.72 (dd, J=8.67, 2.20 Hz, 1 H) 7.40 (s, 1 H) 7.71 (d, J=8.67 Hz, 1 H). MS (ESI+) m/z 438 [M+H]$^+$.

Example 68

Isopropyl 4-{[(4,5-dichloro-2-thienyl)sulfonyl]amino}-2-hydroxybenzoate

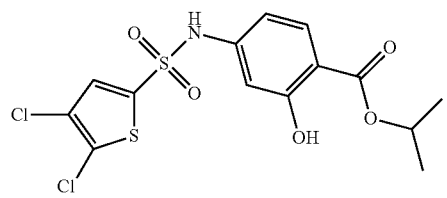 [SMILES: CC(C)OC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 2-propanol (50 μL, 0.654 mmol) according to the General Procedure 8, described in Example 60. The title compound was obtained in 80% yield (16.4 mg). $^1$H NMR (500 MHz, CDCl$_3$) δ ppm 1.38 (d, J=6.23 Hz, 6 H) 5.27 (spt, J=6.27 Hz, 1 H) 6.67 (dd, J=8.67, 2.20 Hz, 1 H) 6.72 (d, J=2.20 Hz, 1 H) 6.95 (br. s., 1 H) 7.41 (s, 1 H) 7.79 (d, J=8.67 Hz, 1 H) 11.10 (s, 1 H). MS (ESI+) m/z 410 [M+H]$^+$.

Example 69

2-Methoxyethyl 4-{[(4,5-dichloro-2-thienyl)sulfonyl]amino}-2-hydroxybenzoate

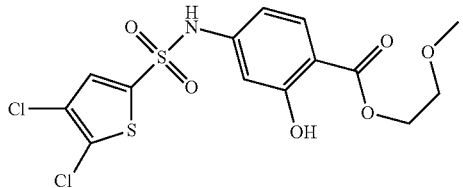 [SMILES: COCCOC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 2-methoxyethanol (50 μL, 0.634 mmol) according to the General Procedure 8, described in Example 60. The title compound was obtained in 68% yield (14.6 mg). $^1$H NMR (500 MHz, CDCl$_3$) δ ppm 3.42 (s, 3 H) 3.70-3.74 (m, 2 H) 4.47-4.50 (m, 2 H) 6.68 (dd, J=8.67, 2.32 Hz, 1 H) 6.73 (d, J=2.32 Hz, 1 H) 6.91 (br. s., 1 H) 7.41 (s, 1 H) 7.84 (d, J=8.67 Hz, 1 H) 10.86 (s, 1 H). MS (ESI+) m/z 426 [M+H]$^+$.

Example 70

Butyl 4-{[(4,5-dichloro-2-thienyl)sulfonyl]amino}-2-hydroxybenzoate

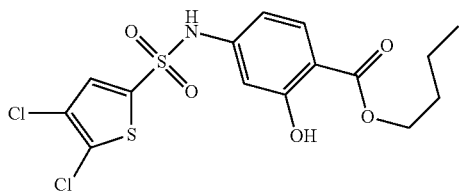 [SMILES: CCCCOC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 1-butanol (50 μL, 0.546 mmol) according to the General Procedure 8, described in Example 60. The title compound was obtained in 60% yield (12.8 mg). $^1$H NMR (500 MHz, CDCl$_3$) δ ppm 0.98 (t, J=7.45 Hz, 3 H) 1.43-1.51 (m, 2 H) 1.71-1.79 (m, 2 H) 4.34 (t, J=6.65 Hz, 2 H) 6.68 (dd, J=8.61, 2.26 Hz, 1 H) 6.72 (d, J=2.26 Hz, 1 H) 6.87 (br. s., 1 H) 7.42 (s, 1 H) 7.80 (d, J=8.61 Hz, 1 H) 11.02 (s, 1 H). MS (ESI+) m/z 424 [M+H]$^+$.

Example 71

Benzyl 4-{[(4,5-dichloro-2-thienyl)sulfonyl]amino}-2-hydroxybenzoate

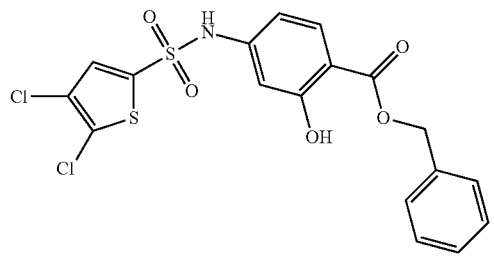 [SMILES: O=C(OCc1ccccc1)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and benzyl alcohol (50 μL, 0.483 mmol) according to the General Procedure 8, described in Example 60. The title compound was obtained in 55% yield (12.7 mg). $^1$H NMR (500 MHz, CDCl$_3$) δ ppm 5.37 (s, 2 H) 6.67 (dd, J=8.67, 2.20 Hz, 1 H) 6.75 (d, J=2.20 Hz, 1 H) 7.03 (br. s., 1 H) 7.35-7.46 (m, 5 H) 7.42 (s, 1 H) 7.84 (d, J=8.67 Hz, 1 H) 10.92 (s, 1 H). MS (ESI+) m/z 458 [M+H]$^+$.

Example 72

Hexyl 4-{[(4,5-dichloro-2-thienyl)sulfonyl]amino}-2-hydroxybenzoate

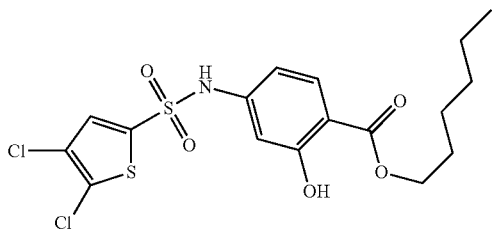 [SMILES: CCCCCCOC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 1-hexanol (50 μL, 0.398 mmol) according to the General Procedure 8, described in Example 60. The title compound was obtained in 71% yield (16.0 mg). $^1$H NMR (500 MHz, CDCl$_3$) δ ppm 0.87-0.94 (m, 3 H) 1.29-1.38 (m, 4 H) 1.38-1.47 (m, 2 H) 1.72-1.80 (m, 2 H) 4.32 (t, J=6.71 Hz, 2 H) 6.68 (dd, J=8.61, 2.26 Hz, 1 H) 6.72 (d, J=2.26 Hz, 1 H) 6.87 (br. s., 1 H) 7.41 (s, 1 H) 7.79 (d, J=8.61 Hz, 1 H) 11.02 (s, 1 H). MS (ESI+) m/z 452 [M+H]$^+$.

Example 73

Phenyl 4-{[(4,5-dichloro-2-thienyl)sulfonyl]amino}-2-hydroxybenzoate

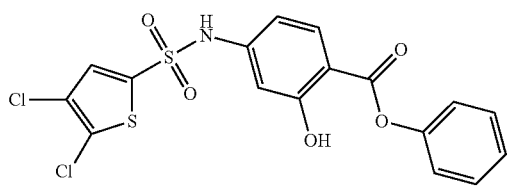 [SMILES: O=C(Oc1ccccc1)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and phenol (50 μL, 0.568 mmol) according to the General Procedure 8, described in Example 60. The title compound was obtained in 75% yield (16.7 mg). ¹H NMR (500 MHz, CDCl₃) δ ppm 6.78 (dd, J=8.67, 2.20 Hz, 1 H) 6.81 (d, J=2.20 Hz, 1 H) 7.17-7.21 (m, 2 H) 7.29-7.34 (m, 1 H) 7.33 (br. s., 1 H) 7.42-7.47 (m, 2 H) 7.45 (s, 1 H) 8.03 (d, J=8.67 Hz, 1 H) 10.66 (s, 1 H). MS (ESI+) m/z 444 [M+H]⁺.

Example 74

Tetrahydrofuran-3-yl 4-{[(4,5-dichloro-2-thienyl)sulfonyl]amino}-2-hydroxybenzoate

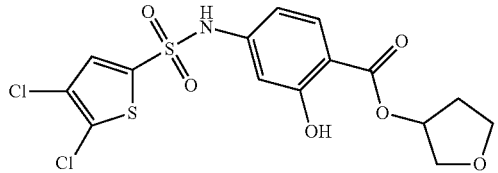 [SMILES: O=C(OC1CCOC1)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 3-hydroxytetrahydrofuran (50 μL, 0.619 mmol) according to the General Procedure 8, described in Example 60. The title compound was obtained in 78% yield (17.0 mg). ¹H NMR (500 MHz, CDCl₃) δ ppm 2.12-2.19 (m, 1 H) 2.25-2.34 (m, 1 H) 3.92 (td, J=8.48, 4.39 Hz, 1 H) 3.95-4.03 (m, 3 H) 5.55 (dddd, J=6.27, 4.27, 2.01, 1.89 Hz, 1 H) 6.68 (dd, J=8.67, 2.32 Hz, 1 H) 6.75 (d, J=2.32 Hz, 1 H) 7.14 (br. s., 1 H) 7.42 (s, 1 H) 7.78 (d, J=8.67 Hz, 1 H) 10.85 (s, 1 H). MS (ESI+) m/z 438 [M+H]⁺.

Example 75

Tetrahydrofuran-3-ylmethyl 4-{[(4,5-dichloro-2-thienyl)sulfonyl]amino}-2-hydroxybenzoate

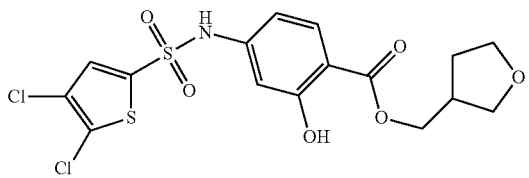 [SMILES: O=C(OCC1CCOC1)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and tetrahydro-3-furanmethanol (50 μL, 0.519 mmol) according to the General Procedure 8, described in Example 60. The title compound was obtained in 72% yield (16.3 mg). ¹H NMR (500 MHz, CDCl₃) δ ppm 1.72 (dddd, J=12.68, 7.95, 6.95, 5.83 Hz, 1 H) 2.12 (dddd, J=12.68, 8.40, 7.73, 5.44 Hz, 1 H) 2.67-2.77 (m, 1 H) 3.68 (dd, J=8.97, 5.25 Hz, 1 H) 3.79 (dddd, J=8.58, 7.73, 6.95, 1 H) 3.89 (dd, J=8.97, 7.07 Hz, 1 H) 3.92 (ddd, J=8.58, 7.95, 5.44 Hz, 1 H) 4.25 (dd, J=10.86, 7.81 Hz, 1 H) 4.34 (dd, J=10.86, 6.47 Hz, 1 H) 6.69 (dd, J=8.67, 2.26 Hz, 1 H) 6.74 (d, J=2.26 Hz, 1 H) 7.09 (br. s., 1 H) 7.42 (s, 1 H) 7.77 (d, J=8.67 Hz, 1 H) 10.88 (s, 1 H). MS (ESI+) m/z 452 [M+H]⁺.

Example 76

2-Methoxyethyl 4-({[5-chloro-4-(2,3-dihydro-1-benzofuran-5-yl)-2-thienyl]sulfonyl}amino)-2-hydroxybenzoate

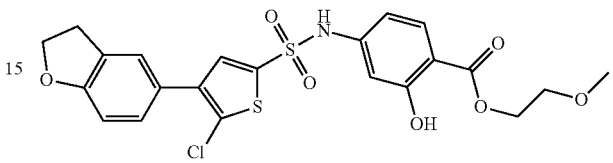

The product was prepared from 4-({[5-chloro-4-(2,3-dihydro-1-benzofuran-5-yl)thiophen-2-yl]sulfonyl}amino)-2-hydroxybenzoic acid (13 mg, 0.022 mmol) (Intermediate 2), 1,1'-carbonyldiimidazole (16 mg, 0.100 mmol), pyridine (8 mg, 0.100 mmol) and 2-methoxyethanol (50 μL, 0.63 mmol) according to the General Procedure 8, described in Example 60, using 0.5 mL MeCN. The title compound was obtained in 91% yield (10 mg). ¹H NMR (500 MHz, CDCl₃) δ ppm 3.25 (t, J=8.73 Hz, 2 H) 3.41 (s, 3 H) 3.69-3.73 (m, 2 H) 4.45-4.49 (m, 2 H) 4.62 (t, J=8.73 Hz, 2 H) 6.71 (dd, J=8.67, 2.32 Hz, 1 H) 6.75 (d, J=2.32 Hz, 1 H) 6.83 (d, J=8.30 Hz, 1 H) 7.06 (s, 1 H) 7.19-7.23 (m, 1 H) 7.29-7.31 (m, 1 H) 7.54 (s, 1 H) 7.82 (d, J=8.67 Hz, 1 H) 10.84 (s, 1 H). MS (ESI+) m/z 510 [M+H]⁺.

Example 77

Methyl 4-[({5-chloro-4-[3-(methoxycarbonyl)phenyl]thiophen-2-yl}sulfonyl)amino]-2-hydroxybenzoate

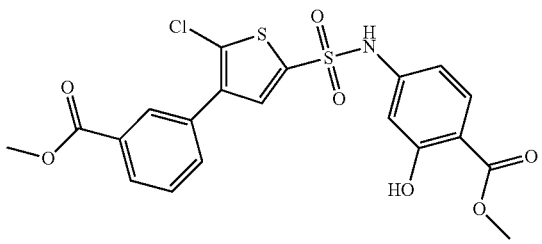 [SMILES: COC(=O)c1cccc(-c2cc(S(=O)(=O)Nc3ccc(C(=O)OC)c(O)c3)sc2Cl)c1]

The product was prepared from 3-(2-chloro-5-{[3-hydroxy-4-(methoxycarbonyl)phenyl]sulfamoyl}thiophen-3-yl)benzoic acid (14 mg, 0.030 mmol) (Intermediate 13), 1,1'-carbonyldiimidazole (16 mg, 0.100 mmol), pyridine (8 mg, 0.100 mmol) and MeOH (100 μL, 2.49 mmol) according to the General Procedure 8, described in Example 60. The title compound was obtained in 72% yield (10.4 mg). ¹H NMR (600 MHz, CDCl₃) δ ppm 3.92 (s, 3 H) 3.94 (s, 3 H) 6.72 (dd, J=8.70, 2.29 Hz, 1 H) 6.76 (d, J=2.29 Hz, 1 H) 6.99 (br. s., 1 H) 7.52 (td, J=7.77, 0.57 Hz, 1 H) 7.61 (s, 1 H) 7.67 (ddd, J=7.77, 1.90, 1.21 Hz, 1 H) 7.79 (d, J=8.70 Hz, 1 H) 8.06 (ddd, J=7.77, 1.67, 1.21 Hz, 1 H) 8.13 (ddd, J=1.90, 0.57 Hz, 1 H) 10.91 (s, 1 H). MS (ESI+) m/z 482 [M+H]⁺.

Example 78

Methyl 4-{[(5-chloro-4-{3-[(1-methylethoxy)carbonyl]phenyl}thiophen-2-yl)sulfonyl]amino}-2-hydroxybenzoate

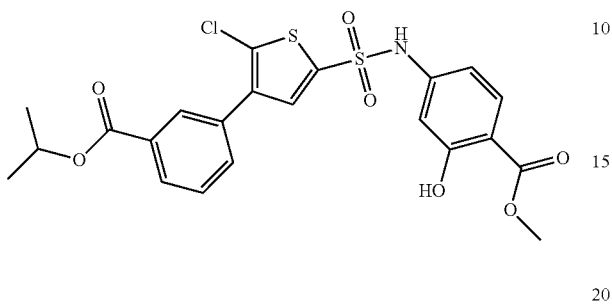

The product was prepared from 3-(2-chloro-5-{[3-hydroxy-4-(methoxycarbonyl)phenyl]sulfamoyl}thiophen-3-yl)benzoic acid (14 mg, 0.030 mmol) (Intermediate 13), 1,1'-carbonyldiimidazole (16 mg, 0.100 mmol), pyridine (8 mg, 0.100 mmol) and 2-propanol (100 µL, 1.31 mmol) according to the General Procedure 8, described in Example 60. The title compound was obtained in 42% yield (6.4 mg). $^1$H NMR (600 MHz, CDCl$_3$) δ ppm 1.38 (d, J=6.26 Hz, 6 H) 3.92 (s, 3 H) 5.27 (spt, J=6.26 Hz, 1 H) 6.72 (dd, J=8.62, 2.25 Hz, 1 H) 6.77 (d, J=2.25 Hz, 1 H) 7.02 (br. s., 1 H) 7.51 (td, J=7.77, 0.55 Hz, 1 H) 7.62 (s, 1 H) 7.65 (ddd, J=7.77, 1.90, 1.18 Hz, 1 H) 7.79 (d, J=8.62 Hz, 1 H) 8.06 (ddd-, J=7.77, 1.65, 1.18 Hz, 1 H) 8.11 (ddd, J=1.90, 1.65, 0.55 Hz, 1 H) 10.91 (s, 1 H). MS (ESI+) m/z 510 [M+H]$^+$.

Example 79

3-Hydroxypropyl 4-{[(4,5-dichlorothiophen-2-yl)sulfonyl]amino}-2-hydroxybenzoate

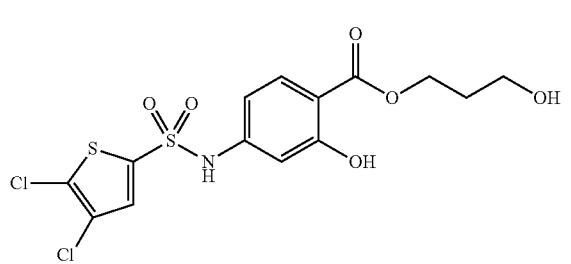 [SMILES: O=C(OCCCO)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.050 mmol) (Intermediate 7) and 1-propanediol (158 mg, 2.1 mmol) according to the General Procedure 8, described in Example 60. The title compound was obtained in 59% yield (12 mg). $^1$H NMR (600 MHz, CDCl$_3$) δ ppm 2.03 (quin, J=6.10 Hz, 2 H) 3.80 (t, J=5.95 Hz, 2 H) 4.52 (t, J=6.26 Hz, 2 H) 6.69 (dd, J=8.70, 2.29 Hz, 1 H) 6.74 (d, J=2.14 Hz, 1 H) 6.77 (br. s., 1 H) 7.43 (s, 1 H) 7.80 (d, J=8.55 Hz, 1 H) 10.91 (s, 1 H). MS (ESI+) m/z 426 [M+H]$^+$.

Example 80

3-(Dimethylamino)propyl 4-{[(4,5-dichloro-2-thienyl)sulfonyl]amino}-2-hydroxybenzoate trifluoroacetate

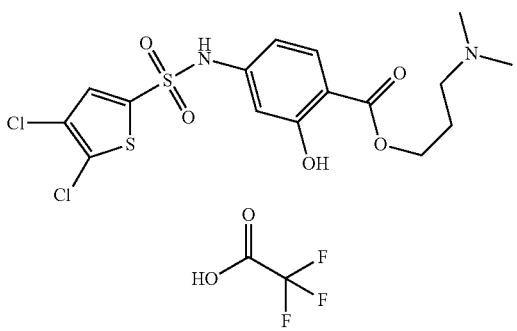

A solution of 4-{[(4,5-dichlorothiophen-2-yl)sulfonyl]amino}-2-hydroxybenzoic acid (Intermediate 7) (18 mg, 0.050 mmol), pyridine (8 mg, 0.10 mmol) and 1,1'-carbonyldiimidazole (16 mg, 0.10 mmol) in 700 µL of MeCN was prepared. After 30 minutes was 3-dimethylamino-1-propanol (50 µL, excess) added. The reaction was shaken at 50° C. overnight. The reaction was acidified by addition of TFA, diluted with water/MeCN and purified by preparative HPLC (acidic system). The title compound was obtained in 56% yield (15.8 mg). $^1$H NMR (500 MHz, CDCl$_3$) δ ppm 2.26-2.35 (m, 2 H) 2.87 (s, 6 H) 3.15-3.23 (m, 2 H) 4.42 (t, J=6.10 Hz, 2 H) 6.68 (dd, J=8.67, 2.26 Hz, 1 H) 6.78 (d, J=2.26 Hz, 1 H) 7.43 (s, 1 H) 7.56 (br. s., 1 H) 7.73 (d, J=8.67 Hz, 1 H) 10.71 (br. s., 1 H). MS (ESI+) m/z 453 [M+H]$^+$.

Example 81

Methyl 4-({[6-chloro-5-(2-fluoro-3-methoxyphenyl)pyridin-3-yl]sulfonyl}amino)-2-hydroxybenzoate

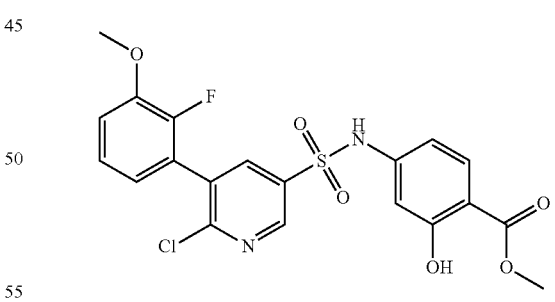

A mixture of methyl 4-{[(5-bromo-6-chloropyridin-3-yl)sulfonyl]amino}-2-hydroxybenzoate (Intermediate 8) (21.1 mg, 0.050 mmol), 2-fluoro-3-methoxyphenylboronic acid (9.7 mg, 0.055 mmol), DIPEA (35 µL, 0.200 mmol) and Pd(dppf)Cl$_2$.CH$_2$Cl$_2$ (2 mg, 0.002 mmol) in aqueous dioxane (1 mL, 9:1 dioxane/water) was heated at 80° C. under nitrogen atmosphere for 1 day. The reaction mixture was acidified by addition of TFA (50 µL). After being allowed to settle overnight the reaction mixture was filtered, diluted with MeOH and purified by preparative HPLC (acidic system). The product was further purified by preparative HPLC (Basic system 2) to give the title compound in 7% yield (1.6 mg). $^1$H NMR (600 MHz, CDCl$_3$) δ ppm 3.93 (s, 3 H) 3.94 (s, 3 H) 6.65 (dd, J=8.68, 2.25 Hz, 1 H) 6.72 (d, J=2.25 Hz, 1 H) 6.82 (ddd, J=7.76, 6.08, 1.57 Hz, 1 H) 6.93 (br. s., 1 H) 7.09 (td, J=8.12, 1.57 Hz, 1 H) 7.18 (ddd, J=8.12, 7.76, 1.45 Hz, 1 H) 7.76 (d, J=8.68 Hz, 1 H) 8.08 (d, J=2.44 Hz, 1 H) 8.84 (d, J=2.44 Hz, 1 H) 10.89 (s, 1 H). MS (ESI+) m/z 467 [M+H]$^+$.

Example 82

General Procedure 9

Methyl 2-hydroxy-4-{[(2'-hydroxybiphenyl-3-yl)sulfonyl]amino}benzoate

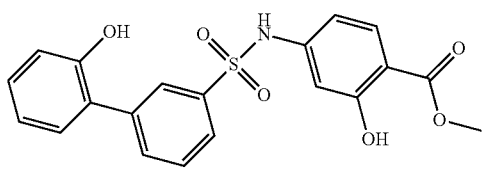 [SMILES: COC(=O)c1ccc(NS(=O)(=O)c2cccc(-c3ccccc3O)c2)cc1O]

A mixture of methyl 4-{[(3-bromophenyl)sulfonyl]amino}-2-hydroxybenzoate (Intermediate 4) (19 mg, 0.050 mmol), 2-(4,4,5,5-tetramethyl-1,3,2-dioxaborolan-2-yl)phenol (12.1 mg, 0.055 mmol), DIPEA (26 mg, 0.200 mmol) and Pd(dppf)Cl$_2$·CH$_2$Cl$_2$ (2 mg, 0.002 mmol) in aqueous dioxane (0.8 mL, 9:1 dioxane/water) was heated at 80° C. under nitrogen atmosphere for 1 day. The reaction mixture was acidified by addition of TFA (50 μL). The reaction mixture was filtered, diluted with MeOH/MeCN/water and purified by preparative HPLC (acidic system). The title compound was obtained in 82% yield (16.2 mg). $^1$H NMR (500 MHz, CDCl$_3$) δ ppm 3.90 (s, 3 H) 5.22 (br. s., 1 H) 6.64 (dd, J=8.67, 2.20 Hz, 1 H) 6.73 (d, J=2.20 Hz, 1 H) 6.93 (d, J=8.09 Hz, 1 H) 7.01 (ddd, J=7.69, 7.50, 0.55 Hz, 1 H) 7.06 (s, 1 H) 7.23 (dd, J=7.69, 1.59 Hz, 1 H) 7.27 (ddd, J=8.09, 7.50, 1.59 Hz, 1 H) 7.56 (dd, J=7.98, 7.74 Hz, 1 H) 7.70 (d, J=8.67 Hz, 1 H) 7.73 (ddd, J=7.74, 1.40, 1.19 Hz, 1 H) 7.85 (ddd, J=7.98, 1.89, 1.19 Hz, 1 H) 8.11 (dd, J=1.89, 1.40 Hz, 1 H) 10.86 (s, 1 H). MS (ESI+) m/z 400 [M+H]$^+$.

Example 83

Methyl 4-({[6-chloro-5-(3-fluorophenyl)pyridin-3-yl]sulfonyl}amino)-2-hydroxybenzoate

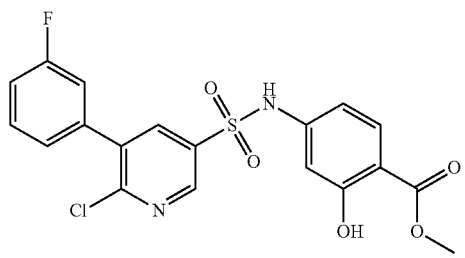 [SMILES: COC(=O)c1ccc(NS(=O)(=O)c2cnc(Cl)c(-c3cccc(F)c3)c2)cc1O]

The product was prepared from methyl 4-{[(5-bromo-6-chloropyridin-3-yl)sulfonyl]amino}-2-hydroxybenzoate (Intermediate 8) (21.1 mg, 0.050 mmol) and 3-fluorobenzeneboronic acid (7.7 mg, 0.055 mmol) according to the General Procedure 9, described in Example 82. The title compound was obtained in 29% yield (6.4 mg). $^1$H NMR (600 MHz, CDCl$_3$) δ ppm 3.93 (s, 3 H) 6.67 (dd, J=8.66, 2.20 Hz, 1 H) 6.71 (d, J=2.20 Hz, 1 H) 6.97 (br. s., 1 H) 7.09 (ddd, J=9.28, 2.55, 1.68 Hz, 1 H) 7.16 (ddd, J=7.68, 1.68, 0.98 Hz, 1 H) 7.17 (tdd, J=8.45, 2.55, 0.98 Hz, 1 H) 7.45 (ddd, J=8.45, 7.68, 5.80 Hz, 1 H) 7.77 (d, J=8.66 Hz, 1 H) 8.04 (d, J=2.44 Hz, 1 H) 8.82 (d, J=2.44 Hz, 1 H) 10.91 (s, 1 H). MS (ESI+) m/z 437 [M+H]$^+$.

Example 84

Methyl 4-({[5-(3-aminophenyl)-6-chloropyridin-3-yl]sulfonyl}amino)-2-hydroxybenzoate

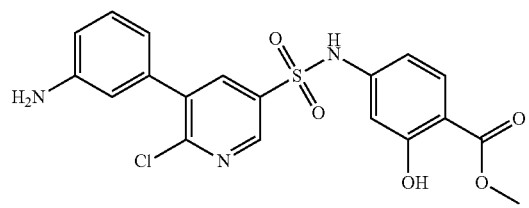 [SMILES: COC(=O)c1ccc(NS(=O)(=O)c2cnc(Cl)c(-c3cccc(N)c3)c2)cc1O]

The product was prepared from methyl 4-{[(5-bromo-6-chloropyridin-3-yl)sulfonyl]amino}-2-hydroxybenzoate (Intermediate 8) (21.1 mg, 0.050 mmol) and 3-(4,4,5,5-tetramethyl-1,3,2-dioxaborolan-2-yl)aniline (12 mg, 0.055 mmol) according to the General Procedure 9, described in Example 82. The title compound was obtained in 43% yield (9.4 mg). $^1$H NMR (600 MHz, CD$_3$OD) δ ppm 3.91 (s, 3 H) 6.72 (dd, J=8.70, 2.29 Hz, 1 H) 6.76 (d, J=2.29 Hz, 1 H) 7.14-7.17 (m, 1 H) 7.17-7.18 (m, 1 H) 7.21 (ddd, J=8.12, 2.21, 0.75 Hz, 1 H) 7.48 (dd, J=8.12, 7.70 Hz, 1 H) 7.76 (d, J=8.70 Hz, 1 H) 8.13 (d, J=2.44 Hz, 1 H) 8.80 (d, J=2.44 Hz, 1 H). MS (ESI+) m/z 434 [M+H]$^+$.

Example 85

Methyl 4-({[6-chloro-5-(4-fluoro-3-methylphenyl)pyridin-3-yl]sulfonyl}amino)-2-hydroxybenzoate

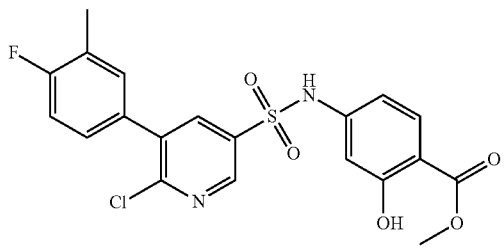 [SMILES: COC(=O)c1ccc(NS(=O)(=O)c2cnc(Cl)c(-c3ccc(F)c(C)c3)c2)cc1O]

The product was prepared from methyl 4-{[(5-bromo-6-chloropyridin-3-yl)sulfonyl]amino}-2-hydroxybenzoate (Intermediate 8) (21.1 mg, 0.050 mmol) and 4-fluoro-3-methylphenylboronic acid (8.5 mg, 0.055 mmol) according to the General Procedure 9, described in Example 82. The title compound was obtained in 38% yield (8.5 mg). $^1$H NMR (600 MHz, CDCl$_3$) δ ppm 2.33 (d, J=1.91 Hz, 3 H) 3.93 (s, 3 H) 6.67 (dd, J=8.65, 2.26 Hz, 1 H) 6.71 (d, J=2.26 Hz, 1 H) 7.03 (br. s., 1 H) 7.10 (dd, J=9.20, 8.30 Hz, 1 H) 7.16-7.19 (m, 1 H) 7.20 (dddd, J=8.30, 4.76, 2.44, 0.59 Hz, 1 H) 7.77 (d, J=8.65 Hz, 1 H) 8.02 (d, J=2.48 Hz, 1 H) 8.79 (d, J=2.48 Hz, 1 H) 10.92 (s, 1 H). MS (ESI+) m/z 451 [M+H]$^+$.

Example 86

Methyl 4-{[(3'-chlorobiphenyl-3-yl)sulfonyl]amino}-2-hydroxybenzoate

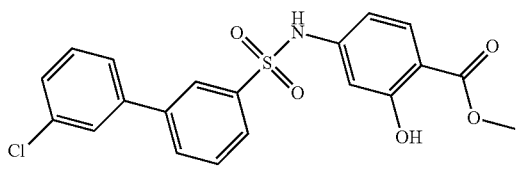 [SMILES: COC(=O)c1ccc(NS(=O)(=O)c2cccc(-c3cccc(Cl)c3)c2)cc1O]

The product was prepared from methyl 4-{[(3-bromophenyl)sulfonyl]amino}-2-hydroxybenzoate (Intermediate 4) (19 mg, 0.050 mmol) and (3-chlorophenyl)boronic acid (8.6 mg, 0.055 mmol) according to the General Procedure 9, described in Example 82. The title compound was obtained in 70% yield (15 mg). $^1$H NMR (500 MHz, CDCl$_3$) δ ppm 3.90 (s, 3 H) 6.66 (dd, J=8.61, 2.20 Hz, 1 H) 6.70 (d, J=2.20 Hz, 1 H) 6.98 (br. s., 1 H) 7.36-7.43 (m, 3 H) 7.47-7.49 (m, 1 H) 7.56 (td, J=7.82, 0.47 Hz, 1 H) 7.72 (d, J=8.61 Hz, 1 H) 7.74 (ddd, J=7.82, 1.86, 1.07 Hz, 1 H) 7.86 (ddd, J=7.82, 1.91, 1.04 Hz, 1 H) 8.03 (ddd, J=1.91, 1.86, 0.47 Hz, 1 H) 10.85 (s, 1 H). MS (ESI+) m/z 418 [M+H]$^+$.

Example 87

Methyl 4-[(biphenyl-3-ylsulfonyl)amino]-2-hydroxybenzoate

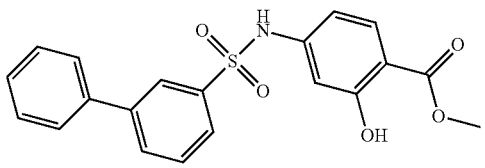 [SMILES: COC(=O)c1ccc(NS(=O)(=O)c2cccc(-c3ccccc3)c2)cc1O]

The product was prepared from methyl 4-{[(3-bromophenyl)sulfonyl]amino}-2-hydroxybenzoate (Intermediate 4) (19 mg, 0.050 mmol) and phenylboronic acid (6.7 mg, 0.055 mmol) according to the General Procedure 9, described in Example 82. The title compound was obtained in 70% yield (13 mg). $^1$H NMR (500 MHz, CDCl$_3$) δ ppm 3.89 (s, 3 H) 6.65 (dd, J=8.67, 2.20 Hz, 1 H) 6.70 (d, J=2.20 Hz, 1 H) 6.94 (s, 1 H) 7.37-7.43 (m, 1 H) 7.44-7.48 (m, 2 H) 7.52-7.55 (m, 2 H) 7.55 (ddd, J=7.87, 7.78, 0.46 Hz, 1 H) 7.71 (d, J=8.67 Hz, 1 H) 7.78 (ddd, J=7.78, 1.74, 1.10 Hz, 1 H) 7.83 (ddd, J=7.87, 1.89, 1.10 Hz, 1 H) 8.09 (ddd, J=1.89, 1.74, 0.46 Hz, 1 H) 10.84 (s, 1 H). MS (ESI+) m/z 384 [M+H]$^+$.

Example 88

Methyl 2-hydroxy-4-{[(3-pyridin-3-ylphenyl)sulfonyl]amino}benzoate trifluoroacetate

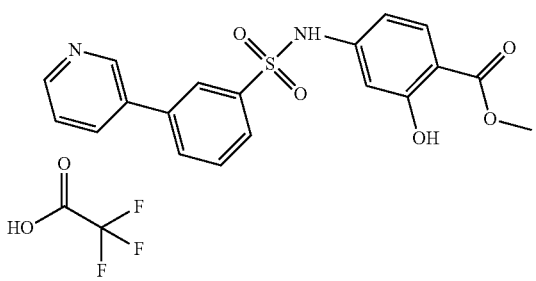

The product was prepared from methyl 4-{[(3-bromophenyl)sulfonyl]amino}-2-hydroxybenzoate (Intermediate 4) (19 mg, 0.050 mmol) and pyridin-3-ylboronic acid (6.8 mg, 0.055 mmol) according to the General Procedure 9, described in Example 82. The title compound was obtained in 69% yield (17 mg). $^1$H NMR (500 MHz, CDCl$_3$) δ ppm 3.90 (s, 3 H) 6.68 (dd, J=8.67, 2.20 Hz, 1 H) 6.71 (d, J=2.20 Hz, 1 H) 7.30 (br. s., 1 H) 7.43 (ddd, J=7.95, 4.87, 0.80 Hz, 1 H) 7.61 (dd, J=7.90, 7.80 Hz, 1 H) 7.72 (d, J=8.67 Hz, 1 H) 7.78 (ddd, J=7.80, 1.83, 1.07 Hz, 1 H) 7.86 (ddd, J=7.95, 2.40, 1.60 Hz, 1 H) 7.91 (ddd, J=7.90, 1.90, 1.07 Hz, 1 H) 8.07 (dd, J=1.90, 1.83 Hz, 1 H) 8.67 (dd, J=4.87, 1.60 Hz, 1 H) 8.81 (dd, J=2.40, 0.80 Hz, 1 H) 10.85 (s, 1 H). MS (ESI+) m/z 385 [M+H]$^+$.

Example 89

Methyl 2-hydroxy-4-{[(3-pyridin-4-ylphenyl)sulfonyl]amino}benzoate trifluoroacetate

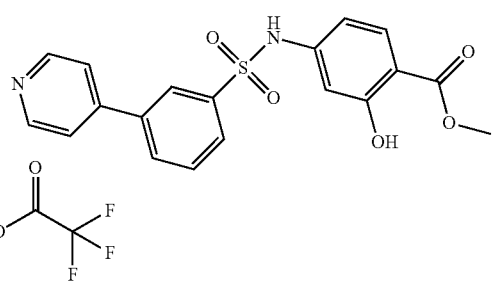

The product was prepared from methyl 4-{[(3-bromophenyl)sulfonyl]amino}-2-hydroxybenzoate (Intermediate 4) (19 mg, 0.050 mmol) and pyridin-4-ylboronic acid (6.8 mg, 0.055 mmol) according to the General Procedure 9, described in Example 82. The title compound was obtained in 73% yield (18 mg). $^1$H NMR (500 MHz, CDCl$_3$) δ ppm 3.80 (s, 3 H) 6.73 (dd, J=2.20, 0.53 Hz, 1 H) 6.74 (dd, J=8.49, 2.20 Hz, 1 H) 7.65 (dd, J=8.49, 0.53 Hz, 1 H) 7.70-7.73 (m, 2 H) 7.75 (dd, J=7.91, 7.81 Hz, 1 H) 7.92 (ddd, J=7.91, 1.85, 1.04 Hz, 1 H) 8.08 (ddd, J=7.81, 1.85, 1.04 Hz, 1 H) 8.19 (t, J=1.85 Hz, 1 H) 8.68-8.73 (m, 2 H) 10.55 (s, 1 H) 10.94 (s, 1 H). MS (ESI+) m/z 385 [M+H]$^+$.

Example 90

Methyl 4-({[3-(1-benzofuran-2-yl)phenyl]sulfonyl}amino)-2-hydroxybenzoate

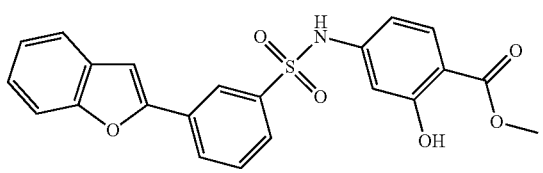 [SMILES: COC(=O)c1ccc(NS(=O)(=O)c2cccc(-c3cc4ccccc4o3)c2)cc1O]

The product was prepared from methyl 4-{[(3-bromophenyl)sulfonyl]amino}-2-hydroxybenzoate (Intermediate 4) (19 mg, 0.050 mmol) and 1-benzofuran-2-ylboronic acid (8.9 mg, 0.055 mmol) according to the General Procedure 9, described in Example 82. The title compound was obtained in 72% yield (15 mg). $^1$H NMR (500 MHz, CDCl$_3$) δ ppm 3.88 (s, 3 H) 6.67 (dd, J=8.67, 2.20 Hz, 1 H) 6.72 (d, J=2.20 Hz, 1 H) 7.06 (br. s., 1 H) 7.11 (d, J=0.92 Hz, 1 H) 7.26 (ddd, J=7.72, 7.26, 0.98 Hz, 1 H) 7.33 (ddd, J=8.21, 7.26, 1.35 Hz, 1 H) 7.53 (dddd, J=8.21, 0.98, 0.92, 0.77 Hz, 1 H) 7.55 (t, J=7.85 Hz, 1 H) 7.61 (ddd, J=7.72, 1.35, 0.77 Hz, 1 H) 7.71 (d, J=8.67 Hz, 1 H) 7.81 (ddd, J=7.85, 1.88, 1.05 Hz, 1 H) 8.02 (ddd, J=7.85, 1.66, 1.05 Hz, 1 H) 8.36 (dd, J=1.88, 1.66 Hz, 1 H) 10.84 (s, 1 H). MS (ESI+) m/z 424 [M+H]+.

Example 91

Methyl 2-hydroxy-4-{[(3-quinolin-6-ylphenyl)sulfonyl]amino}benzoate trifluoroacetate

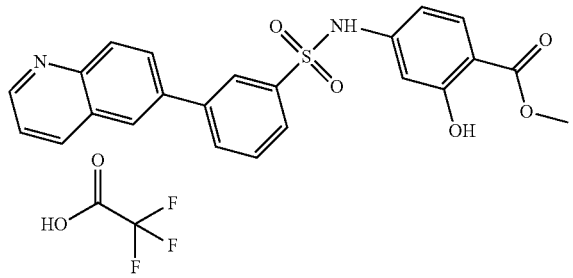

The product was prepared from methyl 4-{[(3-bromophenyl)sulfonyl]amino}-2-hydroxybenzoate (Intermediate 4) (19 mg, 0.050 mmol) and 6-(4,4,5,5-tetramethyl-1,3,2-dioxaborolan-2-yl)quinoline (14 mg, 0.055 mmol) according to the General Procedure 9, described in Example 82. The title compound was obtained in 58% yield (16 mg). 1H NMR (500 MHz, CDCl3:DMSO-d6 6:1) δ ppm 3.57 (s, 3 H) 6.46 (dd, J=8.75, 2.14 Hz, 1 H) 6.55 (d, J=2.14 Hz, 1 H) 7.20 (dd, J=8.26, 4.20 Hz, 1 H) 7.32 (t, J=7.82 Hz, 1 H) 7.36 (d, J=8.75 Hz, 1 H) 7.59 (ddd, J=7.82, 1.86, 1.04 Hz, 1 H) 7.61 (ddd, J=7.82, 1.86, 1.04 Hz, 1 H) 7.64 (dd, J=8.76, 2.14 Hz, 1 H) 7.73 (d, J=2.14 Hz, 1 H) 7.87 (d, J=8.76 Hz, 1 H) 7.94 (t, J=1.86 Hz, 1 H) 7.96-8.00 (m, 1 H) 8.64 (dd, J=4.20, 1.73 Hz, 1 H) 10.23 (s, 1 H) 10.48 (s, 1 H). MS (ESI+) m/z 435 [M+H]+.

Example 92

Methyl 4-{[(3'-aminobiphenyl-3-yl)sulfonyl]amino}-2-hydroxybenzoate trifluoroacetate

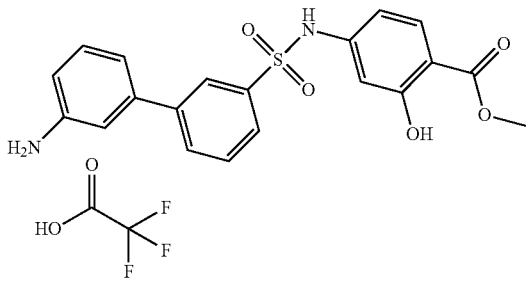

The product was prepared from methyl 4-{[(3-bromophenyl)sulfonyl]amino}-2-hydroxybenzoate (Intermediate 4) (19 mg, 0.050 mmol) and (3-(4,4,5,5-tetramethyl-1,3,2-dioxaborolan-2-yl)aniline (11 mg, 0.050 mmol) according to the General Procedure 9, described in Example 82. The title compound was obtained in 80% yield (21 mg). 1H NMR (600 MHz, CDCl3) δ ppm 3.78 (br. s., 2 H) 3.90 (s, 3 H) 6.63 (dd, J=8.65, 2.23 Hz, 1 H) 6.70 (d, J=2.23 Hz, 1 H) 6.72 (ddd, J=7.96, 2.29, 0.92 Hz, 1 H) 6.80 (br. s., 1 H) 6.82 (dd, J=2.29, 1.72 Hz, 1 H) 6.91 (ddd, J=7.65, 1.72, 0.92 Hz, 1 H) 7.23 (dd, J=7.96, 7.65 Hz, 1 H) 7.52 (t, J=7.86 Hz, 1 H) 7.71 (d, J=8.65 Hz, 1 H) 7.74 (ddd, J=7.86, 1.86, 1.07 Hz, 1 H) 7.81 (ddd, J=7.86, 1.86, 1.07 Hz, 1 H) 8.04 (t, J=1.86 Hz, 1 H) 10.85 (s, 1 H). MS (ESI+) m/z 399 [M+H]+.

Example 93

Methyl 4-{[(3'-acetamidobiphenyl-3-yl)sulfonyl]amino}-2-hydroxybenzoate

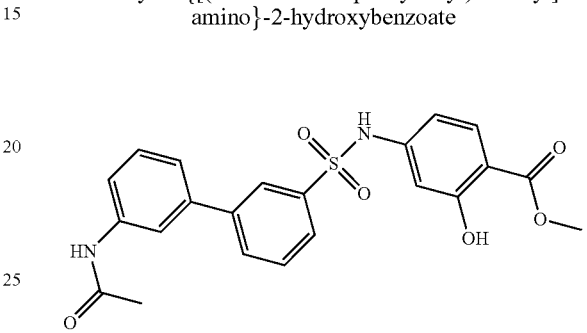

The product was prepared from methyl 4-{[(3-bromophenyl)sulfonyl]amino}-2-hydroxybenzoate (Intermediate 4) (19 mg, 0.050 mmol) and 3-acetamidobenzeneboronic acid (9 mg, 0.050 mmol) according to the General Procedure 9, described in Example 82. The title compound was obtained in 79% yield (17 mg). 1H NMR (600 MHz, CDCl3) δ ppm 2.22 (s, 3 H) 3.89 (s, 3 H) 6.63 (dd, J=8.70, 2.14 Hz, 1 H) 6.75 (d, J=2.14 Hz, 1 H) 6.96 (br. s., 1 H) 7.26-7.30 (m, 1 H) 7.40 (t, J=7.94 Hz, 1 H) 7.53 (t, J=7.78 Hz, 1H) 7.52-7.55 (m, 1H) 7.68-7.71 (m, 1 H) 7.71 (d, J=8.70 Hz, 1 H) 7.77 (ddd, J=7.78, 1.78, 0.99 Hz, 1 H) 7.83 (d, J=7.78 Hz, 1 H) 8.07 (t, J=1.78 Hz, 1 H) 10.88 (s, 1 H). MS (ESI+) m/z 441 [M+H]+.

Example 94

Methyl 2-hydroxy-4-{[(2'-nitrobiphenyl-3-yl)sulfonyl]amino}benzoate

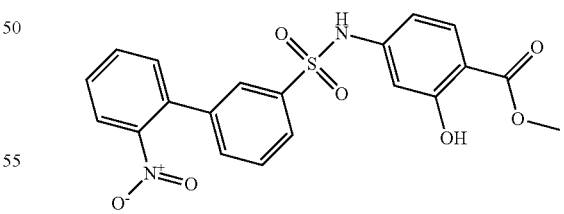

The product was prepared from methyl 4-{[(3-bromophenyl)sulfonyl]amino}-2-hydroxybenzoate (Intermediate 4) (19 mg, 0.050 mmol) and 2-nitrobenzeneboronic acid (8 mg, 0.050 mmol) according to the General Procedure 9, described in Example 82. The title compound was obtained in 64% yield (14 mg). 1H NMR (600 MHz, CDCl3) δ ppm 3.91 (s, 3 H) 6.62 (dd, J=8.70, 2.29 Hz, 1 H) 6.72 (d, J=2.29 Hz, 1 H) 6.81 (br. s., 1 H) 7.36 (dd, J=7.55, 1.40 Hz, 1 H) 7.49 (ddd, J=7.78, 1.82, 1.27 Hz, 1 H) 7.53 (t, J=7.78 Hz, 1

H) 7.56 (ddd, J=8.13, 7.55, 1.40 Hz, 1 H) 7.66 (td, J=7.55, 1.36 Hz, 1 H) 7.73 (d, J=8.70 Hz, 1 H) 7.83 (t, J=1.82 Hz, 1 H) 7.87 (ddd, J=7.78, 1.82, 1.27 Hz, 1 H) 7.97 (dd, J=8.13, 1.36 Hz, 1 H) 10.86 (s, 1 H). MS (ESI+) m/z 429 [M+H]$^+$.

Example 95

Methyl 4-({[3-(5-acetyl-2-thienyl)phenyl]sulfonyl}amino)-2-hydroxybenzoate

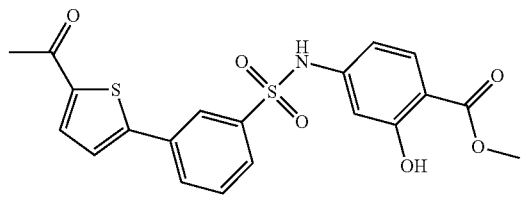 [SMILES: COC(=O)c1ccc(NS(=O)(=O)c2cccc(-c3ccc(C(C)=O)s3)c2)cc1O]

The product was prepared from methyl 4-{[(3-bromophenyl)sulfonyl]amino}-2-hydroxybenzoate (Intermediate 4) (19 mg, 0.050 mmol) and 5-acetyl-2-thiopheneboronic acid (8 mg, 0.050 mmol) according to the General Procedure 9, described in Example 82. The title compound was obtained in 66% yield (14 mg). $^1$H NMR (600 MHz, CDCl$_3$) δ ppm 2.58 (s, 3 H) 3.90 (s, 3 H) 6.66 (dd, J=8.62, 2.21 Hz, 1 H) 6.69 (d, J=2.21 Hz, 1 H) 6.90 (br. s., 1 H) 7.36 (d, J=3.97 Hz, 1 H) 7.54 (t, J=7.88 Hz, 1 H) 7.67 (d, J=3.97 Hz, 1 H) 7.73 (d, J=8.62 Hz, 1 H) 7.81 (ddd, J=7.88, 1.79, 0.99 Hz, 1 H) 7.83 (ddd, J=7.88, 1.68, 0.99 Hz, 1 H) 8.12 (dd, J=1.79, 1.68 Hz, 1 H) 10.85 (s, 1 H). MS (ESI+) m/z 432 [M+H]$^+$.

Example 96

Methyl 2-hydroxy-4-({[2'-(hydroxymethyl)biphenyl-3-yl]sulfonyl}amino)benzoate

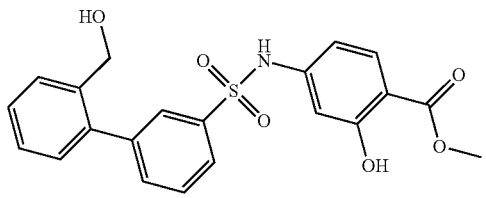 [SMILES: COC(=O)c1ccc(NS(=O)(=O)c2cccc(-c3ccccc3CO)c2)cc1O]

The product was prepared from methyl 4-{[(3-bromophenyl)sulfonyl]amino}-2-hydroxybenzoate (Intermediate 4) (19 mg, 0.050 mmol) and 2-hydroxymethylphenylboronic acid (8 mg, 0.050 mmol) according to the General Procedure 9, described in Example 82. The title compound was obtained in 83% yield (17 mg). $^1$H NMR (600 MHz, CDCl$_3$) δ ppm 2.00 (br. s., 1 H) 3.91 (s, 3 H) 4.45 (br. s., 2 H) 6.62 (dd, J=8.70, 2.24 Hz, 1 H) 6.77 (d, J=2.24 Hz, 1 H) 7.03 (br. s., 1 H) 7.23 (dd, J=7.49, 1.35 Hz, 1 H) 7.38 (td, J=7.49, 1.35 Hz, 1 H) 7.43 (td, J=7.49, 1.35 Hz, 1 H) 7.55 (dd, J=7.86, 7.64 Hz, 1 H) 7.56 (dd, J=7.49, 1.35 Hz, 1 H) 7.60 (ddd, J=7.64, 1.66, 1.20 Hz, 1 H) 7.71 (d, J=8.70 Hz, 1 H) 7.88 (ddd, J=7.86, 1.85, 1.20 Hz, 1 H) 8.05 (dd, J=1.85, 1.66 Hz, 1 H) 10.93 (s, 1 H). MS (ESI+) m/z 396 [M−OH]$^+$.

Example 97

Methyl 4-{[(3'-cyanobiphenyl-3-yl)sulfonyl]amino}-2-hydroxybenzoate

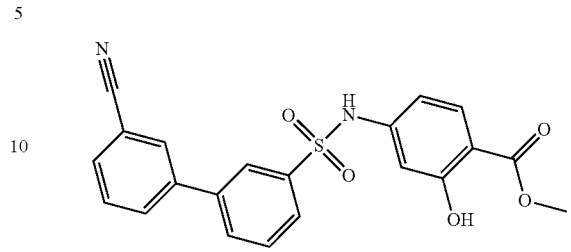

The product was prepared from methyl 4-{[(3-bromophenyl)sulfonyl]amino}-2-hydroxybenzoate (Intermediate 4) (19 mg, 0.050 mmol) and 3-cyanophenylboronic acid (7 mg, 0.050 mmol) according to the General Procedure 9, described in Example 82. The title compound was obtained in 59% yield (12 mg). $^1$H NMR (600 MHz, CDCl$_3$) δ ppm 3.91 (s, 3 H) 6.67 (dd, J=8.62, 2.21 Hz, 1 H) 6.69 (d, J=2.21 Hz, 1 H) 6.90 (br. s., 1 H) 7.59 (td, J=7.70, 0.61 Hz, 1 H) 7.61 (t, J=7.81 Hz, 1 H) 7.70 (ddd, J=7.72, 1.50, 1.20 Hz, 1 H) 7.74 (d, J=8.62 Hz, 1 H) 7.74-7.79 (m, 3 H) 7.91 (ddd, J=7.86, 1.83, 1.11 Hz, 1 H) 8.04 (t, J=1.83 Hz, 1 H) 10.87 (s, 1 H). MS (ESI+) m/z 409 [M+H]$^+$.

Example 98

Methyl 2-hydroxy-4-({[4'-(methylsulfanyl)biphenyl-3-yl]sulfonyl}amino)benzoate

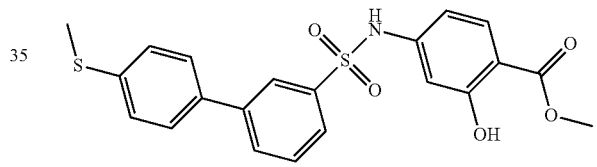

The product was prepared from methyl 4-{[(3-bromophenyl)sulfonyl]amino}-2-hydroxybenzoate (Intermediate 4) (19 mg, 0.050 mmol) and (4-methylthio)phenylboronic acid (8 mg, 0.050 mmol) according to the General Procedure 9, described in Example 82. The title compound was obtained in 62% yield (13 mg). $^1$H NMR (600 MHz, CDCl$_3$) δ ppm 2.53 (s, 3 H) 3.90 (s, 3 H) 6.65 (dd, J=8.70, 2.20 Hz, 1 H) 6.69 (d, J=2.20 Hz, 1 H) 6.82 (br. s., 1 H) 7.31-7.35 (m, 2 H) 7.44-7.48 (m, 2 H) 7.53 (dd, J=7.92, 7.82 Hz, 1 H) 7.71 (d, J=8.70 Hz, 1 H) 7.75 (ddd, J=7.82, 1.85, 1.06 Hz, 1 H) 7.81 (ddd, J=7.92, 1.85, 1.06 Hz, 1 H) 8.05 (t, J=1.85 Hz, 1 H) 10.84 (s, 1 H). MS (ESI+) m/z 430 [M+H]$^+$.

Example 99

Methyl 2-hydroxy-4-({[4'-(trifluoromethoxy)biphenyl-3-yl]sulfonyl}amino)benzoate

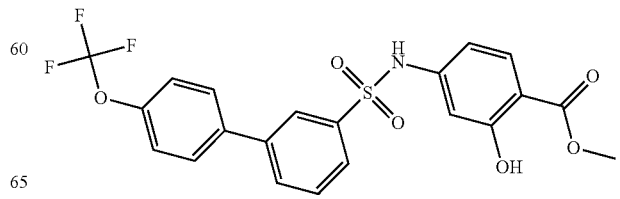

The product was prepared from methyl 4-{[(3-bromophenyl)sulfonyl]amino}-2-hydroxybenzoate (Intermediate 4) (19 mg, 0.050 mmol) and 4-(trifluoromethoxy)benzeneboronic acid (10 mg, 0.050 mmol) according to the General Procedure 9, described in Example 82. The title compound was obtained in 73% yield (17 mg). ¹H NMR (600 MHz, CDCl₃) δ ppm 3.90 (s, 3 H) 6.65 (dd, J=8.70, 2.20 Hz, 1 H) 6.69 (d, J=2.20 Hz, 1 H) 6.83 (br. s., 1 H) 7.29-7.34 (m, 2 H) 7.53-7.57 (m, 2 H) 7.57 (dd, J=7.89, 7.79 Hz, 1 H) 7.72 (d, J=8.70 Hz, 1 H) 7.75 (ddd, J=7.79, 1.83, 1.10 Hz, 1 H) 7.86 (ddd, J=7.89, 1.83, 1.10 Hz, 1 H) 8.05 (t, J=1.83 Hz, 1 H) 10.85 (s, 1 H). MS (ESI+) m/z 468 [M+H]⁺.

Example 100

Methyl 2-hydroxy-4-({[4'-(trifluoromethyl)biphenyl-3-yl]sulfonyl}amino)benzoate

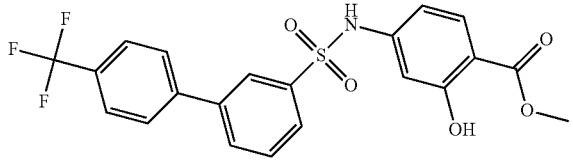 [SMILES: COC(=O)c1ccc(NS(=O)(=O)c2cccc(-c3ccc(C(F)(F)F)cc3)c2)cc1O]

The product was prepared from methyl 4-{[(3-bromophenyl)sulfonyl]amino}-2-hydroxybenzoate (Intermediate 4) (19 mg, 0.050 mmol) and 4-(trifluoromethyl)benzeneboronic acid (9 mg, 0.050 mmol) according to the General Procedure 9, described in Example 82. The title compound was obtained in 77% yield (17 mg). ¹H NMR (600 MHz, CDCl₃) δ ppm 3.90 (s, 3 H) 6.66 (dd, J=8.70, 2.25 Hz, 1 H) 6.70 (d, J=2.25 Hz, 1 H) 6.86 (br. s., 1 H) 7.59 (dd, J=7.89, 7.78 Hz, 1 H) 7.62-7.66 (m, 2 H) 7.70-7.74 (m, 2 H) 7.72 (d, J=8.70 Hz, 1 H) 7.79 (ddd, J=7.78, 1.85, 1.10 Hz, 1 H) 7.89 (ddd, J=7.89, 1.85, 1.10 Hz, 1 H) 8.09 (t, J=1.85 Hz, 1 H) 10.86 (s, 1 H). MS (ESI+) m/z 452 [M+H]⁺.

Example 101

Methyl 4-({[4'-(dimethylcarbamoyl)biphenyl-3-yl]sulfonyl}amino)-2-hydroxybenzoate

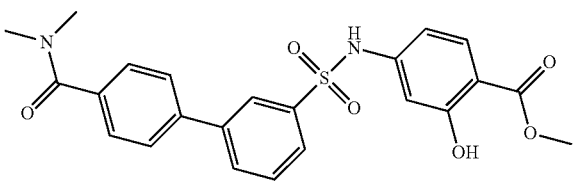

The product was prepared from methyl 4-{[(3-bromophenyl)sulfonyl]amino}-2-hydroxybenzoate (Intermediate 4) (19 mg, 0.050 mmol) and [4-(N,N-dimethylaminocarbonyl)phenyl]boronic acid (10 mg, 0.050 mmol) according to the General Procedure 9, described in Example 82. The title compound was obtained in 77% yield (17 mg). ¹H NMR (600 MHz, CDCl₃) δ ppm 3.03 (br. s., 3 H) 3.15 (br. s., 3 H) 3.90 (s, 3 H) 6.67 (dd, J=8.70, 2.25 Hz, 1 H) 6.71 (d, J=2.25 Hz, 1 H) 7.14 (br. s., 1 H) 7.49-7.53 (m, 2 H) 7.53-7.57 (m, 2 H) 7.56 (dd, J=7.90, 7.78 Hz, 1 H) 7.71 (d, J=8.70 Hz, 1H) 7.77 (ddd, J=7.78, 1.85, 1.10 Hz, 1 H) 7.86 (ddd, J=7.90, 1.85, 1.10 Hz, 1 H) 8.07 (t, J=1.85 Hz, 1 H) 10.85 (s, 1 H). MS (ESI+) m/z 455 [M+H]⁺.

Example 102

Methyl 4-{[(4'-carbamoylbiphenyl-3-yl)sulfonyl]amino}-2-hydroxybenzoate

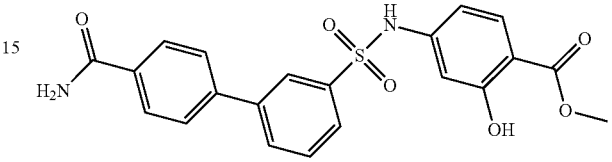

The product was prepared from methyl 4-{[(3-bromophenyl)sulfonyl]amino}-2-hydroxybenzoate (Intermediate 4) (19 mg, 0.050 mmol) and (4-aminocarbonylphenyl)boronic acid (8 mg, 0.050 mmol) according to the General Procedure 9, described in Example 82. The title compound was obtained in 72% yield (15 mg). ¹H NMR (600 MHz, CDCl₃) δ ppm 3.90 (s, 3 H) 5.70 (br. s., 1 H) 6.12 (br. s., 1 H) 6.69 (dd, J=8.70, 2.21 Hz, 1 H) 6.73 (d, J=2.21 Hz, 1 H) 7.32 (br. s., 1 H) 7.58 (dd, J=7.89, 7.78 Hz, 1 H) 7.59-7.63 (m, 2 H) 7.72 (d, J=8.70 Hz, 1 H) 7.79 (ddd, J=7.78, 1.83, 1.07 Hz, 1 H) 7.89 (ddd, J=7.89, 1.83, 1.07 Hz, 1 H) 7.88-7.91 (m, 2 H) 8.10 (t, J=1.83 Hz, 1 H) 10.85 (s, 1 H). MS (ESI+) m/z 427 [M+H]⁺.

Example 103

Methyl 4-({[5-chloro-4-(4-methoxy-3,5-dimethylphenyl)thiophen-2-yl]sulfonyl}amino)-2-hydroxybenzoate

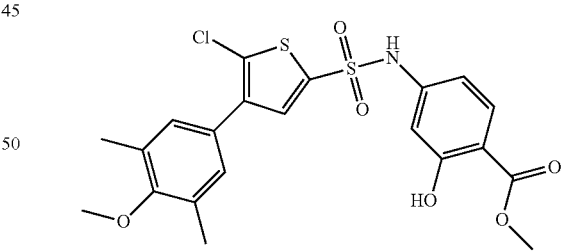

The product was prepared from methyl 4-{[(4-bromo-5-chloro-2-thienyl)sulfonyl]amino}-2-hydroxybenzoate (Intermediate 3) (21 mg, 0.050 mmol) and 4-methoxy-3,5-dimethylbenzeneboronic acid (9 mg, 0.050 mmol) according to the General Procedure 9, described in Example 82. The title compound was obtained in 44% yield (10.6 mg). ¹H NMR (600 MHz, CDCl₃) δ ppm 2.31 (s, 6 H) 3.75 (s, 3 H) 3.92 (s, 3 H) 6.70 (dd, J=8.62, 2.21 Hz, 1 H) 6.75 (d, J=2.21 Hz, 1 H) 6.90 (br. s., 1 H) 7.11 (s, 2 H) 7.54 (s, 1 H) 7.78 (d, J=8.62 Hz, 1 H) 10.90 (s, 1 H). MS (ESI+) m/z 482 [M+H]⁺.

Example 104

Methyl 4-({[4-(3-acetylphenyl)-5-chloro-2-thienyl]sulfonyl}amino)-2-hydroxybenzoate

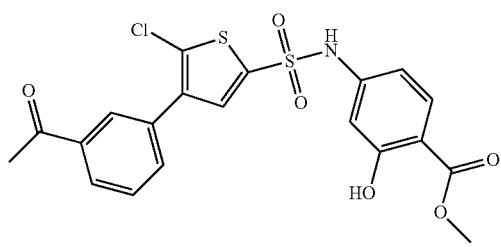 [SMILES: COC(=O)c1ccc(NS(=O)(=O)c2cc(-c3cccc(C(C)=O)c3)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and 3-acetylphenylboronic acid (8 mg, 0.050 mmol) according to the General Procedure 9, described in Example 82. The title compound was obtained in 21% yield (4.9 mg). $^1$H NMR (600 MHz, CD$_3$OD) δ ppm 2.63 (s, 3 H) 3.91 (s, 3 H) 6.77 (dd, J=8.70, 2.20 Hz, 1 H) 6.82 (d, J=2.20 Hz, 1 H) 7.60 (t, J=7.78 Hz, 1 H) 7.70 (s, 1 H) 7.75 (ddd, J=7.63, 1.83, 1.22 Hz, 1 H) 7.78 (d, J=8.70 Hz, 1 H) 8.03 (ddd, J=7.93, 1.83, 1.22 Hz, 1 H) 8.08 (td, J=1.83, 0.61 Hz, 1 H). MS (ESI+) m/z 466 [M+H]$^+$.

Example 105

Methyl 4-[({5-chloro-4-[2-(hydroxymethyl)phenyl]thiophen-2-yl}sulfonyl)amino]-2-hydroxybenzoate

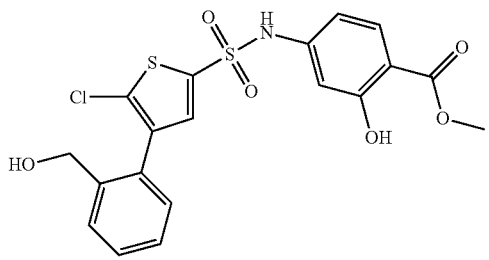 [SMILES: COC(=O)c1ccc(NS(=O)(=O)c2cc(-c3ccccc3CO)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and 2-hydroxymethylphenylboronic acid (8 mg, 0.050 mmol) according to the General Procedure 9, described in Example 82. The title compound was obtained in 52% yield (11.9 mg). $^1$H NMR (600 MHz, CDCl$_3$) δ ppm 1.98 (t, J=4.27 Hz, 1 H) 3.94 (s, 3 H) 4.38 (d, J=4.27 Hz, 2 H) 6.66 (dd, J=8.62, 2.21 Hz, 1 H) 6.82 (d, J=2.21 Hz, 1 H) 7.05 (br. s., 1 H) 7.24 (dd, J=7.55, 1.37 Hz, 1 H) 7.37 (td, J=7.55, 1.37 Hz, 1 H) 7.44 (td, J=7.55, 1.37 Hz, 1 H) 7.54-7.57 (m, 1H) 7.67 (s, 1H) 7.79 (d, J=8.62 Hz, 1 H) 11.02 (s, 1 H). MS (ESI+) m/z 436 [M−OH]$^+$.

Example 106

Methyl 4-({[5-chloro-4-(6-methoxypyridin-3-yl)-2-thienyl]sulfonyl}amino)-2-hydroxybenzoate

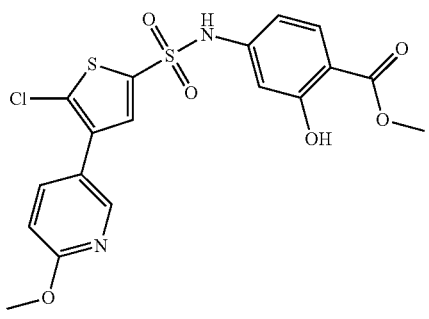

The product was prepared from methyl 4-{[(4-bromo-5-chloro-2-thienyl)sulfonyl]amino}-2-hydroxybenzoate (Intermediate 3) (21 mg, 0.050 mmol) and 6-methoxypyridine-3-boronic acid (8 mg, 0.050 mmol) according to the General Procedure 9, described in Example 82. The product was further purified by preparative TLC (silica, 20% EtOAc in hexane). The title compound was obtained in 28% yield (6.4 mg). $^1$H NMR (600 MHz, CD$_3$OD) δ ppm 3.91 (s, 3 H) 3.94 (s, 3 H) 6.75 (dd, J=8.70, 2.20 Hz, 1 H) 6.80 (d, J=2.20 Hz, 1 H) 6.88 (dd, J=8.62, 0.72 Hz, 1 H) 7.66 (s, 1 H) 7.77 (d, J=8.70 Hz, 1 H) 7.83 (dd, J=8.62, 2.52 Hz, 1 H) 8.28 (dd, J=2.52, 0.72 Hz, 1 H). MS (ESI+) m/z 455 [M+H]$^+$.

Example 107

Methyl 4-({[4-(3-aminophenyl)-5-chlorothiophen-2-yl]sulfonyl}amino)-2-hydroxybenzoate trifluoroacetate

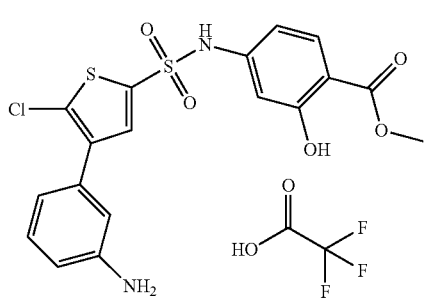

The product was prepared from methyl 4-{[(4-bromo-5-chloro-2-thienyl)sulfonyl]amino}-2-hydroxybenzoate (Intermediate 3) (21 mg, 0.050 mmol) and 3-(4,4,5,5-tetramethyl-1,3,2-dioxaborolan-2-yl)aniline (11 mg, 0.050 mmol) according to the General Procedure 9, described in Example 82. The title compound was obtained in 25% yield (6.8 mg). $^1$H NMR (600 MHz, CD$_3$OD) δ ppm 3.90 (s, 3 H) 6.73 (dd, J=8.70, 2.20 Hz, 1 H) 6.73 (ddd, J=8.08, 2.29, 0.95 Hz, 1 H) 6.76 (dd, J=7.64, 1.71, 0.95 Hz, 1 H) 6.79 (d, J=2.20 Hz, 1 H) 6.83 (ddd, J=2.29, 1.71, 0.45 Hz, 1 H) 7.15 (ddd, J=8.08, 7.64, 0.45 Hz, 1 H) 7.54 (s, 1 H) 7.75 (d, J=8.70 Hz, 1 H). MS (ESI+) m/z 439 [M+H]$^+$.

Example 108

Methyl 4-{[(5-chloro-4-{4-[(methylsulfonyl)amino]phenyl}thiophen-2-yl)sulfonyl]amino}-2-hydroxybenzoate

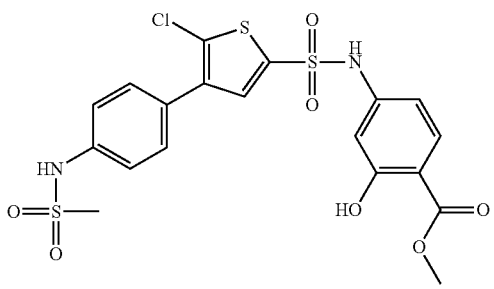 [SMILES: COC(=O)c1ccc(NS(=O)(=O)c2cc(-c3ccc(NS(C)(=O)=O)cc3)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and 4-methanesulfonylaminophenylboronic acid pinacol ester (15 mg, 0.050 mmol) according to the General Procedure 9, described in Example 82. The title compound was obtained in 6% yield (1.6 mg). $^1$H NMR (600 MHz, CD$_3$OD) δ ppm 3.00 (s, 3 H) 3.91 (s, 3 H) 6.74 (dd, J=8.70, 2.20 Hz, 1 H) 6.80 (d, J=2.20 Hz, 1 H) 7.30-7.35 (m, 2 H) 7.48-7.51 (m, 2H) 7.62 (s, 1 H) 7.76 (d, J=8.70 Hz, 1 H). MS (ESI+) m/z 517 [M+H]$^+$.

Example 109

Methyl 4-({[4-(4-carbamoylphenyl)-5-chlorothiophen-2-yl]sulfonyl}amino)-2-hydroxybenzoate

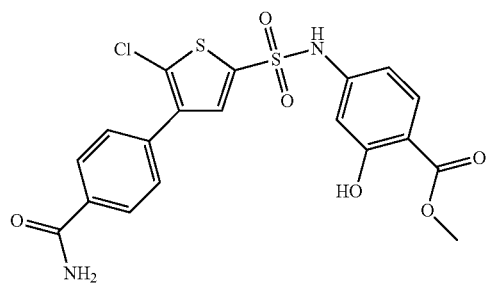 [SMILES: COC(=O)c1ccc(NS(=O)(=O)c2cc(-c3ccc(C(N)=O)cc3)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and (4-aminocarbonylphenyl)boronic acid (8 mg, 0.050 mmol) according to the General Procedure 9, described in Example 82. The title compound was obtained in 36% yield (8.4 mg). $^1$H NMR (600 MHz, CD$_3$OD) δ ppm 3.91 (s, 3 H) 6.75 (dd, J=8.70, 2.20 Hz, 1 H) 6.81 (d, J=2.20 Hz, 1 H) 7.60-7.65 (m, 2 H) 7.68 (s, 1 H) 7.77 (d, J=8.70 Hz, 1 H) 7.94-7.97 (m, 2 H). MS (ESI+) m/z 467 [M+H]$^+$.

Example 110

Methyl 4-({[5-chloro-4-(3-fluoro-4-methoxyphenyl)thiophen-2-yl]sulfonyl}amino)-2-hydroxybenzoate

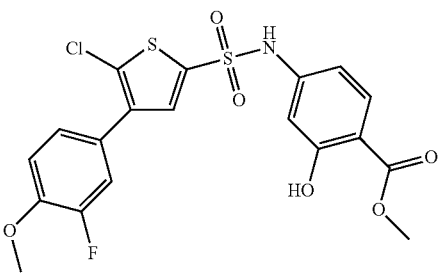 [SMILES: COC(=O)c1ccc(NS(=O)(=O)c2cc(-c3ccc(OC)c(F)c3)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and 3-fluoro-4-methoxyphenylboronic acid (8 mg, 0.050 mmol) according to the General Procedure 9, described in Example 82. The title compound was obtained in 38% yield (9 mg). $^1$H (600 MHz, CD$_3$OD) δ ppm 3.91 (s, 3 H) 3.91 (s, 3 H) 6.74 (dd, J=8.70, 2.20 Hz, 1 H) 6.80 (d, J=2.20 Hz, 1 H) 7.17 (t, J=8.47 Hz, 1 H) 7.25-7.31 (m, 2 H) 7.60 (s, 1 H) 7.77 (d, J=8.70 Hz, 1 H). MS (ESI+) m/z 472 [M+H]$^+$.

Example 111

Methyl 4-{[(5-chloro-4-pyridin-3-ylthiophen-2-yl)sulfonyl]amino}-2-hydroxybenzoate

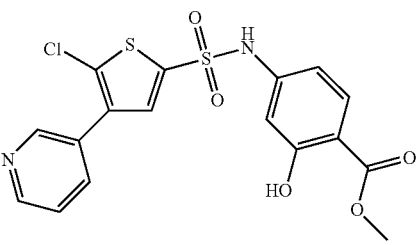 [SMILES: COC(=O)c1ccc(NS(=O)(=O)c2cc(-c3cccnc3)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and pyridin-3-ylboronic acid (6 mg, 0.049 mmol) according to the General Procedure 9, described in Example 82. The title compound was obtained in 16% yield (3.4 mg). $^1$H NMR (600 MHz, CDCl$_3$) δ ppm 3.93 (s, 3 H) 6.73 (dd, J=8.60, 2.24 Hz, 1 H) 6.76 (d, J=2.24 Hz, 1 H) 7.00 (br. s., 1 H) 7.39 (ddd, J=7.90, 4.88, 0.87 Hz, 1 H) 7.59 (s, 1 H) 7.80 (d, J=8.60 Hz, 1 H) 7.81 (ddd, J=7.90, 2.28, 1.68 Hz, 1 H) 8.64 (dd, J=4.88, 1.68 Hz, 1 H) 8.72 (dd, J=2.28, 0.87 Hz, 1 H) 10.93 (s, 1 H). MS (ESI+) m/z 425 [M+H]$^+$.

Example 112

Methyl 2-hydroxy-4-({[3'-(methylsulfonyl)biphenyl-3-yl]sulfonyl}amino)benzoate

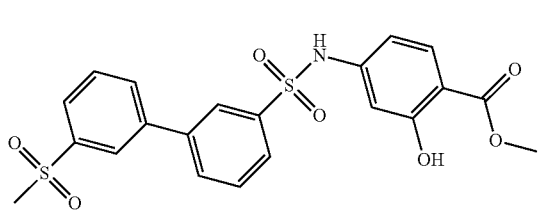 [SMILES: COC(=O)c1ccc(NS(=O)(=O)c2cccc(-c3cccc(S(C)(=O)=O)c3)c2)cc1O]

The product was prepared from methyl 4-{[(3-bromophenyl)sulfonyl]amino}-2-hydroxybenzoate (Intermediate 4) (21 mg, 0.050 mmol) and (3-methylsulphonyl)phenylboronic acid (10 mg, 0.050 mmol) according to the General Procedure 9, described in Example 82. The title compound was obtained in 75% yield (17.2 mg). $^1$H NMR (600 MHz, CD$_3$OD) δ ppm 3.18 (s, 3 H) 3.88 (s, 3 H) 6.71 (dd, J=8.70, 2.20 Hz, 1 H) 6.76 (d, J=2.20 Hz, 1 H) 7.68 (td, J=7.85, 0.45 Hz, 1 H) 7.71 (d, J=8.70 Hz, 1 H) 7.76 (td, J=7.85, 0.45 Hz, 1 H) 7.92 (ddd, J=7.85, 1.82, 1.05 Hz, 1 H) 7.94 (ddd, J=7.85, 1.87, 1.05 Hz, 1 H) 7.96 (ddd, J=7.85, 1.87, 1.05 Hz, 1 H) 8.01 (ddd, J=7.85, 1.82, 1.05 Hz, 1 H) 8.11 (td, J=1.82, 0.45 Hz, 1 H) 8.11 (td, J=1.85, 0.45 Hz, 1 H). MS (ESI+) m/z 462 [M+H]$^+$.

Example 113

Methyl 4-{[(3'-carbamoylbiphenyl-3-yl)sulfonyl]amino}-2-hydroxybenzoate

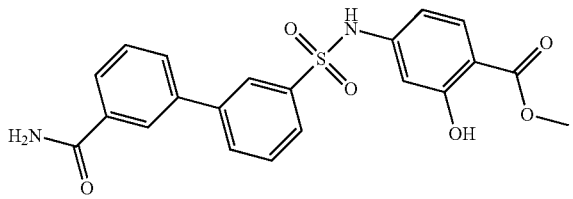 [SMILES: COC(=O)c1ccc(NS(=O)(=O)c2cccc(-c3cccc(C(N)=O)c3)c2)cc1O]

The product was prepared from methyl 4-{[(3-bromophenyl)sulfonyl]amino}-2-hydroxybenzoate (Intermediate 4) (21 mg, 0.050 mmol) and (3-carbamoylphenylboronic acid (8 mg, 0.050 mmol) according to the General Procedure 9, described in Example 82. The title compound was obtained in 43% yield (9.1 mg). $^1$H NMR (600 MHz, CD$_3$OD) δ ppm 3.88 (s, 3 H) 6.70 (dd, J=8.70, 2.20 Hz, 1 H) 6.75 (d, J=2.20 Hz, 1 H) 7.59 (td, J=7.78, 0.45 Hz, 1 H) 7.64 (ddd, J=7.87, 7.78, 0.45 Hz, 1 H) 7.70 (d, J=8.70 Hz, 1 H) 7.79 (ddd, J=7.78, 1.91, 1.06 Hz, 1 H) 7.88 (ddd, J=7.87, 1.87, 1.06 Hz, 1 H) 7.91 (ddd, J=7.78, 1.72, 1.06 Hz, 1 H) 7.92 (ddd, J=7.78, 1.87, 1.07 Hz, 1 H) 8.12 (td, J=1.84, 0.45 Hz, 1 H) 8.15 (td, J=1.89, 0.45 Hz, 1H). MS (ESI+) m/z 427 [M+H]$^+$.

Example 114

Methyl 2-hydroxy-4-({[5-(trifluoromethyl)biphenyl-3-yl]sulfonyl}amino)benzoate

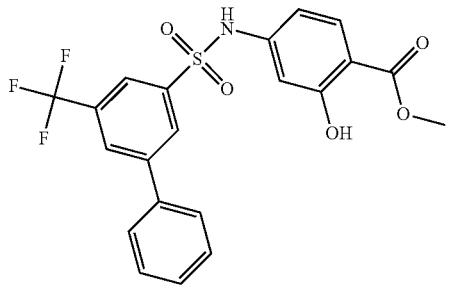 [SMILES: COC(=O)c1ccc(NS(=O)(=O)c2cc(-c3ccccc3)cc(C(F)(F)F)c2)cc1O]

The product was synthesized from methyl 4-({[3-bromo-5-(trifluoromethyl)phenyl]sulfonyl}amino)-2-hydroxybenzoate (Intermediate 5) (23 mg, 0.050 mmol) and phenylboronic acid (7 mg, 0.06 mmol) according to the General Procedure 9, described in Example 82, but without purification. The ester intermediate was treated with 1 M NaOH (300 μL) at 60° C. overnight. The crude product was purified by preparative HPLC (acidic system) and 2-hydroxy-4-({[5-(trifluoromethyl)biphenyl-3-yl]sulfonyl}amino)benzoic acid was obtained in 73% yield over two steps (15.9 mg). $^1$H NMR (500 MHz, CD$_3$OD) δ ppm 6.69 (dd, J=8.64, 2.20 Hz, 1 H) 6.74 (d, J=2.20 Hz, 1 H) 7.43-7.48 (m, 1 H) 7.48-7.53 (m, 2 H) 7.58-7.63 (m, 2 H) 7.74 (d, J=8.64 Hz, 1 H) 8.06 (dq, J=1.73, 0.75 Hz, 1 H) 8.11 (dq, J=1.73, 0.75 Hz, 1 H) 8.24 (t, J=1.73 Hz, 1 H). MS (ESI+) m/z 437 [M+H]$^+$.

The title compound was prepared from 2-hydroxy-4-({[5-(trifluoromethyl)biphenyl-3-yl]sulfonyl}amino)benzoic acid (14.2 mg, 0.032 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 56% yield (8.2 mg) $^1$H NMR (600 MHz, CDCl$_3$) δ ppm 3.91 (s, 3 H) 6.68 (dd, J=8.66, 2.20 Hz, 1 H) 6.70 (d, J=2.20 Hz, 1 H) 7.05 (br. s., 1 H) 7.44-7.47 (m, 1 H) 7.47-7.52 (m, 2 H) 7.52-7.55 (m, 2 H) 7.74 (d, J=8.66 Hz, 1 H) 7.99-8.01 (m, 1 H) 8.06-8.09 (m, 1 H) 8.23 (t, J=1.59 Hz, 1 H) 10.88 (s, 1 H). MS (ESI+) m/z 452 [M+H]$^+$.

Example 115

Methyl 4-({[2',5'-difluoro-5-(trifluoromethyl)biphenyl-3-yl]sulfonyl}amino)-2-hydroxybenzoate

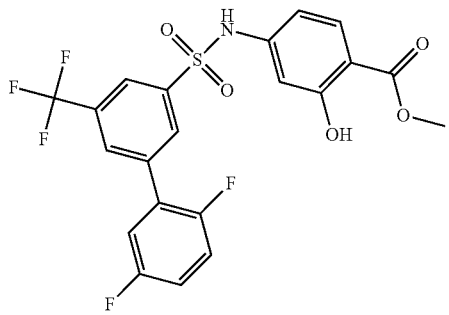 [SMILES: COC(=O)c1ccc(NS(=O)(=O)c2cc(-c3cc(F)ccc3F)cc(C(F)(F)F)c2)cc1O]

The product was synthesized from methyl 4-({[3-bromo-5-(trifluoromethyl)phenyl]sulfonyl}amino)-2-hydroxybenzoate (Intermediate 5) (23 mg, 0.050 mmol) and 2,5-difluorophenylboronic acid (9 mg, 0.06 mmol) according to the General Procedure 9, described in Example 82, but without purification. The ester intermediate was treated with 1 M NaOH (300 μL) at 60° C. overnight. The crude product was purified by preparative HPLC (acidic system) and 4-({[2',5'-difluoro-5-(trifluoromethyl)biphenyl-3-yl]sulfonyl}amino)-2-hydroxybenzoic acid was obtained in 81% yield over two steps (19.2 mg). $^1$H NMR (500 MHz, CD$_3$OD) δ ppm 6.68 (dd, J=8.67, 2.20 Hz, 1 H) 6.72 (d, J=2.20 Hz, 1 H) 7.20-7.30 (m, 2 H) 7.30 (td, J=9.40, 4.52 Hz, 1 H) 7.74 (d, J=8.67 Hz, 1 H) 8.08 (br. s., 1 H) 8.13 (br. s., 1 H) 8.21-8.23 (m, 1 H). MS (ESI+) m/z 474 [M+H]$^+$.

The title compound was prepared from 4-({[2',5'-difluoro-5-(trifluoromethyl)biphenyl-3-yl]sulfonyl}amino)-2-hydroxybenzoic acid (17.8 mg, 0.038 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7 described in Example 59. The title compound was obtained in 62% yield (11.3 mg). $^1$H NMR (600 MHz, CDCl$_3$) δ ppm 3.91 (s, 3 H) 6.67-6.71 (m, 2 H) 7.06 (ddd, J=8.41, 5.95, 3.12 Hz, 1 H) 7.11 (dddd, J=9.11, 7.30, 3.80, 3.12 Hz, 1 H) 7.13 (br. s., 1 H) 7.17 (ddd, J=9.50, 9.11, 4.46 Hz, 1 H) 7.73-7.78 (m, 1 H) 7.95-7.97 (m, 1 H) 8.12-8.14 (m, 1 H) 8.17-8.19 (m, 1 H) 10.88 (s, 1 H). MS (ESI+) m/z 488 [M+H]$^+$.

Example 116

Methyl 4-({[3-(2,3-dihydro-1-benzofuran-5-yl)-5-(trifluoromethyl)phenyl]sulfonyl}amino)-2-hydroxybenzoate

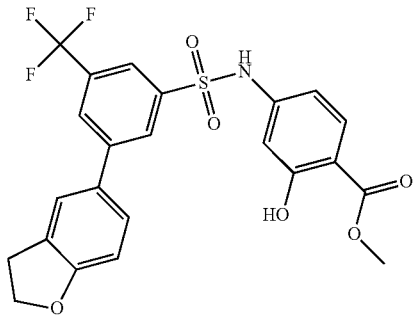 [SMILES: COC(=O)c1ccc(NS(=O)(=O)c2cc(-c3ccc4c(c3)CCO4)cc(C(F)(F)F)c2)cc1O]

The product was synthesized from methyl 4-({[3-bromo-5-(trifluoromethyl)phenyl]sulfonyl}amino)-2-hydroxybenzoate (Intermediate 5) (23 mg, 0.050 mmol) and 2,3-dihydrobenzofuran-5-boronic acid (10 mg, 0.06 mmol) according to the General Procedure 9, described in Example 82, but without purification. The ester intermediate was treated with 1 M NaOH (300 μL) at 60° C. overnight. The crude product was purified by preparative HPLC (acidic system) and 4-({[3-(2,3-dihydro-1-benzofuran-5-yl)-5-(trifluoromethyl)phenyl]sulfonyl}amino)-2-hydroxybenzoic acid was obtained in 83% yield (19.8 mg) over two steps. $^1$H NMR (500 MHz, CD$_3$OD) δ ppm 3.27 (t, J=8.76 Hz, 2 H) 4.61 (t, J=8.76 Hz, 2 H) 6.68 (dd, J=8.67, 2.20 Hz, 1 H) 6.74 (d, J=2.20 Hz, 1 H) 6.84 (d, J=8.30 Hz, 1 H) 7.35 (ddt, J=8.30, 2.14, 0.70 Hz, 1 H) 7.42 (dt, J=2.14, 1.20 Hz, 1H) 7.74 (d, J=8.67 Hz, 1H) 7.98 (dq, J=1.68, 0.74 Hz, 1 H) 8.03 (dq, J=1.68, 0.74 Hz, 1 H) 8.14 (t, J=1.68 Hz, 1 H). MS (ESI+) m/z 480 [M+H]$^+$.

The title compound was prepared from 4-({[3-(2,3-dihydro-1-benzofuran-5-yl)-5-(trifluoromethyl)phenyl]sulfonyl}amino)-2-hydroxybenzoic acid (18.5 mg, 0.039 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 40% yield (7.6 mg). $^1$H NMR (600 MHz, CDCl$_3$) δ ppm 3.28 (t, J=8.79 Hz, 2 H) 3.90 (s, 3 H) 4.65 (t, J=8.79 Hz, 2 H) 6.67 (dd, J=8.66, 2.20 Hz, 1 H) 6.71 (d, J=2.20 Hz, 1 H) 6.87 (d, J=8.30 Hz, 1 H) 7.10 (br. s., 1 H) 7.28-7.31 (ddt, J=8.30, 2.11, 0.70 Hz, 1 H) 7.36 (dq, J=2.11, 0.45 Hz, 1 H) 7.73 (d, J=8.66 Hz, 1 H) 7.91-7.94 (m, 1 H) 7.99-8.01 (m, 1 H) 8.15 (t, J=1.78 Hz, 1 H) 10.87 (s, 1 H). MS (ESI+) m/z 494 [M+H]$^+$.

Example 117

Methyl 2-hydroxy-4-({[2'-hydroxy-5-(trifluoromethyl)biphenyl-3-yl]sulfonyl}amino)benzoate

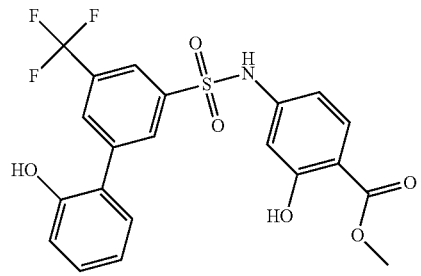 [SMILES: COC(=O)c1ccc(NS(=O)(=O)c2cc(-c3ccccc3O)cc(C(F)(F)F)c2)cc1O]

The product was synthesized from methyl 4-({[3-bromo-5-(trifluoromethyl)phenyl]sulfonyl}amino)-2-hydroxybenzoate (Intermediate 5) (23 mg, 0.050 mmol) and 2-hydroxyphenylboronic acid pinacol ester (13 mg, 0.06 mmol) according to the General Procedure 9, described in Example 82, but without purification. The ester intermediate was treated with 1 M NaOH (300 μL) at 60° C. overnight. The crude product was purified by preparative HPLC (acidic system) and 2-hydroxy-4-({[2'-hydroxy-5-(trifluoromethyl)biphenyl-3-yl]sulfonyl}amino)benzoic acid was obtained in 72% yield over two steps (16.3 mg). $^1$H NMR (500 MHz, CD$_3$OD) δ ppm 6.69 (dd, J=8.67, 2.18 Hz, 1 H) 6.73 (d, J=2.18 Hz, 1 H) 6.92-6.96 (m, 2 H) 7.22-7.27 (m, 2 H) 7.73 (d, J=8.67 Hz, 1 H) 8.00 (dq, J=1.76, 0.75 Hz, 1 H) 8.11 (dq, J=1.67, 0.78 Hz, 1 H) 8.29 (t, J=1.67 Hz, 1 H). MS (ESI+) m/z 454 [M+H]$^+$.

The title compound was prepared from 2-hydroxy-4-({[2'-hydroxy-5-(trifluoromethyl)biphenyl-3-yl]sulfonyl}amino)benzoic acid (15.8 mg, 0.035 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 45% yield (7.4 mg). $^1$H NMR (600 MHz, CDCl$_3$) δ ppm 3.91 (s, 3 H) 5.51 (br. s., 1 H) 6.64 (dd, J=8.66, 2.26 Hz, 1 H) 6.76 (d, J=2.26 Hz, 1 H) 6.91 (dd, J=8.06, 1.12 Hz, 1 H) 7.04 (ddd, J=7.66, 7.38, 1.12 Hz, 1 H) 7.12 (br. s., 1 H) 7.28 (dd, J=7.66, 1.67 Hz, 1 H) 7.30 (ddd, J=8.06, 7.38, 1.67 Hz, 1 H) 7.73 (d, J=8.66

Hz, 1 H) 7.99-8.01 (m, 1 H) 8.06-8.07 (m, 1 H) 8.36 (t, J=1.70 Hz, 1 H) 10.92 (s, 1 H). MS (ESI+) m/z 468 [M+H]⁺.

Example 118

Methyl 4-({[5-(2,5-difluorophenyl)thiophen-2-yl]sulfonyl}amino)-2-hydroxybenzoate

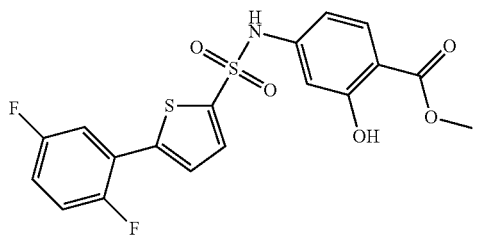 [SMILES: COC(=O)c1ccc(NS(=O)(=O)c2ccc(-c3cc(F)ccc3F)s2)cc1O]

The product was synthesized from 4-{[(5-bromothiophen-2-yl)sulfonyl]amino}-2-hydroxybenzoic acid (Intermediate 9) (19 mg, 0.050 mmol) and 2,5-difluorophenylboronic acid (9 mg, 0.06 mmol) according to the General Procedure 9, described in Example 82. The crude product was purified by preparative HPLC (acidic system) and 4-({[5-(2,5-difluorophenyl)thiophen-2-yl]sulfonyl}amino)-2-hydroxybenzoic acid was obtained in 74% yield (15.3 mg). ¹H NMR (500 MHz, CD₃OD) δ ppm 6.72 (dd, J=8.63, 2.17 Hz, 1 H) 6.78 (d, J=2.17 Hz, 1 H) 7.15 (dddd, J=9.15, 7.53, 3.86, 3.16 Hz, 1 H) 7.27 (dddd, J=10.54, 9.15, 4.58 Hz, 1 H) 7.53 (dddd, J=9.15, 5.99, 3.16 Hz, 1 H) 7.52 (d, J=4.02 Hz, 1 H) 7.63 (dd, J=4.02, 1.40 Hz, 1 H) 7.75 (d, J=8.63 Hz, 1 H). MS (ESI+) m/z 412 [M+H]⁺.

The title compound was prepared from 4-({[5-(2,5-difluorophenyl)thiophen-2-yl]sulfonyl}amino)-2-hydroxybenzoic acid (13.9 mg, 0.034 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 57% yield (8.2 mg). ¹H NMR (600 MHz, CDCl₃) δ ppm 3.91 (s, 3H) 6.71 (dd, J=8.66, 2.26 Hz, 1 H) 6.75 (d, J=2.26 Hz, 1 H) 6.96 (br. s., 1 H) 7.03 (dddd, J=9.13, 7.32, 3.84, 3.09 Hz, 1 H) 7.14 (ddd, J=10.14, 9.13, 4.55 Hz, 1 H) 7.26 (ddd, J=8.80, 5.74, 3.09 Hz, 1 H) 7.35 (dd, J=4.04, 0.74 Hz, 1 H) 7.63 (dd, J=4.04, 1.07 Hz, 1 H) 7.76 (d, J=8.66 Hz, 1 H) 10.88 (s, 1 H). MS (ESI+) m/z 426 [M+H]⁺.

Example 119

Methyl 4-({[5-(2,3-dihydro-1-benzofuran-5-yl)thiophen-2-yl]sulfonyl}amino)-2-hydroxybenzoate

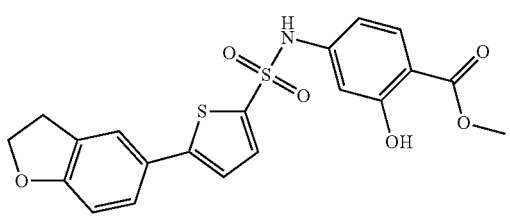 [SMILES: COC(=O)c1ccc(NS(=O)(=O)c2ccc(-c3ccc4c(c3)CCO4)s2)cc1O]

The product was synthesized from 4-{[(5-bromothiophen-2-yl)sulfonyl]amino}-2-hydroxybenzoic acid (Intermediate 9) (19 mg, 0.050 mmol) and 2,3-dihydrobenzofuran-5-boronic acid (10 mg, 0.06 mmol) according to the General Procedure 9, described in Example 82. The crude product was purified by preparative HPLC (acidic system) and 4-({[5-(2,3-dihydro-1-benzofuran-5-yl)thiophen-2-yl]sulfonyl}amino)-2-hydroxybenzoic acid was obtained in 73% yield (15.2 mg). ¹H NMR (500 MHz, CD₃OD) δ ppm 3.23 (t, J=8.73 Hz, 2H) 4.58 (t, J=8.73 Hz, 2 H) 6.70 (dd, J=8.67, 2.14 Hz, 1 H) 6.75 (d, J=8.31 Hz, 1 H) 6.78 (d, J=2.14 Hz, 1 H) 7.19 (d, J=4.03 Hz, 1 H) 7.37 (ddt, J=8.31, 2.08, 0.70 Hz, 1 H) 7.48 (dt, J=2.08, 1.15 Hz, 1 H) 7.54 (d, J=4.03 Hz, 1 H) 7.74 (d, J=8.67 Hz, 1 H). MS (ESI+) m/z 418 [M+H]⁺.

The title compound was prepared from 4-({[5-(2,3-dihydro-1-benzofuran-5-yl)thiophen-2-yl]sulfonyl}amino)-2-hydroxybenzoic acid (14.4 mg, 0.034 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 52% yield (7.8 mg). ¹H NMR (600 MHz, CDCl₃) δ ppm 3.24 (t, J=8.73 Hz, 2 H) 3.91 (s, 3 H) 4.62 (t, J=8.73 Hz, 2 H) 6.69 (dd, J=8.66, 2.20 Hz, 1 H) 6.75 (d, J=2.20 Hz, 1 H) 6.79 (d, J=8.30 Hz, 1 H) 6.91 (br. s., 1 H) 7.04 (d, J=4.03 Hz, 1 H) 7.29-7.32 (ddt, J=8.30, 2.08, 0.74 Hz, 1 H) 7.37 (dq, J=2.08, 0.51 Hz, 1 H) 7.57 (d, J=4.03 Hz, 1 H) 7.74 (d, J=8.66 Hz, 1 H) 10.87 (s, 1 H). MS (ESI+) m/z 432 [M+H]⁺.

Example 120

Methyl 2-hydroxy-4-({[3-(1-hydroxyethyl)phenyl]sulfonyl}amino)benzoate

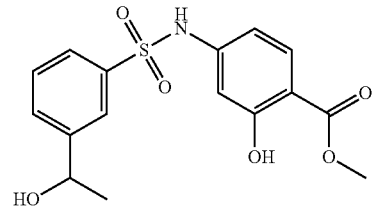 [SMILES: COC(=O)c1ccc(NS(=O)(=O)c2cccc(C(C)O)c2)cc1O]

The intermediate 4-{[(3-acetylphenyl)sulfonyl]amino}-2-hydroxybenzoic acid was synthesized in 21% yield (71 mg) from 3-acetylbenzenesulfonyl chloride (220 mg, 1.0 mmol) and 4-aminosalicylic acid (150 mg, 1.0 mmol) according to the General Procedure 4, described in Example 7. ¹H NMR (500 MHz, CD₃OD) δ ppm 2.61 (s, 3H) 6.66 (dd, J=8.55, 2.20 Hz, 1 H) 6.69 (d, J=2.20 Hz, 1 H) 7.68 (td, J=7.84, 0.54 Hz, 1 H) 7.69 (d, J=8.55 Hz, 1 H) 8.07 (ddd, J=7.87, 1.96, 1.10 Hz, 1 H) 8.20 (ddd, J=7.81, 1.69, 1.10 Hz, 1 H) 8.42 (ddd, J=1.96, 1.69, 0.54 Hz, 1 H). MS (ESI+) m/z 336 [M+H]⁺.

A mixture of 4-{[(3-acetylphenyl)sulfonyl]amino}-2-hydroxybenzoic acid (12 mg, 0.036 mmol) and NaBH₄ (5 mg, 0.132 mmol) in MeOH (1 mL) was stirred at room temperature for 1 h. The reaction was quenched with 1 M HCl (2 mL) and the product was extracted with EtOAc. The organic phase was concentrated and the crude product was purified by preparative HPLC (acidic system) and 2-hydroxy-4-({[3-(1-hydroxyethyl)phenyl]sulfonyl}amino)benzoic acid was obtained in 70% yield (8.5 mg). ¹H NMR (500 MHz, CD₃OD) δ ppm 1.39 (d, J=6.47 Hz, 3 H) 4.83-4.89 (m, 1 H) 6.63 (dd, J=8.64, 2.18 Hz, 1 H) 6.66 (dd, J=2.18, 0.36 Hz, 1 H) 7.49 (ddd, J=7.81, 7.74, 0.57 Hz, 1 H) 7.59 (dddd, J=7.74, 1.72, 1.16, 0.63 Hz, 1 H) 7.67 (dd, J=8.64, 0.36 Hz, 1 H) 7.74 (ddd, J=7.81, 1.93, 1.16 Hz, 1 H) 7.89 (dddd, J=1.93, 1.72, 0.57, 0.57 Hz, 1 H). MS (ESI+) m/z 338 [M+H]⁺.

The title compound was prepared from 2-hydroxy-4-({[3-(1-hydroxyethyl)phenyl]sulfonyl}amino)benzoic acid (7.7 mg, 0.023 mmol), 1,1'-carbonyldiimidazole (16 mg, 0.100 mmol), MeOH (20 µL, 0.5 mmol) and pyridine (8 mg, 0.100 mmol) in MeCN, according to the General Procedure 7, described in Example 59. The title compound was obtained in 34% yield (2.7 mg). ¹H NMR (600 MHz, CDCl₃) δ ppm 1.47 (d, J=6.47 Hz, 3 H) 3.90 (s, 3 H) 4.94 (q, J=6.47 Hz, 1 H) 6.63 (dd, J=8.51, 2.27 Hz, 1 H) 6.64 (dd, J=2.27, 0.55 Hz, 1 H) 6.82 (br. s., 1 H) 7.46 (ddd, J=7.87, 7.71, 0.48 Hz, 1 H) 7.58 (dddd, J=7.71, 1.72, 1.11, 0.61 Hz, 1 H) 7.70 (dd, J=8.51, 0.55 Hz, 1 H) 7.77 (ddd, J=7.87, 1.98, 1.11 Hz, 1 H) 7.89 (dddd, J=1.98, 1.72, 0.57, 0.48 Hz, 1 H) 10.83 (s, 1 H). MS (ESI+) m/z 334 [M−OH]⁺.

Example 121

Methyl 2-hydroxy-4-{[(3-methoxyphenyl)sulfonyl]amino}benzoate

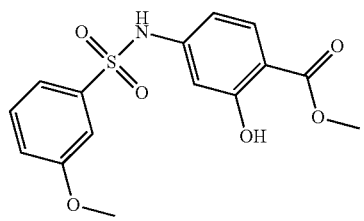 [SMILES: COC(=O)c1ccc(NS(=O)(=O)c2cccc(OC)c2)cc1O]

The intermediate 2-hydroxy-4-{[(3-methoxyphenyl)sulfonyl]amino}benzoic acid was synthesized in 25% yield (81 mg) from 3-methoxybenzenesulfonyl chloride (210 mg, 1.0 mmol) and 4-aminosalicylic acid (150 mg, 1.0 mmol) according to the General Procedure 4, described in Example 7. ¹H NMR (500 MHz, CD₃OD) δ ppm 3.81 (s, 3 H) 6.64 (dd, J=8.67, 2.20 Hz, 1 H) 6.69 (d, J=2.20 Hz, 1 H) 7.12-7.17 (m, 1 H) 7.35-7.37 (m, 1 H) 7.41-7.45 (m, 2H) 7.69 (d, J=8.67 Hz, 1 H). MS (ESI+) m/z 324 [M+H]⁺.

The title compound was prepared from 2-hydroxy-4-{[(3-methoxyphenyl)sulfonyl]amino}benzoic acid (12.0 mg, 0.037 mmol), 1,1'-carbonyldiimidazole (16 mg, 0.100 mmol), MeOH (20 µL, 0.5 mmol) and pyridine (8 mg, 0.100 mmol) in MeCN, according to the General Procedure 7, described in Example 59. The title compound was obtained in 77% yield (9.6 mg). ¹H NMR (600 MHz, CDCl₃) δ ppm 3.81 (s, 3 H) 3.90 (s, 3 H) 6.63 (dd, J=8.66, 2.25 Hz, 1 H) 6.66 (d, J=2.25 Hz, 1 H) 6.77 (br. s., 1 H) 7.08 (ddd, J=8.28, 2.59, 1.00 Hz, 1 H) 7.36 (ddd, J=2.59, 1.70, 0.36 Hz, 1 H) 7.38 (ddd, J=8.28, 7.77, 0.36 Hz, 1H) 7.44 (ddd, J=7.77, 1.70, 1.00 Hz, 1 H) 7.71 (d, J=8.66 Hz, 1 H) 10.84 (s, 1H). MS (ESI+) m/z 338 [M+H]⁺.

Example 122

Methyl 4-({[3-(2,3-dihydro-1-benzofuran-5-yl)benzyl]sulfonyl}amino)-2-hydroxybenzoate

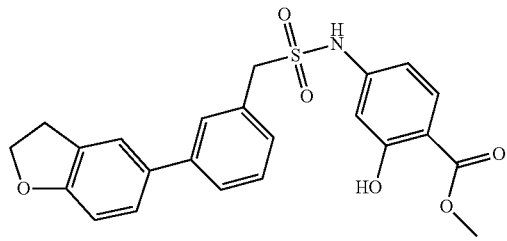 [SMILES: COC(=O)c1ccc(NS(=O)(=O)Cc2cccc(-c3ccc4c(c3)CCO4)c2)cc1O]

4-{[(3-Bromobenzyl)sulfonyl]amino}-2-hydroxybenzoic acid (Intermediate 10) (12 mg, 0.030 mmol), 2,3-dihydrobenzofuran-5-boronic acid (6 mg, 0.036 mmol), DIPEA (15 mg, 0.12 mmol) and Pd(dppf)Cl₂·CH₂Cl₂ (1 mg, 0.0012 mmol) were allowed to react according to the General Procedure 9, described in Example 82. The crude product was purified by preparative HPLC (acidic system) and 4-({[3-(2,3-dihydro-1-benzofuran-5-yl)benzyl]sulfonyl}amino)-2-hydroxybenzoic acid was obtained in 72% yield (9.2 mg). ¹H NMR (500 MHz, CD₃OD) δ ppm 3.23 (t, J=8.70 Hz, 2 H) 4.57 (t, J=8.70 Hz, 2 H) 4.56 (s, 2 H) 6.65 (dd, J=8.67, 2.20 Hz, 1 H) 6.70 (d, J=2.20 Hz, 1 H) 6.74 (d, J=8.30 Hz, 1 H) 7.20-7.25 (m, 2 H) 7.27-7.29 (m, 1 H) 7.31 (t, J=1.47 Hz, 1 H) 7.36 (t, J=7.80 Hz, 1 H) 7.50 (ddd, J=7.80, 1.47, 1.05 Hz, 1 H) 7.73 (d, J=8.67 Hz, 1 H). (ESI+) m/z 426 [M+H]⁺.

The title compound was prepared from 4-({[3-(2,3-dihydro-1-benzofuran-5-yl)benzyl]sulfonyl}amino)-2-hydroxybenzoic acid (6.1 mg, 0.014 mmol), 1,1'-carbonyldiimidazole (16 mg, 0.100 mmol), MeOH (20 µL, 0.5 mmol) and pyridine (8 mg, 0.100 mmol) in MeCN, according to the General Procedure 7, described in Example 59. The title compound was obtained in 24% yield (1.5 mg). ¹H NMR (600 MHz, CDCl₃) δ ppm 3.26 (t, J=8.73 Hz, 2 H) 3.95 (s, 3 H) 4.47 (s, 2 H) 4.62 (t, J=8.73 Hz, 2 H) 6.53 (br. s., 1 H) 6.64 (dd, J=8.66, 2.26 Hz, 1 H) 6.73 (d, J=2.26 Hz, 1 H) 6.82 (d, J=8.30 Hz, 1 H) 7.13-7.17 (m, 1 H) 7.23-7.26 (m, 1 H) 7.30-7.32 (m, 1 H) 7.33 (t, J=1.85 Hz, 1 H) 7.38 (t, J=7.77 Hz, 1 H) 7.53 (ddd, J=7.77, 1.85, 1.10 Hz, 1 H) 7.78 (d, J=8.66 Hz, 1 H) 10.95 (s, 1 H). MS (ESI+) m/z 440 [M+H]⁺.

Example 123

Methyl 4-({[(2',5'-difluorobiphenyl-4-yl)methyl]sulfonyl}amino)-2-hydroxybenzoate

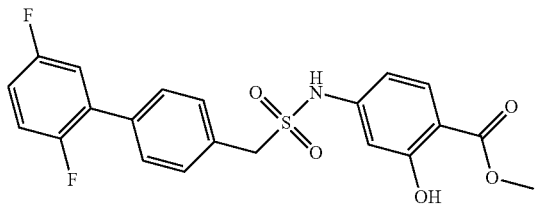 [SMILES: COC(=O)c1ccc(NS(=O)(=O)Cc2ccc(-c3cc(F)ccc3F)cc2)cc1O]

4-{[(4-Bromobenzyl)sulfonyl]amino}-2-hydroxybenzoic acid (Intermediate 11) (12 mg, 0.030 mmol), 2,5-difluorophenylboronic acid (6 mg, 0.036 mmol), DIPEA (15 mg, 0.12 mmol) and Pd(dppf)Cl₂·CH₂Cl₂ (1 mg, 0.0012 mmol) were allowed to react according to the General Procedure 9, described in Example 82. The crude product was purified by preparative HPLC (acidic system) and 4-({[(2',5'-difluorobiphenyl-4-yl)methyl]sulfonyl}amino)-2-hydroxybenzoic acid was obtained in 95% yield (11.9 mg). $^1$H NMR (500 MHz, CD$_3$OD) δ ppm 4.56 (s, 2 H) 6.66 (dd, J=8.50, 2.00 Hz, 1 H) 6.73 (br. s., 1 H) 7.07-7.13 (m, 1 H) 0.17-7.23 (m, 2 H) 7.36-7.41 (m, 2 H) 7.48-7.52 (m, 2 H) 7.76 (d, J=8.50 Hz, 1 H). MS (ESI+) m/z 420 [M+H]$^+$.

The title compound was prepared from 4-({[(2',5'-difluorobiphenyl-4-yl)methyl]sulfonyl}amino)-2-hydroxybenzoic acid (9.5 mg, 0.023 mmol), 1,1'-carbonyldiimidazole (16 mg, 0.100 mmol), MeOH (20 µL, 0.5 mmol) and pyridine (8 mg, 0.100 mmol) in MeCN, according to the General Procedure 7, described in Example 59. The title compound was obtained in 52% yield (5.1 mg). $^1$H NMR (600 MHz, CDCl$_3$) δ ppm 3.95 (s, 3 H) 4.47 (s, 2 H) 6.53 (br. s., 1 H) 6.61 (dd, J=8.66, 2.26 Hz, 1 H) 6.75 (d, J=2.26 Hz, 1 H) 7.00-7.05 (m, 1 H) 7.08-7.12 (m, 1 H) 7.12 (td, J=9.33, 4.52 Hz, 1 H) 7.30-7.34 (m, 2 H) 7.49-7.53 (m, 2 H) 7.79 (d, J=8.66 Hz, 1 H) 10.95 (s, 1 H). MS (ESI+) m/z 434 [M+H]$^+$.

Example 124

Methyl 4-({[4-(2,3-dihydro-1-benzofuran-5-yl)benzyl]sulfonyl}amino)-2-hydroxybenzoate

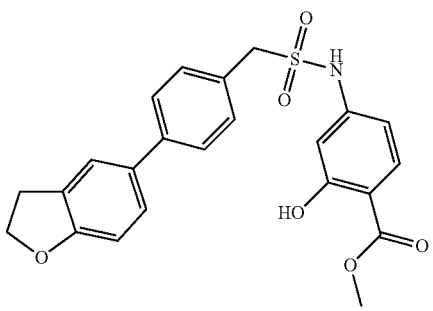 [SMILES: COC(=O)c1ccc(NS(=O)(=O)Cc2ccc(-c3ccc4c(c3)CCO4)cc2)cc1O]

4-{[(4-Bromobenzyl)sulfonyl]amino}-2-hydroxybenzoic acid (Intermediate 11) (12 mg, 0.030 mmol), 2,3-dihydrobenzofuran-5-boronic acid (6 mg, 0.036 mmol), DIPEA (15 mg, 0.12 mmol) and Pd(dppf)Cl$_2$.CH$_2$Cl$_2$ (1 mg, 0.0012 mmol) were allowed to react according to the General Procedure 9, described in Example 82. The crude product was purified by preparative HPLC (acidic system) and 4-({[4-(2,3-dihydro-1-benzofuran-5-yl)benzyl]sulfonyl}amino)-2-hydroxybenzoic acid was obtained in 96% yield (12.2 mg). $^1$H NMR (500 MHz, CD$_3$OD) δ ppm 3.25 (t, J=8.70 Hz, 2 H) 4.51 (s, 2 H) 4.58 (t, J=8.70 Hz, 2 H) 6.65 (dd, J=8.67, 2.14 Hz, 1 H) 6.72 (d, J=2.14 Hz, 1 H) 6.77 (d, J=8.18 Hz, 1 H) 7.27-7.31 (m, 2 H) 7.30 (dd, J=8.18, 1.83 Hz, 1 H) 7.42 (d, J=1.83 Hz, 1 H) 7.45-7.50 (m, 2 H) 7.74 (d, J=8.67 Hz, 1 H). MS (ESI+) m/z 426 [M+H]$^+$.

The title compound was prepared from 4-({[4-(2,3-dihydro-1-benzofuran-5-yl)benzyl]sulfonyl}amino)-2-hydroxybenzoic acid (10.4 mg, 0.024 mmol), 1,1'-carbonyldiimidazole (16 mg, 0.100 mmol), MeOH (20 µL, 0.5 mmol) and pyridine (8 mg, 0.100 mmol) in MeCN, according to the General Procedure 7, described in Example 59. The title compound was obtained in 27% yield (2.9 mg). $^1$H NMR (600 MHz, CDCl$_3$) δ ppm 3.27 (t, J=8.66 Hz, 2 H) 3.95 (s, 3 H) 4.45 (s, 2 H) 4.63 (t, J=8.66 Hz, 2 H) 6.47 (br. s., 1 H) 6.63 (dd, J=8.66, 2.26 Hz, 1 H) 6.75 (d, J=2.26 Hz, 1 H) 6.85 (d, J=8.25 Hz, 1 H) 7.24-7.27 (m, 2 H) 7.29-7.33 (ddt, J=8.30, 2.07, 0.71 Hz, 1 H) 7.39-7.41 (m, 1 H) 7.48-7.52 (m, 2 H) 7.79 (d, J=8.66 Hz, 1 H) 10.95 (s, 1 H). MS (ESI+) m/z 440 [M+H]$^+$.

Example 125

Methyl 4-{[(biphenyl-4-ylmethyl)sulfonyl]amino}-2-hydroxybenzoate

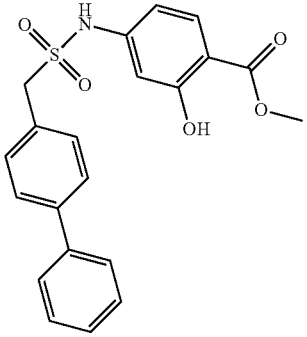 [SMILES: COC(=O)c1ccc(NS(=O)(=O)Cc2ccc(-c3ccccc3)cc2)cc1O]

4-{[(4-Bromobenzyl)sulfonyl]amino}-2-hydroxybenzoic acid (Intermediate 11) (12 mg, 0.030 mmol), phenylboronic acid (4 mg, 0.036 mmol), DIPEA (15 mg, 0.12 mmol) and Pd(dppf)Cl$_2$.CH$_2$Cl$_2$ (1 mg, 0.0012 mmol) were allowed to react according to the General Procedure 9, described in Example 82. The crude product was purified by preparative HPLC (acidic system) and 4-{[(biphenyl-4-ylmethyl)sulfonyl]amino}-2-hydroxybenzoic acid was obtained in 90% yield (10.3 mg). $^1$H NMR (500 MHz, CD$_3$OD) δ ppm 4.54 (s, 2 H) 6.67 (dd, J=8.67, 1.83 Hz, 1 H) 6.74 (br. s., 1 H) 7.31-7.37 (m, 1 H) 7.33-7.37 (m, 2 H) 7.40-7.45 (m, 2 H) 7.54-7.58 (m, 2 H) 7.56-7.59 (m, 2 H) 7.76 (d, J=8.67 Hz, 1 H). MS (ESI+) m/z 384 [M+H]$^+$.

The title compound was prepared from 4-{[(biphenyl-4-ylmethyl)sulfonyl]amino}-2-hydroxybenzoic acid (8.4 mg, 0.022 mmol), 1,1'-carbonyldiimidazole (16 mg, 0.100 mmol), MeOH (20 µL, 0.5 mmol) and pyridine (8 mg, 0.100 mmol) in MeCN, according to the General Procedure 7, described in Example 59. The title compound was obtained in 49% yield (4.3 mg). $^1$H NMR (600 MHz, CDCl$_3$) δ ppm 3.95 (s, 3 H) 4.47 (s, 2 H) 6.47 (br. s., 1 H) 6.62 (dd, J=8.66, 2.26 Hz, 1 H) 6.76 (d, J=2.26 Hz, 1 H) 7.28-7.33 (m, 2 H) 7.36-7.40 (m, 1 H) 7.43-7.47 (m, 2 H) 7.54-7.59 (m, 4 H) 7.79 (d, J=8.66 Hz, 1 H) 10.95 (s, 1 H). MS (ESI+) m/z 398 [M+H]$^+$.

Example 126

Methyl 2-hydroxy-4-({[(2'-hydroxybiphenyl-4-yl)methyl]sulfonyl}amino)benzoate

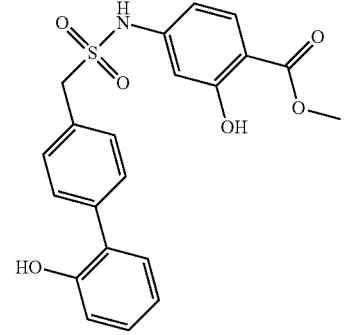 [SMILES: COC(=O)c1ccc(NS(=O)(=O)Cc2ccc(-c3ccccc3O)cc2)cc1O]

4-{[(4-Bromobenzyl)sulfonyl]amino}-2-hydroxybenzoic acid (Intermediate 11) (12 mg, 0.030 mmol), 2-hydroxyphenylboronic acid pinacol ester (8 mg, 0.036 mmol), DIPEA (15 mg, 0.12 mmol) and Pd(dppf)Cl$_2$·CH$_2$Cl$_2$ (1 mg, 0.0012 mmol) were allowed to react according to the General Procedure 9, described in Example 82. The crude product was purified by preparative HPLC (acidic system) giving 2-hydroxy-4-({[(2'-hydroxybiphenyl-4-yl)methyl]sulfonyl}amino)benzoic acid (12.8 mg). $^1$H NMR (500 MHz, CD$_3$OD) δ ppm 4.52 (s, 2 H) 6.69 (dd, J=8.67, 2.20 Hz, 1 H) 6.77 (d, J=2.20 Hz, 1 H) 6.86-6.90 (m, 2 H) 7.13-7.17 (m, 1 H) 7.18-7.21 (m, 1 H) 7.26-7.31 (m, 2 H) 7.49-7.53 (m, 2 H) 7.78 (d, J=8.67 Hz, 1H). MS (ESI+) m/z 400 [M+H]$^+$.

The title compound was prepared from 2-hydroxy-4-({[(2'-hydroxybiphenyl-4-yl)methyl]sulfonyl}amino)benzoic acid (11.7 mg, 0.029 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 45% yield (5.5 mg). $^1$H NMR (600 MHz, CDCl$_3$) δ ppm 3.94 (s, 3H) 4.48 (s, 2H) 5.22 (s, 1 H) 6.60 (dd, J=8.66, 2.26 Hz, 1 H) 6.68 (br. s., 1 H) 6.68 (d, J=2.26 Hz, 1 H) 6.97 (dd, J=8.11, 1.20 Hz, 1 H) 7.00 (ddd, J=7.58, 7.37, 1.20 Hz, 1 H) 7.21 (dd, J=7.58, 1.71 Hz, 1 H) 7.27 (ddd, J=8.11, 7.37, 1.71 Hz, 1 H) 7.33-7.37 (m, 2 H) 7.45-7.50 (m, 2 H) 7.78 (d, J=8.66 Hz, 1 H) 10.94 (s, 1 H). MS (ESI+) m/z 414 [M+H]$^+$.

Example 127

Methyl 4-{[(3'-ethoxybiphenyl-3-yl)sulfonyl]amino}-2-hydroxybenzoate

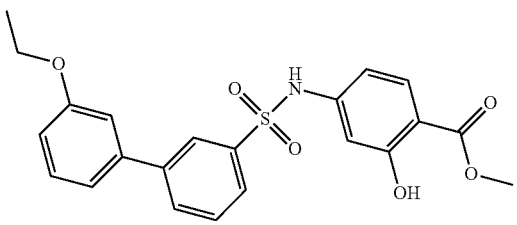 [SMILES: CCOc1cccc(-c2cccc(S(=O)(=O)Nc3ccc(C(=O)OC)c(O)c3)c2)c1]

A mixture of 4-{[(3-bromophenyl)sulfonyl]amino}-2-hydroxybenzoic acid (Intermediate 12) (18.7 mg, 0.05 mmol), 3-ethoxyphenylboronic acid (11.6 mg, 0.07 mmol), K$_2$CO$_3$ (20.7 mg, 0.15 mmol) and Pd(dppf)Cl$_2$:CH$_2$Cl$_2$ (4 mg, 0.005 mmol) in dioxane (3.2 mL) and water (800 μL) was heated at 145° C. for 900 s in a microwave reactor. The reaction mixture was concentrated and the crude product was purified by preparative HPLC (neutral method) to give 4-{[(3'-ethoxybiphenyl-3-yl)sulfonyl]amino}-2-hydroxybenzoic acid in 80% yield (16.6 mg). MS (ESI+) calcd mass for C$_{21}$H$_{19}$NO$_6$S 413.093308, found 413.094308.

The title compound was prepared from 4-{[(3'-ethoxybiphenyl-3-yl)sulfonyl]amino}-2-hydroxybenzoic acid (9.9 mg, 0.024 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 41% yield (4.2 mg). $^1$H NMR (600 MHz, CDCl$_3$) δ ppm 1.45 (t, J=7.03 Hz, 3H) 3.89 (s, 3 H) 4.09 (q, J=7.03 Hz, 2 H) 6.65 (dd, J=8.66, 2.26 Hz, 1 H) 6.69 (d, J=2.26 Hz, 1 H) 6.84 (br. s., 1 H) 6.93 (ddd, J=8.26, 2.54, 0.93 Hz, 1 H) 7.04 (dd, J=2.54, 1.78 Hz, 1 H) 7.10 (ddd, J=7.64, 1.78, 0.93 Hz, 1 H) 7.36 (dd, J=8.26, 7.64 Hz, 1 H) 7.53 (td, J=7.81, 0.50 Hz, 1 H) 7.71 (d, J=8.66 Hz, 1 H) 7.76 (ddd, J=7.81, 1.83, 1.08 Hz, 1 H) 7.83 (ddd, J=7.81, 1.92, 1.08 Hz, 1 H) 8.07 (ddd, J=1.92, 1.83, 0.50 Hz, 1 H) 10.84 (s, 1 H). MS (ESI+) m/z 428 [M+H]$^+$.

Example 128

1-Methylethyl 3'-{[3-hydroxy-4-(methoxycarbonyl)phenyl]sulfamoyl}biphenyl-3-carboxylate

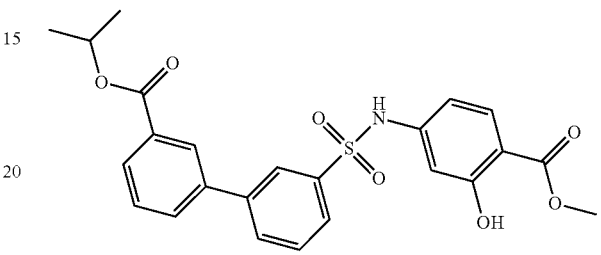

A mixture of 4-{[(3-bromophenyl)sulfonyl]amino}-2-hydroxybenzoic acid (Intermediate 12) (18.7 mg, 0.05 mmol), 3-isopropoxycarbonylphenylboronic acid (14.5 mg, 0.07 mmol), K$_2$CO$_3$ (20.7 mg, 0.15 mmol) and Pd(dppf)Cl$_2$:CH$_2$Cl$_2$ (4 mg, 0.005 mmol) in dioxane (3.2 mL) and water (800 μL) was heated at 145° C. for 900 s in a microwave reactor. The reaction mixture was concentrated and the crude product was purified by preparative HPLC (neutral method) to give 2-hydroxy-4-[({3'-[(1-methylethoxy)carbonyl]biphenyl-3-yl}sulfonyl)amino]benzoic acid in 35% yield (8 mg). MS (ESI+) calcd for C$_{23}$H$_{21}$NO$_7$S 455.103873, found 455.104263.

The title compound was prepared from 2-hydroxy-4-[({3'-[(1-methylethoxy)carbonyl]biphenyl-3-yl}sulfonyl)amino]benzoic acid (3.9 mg, 0.009 mmol), 1,1'-carbonyldiimidazole (16 mg, 0.100 mmol), MeOH (20 μL, 0.5 mmol) and pyridine (8 mg, 0.100 mmol) in MeCN, according to the General Procedure 7, described in Example 59. The title compound was obtained in 40% yield (1.6 mg). $^1$H NMR (600 MHz, CDCl$_3$) δ ppm 1.40 (d, J=6.22 Hz, 6 H) 3.89 (s, 3 H) 5.29 (spt, J=6.22 Hz, 1 H) 6.66 (dd, J=8.66, 2.25 Hz, 1 H) 6.69 (d, J=2.25 Hz, 1 H) 6.91 (br. s., 1 H) 7.53 (td, J=7.73, 0.50 Hz, 1 H) 7.58 (ddd, J=7.81, 7.75, 0.45 Hz, 1 H) 7.71 (ddd, J=7.73, 1.96, 1.15 Hz, 1 H) 7.72 (d, J=8.66 Hz, 1 H) 7.81 (ddd, J=7.75, 1.85, 1.05 Hz, 1 H) 7.87 (ddd, J=7.87, 1.85, 1.05 Hz, 1 H) 8.07 (ddd, J=7.73, 1.67, 1.15 Hz, 1 H) 8.10 (td, J=1.85, 0.45 Hz, 1 H) 8.19 (ddd, J=1.96, 1.67, 0.50 Hz, 1 H) 10.84 (s, 1 H). MS (ESI+) m/z 470 [M+H]$^+$.

Example 129

Methyl 4-{[(3-acetylphenyl)sulfonyl]amino}-2-hydroxybenzoate

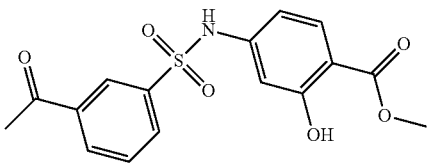 [SMILES: COC(=O)c1ccc(NS(=O)(=O)c2cccc(C(C)=O)c2)cc1O]

A mixture of 3-acetylbenzenesulfonyl chloride (109 mg, 0.5 mmol), 4-aminosalicylic acid (153 mg, 1 mmol) and pyridine (0.4 mL, 5 mmol) in $CH_2Cl_2$ (10 mL) was stirred at 60° C. for 2 h. The reaction mixture was diluted with EtOAc and the organic phase was washed with 1 M HCl, dried and concentrated. The residue was purified by preparative HPLC (acidic system) giving 155 mg of the intermediate 4-{[(3-acetylphenyl)sulfonyl]amino}-2-hydroxybenzoic acid. MS (ESI+) calcd for $C_{15}H_{13}NO_6S$ 335.046358, found 335.045738.

$H_2SO_4$ (170 µL) was added to a solution of 4-{[(3-acetylphenyl)sulfonyl]amino}-2-hydroxybenzoic acid (22 mg, 0.065 mmol) in dry MeOH (2.1 mL). The mixture was heated at 60° C. for 3 days. The reaction mixture was diluted with EtOAc and the organic phase was washed with water, dried and concentrated. The crude product was purified by preparative HPLC (acidic system). The fractions were neutralized with aqueous $NH_4OAc$ (sat) before evaporation. The residue was dissolved in EtOAc. The organic solution was washed with diluted HCl to remove the salts, dried and concentrated to give the title compound in 31% yield (7.1 mg). MS (ESI+) calcd for $C_{16}H_{15}NO_6S$ 349.062008, found 349.062218.

Example 130

Methyl 4-({[5-(2-fluoro-3-methoxyphenyl)pyridin-3-yl]sulfonyl}amino)-2-hydroxybenzoate

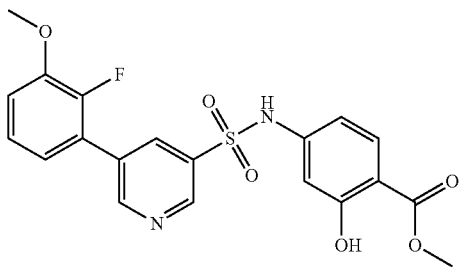 [SMILES: COC(=O)c1ccc(NS(=O)(=O)c2cncc(-c3cccc(OC)c3F)c2)cc1O]

A mixture of methyl 4-{[(5-bromo-6-chloropyridin-3-yl)sulfonyl]amino}-2-hydroxybenzoate (Intermediate 8) (42 mg, 0.100 mmol), 2-fluoro-3-methoxyphenylboronic acid (19.4 mg, 0.110 mmol), DIPEA (70 µL, 0.400 mmol) and $Pd(dppf)Cl_2 \cdot CH_2Cl_2$ (4 mg, 0.005 mmol) in aqueous dioxane (2 mL, 9:1 dioxane/water) was heated at 80° C. under nitrogen atmosphere for 1 day. After additional 2 days stirring at room temperature, the solvent was removed by evaporation giving the intermediate methyl 4-({[6-chloro-5-(2-fluoro-3-methoxyphenyl)pyridin-3-yl]sulfonyl}amino)-2-hydroxybenzoate.

The methyl 4-({[6-chloro-5-(2-fluoro-3-methoxyphenyl)pyridin-3-yl]sulfonyl}amino)-2-hydroxybenzoate together with a spatula of Pd/C (10%) were slurried in MeOH. The tube was sealed and a hydrogen atmosphere was applied with a balloon. The reaction mixture was stirred at room temperature overnight. More Pd/C (10%) was added and the reaction was stirred under hydrogen atmosphere for additional 3 days. The reaction mixture was filtered and the crude product was purified by preparative HPLC (acidic system). The title compound was obtained in 6% yield (2.6 mg). $^1$H NMR (600 MHz, $CDCl_3$) δ ppm 3.91 (s, 3 H) 3.94 (s, 3 H) 6.68 (dd, J=8.66, 2.20 Hz, 1 H) 6.72 (d, J=2.20 Hz, 1 H) 6.95 (ddd, J=8.02, 6.46, 1.46 Hz, 1 H) 7.06 (td, J=8.02, 1.46 Hz, 1 H) 7.20 (td, J=8.02, 1.46 Hz, 1H) 7.21 (br. s., 1 H) 7.74 (d, J=8.66 Hz, 1H) 8.30-8.35 (m, 1 H) 8.95 (s, 1 H) 9.04 (s, 1 H) 10.86 (s, 1 H). MS (ESI+) m/z 433 [M+H]$^+$.

Example 131

Methyl 2-hydroxy-4-({[3-methyl-5-(1-methylethyl)-1-benzofuran-2-yl]sulfonyl}amino)benzoate

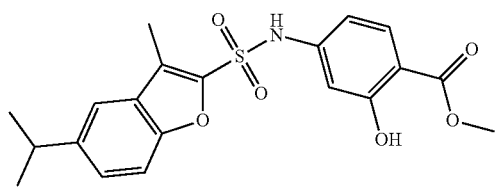 [SMILES: COC(=O)c1ccc(NS(=O)(=O)c2oc3ccc(C(C)C)cc3c2C)cc1O]

The intermediate 5-isopropyl-3-methylbenzofuran-2-sulfonyl chloride was prepared according to the following multistep procedure. A solution of 4-isopropylphenol (500 mg, 3.67 mmol), N-iodosuccinimide (838 mg, 3.72 mmol) and p-TsOH (70 mg, 0.37 mmol) in $CH_2Cl_2$ (25 mL) was stirred at room temperature overnight. The reaction mixture was diluted with $CH_2Cl_2$ and washed with water. The organic phase was dried and evaporated to give 820 mg of 2-iodo-4-isopropylphenol (85%). $^1$H NMR (400 MHz, $CDCl_3$) δ ppm 1.22 (d, J=7.03 Hz, 6 H) 2.82 (spt, J=7.03 Hz, 1 H) 6.92 (d, J=8.53 Hz, 1 H) 7.11 (dd, J=8.28, 2.01 Hz, 1 H) 7.50 (d, J=2.01 Hz, 1 H).

A mixture of 2-iodo-4-isopropylphenol (820 mg, 3.13 mmol), allylbromide (800 µL, 9.46 mmol) and $K_2CO_3$ (530 mg, 3.83 mmol) in THF (40 mL) was refluxed for 24 h and then stirred at room temperature for 48 h. The reaction mixture was diluted with $CH_2Cl_2$. The organic phase was washed with water followed by aqueous $NaHCO_3$ (sat) and then dried. Evaporation of the solvent gave allyl-2-iodo-4-isopropylphenyl ether (892 mg) which was used without further purification. MS (ESI+) m/z 303 [M+H]$^+$.

According to the method described by Xie et al. (Xie et al., (2004) Tetrahedron Lett. 45, 6235-6237) a mixture of allyl-2-iodo-4-isopropylphenyl ether (300 mg, 0.99 mmol), NBu$_3$ (350 µL, 1.49 mmol), ammonium formate (65 mg, 1.03 mmol) and $PdCl_2$ (10 mg, 0.06 mmol) in 1-butyl-3-methylimidazolium tetrafluoroborate (1.5 mL) was heated at 60° C. for 2 days. A second portion of $PdCl_2$ (24 mg) was added and the mixture was heated at 60° C. additional 5 h. The reaction mixture was extracted with $Et_2O$. Evaporation of the solvent afforded 220 mg of crude product, which was purified on silica using heptane as eluent giving the 5-isopropyl-3-methylbenzofuran in 30% yield (55 mg). $^1$H NMR (400 MHz, $CDCl_3$) δ ppm 1.31 (d, J=6.90 Hz, 6 H) 2.24 (d, J=1.25 Hz, 3 H) 3.03 (spt, J=6.90 Hz, 1 H) 7.17 (dd, J=8.34, 1.94 Hz, 1 H) 7.34-7.39 (m, 3 H). The synthesis was repeated on a larger scale before the sulfonylation step was carried out.

The 5-isopropyl-3-methylbenzofuran (8.7 g, 50 mmol) was dissolved in EtOAc (100 mL) and $Ac_2O$ (14 mL, 148 mmol) was added. Conc. $H_2SO_4$ (3 mL, 53 mmol) was added dropwise. The mixture was stirred at room temperature for 1 h. The product was precipitated by the dropwise addition of KOAc (5.0 g) in EtOH (50 mL) and separated by centrifugation. The solvent was decanted giving 5.02 g of potassium 5-isopropyl-3-methylbenzofuran-2-sulfonate (39%). $^1$H NMR (400 MHz, DMSO-d$_6$) δ ppm 1.25 (d, J=7.03 Hz, 6 H) 2.33 (s, 3 H) 3.00 (spt, J=7.03 Hz, 1 H) 7.21 (dd, J=8.66, 1.38 Hz, 1 H) 7.36-7.41 (m, 2 H). The NMR spectra showed 2.7 equiv of EtOH in the crystals.

The potassium salt of 5-isopropyl-3-methylbenzofuran-2-sulfonic acid (100 mg, 0.34 mmol) was mixed with POCl$_3$ (5 mL) and the reaction mixture was heated at 60° C. overnight. The POCl$_3$ was evaporated and the crude product was dissolved in CH$_2$Cl$_2$ and passed through a short plug of silica to give the 5-isopropyl-3-methylbenzofuran-2-sulfonyl chloride (30 mg, 33%).

The title compound was prepared from methyl 4-aminosalicylate (22 mg, 0.132 mmol) and 5-isopropyl-3-methylbenzofuran-2-sulfonyl chloride (50 mg, 0.183 mmol) according to the General Procedure 4, described in Example 7. The title compound was obtained in 13% yield (5.2 mg). $^1$H NMR (500 MHz, CD$_3$OD) δ ppm 1.28 (d, J=6.96 Hz, 6 H) 2.54 (s, 3 H) 3.02 (spt, J=6.96 Hz, 1 H) 3.87 (s, 3 H) 6.69 (dd, J=8.67, 2.20 Hz, 1 H) 6.77 (d, J=2.20 Hz, 1 H) 7.37 (dd, J=8.68, 1.65 Hz, 1 H) 7.38 (dd, J=8.68, 0.82 Hz, 1 H) 7.50 (dt, J=1.65, 0.82 Hz, 1 H) 7.69 (d, J=8.67 Hz, 1 H). MS (ESI+) m/z 404 [M+H]$^+$.

Example 132

Methyl 2-(acetyloxy)-4-{[(4,5-dichlorothiophen-2-yl)sulfonyl]amino}benzoate

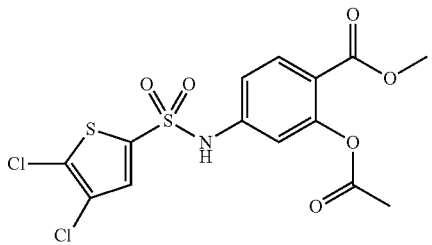 [SMILES: COC(=O)c1ccc(NS(=O)(=O)c2cc(Cl)c(Cl)s2)cc1OC(C)=O]

A mixture of methyl 4-[(tert-butoxycarbonyl)amino]-2-hydroxybenzoate (Intermediate 14) (150 mg, 0.56 mmol), pyridine (49 mg, 0.62 mmol) and acetic anhydride (65 mg, 0.64 mmol) was stirred in MeCN (5 mL) at 70° C. for 2 weeks. The solvent was removed under vacuum. The residue was dissolved in EtOAc, washed with 1 M HCl, water and brine. The solution was dried (MgSO$_4$) and concentrated under vacuum. The crude, methyl 2-(acetyloxy)-4-[(tert-butoxycarbonyl)amino]benzoate, was obtained as an oil (191 mg) and was used without further purification in the next step. $^1$H NMR (600 MHz, CDCl$_3$) δ ppm 1.51 (s, 9 H) 2.33 (s, 3 H) 3.84 (s, 3 H) 6.71 (s, 1 H) 7.11 (dd, J=8.66, 2.20 Hz, 1 H) 7.37 (br. s., 1 H) 7.94 (d, J=8.66 Hz, 1 H). MS (ESI+) m/z 327 [M+NH$_4$]$^+$. The position of the acetyl group was confirmed by DPFGSE-NOE experiments.

A solution of methyl 2-(acetyloxy)-4-[(tert-butoxycarbonyl)amino]benzoate (87 mg, 0.28 mmol) and TFA (230 mg, 2.0 mmol) in CH$_2$Cl$_2$ (1.3 mL) was stirred overnight at room temperature. The solution was diluted with more CH$_2$Cl$_2$, washed with saturated NaHCO$_3$ and brine, dried over MgSO$_4$, filtered and concentrated. The product, methyl 2-(acetyloxy)-4-aminobenzoate, was obtained in 69% yield (41 mg). MS (ESI+) m/z 210 [M+H]$^+$.

A mixture of methyl 2-(acetyloxy)-4-aminobenzoate (15 mg, 0.072 mmol), 2,3-dichlorothiophene-5-sulfonyl chloride (29 mg, 0.115 mmol) and pyridine (29 mg, 0.37 mmol) in MeCN (0.7 mL) was shaken at room temperature for 1 day. The solvent was removed under vacuum and the residue dissolved in DMSO. The sample was purified by preparative HPLC (acidic system). The title compound was obtained in 47% yield (20.1 mg). $^1$H NMR (600 MHz, CDCl$_3$) δ ppm 2.36 (s, 3 H) 3.85 (s, 3 H) 6.97 (d, J=2.14 Hz, 1 H) 7.01 (dd, J=8.54, 2.14 Hz, 1 H) 7.02 (br.s., 1 H) 7.38 (s, 1 H) 7.98 (d, J=8.54 Hz, 1 H). MS (ESI+) m/z 441 [M+NH$_4$]$^+$.

Example 133

2-Methoxyethyl 4-({[5-chloro-4-(2-hydroxyphenyl)-2-thienyl]sulfonyl}amino)-2-hydroxybenzoate

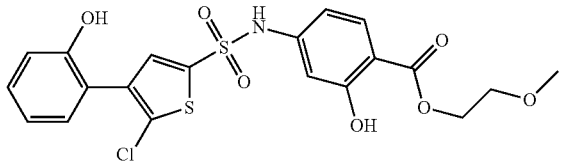 [SMILES: COCCOC(=O)c1ccc(NS(=O)(=O)c2cc(-c3ccccc3O)c(Cl)s2)cc1O]

A mixture of 4-{[(4-bromo-5-chlorothiophen-2-yl)sulfonyl]amino}-2-hydroxybenzoic acid (Intermediate 1) (150 mg, 0.36 mmol), 2-(4,4,5,5-tetramethyl-1,3,2-dioxaborolan-2-yl)phenol (87 mg, 0.40 mmol), DIPEA (140 mg, 1.1 mmol) and Pd(dppf)Cl$_2$.CH$_2$Cl$_2$ (15 mg, 0.018 mmol) in aqueous dioxane (5 mL dioxane, 1 mL water) was heated at 80° C. under N$_2$ atmosphere overnight. CH$_2$Cl$_2$ (50 mL) followed by 1 M Na$_2$CO$_3$ (10 mL) were added to the reaction mixture. The aqueous phase was washed with CH$_2$Cl$_2$ (2×50 mL) and then acidified with conc. H$_3$PO$_4$. EtOAc (100 mL) was added. The organic phase was washed with 1 M HCl (2×50 mL) and brine, dried over MgSO$_4$, filtered and concentrated. The crude product was dissolved in water/MeOH and purified by preparative HPLC (acidic system) to give 4-({[5-chloro-4-(2-hydroxyphenyl)thiophen-2-yl]sulfonyl}amino)-2-hydroxybenzoic acid as a white solid (37 mg, 24%). $^1$H NMR (500 MHz, CD$_3$OD) δ ppm 6.72 (dd, J=8.55, 2.20 Hz, 1 H) 6.78 (d, J=1.95 Hz, 1 H) 6.85-6.91 (m, 2 H) 7.19-7.24 (m, 2 H) 7.61 (s, 1H) 7.77 (d, J=8.55 Hz, 1 H). MS (ESI+) m/z 426 [M+H]$^+$.

A reaction mixture containing 4-({[5-chloro-4-(2-hydroxyphenyl)thiophen-2-yl]sulfonyl}amino)-2-hydroxybenzoic acid (5 mg, 0.011 mmol), 1,1'-carbonyldiimidazole (16 mg, 0.100 mmol) and pyridine (8 mg, 0.100 mmol) in MeCN (0.5 mL) was stirred at room temperature for 30 min, and then 2-methoxyethanol (7.6 mg, 0.100 mmol) was added. The reaction mixture was stirred at room temperature overnight, then acidified with TFA and diluted with MeOH. The crude product was purified by preparative HPLC (acidic system). The title compound was obtained in 39% yield (2.1 mg). $^1$H NMR (500 MHz, CDCl$_3$) δ ppm 3.44 (s, 3 H) 3.72-3.79 (m, 2 H) 4.45-4.54 (m, 2 H) 5.25 (br. s., 1 H) 6.70 (dd, J=8.67, 2.32 Hz, 1 H) 6.77 (d, J=2.20 Hz, 1 H) 6.90 (d, J=8.06 Hz, 1 H) 6.95 (br. s., 1 H) 6.96-7.01 (m, 1 H) 7.25 (dd, J=7.69, 1.59 Hz, 1 H) 7.28-7.32 (m, 1 H) 7.59 (s, 1 H) 7.83 (d, J=8.55 Hz, 1 H) 10.83 (s, 1 H). MS (ESI+) m/z 484 [M+H]$^+$.

Example 134

Methyl 4-{[(5'-fluoro-2'-hydroxybiphenyl-3-yl)sulfonyl]amino}-2-hydroxybenzoate

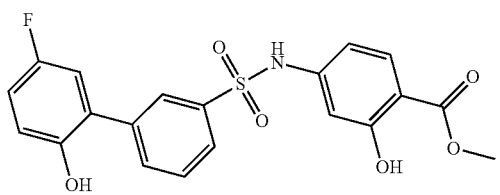 [SMILES: COC(=O)c1ccc(NS(=O)(=O)c2cccc(-c3cc(F)ccc3O)c2)cc1O]

A reaction mixture containing 4-{[(5'-fluoro-2'-hydroxybiphenyl-3-yl)sulfonyl]amino}-2-hydroxybenzoic acid (Intermediate 16) (15 mg, 0.037 mmol), 1,1'-carbonyldiimidazole (16 mg, 0.100 mmol), pyridine (8 mg, 0.100 mmol) and MeOH (20 μL, 0.5 mmol) in MeCN (1 mL) was heated at 60° C. overnight. The mixture was acidified with TFA (30 μL) and diluted with MeOH/water. The crude product was purified by preparative HPLC (acidic system). The title compound was obtained in 27% yield (4.3 mg). $^1$H NMR (600 MHz, CD$_3$OD) δ ppm 3.88 (s, 3 H) 6.70 (dd, J=8.70, 2.20 Hz, 1 H) 6.74 (d, J=2.20 Hz, 1 H) 6.88 (ddd, J=8.54, 4.73, 0.82 Hz, 1 H) 6.91-6.97 (m, 2 H) 7.55 (td, J=7.85, 0.45 Hz, 1H) 7.69 (d, J=8.70 Hz, 1 H) 7.78-7.82 (m, 2H) 8.10 (td, J=1.82, 0.45 Hz, 1H). MS (ESI+) m/z 418 [M+H]$^+$.

Example 135

3-(2-Chloro-5-{[3-hydroxy-4-(methoxycarbonyl)phenyl]sulfamoyl}thiophen-3-yl)benzoic acid

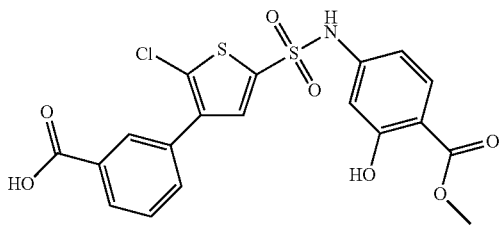 [SMILES: COC(=O)c1ccc(NS(=O)(=O)c2cc(-c3cccc(C(=O)O)c3)c(Cl)s2)cc1O]

The compound was prepared from methyl 4-{[(4-bromo-5-chloro-2-thienyl)sulfonyl]amino}-2-hydroxybenzoate (Intermediate 3) (128 mg, 0.30 mmol) and 3-carboxyphenylboronic acid (50 mg, 0.30 mmol) as described for Intermediate 13. An analytical sample of the crude product (14 mg) was purified by preparative HPLC (acidic system) to give the title compound in 100% purity (5.3 mg, 38%). $^1$H NMR (600 MHz, CD$_3$OD) δ ppm 3.91 (s, 3 H) 6.76 (dd, J=8.70, 2.20 Hz, 1 H) 6.82 (dd, J=2.20, 0.30 Hz, 1 H) 7.57 (td, J=7.78, 0.50 Hz, 1H) 7.68 (s, 1 H) 7.73 (ddd, J=7.78, 1.88, 1.18 Hz, 1 H) 7.79 (dd, J=8.70, 0.30 Hz, 1 H) 8.06 (ddd, J=7.78, 1.65, 1.18 Hz, 1 H) 8.14 (ddd, J=1.88, 1.65, 0.50 Hz, 1 H). MS (ESI+) m/z 468 [M+H]$^+$.

Example 136

Methyl 4-({[3-(ethoxycarbonyl)phenyl]sulfonyl}amino)-2-hydroxybenzoate

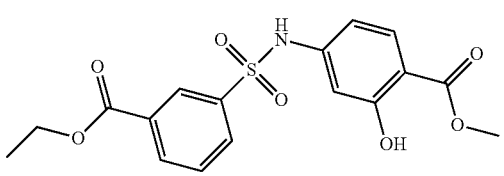 [SMILES: CCOC(=O)c1cccc(S(=O)(=O)Nc2ccc(C(=O)OC)c(O)c2)c1]

A solution of 3-({[3-hydroxy-4-(methoxycarbonyl)phenyl]amino}sulfonyl)benzoic acid (Intermediate 15) (18 mg, 0.050 mmol), pyridine (8 mg, 0.10 mmol) and 1,1'-carbonyldiimidazole (16 mg, 0.10 mmol) in MeCN (700 μL) was prepared. After 30 minutes EtOH (100 μL, excess) was added. The reaction mixture was shaken at 60° C. for 3 days. The reaction was acidified by addition of TFA (30 μL), diluted with water/MeOH and purified by preparative HPLC (acidic system). The title compound was obtained in 57% yield (11 mg). $^1$H NMR (600 MHz, DMSO-d6) δ ppm 1.32 (t, J=7.17 Hz, 3H) 3.81 (s, 3 H) 4.34 (q, J=7.17 Hz, 2 H) 6.67 (br. s., 2 H) 7.63 (d, J=8.09 Hz, 1 H) 7.74 (t, J=7.85 Hz, 1 H) 8.07 (d, J=7.85 Hz, 1 H) 8.17 (d, J=7.85 Hz, 1 H) 8.35 (t, J=1.60 Hz, 1 H) 10.56 (s, 1 H) 11.02 (br. s., 1H). MS (ESI+) m/z 380 [M+H]$^+$.

Example 137

Methyl 2-hydroxy-4-[({3-[(1-methylethoxy)carbonyl]phenyl}sulfonyl)amino]benzoate

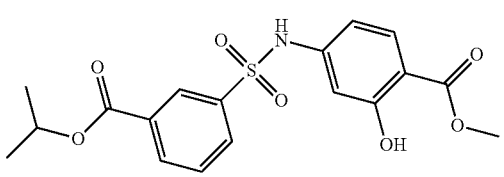 [SMILES: COC(=O)c1ccc(NS(=O)(=O)c2cccc(C(=O)OC(C)C)c2)cc1O]

A solution of 3-({[3-hydroxy-4-(methoxycarbonyl)phenyl]amino}sulfonyl)benzoic acid (Intermediate 15) (18 mg, 0.050 mmol), pyridine (8 mg, 0.10 mmol) and 1,1'-carbonyldiimidazole (16 mg, 0.10 mmol) in MeCN (700 μL) was prepared. After 30 minutes isopropanol (100 μL, excess) was added. The reaction mixture was shaken at 60° C. for 3 days. The reaction was acidified by addition of TFA (30 μL), diluted with water/MeOH and purified by preparative HPLC (acidic system). The title compound was obtained in 61% yield (12 mg). $^1$H NMR (600 MHz, CDCl$_3$) δ ppm 1.37 (d, J=6.26 Hz, 6 H) 3.90 (s, 3 H) 5.26 (spt, J=6.26 Hz, 1 H) 6.64 (dd, J=8.65, 2.25 Hz, 1 H) 6.67 (d, J=2.25 Hz, 1 H) 6.86 (br. s., 1 H) 7.56 (t, J=7.85 Hz, 1 H) 7.71 (d, J=8.65 Hz, 1 H) 8.03 (ddd, J=7.85, 1.91, 1.22 Hz, 1 H) 8.23 (ddd, J=7.85, 1.51, 1.20 Hz, 1 H) 8.50 (dd, J=1.91, 1.51 Hz, 1H) 10.84 (s, 1 H). MS (ESI+) m/z 394 [M+H]$^+$.

Example 138

Methyl 2-hydroxy-4-({[3-(methylcarbamoyl)phenyl]sulfonyl}amino)benzoate

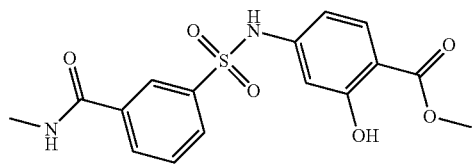

A solution of 3-({[3-hydroxy-4-(methoxycarbonyl)phenyl]amino}sulfonyl)benzoic acid (Intermediate 15) (18 mg, 0.050 mmol), DIPEA (10 mg, 0.075 mmol) and propanephosphonic acid cyclic anhydride (50% in EtOAc, 45 µL, 0.075 mmol) in MeCN (700 µL) was prepared. After 30 minutes was methylamine, 33% in EtOH (100 µL, excess) added. The reaction was shaken at room temperature for 3 days. The reaction mixture was diluted with water/MeOH and purified by preparative HPLC (acidic system). The title compound was obtained in 49% yield (9 mg). $^1$H NMR (600 MHz, CD$_3$OD) δ ppm 2.92 (s, 3 H) 3.88 (s, 3 H) 6.67 (dd, J=8.70, 2.20 Hz, 1 H) 6.70 (d, J=2.20 Hz, 1 H) 7.62 (td, J=7.93, 0.53 Hz, 1 H) 7.68 (d, J=8.70 Hz, 1H) 7.98-8.02 (m, 2 H) 8.33 (td, J=1.83, 0.53 Hz, 1 H). MS (ESI+) m/z 365 [M+H]$^+$.

Example 139

Methyl 2-hydroxy-4-({[3-(piperidin-1-ylcarbonyl)phenyl]sulfonyl}amino)benzoate

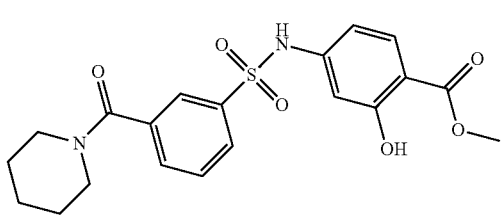 [SMILES: COC(=O)c1ccc(NS(=O)(=O)c2cccc(C(=O)N3CCCCC3)c2)cc1O]

A solution of 3-({[3-hydroxy-4-(methoxycarbonyl)phenyl]amino}sulfonyl)benzoic acid (Intermediate 15) (18 mg, 0.050 mmol), diisopropylethylamine (10 mg, 0.075 mmol) and propanephosphonic acid cyclic anhydride (50% in EtOAc, 45 µL, 0.075 mmol) in MeCN (700 µL) was prepared. After 30 minutes was piperidine (100 µL, excess) added. The reaction mixture was shaken at room temperature for 3 days. The reaction was diluted with water/MeOH and purified by preparative HPLC (acidic system). The title compound was obtained in 53% yield (11.1 mg). $^1$H NMR (600 MHz, CD$_3$OD) δ ppm 1.38-1.49 (m, 2 H) 1.61-1.69 (m, 2 H) 1.66-1.72 (m, 2 H) 3.13-3.21 (m, 2 H) 3.65-3.73 (m, 2 H) 3.89 (s, 3 H) 6.67 (dd, J=8.70, 2.20 Hz, 1H) 6.70 (d, J=2.20 Hz, 1 H) 7.61 (dd, J=7.63, 1.60, 1.50 Hz, 1 H) 7.64 (ddd, J=7.63, 7.50, 0.59 Hz, 1 H) 7.69 (d, J=8.70 Hz, 1 H) 7.81 (ddd, J=1.96, 1.50, 0.59 Hz, 1 H) 7.96 (ddd, J=7.50, 1.96, 1.60 Hz, 1 H). MS (ESI+) m/z 419 [M+H]$^+$.

Example 140

Benzyl 2-acetoxy-4-[(1-naphthylsulfonyl)amino]benzoate

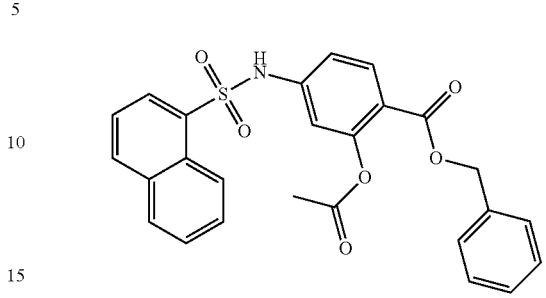

A mixture of methyl 4-[(tert-butoxycarbonyl)amino]-2-hydroxybenzoate (Intermediate 14) (200 mg, 0.75 mmol) in 1 M NaOH (4 mL) and dioxane (2 mL) was stirred at 40° C. overnight. The reaction mixture was first washed with Et$_2$O and then acidified with conc. H$_3$PO$_4$ to pH ~3. EtOAc was added. The organic phase was washed with brine, dried over MgSO$_4$, filtered and concentrated. The 4-[(tert-butoxycarbonyl)amino]-2-hydroxybenzoic acid was obtained in 99% yield (187 mg). MS (ESI+) m/z 254 [M+H]$^+$.

A solution of 4-[(tert-butoxycarbonyl)amino]-2-hydroxybenzoic acid (187 mg, 0.74 mmol), 1,1'-carbonyldiimidazole (162 mg, 1.0 mmol) and pyridine (79 mg, 1.0 mmol) in MeCN (5 mL) was prepared. After 30 minutes benzyl alcohol (108 mg, 1.0 mmol) was added. The reaction mixture was stirred at 50° C. overnight. EtOAc (20 mL) and water (20 mL) was added. The organic phase was washed with 1 M H$_3$PO$_4$ and brine, dried over MgSO$_4$, filtered and concentrated. The residue was purified by flash chromatography (silica, 20% EtOAc in hexane). The benzyl 4-[(tert-butoxycarbonyl)amino]-2-hydroxybenzoate was obtained in 31% yield (72 mg).). MS (ESI+) m/z 288 [M−tBu]$^+$.

A mixture of benzyl 4-[(tert-butoxycarbonyl)amino]-2-hydroxybenzoate (72 mg, 0.23 mmol), DIPEA (89 mg, 0.69 mmol) and acetyl chloride (54 mg, 0.69 mmol) in MeCN (4 mL) was stirred overnight. To the reaction mixture was added water and EtOAc. The organic phase was washed with 1 M H$_3$PO$_4$, water, sat. NaHCO$_3$ and brine, dried over MgSO$_4$, filtered and concentrated. The benzyl 2-acetoxy-4-[(tert-butoxycarbonyl)amino]benzoate was obtained in 78% yield (70 mg). MS (ESI+) m/z 403 [M+NH$_4$]$^+$.

A mixture of benzyl 2-acetoxy-4-[(tert-butoxycarbonyl)amino]benzoate (70 mg, 0.18 mmol) and TFA (500 µL) in 2 mL of dichloromethane was stirred for 1 h. Water (2 mL) was added. The organic phase was washed with sat. NaHCO$_3$ and brine, dried over MgSO$_4$, filtered and concentrated. The benzyl 2-acetoxy-4-aminobenzoate was obtained in 89% yield (46 mg). MS (ESI+) m/z 286 [M+H]$^+$.

A mixture of benzyl 2-acetoxy-4-aminobenzoate (46 mg, 0.16 mmol), pyridine (25 mg, 0.32 mmol) and 1-naphthalenesulfonyl chloride (54 mg, 0.24 mmol) in MeCN (2 mL) was shaken at 60° C. for 2 h. The reaction mixture was acidified with TFA (100 µL) and purified by preparative HPLC (acidic system). The title compound was obtained in 39% yield (30 mg). $^1$H NMR (600 MHz, CDCl$_3$) δ ppm 2.05 (s, 3 H) 5.20 (s, 2 H) 6.81-6.84 (m, 2 H) 7.30-7.38 (m, 5 H) 7.50 (dd, J=8.21, 7.40 Hz, 1 H) 7.60 (ddd, J=8.17, 6.88, 1.07 Hz, 1 H) 7.69 (ddd, J=8.68, 6.88, 1.32 Hz, 1 H) 7.81-7.84 (m, 1 H) 7.91-7.95 (m, 1 H) 8.05 (d, J=8.21 Hz, 1 H) 8.26 (dd, J=7.40, 1.07 Hz, 1 H) 8.63 (dq, J=8.68, 1.07 Hz, 1 H). MS (ESI+) m/z 476 [M+H]$^+$.

Example 141

2-Acetoxy-4-[(1-naphthylsulfonyl)amino]benzoic acid

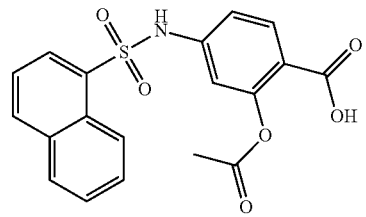 [SMILES: CC(=O)Oc1cc(NS(=O)(=O)c2cccc3ccccc23)ccc1C(=O)O]

A mixture of benzyl 2-acetoxy-4-[(1-naphthylsulfonyl)amino]benzoate (Example 140) (20 mg, 0.042 mmol) and palladium on charcoal (10%, 5 mg) in EtOAc (3 mL) was stirred in an atmosphere of hydrogen for 2 hours. The reaction mixture was filtered and purified by preparative HPLC (acidic system). The title compound was obtained in 48% yield (7.7 mg). $^1$H NMR (600 MHz, CD$_3$OD) δ ppm 2.21 (s, 3 H) 6.84 (dd, J=2.25, 0.31 Hz, 1 H) 6.95 (dd, J=8.70, 2.25 Hz, 1 H) 7.57 (dd, J=8.25, 7.37 Hz, 1 H) 7.62 (ddd, J=8.23, 6.93, 1.00 Hz, 1 H) 7.71 (ddd, J=8.69, 6.93, 1.38 Hz, 1 H) 7.77 (dd, J=8.70, 0.31 Hz, 1 H) 7.98-8.01 (m, 1 H) 8.12-8.16 (m, 1 H) 8.31 (dd, J=7.37, 1.22 Hz, 1 H) 8.72 (dq, J=8.69, 1.00 Hz, 1 H). MS (ESI+) m/z 386 [M+H]$^+$. A $^{15}$N-gHMBC experiment support the position of the acetyl group.

Example 142

Methyl 2-hydroxy-4-({[3-(piperidin-1-yl)phenyl]sulfonyl}amino)benzoate

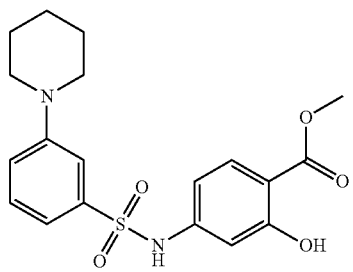 [SMILES: COC(=O)c1ccc(NS(=O)(=O)c2cccc(N3CCCCC3)c2)cc1O]

A mixture of methyl 4-{[(3-bromophenyl)sulfonyl]amino}-2-hydroxybenzoate (Intermediate 4) (40 mg, 0.10 mmol), piperidine (14 µL, 0.14 mmol), Pd$_2$(dba)$_3$ (8 mg, 0.009 mmol) and 2'-(dicyclohexylphosphino)-N,N-dimethyl[1,1'-biphenyl]-2-amine (8 mg, 0.02 mmol) was weighed out in a tube, flushed with N$_2$ and capped. Dry THF (2 mL) was added, followed by lithium bis(trimethylsilyl)amide (0.5 mL, 1 M in THF). The vial was heated for 30 minutes in a microwave reactor at 100° C. The reaction was quenched with saturated NH$_4$Cl (1 mL) and the organic phase was separated. The solvent was evaporated and the residue was dissolved in MeOH together with 2 drops of TFA. The crude product was purified by preparative HPLC (basic system) and the title compound was obtained in 40% yield (7.6 mg). $^1$H NMR (600 MHz, CDCl$_3$) δ ppm 1.56-1.62 (m, 2 H) 1.63-1.70 (m, 4 H) 3.15-3.21 (m, 4 H) 3.90 (s, 3 H) 6.62 (dd, J=8.66, 2.26 Hz, 1 H) 6.66 (d, J=2.26 Hz, 1 H) 6.68 (br. s., 1 H) 7.04 (ddd, J=8.39, 2.50, 0.91 Hz, 1 H) 7.21 (ddd, J=7.72, 1.74, 0.91 Hz, 1 H) 7.29 (dd, J=8.39, 7.72 Hz, 1 H) 7.32 (dd, J=2.50, 1.74 Hz, 1 H) 7.69 (d, J=8.66 Hz, 1 H) 10.82 (s, 1 H). MS (ESI+) m/z 391 [M+H]$^+$.

Example 143

Methyl 4-[({5-chloro-4-[3-(dimethylcarbamoyl)phenyl]thiophen-2-yl}sulfonyl)amino]-2-hydroxybenzoate

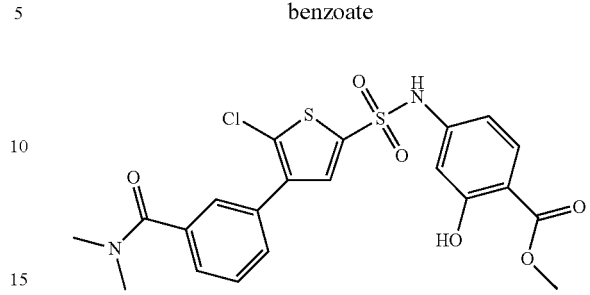

A solution of 3-(2-chloro-5-{[3-hydroxy-4-(methoxycarbonyl)phenyl]sulfamoyl}thiophen-3-yl)benzoic acid (Intermediate 13) (14 mg, 0.030 mmol), pyridine (8 mg, 0.10 mmol) and 1,1'-carbonyldiimidazole (16 mg, 0.10 mmol) in MeCN (700 µL) was prepared. After 30 minutes dimethylamine (40% in water, 100 µL, excess) was added. The reaction mixture was shaken at 60° C. overnight. The reaction was acidified with TFA (30 µL), diluted with water/MeOH and purified by preparative HPLC (acidic system). The title compound was obtained in 14% yield (2.1 mg). $^1$H NMR (600 MHz, CDCl$_3$) δ ppm 3.01 (br. s., 3 H) 3.13 (br. s., 3 H) 3.92 (s, 3 H) 6.72 (dd, J=8.62, 2.25 Hz, 1 H) 6.76 (d, J=2.25 Hz, 1 H) 7.14 (br. s., 1 H) 7.44 (ddd, J=6.90, 2.10, 1.75 Hz, 1 H) 7.46-7.50 (m, 2 H) 7.51 (td, J=1.70, 0.72 Hz, 1 H) 7.55 (s, 1 H) 7.78 (d, J=8.62 Hz, 1 H) 10.91 (s, 1 H). MS (ESI+) m/z 495 [M+H]$^+$.

Example 144

(5-Methyl-2-oxo-1,3-dioxol-4-yl)methyl 4-{[(4,5-dichloro-2-thienyl)sulfonyl]amino}-2-hydroxybenzoate

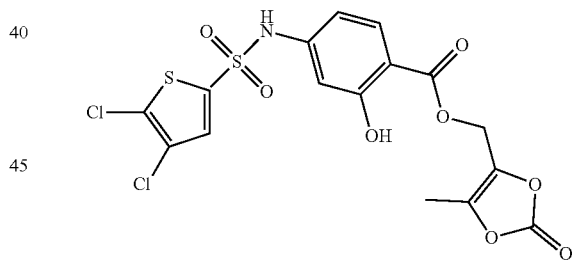

A mixture of 4,5-dimethyl-1,3-dioxol-2-one (1.0 g, 8.8 mmol), benzoylperoxide (60 mg, 0.25 mmol) and N-bromosuccinimide (1.6 g, 9.0 mmol) in carbon tetrachloride (10 mL) was heated at reflux for 2 h. The solid was removed from the reaction mixture by filtration. The mother liquid was washed with sat. NaHCO$_3$ and brine, dried over MgSO$_4$ and concentrated. The crude product, 4-(bromomethyl)-5-methyl-1,3-dioxol-2-one, was obtained as a yellow oil (1.7 g) and was used without further purification in the next step.

A mixture of 4-(bromomethyl)-5-methyl-1,3-dioxol-2-one (10 mg, 0.052 mmol), 4-{[(4,5-dichloro-2-thienyl)sulfonyl]amino}-2-hydroxybenzoic acid (Intermediate 7, 14 mg, 0.037 mmol) and NaHCO$_3$ (2.8 mg, 0.033 mmol) in DMF (0.4 mL) was shaken at room temperature overnight. The reaction mixture was acidified by addition of TFA (50 µL), diluted with water/MeCN and purified by preparative HPLC (acidic system). The title compound was obtained in 38% yield (6.8 mg). $^1$H NMR (600 MHz, CD$_3$OD) δ ppm 2.23 (s, 3 H) 5.19 (s, 2 H) 6.74 (dd, J=8.70, 2.20 Hz, 1 H)

6.79 (d, J=2.20 Hz, 1 H) 7.54 (s, 1 H) 7.79 (d, J=8.70 Hz, 1 H). MS (ESI+) m/z 497 [M+NH$_4$]$^+$. $^{13}$C-gHSQC and $^{13}$C-gHMBC experiments support the structure.

Example 145

3-({[3-Hydroxy-4-(methoxycarbonyl)phenyl]amino}sulfonyl)benzoic acid

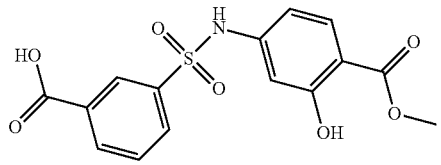 [SMILES: COC(=O)c1ccc(NS(=O)(=O)c2cccc(C(=O)O)c2)cc1O]

The product was prepared from 3-(chlorosulfonyl)benzoic acid (0.50 g, 2.3 mmol) and methyl 4-aminosalicylate (0.38 g, 2.3 mmol) as described for Intermediate 15. The title compound was obtained in 22% yield (180 mg). $^1$H NMR (600 MHz, CD$_3$OD) δ ppm 3.88 (s, 3 H) 6.68 (dd, J=8.70, 2.23 Hz, 1 H) 6.71 (dd, J=2.23, 0.31 Hz, 1 H) 7.64 (td, J=7.86, 0.55 Hz, 1 H) 7.69 (dd, J=8.70, 0.31 Hz, 1 H) 8.05 (ddd, J=7.86, 1.96, 1.15 Hz, 1 H) 8.21 (ddd, J=7.86, 1.67, 1.15 Hz, 1 H) 8.48 (ddd, J=1.96, 1.67, 0.55 Hz, 1 H). MS (ESI+) m/z 352 [M+H]$^+$.

Example 146

2-Amino-2-oxoethyl 4-{[(4,5-dichlorothiophen-2-yl)sulfonyl]amino}-2-hydroxybenzoate

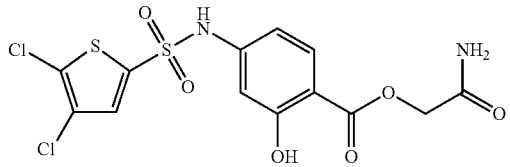 [SMILES: NC(=O)COC(=O)c1ccc(NS(=O)(=O)c2cc(Cl)c(Cl)s2)cc1O]

A mixture of 4-{[(4,5-dichlorothiophen-2-yl)sulfonyl]amino}-2-hydroxybenzoic acid (Intermediate 7) (25 mg, 0.068 mmol), chloroacetamide (5.8 mg, 0.062 mmol), NaHCO$_3$ (5.5 mg, 0.065 mmol) and NaI (0.5 mg, 0.003 mmol) in DMF (500 μL) was shaken at 50° C. overnight. The crude product was purified by preparative HPLC (basic system) and the title product was obtained in 29% yield (8.4 mg). $^1$H NMR (600 MHz, DMSO-d$_6$) δ ppm 4.66 (s, 2 H) 6.72-6.76 (m, 1 H) 6.76 (d, J=8.64 Hz, 1 H) 7.35 (br. s., 1H) 7.56 (br. s., 1 H) 7.77-7.82 (m, 1 H) 7.81 (d, J=8.64 Hz, 1 H) 10.49 (s, 1 H) 11.31 (br. s., 1 H). MS (ESI+) m/z 425 [M+H]$^+$.

Example 147

2-[Bis(2-hydroxyethyl)amino]ethyl 4-{[(2,5-dichloro-3-thienyl)sulfonyl]amino}-2-hydroxybenzoate trifluoroacetate

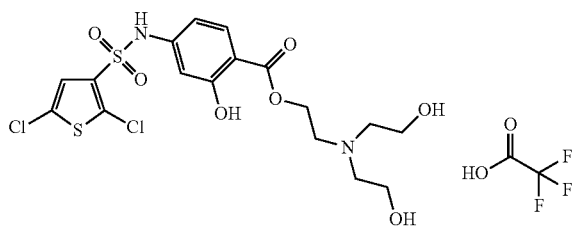 [SMILES: O=C(OCCN(CCO)CCO)c1ccc(NS(=O)(=O)c2cc(Cl)sc2Cl)cc1O ; O=C(O)C(F)(F)F]

A mixture of 4-{[(2,5-dichlorothiophen-3-yl)sulfonyl]amino}-2-hydroxybenzoic acid (Intermediate 6) (18 mg, 0.050 mmol), pyridine (8 mg, 0.10 mmol), carbonyldiimidazole (16 mg, 0.10 mmol) and triethanolamine (15 mg, 0.10 mmol) in 500 μL of MeCN was shaken overnight. The reaction mixture was acidified by addition of TFA, diluted with water/MeOH and purified by preparative HPLC (acidic system). The title compound was obtained in 58% yield (17.9 mg). $^1$H NMR (500 MHz, CDCl$_3$) δ ppm 3.41-3.52 (m, 4 H) 3.71-3.81 (m, 2 H) 3.88-3.94 (m, 4 H) 4.68-4.74 (m, 2 H) 6.72-6.76 (m, 2 H) 7.27 (s, 1 H) 7.86 (m, 1 H). MS (ESI+) m/z 499 [M+H]$^+$.

Example 148

2-(2-Hydroxyethoxy)ethyl 4-{[(2,5-dichloro-3-thienyl)sulfonyl]amino}-2-hydroxybenzoate

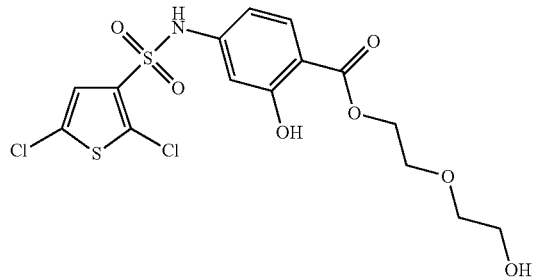 [SMILES: O=C(OCCOCCO)c1ccc(NS(=O)(=O)c2cc(Cl)sc2Cl)cc1O]

A mixture of 4-{[(2,5-dichlorothiophen-3-yl)sulfonyl]amino}-2-hydroxybenzoic acid (Intermediate 6) (18 mg, 0.050 mmol), pyridine (8 mg, 0.10 mmol), 1,1'-carbonyldiimidazole (16 mg, 0.10 mmol) and diethylene glycol (11 mg, 0.10 mmol) in MeCN (500 μL) was shaken overnight. The reaction mixture was acidified by addition of TFA, diluted with water/MeOH and purified by preparative HPLC (acidic system). The title compound was obtained in 25% yield (5.6 mg). $^1$H NMR (500 MHz, DMSO-d$_6$:CD$_3$OD 6:2) δ ppm 3.46-3.52 (m, 4 H) 3.71-3.74 (m, 2 H) 4.36-4.40 (m, 2 H) 6.69 (d, J=2.20 Hz, 1 H) 6.72 (dd, J=8.67, 2.20 Hz, 1 H) 7.37 (s, 1 H) 7.72 (d, J=8.67 Hz, 1 H). MS (ESI+) m/z 456 [M+H]$^+$.

Example 149

Pentyl 4-{[(4,5-dichloro-2-thienyl)sulfonyl]amino}-2-hydroxybenzoate

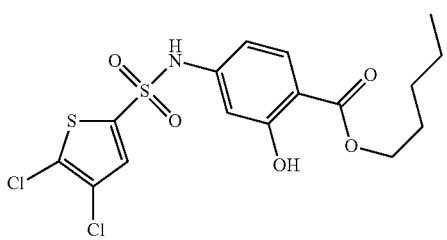 [SMILES: CCCCCOC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 1-pentanol (50 μL, excess) according to the General Procedure 8, described in Example 60. The title compound was obtained in 71% yield (15.5 mg). $^1$H NMR (500 MHz, CDCl$_3$) δ ppm 0.93 (t, J=7.08 Hz, 3 H) 1.35-1.46 (m, 4 H) 1.73-1.81 (m, 2 H) 4.33 (t, J=6.71 Hz, 2 H) 6.68 (dd, J=8.67, 2.26 Hz, 1 H) 6.73 (d, J=2.26 Hz, 1 H) 6.88 (br. s., 1 H) 7.42 (s, 1 H) 7.80 (d, J=8.67 Hz, 1 H) 11.02 (s, 1 H). MS (ESI+) m/z 438 [M+H]+.

Example 150

Propyl 4-{[(4,5-dichloro-2-thienyl)sulfonyl]amino}-2-hydroxybenzoate

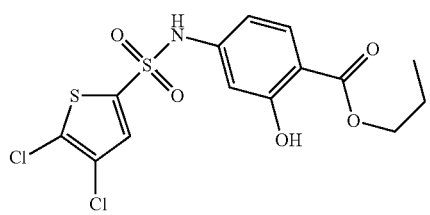 [SMILES: CCCOC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.50 mmol) (Intermediate 7) and 1-propanol (50 µL, excess) according to the General Procedure 8, described in Example 60. The title compound was obtained in 61% yield (12.6 mg). $^1$H NMR (500 MHz, CDCl$_3$) δ ppm 1.03 (t, J=7.45 Hz, 3 H) 1.75-1.84 (m, 2 H) 4.29 (t, J=6.65 Hz, 2 H) 6.68 (dd, J=8.67, 2.26 Hz, 1 H) 6.73 (d, J=2.26 Hz, 1 H) 6.92 (br. s., 1 H) 7.41 (s, 1 H) 7.81 (d, J=8.67 Hz, 1 H) 11.01 (s, 1 H). MS (ESI+) m/z 410 [M+H]+.

Example 151

4-(Dimethylamino)butyl 2-hydroxy-4-({[3-(2-methyl-1,3-thiazol-4-yl)phenyl]sulfonyl}amino)benzoate trifluoroacetate

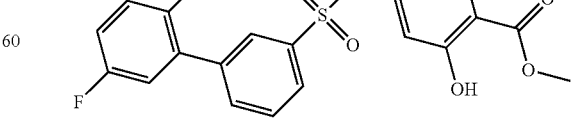

A mixture of 3-(2-methyl-1,3-thiazol-4-yl)benzenesulfonyl chloride (137 mg, 0.5 mmol), 4-aminosalicylic acid (153 mg, 1 mmol) and pyridine (396 mg, 5 mmol) in CH$_2$Cl$_2$ (20 mL) was stirred at room temperature overnight and at 50° C. for 2 h. The reaction was diluted with EtOAc, washed with 1 M HCl, dried and concentrated. The residue was purified by flash chromatography (silica, CHCl$_3$+0.5% formic acid). The intermediate, 2-hydroxy-4-({[3-(2-methyl-1,3-thiazol-4-yl)phenyl]sulfonyl}amino)benzoic acid, was obtained in 41% yield (80 mg). MS (ESI+) m/z 391 [M+H]+.

A mixture of 2-hydroxy-4-({[3-(2-methyl-1,3-thiazol-4-yl)phenyl]sulfonyl}amino)benzoic acid (26 mg, 67 µmol), 4-(dimethylamino)-1-butanol (78 mg, 0.67 mmol), 4-dimethylaminopyridine (2.4 mg, 20 µmol) and N,N'-dicyclohexylcarbodiimide (41 mg, 0.20 mmol) was stirred in THF (1 ml) overnight at room temperature and further at 60° C. for 3 h. The solvent was evaporated and the residue dissolved on MeOH. The compound was purified by preparative HPLC (acidic system). The title compound was obtained in 6% yield (2.5 mg). MS (ESI+) calcd for C$_{23}$H$_{27}$N$_3$O$_5$S$_2$: 489.139212, found 489.140522.

Example 152

Methyl 4-({[5'-fluoro-2'-hydroxy-5-(trifluoromethyl)biphenyl-3-yl]sulfonyl}amino)-2-hydroxybenzoate

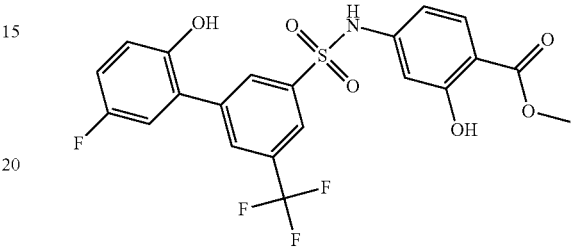

The product was prepared from methyl 4-({[3-bromo-5-(trifluoromethyl)phenyl]sulfonyl}amino)-2-hydroxybenzoate (Intermediate 5) (0.023 g, 0.050 mmol) and (5-fluoro-2-hydroxyphenyl)boronic acid (0.008 g, 0.050 mmol) according to the General Procedure 9, described in Example 82. The title compound was obtained in 79% yield (19.1 mg). $^1$H NMR (600 MHz, CDCl$_3$) δ ppm 3.91 (s, 3 H) 5.51 (br. s., 1 H) 6.65 (dd, J=8.70, 2.22 Hz, 1 H) 6.76 (d, J=2.22 Hz, 1 H) 6.87 (dd, J=8.85, 4.51 Hz, 1 H) 6.96 (dd, J=8.77, 3.05 Hz, 1 H) 7.00 (ddd, J=8.85, 7.74, 3.05 Hz, 1 H) 7.09 (br. s., 1 H) 7.74 (d, J=8.70 Hz, 1 H) 7.97-8.00 (m, 1 H) 8.07-8.11 (m, 1 H) 8.32 (t, J=1.69 Hz, 1 H) 10.92 (s, 1 H). MS (ESI+) m/z 486 [M+H]+.

Example 153

Methyl 4-{[(2',5'-difluorobiphenyl-3-yl)sulfonyl]amino}-2-hydroxybenzoate

The product was prepared from methyl 4-{[(3-bromophenyl)sulfonyl]amino}-2-hydroxybenzoate (Intermediate 4) (0.019 g, 0.050 mmol) and 2,5-difluorophenylboronic acid (0.008 g, 0.050 mmol) according to the General Procedure 9, described in Example 82. The title compound was obtained in 72% yield (15.2 mg). $^1$H NMR (600 MHz, CDCl$_3$) δ ppm 3.90 (s, 3 H) 6.66 (dd, J=8.60, 2.25 Hz, 1 H) 6.69 (d, J=2.25 Hz, 1 H) 6.84 (br. s., 1 H) 7.03-7.09 (m, 2 H) 7.10-7.17 (m, 1 H) 7.57 (dd, J=7.94, 7.81 Hz, 1 H) 7.73 (d, J=8.60 Hz, 1 H) 7.72-7.75 (ddt, J=7.81, 1.66, 1.12 Hz, 1 H) 7.89 (ddd, J=7.94, 1.95, 1.10 Hz, 1 H) 8.01-8.04 (m, 1 H) 10.86 (s, 1 H). MS (ESI+) m/z 420 [M+H]$^+$.

Example 154

Methyl 4-({[3-(2,3-dihydro-1-benzofuran-5-yl)phenyl]sulfonyl}amino)-2-hydroxybenzoate

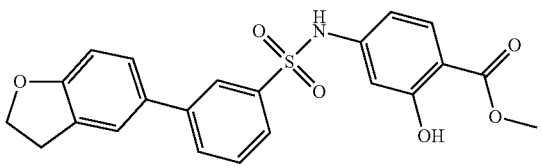 [SMILES: COC(=O)c1ccc(NS(=O)(=O)c2cccc(-c3ccc4c(c3)CCO4)c2)cc1O]

The product was prepared from methyl 4-{[(3-bromophenyl)sulfonyl]amino}-2-hydroxybenzoate (Intermediate 4) (0.019 g, 0.050 mmol) and 2,3-dihydrobenzofuran-5-boronic acid (0.008 g, 0.050 mmol) according to the General Procedure 9, described in Example 82. The title compound was obtained in 82% yield (17.4 mg). $^1$H NMR (600 MHz, CDCl$_3$) δ ppm 3.27 (t, J=8.70 Hz, 2 H) 3.89 (s, 3 H) 4.63 (t, J=8.70 Hz, 2 H) 6.64 (dd, J=8.70, 2.20 Hz, 1 H) 6.69 (d, J=2.20 Hz, 1 H) 6.83 (br. s., 1 H) 6.85 (d, J=8.24 Hz, 1 H) 7.26-7.31 (m, 1 H) 7.34-7.38 (m, 1 H) 7.49 (t, J=7.83 Hz, 1 H) 7.70 (d, J=8.70 Hz, 1 H) 7.70 (ddd, J=7.83, 1.87, 1.06 Hz, 1 H) 7.76 (ddd, J=7.83, 1.87, 1.06 Hz, 1 H) 8.00 (t, J=1.87 Hz, 1 H) 10.84 (s, 1 H). MS (ESI+) m/z 426 [M+H]$^+$.

Example 155

Methyl 4-({[6-chloro-5-(2,3-dihydro-1-benzofuran-5-yl)pyridin-3-yl]sulfonyl}amino)-2-hydroxybenzoate

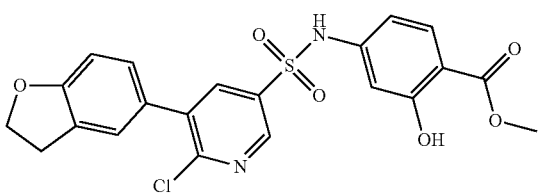 [SMILES: COC(=O)c1ccc(NS(=O)(=O)c2cnc(Cl)c(-c3ccc4c(c3)CCO4)c2)cc1O]

The product was prepared from methyl 4-{[(5-bromo-6-chloropyridin-3-yl)sulfonyl]amino}-2-hydroxybenzoate (Intermediate 8) (0.021 g, 0.050 mmol) and 2,3-dihydrobenzofuran-5-boronic acid (0.008 g, 0.050 mmol) according to the General Procedure 9, described in Example 82. The title compound was obtained in 39% yield (9.0 mg). $^1$H NMR (600 MHz, CDCl$_3$) δ ppm 3.28 (t, J=8.77 Hz, 2 H) 3.93 (s, 3 H) 4.66 (t, J=8.77 Hz, 2 H) 6.67 (dd, J=8.70, 2.25 Hz, 1 H) 6.72 (d, J=2.25 Hz, 1 H) 6.86 (d, J=8.24 Hz, 1 H) 7.09 (br. s., 1 H) 7.12-7.15 (ddt, J=8.24, 2.07, 0.77 Hz, 1 H) 7.21-7.23 (m, 1 H) 7.76 (d, J=8.70 Hz, 1 H) 8.03 (d, J=2.50 Hz, 1 H) 8.75 (d, J=2.50 Hz, 1 H) 10.90 (s, 1 H). MS (ESI+) m/z 461 [M+H]$^+$.

Example 156

General Procedure 10

Methyl 4-({[5-chloro-4-(2-hydroxyphenyl)-2-thienyl]sulfonyl}amino)-2-hydroxybenzoate

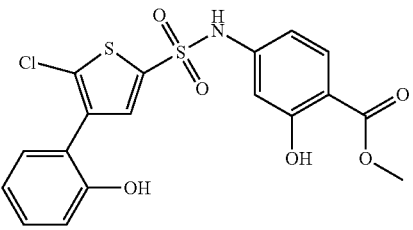 [SMILES: COC(=O)c1ccc(NS(=O)(=O)c2cc(-c3ccccc3O)c(Cl)s2)cc1O]

A mixture of methyl 4-{[(4-bromo-5-chloro-2-thienyl)sulfonyl]amino}-2-hydroxybenzoate (Intermediate 3) (0.21 g, 0.50 mmol), 2-(4,4,5,5-tetramethyl-1,3,2-dioxaborolan-2-yl)phenol (0.11 g, 0.50 mmol), DIPEA (0.26 g, 2.0 mmol) and Pd(dppf)Cl$_2$·CH$_2$Cl$_2$ (8 mg, 0.010 mmol) in aqueous dioxane (5 mL dioxane, 0.7 mL water) was heated at 80° C. under N$_2$ atmosphere for 3 days. EtOAc and water were added to the reaction mixture. The organic phase was washed with 1 M H$_3$PO$_4$, water and brine, dried with MgSO$_4$, filtered and concentrated. The crude product was purified by flash chromatography (silica, 20-40% EtOAc in hexane). The title compound was obtained as an off-white solid (0.12 g, 56%). $^1$H NMR (600 MHz, CDCl$_3$) δ ppm 2.64 (s, 1 H) 3.94 (s, 3 H) 5.00 (br. s., 1 H) 6.71 (dd, J=8.70, 2.29 Hz, 1 H) 6.78 (d, J=2.44 Hz, 1 H) 6.92 (dd, J=8.09, 0.76 Hz, 1 H) 6.97-7.02 (m, 1 H) 7.26 (dd, J=7.63, 1.53 Hz, 1 H) 7.28-7.32 (m, 1 H) 7.65 (s, 1 H) 7.79 (d, J=8.54 Hz, 1 H) 10.93 (s, 1 H). MS (ESI+) m/z 440 [M+H]$^+$.

Example 157

Methyl 4-({[5-chloro-4-(5-fluoro-2-hydroxyphenyl)-2-thienyl]sulfonyl}amino)-2-hydroxybenzoate

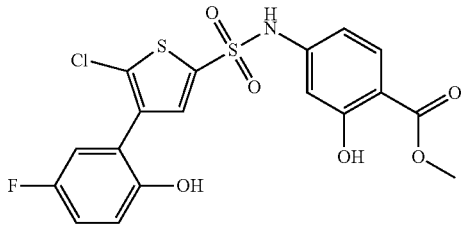 [SMILES: COC(=O)c1ccc(NS(=O)(=O)c2cc(-c3cc(F)ccc3O)c(Cl)s2)cc1O]

The product was prepared from methyl 4-{[(4-bromo-5-chloro-2-thienyl)sulfonyl]amino}-2-hydroxybenzoate (Intermediate 3) (0.21 g, 0.50 mmol) and (5-fluoro-2-hydroxyphenyl)boronic acid (0.078 g, 0.50 mmol) according to the General Procedure 10, described in Example 156, with a modified reaction time (1 day). The crude product was purified by preparative HPLC (acidic system). The title compound was obtained in 44% yield (0.10 g). $^1$H NMR (600 MHz, CDCl₃) δ ppm 3.93 (s, 3H) 5.07 (br. s., 1 H) 6.70 (dd, J=8.67, 2.21 Hz, 1 H) 6.77 (d, J=2.21 Hz, 1 H) 6.84-6.90 (m, 1 H) 6.96-7.02 (m, 2 H) 7.06 (br. s., 1 H) 7.64 (s, 1 H) 7.78 (d, J=8.67 Hz, 1 H) 10.92 (s, 1 H). MS (ESI+) m/z 458 [M+H]⁺.

Example 158

Methyl 4-({[4-(1,3-benzodioxol-5-yl)-5-chloro-2-thienyl]sulfonyl}amino)-2-hydroxybenzoate

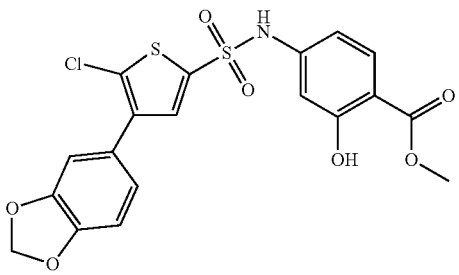 [SMILES: COC(=O)c1ccc(NS(=O)(=O)c2cc(-c3ccc4c(c3)OCO4)c(Cl)s2)cc1O]

The product was prepared from methyl 4-{[(4-bromo-5-chloro-2-thienyl)sulfonyl]amino}-2-hydroxybenzoate (Intermediate 3) (0.21 g, 0.50 mmol) and 3,4-methylenedioxybenzeneboronic acid (0.083 g, 0.50 mmol) according to the General Procedure 10, described in Example 156, with a modified reaction time (1 day). The crude product was purified by preparative HPLC (acidic system). The title compound was obtained in 36% yield (0.085 g). ¹H NMR (600 MHz, CDCl₃) δ ppm 3.92 (s, 3 H) 6.01 (s, 2 H) 6.71 (dd, J=8.70, 2.25 Hz, 1 H) 6.75 (d, J=2.25 Hz, 1 H) 6.86 (d, J=8.05 Hz, 1 H) 6.92 (dd, J=8.05, 1.80 Hz, 1 H) 6.94 (br. s., 1 H) 6.94 (d, J=1.80 Hz, 1 H) 7.53 (s, 1 H) 7.78 (d, J=8.70 Hz, 1 H) 10.90 (s, 1 H). MS (ESI+) m/z 468 [M+H]⁺.

Example 159

3-Morpholin-4-ylpropyl 2-hydroxy-4-{[(2'-hydroxybiphenyl-3-yl)sulfonyl]amino}benzoate trifluoroacetate

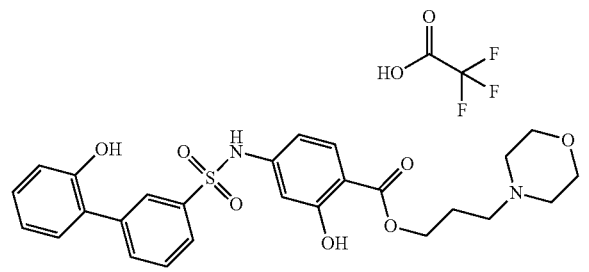 [SMILES: O=C(O)C(F)(F)F ; O=C(OCCCN1CCOCC1)c1ccc(NS(=O)(=O)c2cccc(-c3ccccc3O)c2)cc1O]

A mixture of methyl 2-hydroxy-4-{[(2'-hydroxybiphenyl-3-yl)sulfonyl]amino}benzoate (Example 82) (0.14 g, 0.35 mmol) in 1 M NaOH (2 ml) was stirred at 60° C. for 6 h. The aqueous solution was washed with Et₂O, acidified with conc. H₃PO₄ and extracted with EtOAc. The organic phase was washed with water and brine, dried over MgSO₄, filtered and concentrated. The residue was recrystallized from water/MeOH yielding 2-hydroxy-4-{[(2'-hydroxybiphenyl-3-yl)sulfonyl]amino}benzoic acid (83 mg, 63%). ¹H NMR (600 MHz, CD₃OD) δ ppm 6.68 (dd, J=8.70, 2.29 Hz, 1 H) 6.72 (d, J=2.14 Hz, 1 H) 6.87-6.93 (m, 2 H) 7.16-7.23 (m, 2 H) 7.54 (t, J=7.63 Hz, 1 H) 7.70 (d, J=8.54 Hz, 1 H) 7.75-7.79 (m, 1 H) 7.79-7.83 (m, 1 H) 8.10 (t, J=1.68 Hz, 1 H). MS (ESI+) m/z 386 [M+H]⁺.

The product was prepared from 2-hydroxy-4-{[(2'-hydroxybiphenyl-3-yl)sulfonyl]amino}benzoic acid (0.019 g, 0.050 mmol) and 4-(3-hydroxypropyl)-morpholine (15 mg, 0.10 mmol) according to the General Procedure 7, described in Example 59. The title compound was obtained in 32% yield (9.8 mg). MS (ESI+) m/z 513 [M+H]⁺.

Example 160

3-Morpholin-4-ylpropyl 4-{[(5'-fluoro-2'-hydroxybiphenyl-3-yl)sulfonyl]amino}-2-hydroxybenzoate trifluoroacetate

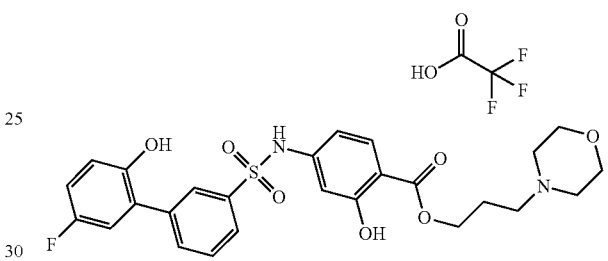

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 4-(3-hydroxypropyl)-morpholine (15 mg, 0.10 mmol) according to the General Procedure 7, described in Example 59. The title compound was obtained in 26% yield (8.1 mg). MS (ESI+) m/z 531 [M+H]⁺.

Example 161

2-Methoxyethyl 4-({[4-(1,3-benzodioxol-5-yl)-5-chloro-2-thienyl]sulfonyl}amino)-2-hydroxybenzoate

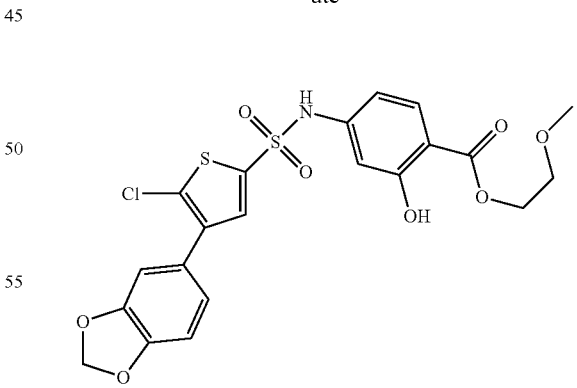

The product was prepared from 4-({[4-(1,3-benzodioxol-5-yl)-5-chloro-2-thienyl]sulfonyl}amino)-2-hydroxybenzoic acid (Intermediate 17) (0.023 g, 0.050 mmol) and methoxyethanol (8 mg, 0.10 mmol) according to the General Procedure 7, described in Example 59. The title compound was obtained in 39% yield (9.9 mg). ¹H NMR (600 MHz, CDCl₃) δ ppm 3.42 (s, 3 H) 3.70-3.74 (m, 2 H) 4.46-4.50 (m, 2 H) 6.02 (s, 2 H) 6.71 (dd, J=8.70, 2.29 Hz, 1 H) 6.76 (d, J=2.14 Hz, 1 H) 6.88 (d, J=7.93 Hz, 1 H) 6.93 (dd, J=8.24, 1.83 Hz, 1 H) 6.96 (d, J=1.53 Hz, 1 H) 7.54 (s, 1 H) 7.84 (d, J=8.54 Hz, 1 H) 10.86 (s, 1 H). MS (ESI+) m/z 512 [M+H]+.

Example 162

3-Morpholin-4-ylpropyl 4-({[4-(1,3-benzodioxol-5-yl)-5-chloro-2-thienyl]sulfonyl}amino)-2-hydroxybenzoate trifluoroacetate

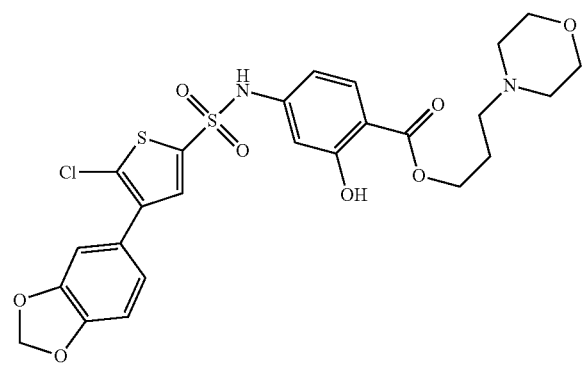

The product was prepared from 4-({[4-(1,3-benzodioxol-5-yl)-5-chloro-2-thienyl]sulfonyl}amino)-2-hydroxybenzoic acid (Intermediate 17) (0.023 g, 0.050 mmol) and 4-(3-hydroxypropyl)-morpholine (15 mg, 0.10 mmol) according to the General Procedure 7, described in Example 59. The title compound was obtained in 28% yield (9.9 mg). ¹H NMR (600 MHz, CDCl₃) δ ppm 2.24 (br. s., 2 H) 2.83 (br. s., 2 H) 3.07 (br. s., 2 H) 3.53 (br. s., 2 H) 3.95 (br. s., 4 H) 4.41 (t, J=6.10 Hz, 2H) 6.02 (s, 2 H) 6.71 (dd, J=8.70, 2.29 Hz, 1 H) 6.80 (d, J=2.14 Hz, 1 H) 6.88 (d, J=7.93 Hz, 1 H) 6.94 (dd, J=7.43, 1.83 Hz, 1 H) 6.96 (d, J=1.53 Hz, 1 H) 7.55 (s, 1 H) 7.75 (d, J=8.85 Hz, 1 H) 10.75 (br. s., 1 H). MS (ESI+) m/z 581 [M+H]+.

Example 163

3-Morpholin-4-ylpropyl 4-({[5-chloro-4-(2,3-dihydro-1-benzofuran-5-yl)-2-thienyl]sulfonyl}amino)-2-hydroxybenzoate trifluoroacetate

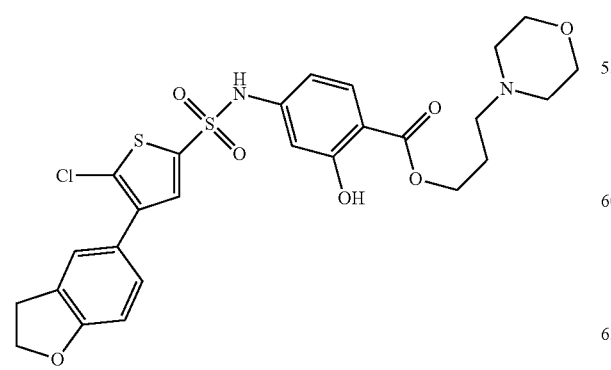

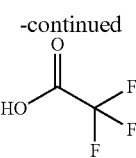

The product was prepared from 4-({[5-chloro-4-(2,3-dihydro-1-benzofuran-5-yl)thiophen-2-yl]sulfonyl}amino)-2-hydroxybenzoic acid (Intermediate 2) (0.023 g, 0.050 mmol) and 4-(3-hydroxypropyl)-morpholine (15 mg, 0.10 mmol) according to the General Procedure 7, described in Example 59. The title compound was obtained in 29% yield (10 mg). ¹H NMR (600 MHz, CDCl₃) δ ppm 2.24 (br. s., 2 H) 2.83 (br. s., 2 H) 3.08 (br. s., 2 H) 3.26 (t, J=8.70 Hz, 2 H) 3.52 (br. s., 2 H) 3.96 (br. s., 4 H) 4.40 (t, J=6.10 Hz, 2 H) 4.63 (t, J=8.70 Hz, 2 H) 6.71 (dd, J=8.70, 2.29 Hz, 1 H) 6.80 (d, J=2.14 Hz, 1 H) 6.84 (d, J=8.24 Hz, 1 H) 7.23 (dd, J=8.24, 1.83 Hz, 1 H) 7.31-7.33 (m, 1 H) 7.57 (s, 1 H) 7.75 (d, J=8.85 Hz, 1 H) 10.75 (br. s., 1 H). MS (ESI+) m/z 579 [M+H]+.

Example 164

3-Morpholin-4-ylpropyl 2-hydroxy-4-{[(2,4,5-trichloro-3-thienyl)sulfonyl]amino}benzoate

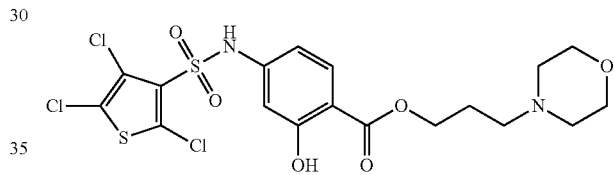

The product was prepared from 2-hydroxy-4-{[(2,4,5-trichloro-3-thienyl)sulfonyl]amino}benzoic acid (Intermediate 18) (0.019 g, 0.048 mmol) and 4-(3-hydroxypropyl)-morpholine (41 mg, 0.28 mmol) according to the General Procedure 7, described in Example 59. After purification the compound was dissolved in EtOAc and washed with Na₂CO₃ (aq. sat.). Concentration of the organic phase gave the title compound in 35% yield (10 mg). ¹H NMR (600 MHz, CDCl₃) δ ppm 1.87-2.07 (m, 2H) 2.19-2.75 (m, 6H) 3.55-3.90 (m, 4 H) 4.39 (t, J=6.33 Hz, 2 H) 6.67 (dd, J=8.70, 2.21 Hz, 1 H) 6.71 (d, J=2.21 Hz, 1 H) 7.75 (d, J=8.70 Hz, 1 H) 10.89 (br. s., 1 H). MS (ESI+) m/z 529 [M+H]+.

Example 165

2-Methoxyethyl 2-hydroxy-4-{[(2,4,5-trichloro-3-thienyl)sulfonyl]amino}benzoate

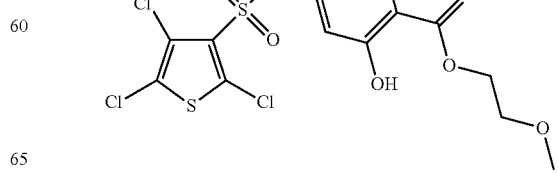

143

The product was prepared from 2-hydroxy-4-{[(2,4,5-trichloro-3-thienyl)sulfonyl]amino}benzoic acid (Intermediate 18) (0.019 g, 0.048 mmol) and methoxy-ethanol (22 mg, 0.28 mmol) according to the General Procedure 7, described in Example 59. The title compound was obtained in 38% yield (8.4 mg). $^1$H NMR (600 MHz, CDCl$_3$) δ ppm 3.41 (s, 3 H) 3.68-3.73 (m, 2 H) 4.45-4.48 (m, 2 H) 6.67 (dd, J=8.70, 2.29 Hz, 1H) 6.70 (d, J=2.29 Hz, 1 H) 7.82 (d, J=8.70 Hz, 1 H) 10.83 (s, 1 H). MS (ESI+) m/z 460 [M+H]$^+$.

Example 166

3-[(Tert-butoxycarbonyl)amino]propyl 2-hydroxy-4-{[(2,4,5-trichloro-3-thienyl)sulfonyl]amino}benzoate

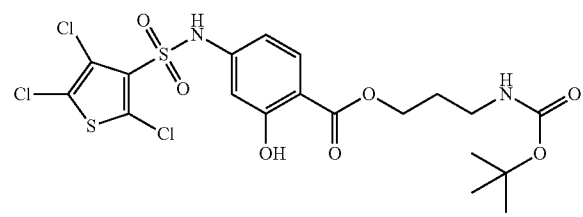 [SMILES: CC(C)(C)OC(=O)NCCCOC(=O)c1ccc(NS(=O)(=O)c2c(Cl)sc(Cl)c2Cl)cc1O]

The product was prepared from 2-hydroxy-4-{[(2,4,5-trichloro-3-thienyl)sulfonyl]amino}benzoic acid (Intermediate 18) (0.019 g, 0.048 mmol) and tert-butyl (3-hydroxypropyl)carbamate (59 mg, 0.34 mmol) according to the General Procedure 7, described in Example 59. The title compound was obtained in 40% yield (11 mg). $^1$H NMR (600 MHz, CDCl$_3$) δ ppm 1.44 (s, 9 H) 1.96 (quin, J=6.33 Hz, 2 H) 3.28 (q, J=6.10 Hz, 2 H) 4.40 (t, J=6.10 Hz, 2 H) 4.69 (br. s., 1 H) 6.67 (dd, J=8.54, 2.14 Hz, 1 H) 6.72 (d, J=2.14 Hz, 1 H) 7.19 (s, 1 H) 7.77 (d, J=8.85 Hz, 1 H) 10.90 (s, 1H). MS (ESI+) m/z 581 [M+Na]$^+$.

Example 167

1-Methylpiperidin-4-yl 2-hydroxy-4-{[(2,4,5-trichloro-3-thienyl)sulfonyl]amino}benzoate

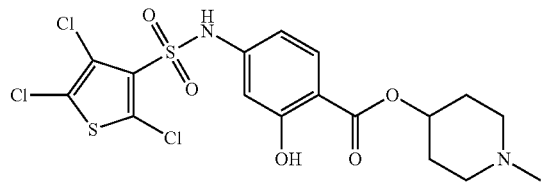 [SMILES: CN1CCC(OC(=O)c2ccc(NS(=O)(=O)c3c(Cl)sc(Cl)c3Cl)cc2O)CC1]

The product was prepared from 2-hydroxy-4-{[(2,4,5-trichloro-3-thienyl)sulfonyl]amino}benzoic acid (Intermediate 18) (0.019 g, 0.048 mmol) and 1-methylpiperidin-4-ol (32 mg, 0.28 mmol) according to the General Procedure 7, described in Example 59. After purification the compound was dissolved in EtOAc and washed with Na$_2$CO$_3$ (aq. sat.). Concentration of the organic phase gave the title compound in 15% yield (3.6 mg). $^1$H NMR (600 MHz, CDCl$_3$) δ ppm 1.81-1.93 (m, 2 H) 1.96-2.07 (m, 2 H) 2.26-2.42 (m, 5 H) 2.63-2.73 (m, 2 H) 5.00-5.13 (m, 1 H) 6.68 (dd, J=8.70, 1.98 Hz, 1 H) 6.72 (d, J=1.83 Hz, 1H) 7.78 (d, J=8.54 Hz, 1 H) 10.99 (br. s., 1 H). MS (ESI+) m/z 499 [M+H]$^+$.

144

Example 168

4-Morpholin-4-ylbutyl 2-hydroxy-4-{[(2,4,5-trichloro-3-thienyl)sulfonyl]amino}benzoate trifluoroacetate

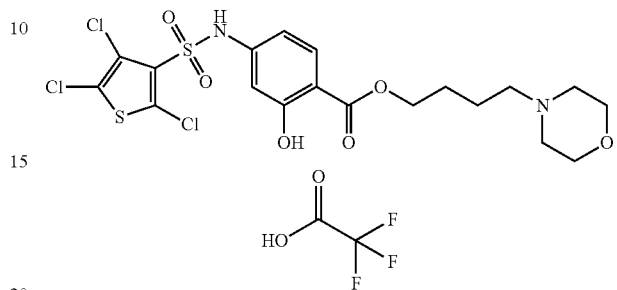

The product was prepared from 2-hydroxy-4-{[(2,4,5-trichloro-3-thienyl)sulfonyl]amino}benzoic acid (Intermediate 18) (0.020 g, 0.050 mmol) and 4-morpholin-4-ylbutan-1-ol (48 mg, 0.30 mmol) according to the General Procedure 7, described in Example 59. The title compound was obtained in 65% yield (18 mg). $^1$H NMR (600 MHz, CDCl$_3$) δ ppm 1.79-1.86 (m, 2 H) 1.92 (br. s., 2 H) 2.77 (br. s., 2 H) 3.00 (br. s., 2 H) 3.46 (br. s., 2 H) 3.97 (br. s., 4 H) 4.29-4.38 (m, 2H) 6.64 (dd, J=8.70, 2.29 Hz, 1 H) 6.73 (d, J=2.14 Hz, 1 H) 7.18 (br. s., 1 H) 7.71 (d, J=8.54 Hz, 1 H) 10.82 (s, 1 H). MS (ESI+) m/z 543 [M+H]$^+$.

Example 169

1-Methylpyrrolidin-3-yl 2-hydroxy-4-{[(2,4,5-trichloro-3-thienyl)sulfonyl]amino}benzoate trifluoroacetate

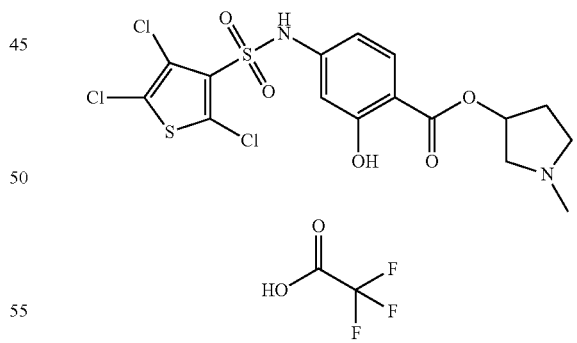

The product was prepared from 2-hydroxy-4-{[(2,4,5-trichloro-3-thienyl)sulfonyl]amino}benzoic acid (Intermediate 18) (0.020 g, 0.050 mmol) and 1-methylpyrrolidin-3-ol (30 mg, 0.30 mmol) according to the General Procedure 7, described in Example 59. The title compound was obtained in 49% yield (12 mg). $^1$H NMR (600 MHz, CD$_3$OD) δ ppm 2.27-2.39 (m, 1 H) 2.50-2.68 (m, 1 H) 2.95 (br. s., 3 H) 3.44-3.86 (m, 4 H) 5.61-5.66 (m, 1 H) 6.71-6.75 (m, 2 H) 7.80-7.85 (m, 1H). MS (ESI+) m/z 485 [M+H]$^+$.

Example 170

General Procedure 11

4-Morpholin-4-ylbutyl 4-{[(5'-fluoro-2'-hydroxybiphenyl-3-yl)sulfonyl]amino}-2-hydroxybenzoate trifluoroacetate

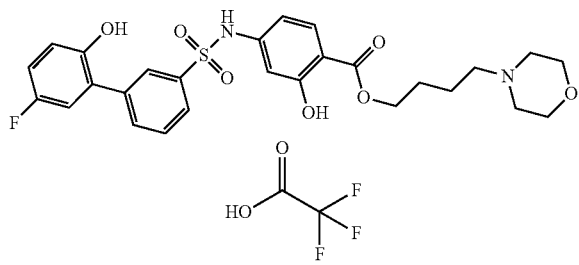

A mixture of 4-{[(5'-fluoro-2'-hydroxybiphenyl-3-yl)sulfonyl]amino}-2-hydroxybenzoic acid (Intermediate 16) (20 mg, 0.050 mmol) and thionyl chloride (18 mg, 0.15 mmol) in MeCN (2 mL) was stirred at room temperature for 20 minutes. The reaction mixture was concentrated to half the volume with a stream of nitrogen and a solution of 4-morpholin-4-ylbutan-1-ol (40 mg, 0.25 mmol) in MeCN (1 mL) was added. The reaction mixture was stirred at room temperature for 3 days, and purified by preparative HPLC (acidic system). The title compound was obtained in 31% yield (10.2 mg). MS (ESI+) m/z 545 [M+H]$^+$.

Example 171

3-Morpholin-4-ylpropyl 4-{[(2',5'-difluorobiphenyl-3-yl)sulfonyl]amino}-2-hydroxybenzoate trifluoroacetate

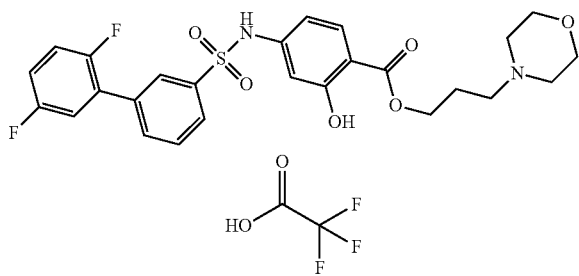

The product was prepared from 4-{[(2',5'-difluorobiphenyl-3-yl)sulfonyl]amino}-2-hydroxybenzoic acid (Intermediate 19) (20 mg, 0.050 mmol) and 4-(3-hydroxypropyl)morpholine (36 mg, 0.25 mmol) according to the General Procedure 11, described in Example 170. The title compound was obtained in 73% yield (24 mg). $^1$H NMR (600 MHz, DMSO-d$_6$) δ ppm 2.04 (br. s., 2 H) 2.93-3.26 (m, 4 H) 3.40-3.69 (m, 4 H) 3.97 (br. s., 2 H) 4.30 (t, J=5.95 Hz, 2 H) 6.71-6.77 (m, 2 H) 7.30-7.38 (m, 1 H) 7.40-7.50 (m, 2 H) 7.69 (d, J=8.24 Hz, 1 H) 7.73 (t, J=7.93 Hz, 1 H) 7.84-7.92 (m, 2 H) 8.00-8.06 (m, 1 H) 9.51 (br. s., 1 H) 10.56 (br. s., 1 H) 10.98 (br. s., 1 H). MS (ESI+) m/z 533 [M+H]$^+$.

Example 172

2-Methoxyethyl 4-{[(2',5'-difluorobiphenyl-3-yl)sulfonyl]amino}-2-hydroxybenzoate

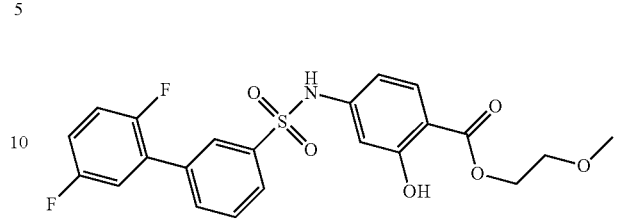

The product was prepared from 4-{[(2',5'-difluorobiphenyl-3-yl)sulfonyl]amino}-2-hydroxybenzoic acid (Intermediate 19) (20 mg, 0.050 mmol) and methoxyethanol (19 mg, 0.25 mmol) according to the General Procedure 11, described in Example 170. The title compound was obtained in 76% yield (18 mg). $^1$H NMR (600 MHz, DMSO-d$_6$) δ ppm 3.27 (s, 3 H) 3.58-3.64 (m, 2 H) 4.32-4.39 (m, 2 H) 6.71 (d, J=1.83 Hz, 1 H) 6.74 (dd, J=8.70, 1.98 Hz, 1 H) 7.29-7.38 (m, 1 H) 7.40-7.49 (m, 2 H) 7.65 (d, J=8.54 Hz, 1 H) 7.72 (t, J=7.78 Hz, 1 H) 7.87 (d, J=7.63 Hz, 1 H) 7.89 (d, J=7.93 Hz, 1 H) 8.00-8.05 (m, 1 H) 10.55 (s, 1 H) 10.96 (br. s., 1 H). MS (ESI+) m/z 464 [M+H]$^+$.

Example 173

4-Morpholin-4-ylbutyl 4-{[(2',5'-difluorobiphenyl-3-yl)sulfonyl]amino}-2-hydroxybenzoate trifluoroacetate

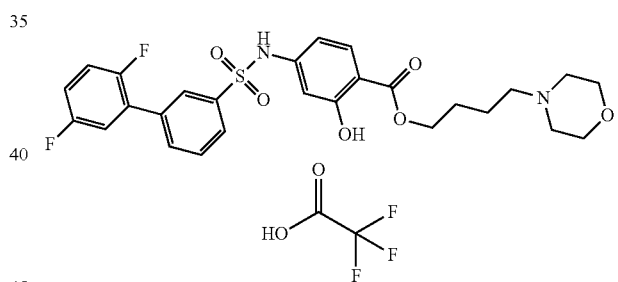

The product was prepared from 4-{[(2',5'-difluorobiphenyl-3-yl)sulfonyl]amino}-2-hydroxybenzoic acid (Intermediate 19) (20 mg, 0.050 mmol) and 4-morpholin-4-ylbutan-1-ol (40 mg, 0.25 mmol) according to the General Procedure 11, described in Example 170. The title compound was obtained in 60% yield (20 mg). MS (ESI+) m/z 547 [M+H]$^+$.

Example 174

3-Morpholin-4-ylpropyl 4-({[3-(2,3-dihydro-1-benzofuran-5-yl)phenyl]sulfonyl}amino)-2-hydroxybenzoate trifluoroacetate

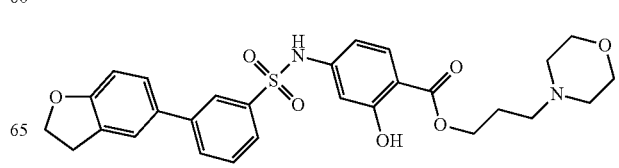

-continued

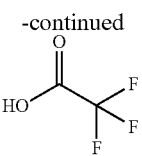

The product was prepared from 4-({[3-(2,3-dihydro-1-benzofuran-5-yl)phenyl]sulfonyl}amino)-2-hydroxybenzoic acid (Intermediate 20) (21 mg, 0.050 mmol) and 4-(3-hydroxypropyl)-morpholine (36 mg, 0.25 mmol) according to the General Procedure 11, described in Example 170. The title compound was obtained in 69% yield (22 mg). $^1$H NMR (600 MHz, DMSO-d$_6$) δ ppm 3.25 (t, J=8.85 Hz, 2 H) 4.29 (t, J=5.95 Hz, 2 H) 4.59 (t, J=8.70 Hz, 2 H) 6.71-6.77 (m, 2 H) 6.88 (d, J=8.24 Hz, 1 H) 7.39 (dd, J=8.24, 2.14 Hz, 1 H) 7.53 (s, 1 H) 7.62 (t, J=7.78 Hz, 1 H) 7.69 (d, J=9.15 Hz, 1 H) 7.73 (d, J=8.54 Hz, 1H) 7.87 (d, J=7.93 Hz, 1 H) 8.00 (s, 1 H) 9.50 (br. s., 1 H) 10.56 (br. s., 1 H) 10.89 (br. s., 1 H). MS (ESI+) m/z 539 [M+H]$^+$.

Example 175

2-Methoxyethyl 4-({[3-(2,3-dihydro-1-benzofuran-5-yl)phenyl]sulfonyl}amino)-2-hydroxybenzoate

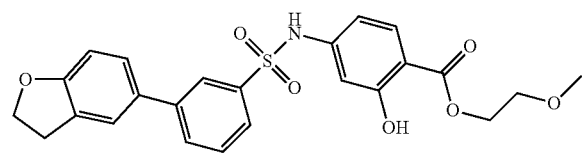 [SMILES: COCCOC(=O)c1ccc(NS(=O)(=O)c2cccc(-c3ccc4c(c3)CCO4)c2)cc1O]

The product was prepared from 4-({[3-(2,3-dihydro-1-benzofuran-5-yl)phenyl]sulfonyl}amino)-2-hydroxybenzoic acid (Intermediate 20) (21 mg, 0.050 mmol) and methoxyethanol (19 mg, 0.25 mmol) according to the General Procedure 11, described in Example 170. The title compound was obtained in 41% yield (9.7 mg). $^1$H NMR (600 MHz, DMSO-d$_6$) δ ppm 3.24 (t, J=8.85 Hz, 2 H) 3.26 (s, 3 H) 3.57-3.64 (m, 2 H) 4.32-4.39 (m, 2 H) 4.59 (t, J=8.70 Hz, 2 H) 6.70-6.73 (m, 1 H) 6.74 (d, J=8.85 Hz, 1 H) 6.88 (d, J=8.24 Hz, 1 H) 7.38 (dd, J=8.24, 2.14 Hz, 1 H) 7.49-7.53 (m, 1 H) 7.62 (t, J=7.78 Hz, 1 H) 7.65 (d, J=8.85 Hz, 1 H) 7.73 (d, J=7.93 Hz, 1 H) 7.86 (d, J=7.93 Hz, 1 H) 7.98 (t, J=1.68 Hz, 1 H) 10.54 (s, 1 H) 10.86 (br. s., 1 H). MS (ESI+) m/z 470 [M+H]$^+$.

Example 176

4-Morpholin-4-ylbutyl 4-({[3-(2,3-dihydro-1-benzofuran-5-yl)phenyl]sulfonyl}amino)-2-hydroxybenzoate trifluoroacetate The product was prepared from 4-({[3-(2,3-dihydro-1-benzofuran-5-yl)phenyl]sulfonyl}amino)-2-hydroxybenzoic acid (Intermediate 20) (21 mg, 0.050 mmol) and 4-morpholin-4-ylbutan-1-ol (40 mg, 0.25 mmol) according to the General Procedure 11, described in Example 170. The title compound was obtained in 69% yield (23 mg). MS (ESI+) m/z 553 [M+H]$^+$.

Example 177

Methyl 4-{[(3-bromo-4-methoxyphenyl)sulfonyl]amino}-2-hydroxybenzoate

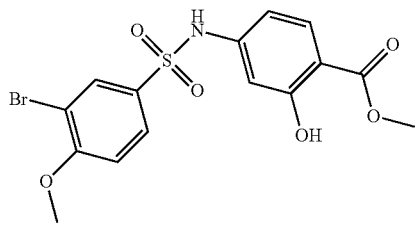 [SMILES: COC(=O)c1ccc(NS(=O)(=O)c2ccc(OC)c(Br)c2)cc1O]

A solution of 2-bromoanisole (5.00 g, 26.7 mmol) in CH$_2$Cl$_2$ (100 mL) was cooled on ice. Chlorosulfonic acid (9.3 g, 80 mmol) in CH$_2$Cl$_2$ (100 mL) was added dropwise at 0° C. The reaction mixture was allowed to reach room temperature overnight and was then added slowly to a stirred solution of brine. The organic phase was separated and washed with brine, dried over MgSO$_4$, filtered and concentrated. The intermediate 3-bromo-4-methoxybenzenesulfonyl chloride was obtained in 97% yield (7.33 g). $^1$H NMR (600 MHz, CDCl$_3$) δ ppm 4.03 (s, 3H) 7.04 (d, J=8.85 Hz, 1 H) 7.99 (dd, J=8.85, 2.44 Hz, 1 H) 8.22 (d, J=2.44 Hz, 1 H). MS (ESI+) m/z 249 [M–Cl]$^+$.

A mixture of 3-bromo-4-methoxybenzenesulfonyl chloride (2.86 g, 10 mmol), methyl 4-amino-salicylate (1.84 g, 11 mmol) and pyridine (0.87 g, 11 mmol) in MeCN (100 mL) was stirred at 80° C. for 1 day. Water and EtOAc were added. The organic phase was washed with 1 M HCl, water and brine, dried over MgSO$_4$, filtered and concentrated. The residue was recrystallized from toluene/heptane. The title compound was obtained in 78% yield (3.26 g). $^1$H NMR (600 MHz, DMSO-d$_6$) δ ppm 3.82 (s, 3 H) 3.91 (s, 3 H) 6.66-6.73 (m, 2 H) 7.28 (d, J=8.85 Hz, 1 H) 7.66 (d, J=8.85 Hz, 1 H) 7.81 (dd, J=8.70, 2.29 Hz, 1 H) 7.96 (d, J=2.14 Hz, 1 H) 10.58 (s, 1 H) 10.81 (s, 1 H). MS (ESI+) m/z 416 [M+H]$^+$.

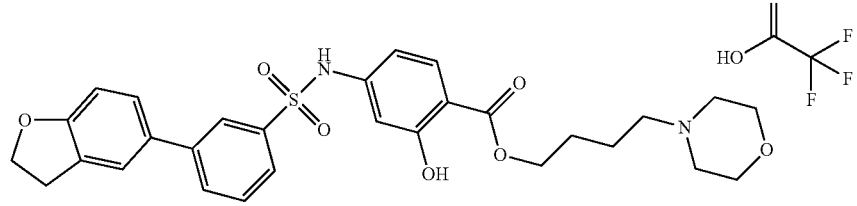

Example 178

General Procedure 12

2-Methoxy-1-methylethyl 4-{[(5'-fluoro-2'-hydroxy-biphenyl-3-yl)sulfonyl]amino}-2-hydroxybenzoate

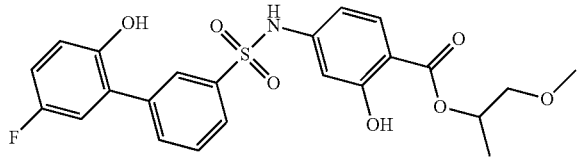 [SMILES: COCC(C)OC(=O)c1ccc(NS(=O)(=O)c2cccc(-c3cc(F)ccc3O)c2)cc1O]

A mixture of 4-{[(5'-fluoro-2'-hydroxybiphenyl-3-yl)sulfonyl]amino}-2-hydroxybenzoic acid (Intermediate 16) (0.020 g, 0.050 mmol), 1-methoxy-2-propanol (400 µL) and conc. sulfuric acid (40 µL) was stirred at 80° C. for 1 week. The reaction mixture was diluted with MeCN and purified by preparative HPLC (acidic system). The title compound was obtained in 33% yield (7.8 mg). $^1$H NMR (600 MHz, DMSO-$d_6$) δ ppm 1.23 (d, J=6.41 Hz, 3 H) 3.25 (s, 3 H) 3.42-3.52 (m, 2 H) 5.16-5.21 (m, 1 H) 6.70 (d, J=2.14 Hz, 1 H) 6.74 (dd, J=8.85, 2.14 Hz, 1 H) 6.96 (dd, J=9.00, 5.03 Hz, 1 H) 7.04-7.09 (m, 1 H) 7.11 (dd, J=9.61, 3.20 Hz, 1H) 7.60-7.65 (m, 2 H) 7.78 (d, J=8.85 Hz, 1 H) 7.83 (d, J=7.93 Hz, 1 H) 8.10 (t, J=1.83 Hz, 1 H) 9.82 (s, 1 H) 10.62 (s, 1 H) 10.91 (s, 1 H). MS (ESI+) m/z 476 [M+H]$^+$.

Example 179

Tetrahydrofuran-3-yl 4-{[(5'-fluoro-2'-hydroxybiphenyl-3-yl)sulfonyl]amino}-2-hydroxybenzoate

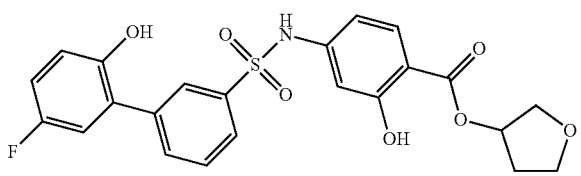 [SMILES: O=C(OC1CCOC1)c1ccc(NS(=O)(=O)c2cccc(-c3cc(F)ccc3O)c2)cc1O]

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 3-hydroxytetrahydrofuran (400 µL) according to the General Procedure 12, described in Example 178. The title compound was obtained in 30% yield (7.2 mg). $^1$H NMR (600 MHz, DMSO-$d_6$) δ ppm 1.98-2.05 (m, 1 H) 2.15-2.23 (m, 1 H) 3.71-3.76 (m, 1 H) 3.78-3.86 (m, 3 H) 5.40-5.44 (m, 1 H) 6.70 (d, J=1.83 Hz, 1 H) 6.73 (dd, J=8.54, 2.14 Hz, 1 H) 6.96 (dd, J=8.85, 4.88 Hz, 1 H) 7.04-7.09 (m, 1 H) 7.11 (dd, J=9.46, 3.05 Hz, 1 H) 7.59-7.66 (m, 2 H) 7.75-7.80 (m, 1 H) 7.81-7.86 (m, 1 H) 8.10 (t, J=1.83 Hz, 1 H) 9.82 (s, 1 H) 10.56 (s, 1 H) 10.91 (s, 1 H). MS (ESI+) m/z 474 [M+H]$^+$.

Example 180

1-(Methoxymethyl)propyl 4-{[(5'-fluoro-2'-hydroxybiphenyl-3-yl)sulfonyl]amino}-2-hydroxybenzoate

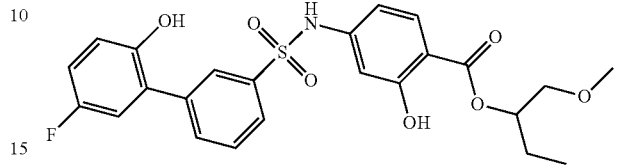

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 1-methoxy-2-butanol (400 µL) according to the General Procedure 12, described in Example 178. The title compound was obtained in 18% yield (4.3 mg). $^1$H NMR (600 MHz, DMSO-$d_6$) δ ppm 0.86 (t, J=7.48 Hz, 3 H) 1.56-1.70 (m, 2 H) 3.24 (s, 3 H) 3.45-3.49 (m, 1 H) 3.49-3.55 (m, 1 H) 5.06-5.12 (m, 1 H) 6.71 (d, J=2.14 Hz, 1 H) 6.74 (dd, J=8.85, 2.14 Hz, 1 H) 6.96 (dd, J=8.85, 4.88 Hz, 1 H) 7.03-7.09 (m, 1 H) 7.11 (dd, J=9.46, 3.36 Hz, 1 H) 7.58-7.68 (m, 2 H) 7.75-7.80 (m, 1H) 7.82-7.86 (m, 1 H) 8.11 (t, J=1.83 Hz, 1 H) 9.82 (s, 1H) 10.63 (s, 1 H) 10.92 (s, 1 H). MS (ESI+) m/z 490 [M+H]$^+$.

Example 181

2-Ethoxy-1-(ethoxymethyl)ethyl 4-{[(5'-fluoro-2'-hydroxybiphenyl-3-yl)sulfonyl]amino}-2-hydroxybenzoate

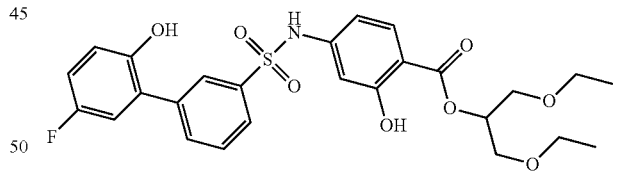

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 1,3-diethoxy-2-propanol (400 µL) according to the General Procedure 12, described in Example 178. The title compound was obtained in 17% yield (4.6 mg). $^1$H NMR (600 MHz, DMSO-$d_6$) δ ppm 1.05 (t, J=7.02 Hz, 6 H) 3.37-3.50 (m, 4 H) 3.53-3.61 (m, 4 H) 5.18-5.27 (m, 1 H) 6.71 (d, J=2.14 Hz, 1 H) 6.74 (dd, J=8.54, 2.14 Hz, 1 H) 6.96 (dd, J=8.85, 4.88 Hz, 1 H) 7.02-7.10 (m, 1 H) 7.11 (dd, J=9.46, 3.05 Hz, 1 H) 7.59-7.68 (m, 2 H) 7.78 (d, J=8.85 Hz, 1 H) 7.84 (d, J=7.63 Hz, 1 H) 8.11 (t, J=1.83 Hz, 1 H) 9.82 (s, 1 H) 10.53 (s, 1 H) 10.93 (s, 1 H). MS (ESI+) m/z 534 [M+H]$^+$.

Example 182

2-Methoxybutyl 4-{[(5'-fluoro-2'-hydroxybiphenyl-3-yl)sulfonyl]amino}-2-hydroxybenzoate

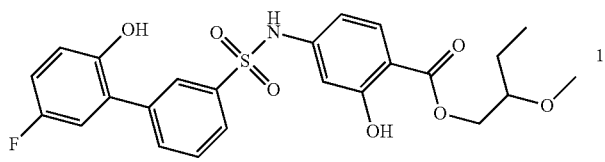

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 2-methoxy-1-butanol (400 µL) according to the General Procedure 12, described in Example 178. The title compound was obtained in 57% yield (14 mg). $^1$H NMR (600 MHz, DMSO-$d_6$) δ ppm 0.88 (t, J=7.48 Hz, 3 H) 1.46-1.55 (m, 2 H) 3.30 (s, 3 H) 3.36-3.42 (m, 1 H) 4.18 (dd, J=11.75, 5.65 Hz, 1 H) 4.34 (dd, J=11.75, 3.81 Hz, 1 H) 6.71 (d, J=2.14 Hz, 1 H) 6.74 (dd, J=8.85, 2.14 Hz, 1 H) 6.96 (dd, J=8.85, 4.88 Hz, 1 H) 7.04-7.09 (m, 1 H) 7.11 (dd, J=9.46, 3.36 Hz, 1 H) 7.59-7.69 (m, 2 H) 7.79 (d, J=8.54 Hz, 1 H) 7.84 (d, J=7.93 Hz, 1 H) 8.11 (t, J=1.68 Hz, 1 H) 9.82 (s, 1 H) 10.56 (s, 1 H) 10.92 (s, 1 H). MS (ESI+) m/z 490 [M+H]$^+$.

Example 183

2-Hydroxyethyl 4-{[(5'-fluoro-2'-hydroxybiphenyl-3-yl)sulfonyl]amino}-2-hydroxybenzoate

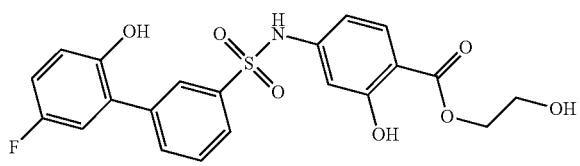 [SMILES: O=C(OCCO)c1ccc(NS(=O)(=O)c2cccc(-c3cc(F)ccc3O)c2)cc1O]

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and ethylene glycol (400 µL) according to the General Procedure 12, described in Example 178 with a modified reaction time of 1 day. The title compound was obtained in 100% yield (22 mg). $^1$H NMR (600 MHz, DMSO-$d_6$) δ ppm 3.60-3.70 (m, 2 H) 4.23-4.29 (m, 2 H) 4.90 (t, J=5.65 Hz, 1 H) 6.70 (d, J=2.14 Hz, 1 H) 6.73 (dd, J=8.70, 1.98 Hz, 1 H) 6.96 (dd, J=9.15, 4.88 Hz, 1 H) 7.03-7.09 (m, 1 H) 7.12 (dd, J=9.46, 3.05 Hz, 1 H) 7.63 (t, J=7.93 Hz, 1 H) 7.71 (d, J=8.54 Hz, 1 H) 7.78 (d, J=8.85 Hz, 1 H) 7.83 (d, J=7.63 Hz, 1 H) 8.11 (t, J=1.68 Hz, 1 H) 9.82 (s, 1 H) 10.60 (s, 1 H) 10.91 (s, 1 H). MS (ESI+) m/z 448 [M+H]$^+$.

Example 183 was also prepared on an 6-g scale according to a similar protocol with some minor changes, such as a lower temperature (50° C. for 1 week) and extractive workup (EtOAc).

Example 184

3-Hydroxypropyl 4-{[(5'-fluoro-2'-hydroxybiphenyl-3-yl)sulfonyl]amino}-2-hydroxybenzoate

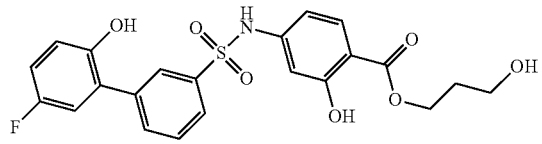 [SMILES: O=C(OCCCO)c1ccc(NS(=O)(=O)c2cccc(-c3cc(F)ccc3O)c2)cc1O]

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 1,3-propandiol (400 µL) according to the General Procedure 12, described in Example 178 with a modified reaction time of 1 day. The title compound was obtained in 70% yield (16 mg). $^1$H NMR (600 MHz, DMSO-$d_6$) δ ppm 1.77-1.86 (m, 2 H) 3.46-3.55 (m, 2 H) 4.30 (t, J=6.41 Hz, 2 H) 4.57 (t, J=5.03 Hz, 1 H) 6.70 (d, J=2.14 Hz, 1 H) 6.73 (dd, J=8.85, 2.14 Hz, 1 H) 6.96 (dd, J=8.85, 4.88 Hz, 1 H) 7.04-7.09 (m, 1 H) 7.11 (dd, J=9.46, 3.36 Hz, 1 H) 7.63 (t, J=7.78 Hz, 1 H) 7.65 (d, J=8.54 Hz, 1 H) 7.75-7.80 (m, 1 H) 7.82-7.86 (m, 1 H) 8.10 (t, J=1.68 Hz, 1 H) 9.82 (s, 1 H) 10.62 (s, 1 H) 10.90 (s, 1 H). MS (ESI+) m/z 462 [M+H]$^+$.

Example 185

2-Methoxyethyl 4-{[(5'-fluoro-2'-hydroxybiphenyl-3-yl)sulfonyl]amino}-2-hydroxybenzoate

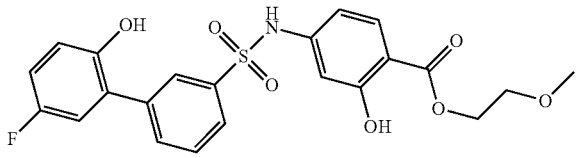 [SMILES: COCCOC(=O)c1ccc(NS(=O)(=O)c2cccc(-c3cc(F)ccc3O)c2)cc1O]

The product was prepared from 4-{[(5'-fluoro-2'-hydroxybiphenyl-3-yl)sulfonyl]amino}-2-hydroxybenzoic acid (Intermediate 16) (0.040 g, 0.10 mmol) and methoxyethanol (0.038 g, 0.5 mmol) according to the General Procedure 11, described in Example 170, with a modified reaction time (1 h). The title compound was obtained in 74% yield (34 mg). $^1$H NMR (600 MHz, CDCl$_3$) δ ppm 3.42 (s, 3 H) 3.69-3.75 (m, 2 H) 4.42-4.52 (m, 2 H) 4.99 (br. s., 1 H) 6.62 (d, J=8.54 Hz, 1 H) 6.71-6.75 (m, 1 H) 6.82 (s, 1 H) 6.86 (dd, J=8.85, 4.58 Hz, 1 H) 6.93 (dd, J=8.70, 2.90 Hz, 1 H) 6.95-7.01 (m, 1 H) 7.58 (t, J=7.93 Hz, 1 H) 7.71 (d, J=6.71 Hz, 1 H) 7.77 (d, J=8.54 Hz, 1 H) 7.88 (d, J=7.93 Hz, 1 H) 8.06 (s, 1 H) 10.82 (s, 1 H). MS (ESI+) m/z 462 [M+H]$^+$.

Example 186

2-Methoxyethyl 4-{[(3,5-dichlorophenyl)sulfonyl]amino}-2-hydroxybenzoate

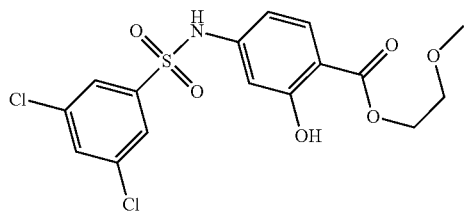 [SMILES: COCCOC(=O)c1ccc(NS(=O)(=O)c2cc(Cl)cc(Cl)c2)cc1O]

The product was prepared from 4-{[(3,5-dichlorophenyl)sulfonyl]amino}-2-hydroxybenzoic acid (Intermediate 21) (0.018 g, 0.050 mmol) and 2-methoxyethanol (15 mg, 0.20 mmol) according to the General Procedure 8, described in Example 60. The title compound was obtained in 58% yield (12 mg). $^1$H NMR (600 MHz, CDCl$_3$) δ ppm 3.41 (s, 3 H) 3.69-3.72 (m, 2 H) 4.45-4.49 (m, 2 H) 6.63 (dd, J=8.54, 2.44 Hz, 1 H) 6.65 (d, J=2.14 Hz, 1 H) 6.74 (br. s., 1 H) 7.54 (t, J=1.83 Hz, 1 H) 7.73 (d, J=1.83 Hz, 2 H) 7.81 (d, J=8.54 Hz, 1 H) 10.83 (s, 1 H). MS (ESI+) m/z 420 [M+H]$^+$.

Example 187

3-Morpholin-4-ylpropyl 4-{[(3,5-dichlorophenyl)sulfonyl]amino}-2-hydroxybenzoate trifluoroacetate

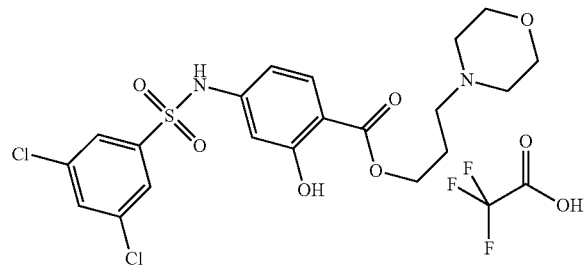

The product was prepared from 4-{[(3,5-dichlorophenyl)sulfonyl]amino}-2-hydroxybenzoic acid (Intermediate 21) (0.018 g, 0.050 mmol) and 4-(3-hydroxypropyl)morpholine (29 mg, 0.20 mmol) according to the General Procedure 8, described in Example 60. The title compound was obtained in 65% yield (19 mg). $^1$H NMR (600 MHz, CDCl$_3$) δ ppm 2.21-2.35 (m, 2 H) 2.74-2.99 (m, 2 H) 3.11-3.22 (m, 2 H) 3.45-3.67 (m, 2 H) 3.90-4.09 (m, 4 H) 4.39 (t, J=5.95 Hz, 2 H) 6.62 (dd, J=8.70, 2.29 Hz, 1 H) 6.70 (d, J=2.14 Hz, 1 H) 7.17 (br. s., 1 H) 7.54 (t, J=1.83 Hz, 1 H) 7.70 (d, J=8.54 Hz, 1 H) 7.74 (d, J=1.83 Hz, 2 H) 10.68 (br. s., 1 H). MS (ESI+) m/z 489 [M+H]$^+$.

Example 188

Tetrahydrofuran-3-yl 4-{[(3,5-dichlorophenyl)sulfonyl]amino}-2-hydroxybenzoate

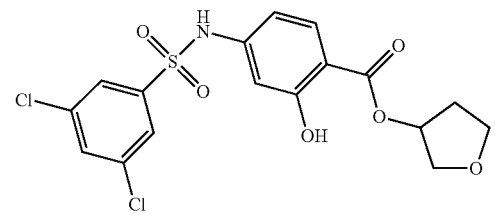 [SMILES: O=C(OC1CCOC1)c1ccc(NS(=O)(=O)c2cc(Cl)cc(Cl)c2)cc1O]

The product was prepared from 4-{[(3,5-dichlorophenyl)sulfonyl]amino}-2-hydroxybenzoic acid (Intermediate 21) (0.018 g, 0.050 mmol) and 3-hydroxytetrahydrofuran (18 mg, 0.20 mmol) according to the General Procedure 8, described in Example 60. The title compound was obtained in 67% yield (14 mg). $^1$H NMR (600 MHz, CDCl$_3$) δ ppm 2.11-2.18 (m, 1 H) 2.25-2.32 (m, 1 H) 3.90 (td, J=8.47, 4.42 Hz, 1 H) 3.93-4.01 (m, 3 H) 5.53 (dddd, J=6.37, 4.31, 1.98, 1.68 Hz, 1 H) 6.63 (dd, J=8.70, 2.29 Hz, 1 H) 6.66 (d, J=2.14 Hz, 1 H) 6.75 (br. s., 1 H) 7.55 (t, J=1.83 Hz, 1 H) 7.73 (d, J=1.83 Hz, 2 H) 7.75 (d, J=8.85 Hz, 1 H) 10.83 (s, 1 H). MS (ESI+) m/z 432 [M+H]$^+$.

Example 189

1-(Methoxymethyl)propyl 4-{[(3,5-dichlorophenyl)sulfonyl]amino}-2-hydroxybenzoate

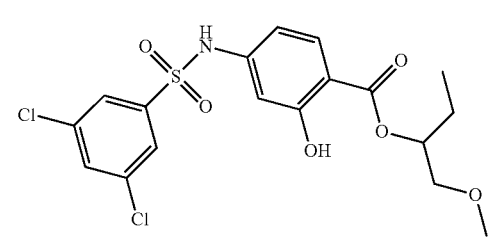 [SMILES: CCC(COC)OC(=O)c1ccc(NS(=O)(=O)c2cc(Cl)cc(Cl)c2)cc1O]

The product was prepared from 4-{[(3,5-dichlorophenyl)sulfonyl]amino}-2-hydroxybenzoic acid (Intermediate 21) (0.018 g, 0.050 mmol) and 1-methoxy-2-butanol (21 mg, 0.20 mmol) according to the General Procedure 8, described in Example 60. The title compound was obtained in 60% yield (13 mg). $^1$H NMR (600 MHz, CDCl$_3$) δ ppm 0.96 (t, J=7.48 Hz, 3 H) 1.73 (quin, J=7.25 Hz, 2 H) 3.36 (s, 3 H) 3.53 (dd, J=10.68, 3.66 Hz, 1 H) 3.57 (dd, J=10.68, 6.10 Hz, 1 H) 5.18-5.23 (m, 1 H) 6.63 (dd, J=8.54, 2.44 Hz, 1 H) 6.65 (d, J=1.83 Hz, 1 H) 6.73 (br. s., 1 H) 7.55 (t, J=1.83 Hz, 1 H) 7.73 (d, J=1.83 Hz, 2 H) 7.79 (d, J=8.85 Hz, 1 H) 10.96 (s, 1 H). MS (ESI+) m/z 448 [M+H]$^+$.

Example 190

2-Methoxybutyl 4-{[(3,5-dichlorophenyl)sulfonyl]amino}-2-hydroxybenzoate

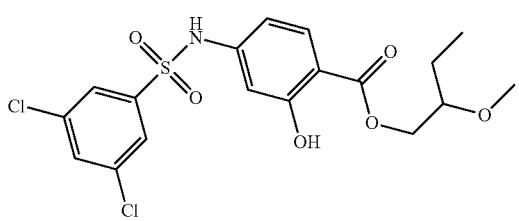 [SMILES: CCC(COC(=O)c1ccc(NS(=O)(=O)c2cc(Cl)cc(Cl)c2)cc1O)OC]

The product was prepared from 4-{[(3,5-dichlorophenyl)sulfonyl]amino}-2-hydroxybenzoic acid (Intermediate 21) (0.018 g, 0.050 mmol) and 2-methoxy-1-butanol (21 mg, 0.20 mmol) according to the General Procedure 8, described in Example 60. The title compound was obtained in 70% yield (16 mg). $^1$H NMR (600 MHz, CDCl$_3$) δ ppm 0.98 (t, J=7.48 Hz, 3 H) 1.62 (qd, J=7.07, 2.59 Hz, 2 H) 3.39-3.43 (m, 1 H) 3.43 (s, 3 H) 4.27 (dd, J=11.60, 5.80 Hz, 1 H) 4.41 (dd, J=11.75, 3.81 Hz, 1 H) 6.63 (dd, J=8.54, 2.44 Hz, 1 H) 6.66 (d, J=2.14 Hz, 1 H) 6.73 (br. s., 1 H) 7.55 (t, J=1.83 Hz, 1 H) 7.73 (d, J=1.83 Hz, 2 H) 7.78 (d, J=8.85 Hz, 1 H) 10.86 (s, 1 H). MS (ESI+) m/z 448 [M+H]$^+$.

Example 191

2-Methoxy-1-(methoxymethyl)ethyl 4-{[(3,5-dichlorophenyl)sulfonyl]amino}-2-hydroxybenzoate

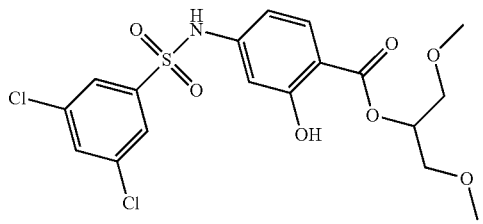 [SMILES: COCC(COC)OC(=O)c1ccc(NS(=O)(=O)c2cc(Cl)cc(Cl)c2)cc1O]

The product was prepared from 4-{[(3,5-dichlorophenyl)sulfonyl]amino}-2-hydroxybenzoic acid (Intermediate 21) (0.018 g, 0.050 mmol) and 1,3-dimethoxypropan-2-ol (24 mg, 0.20 mmol) according to the General Procedure 8, described in Example 60. The title compound was obtained in 71% yield (16 mg). $^1$H NMR (600 MHz, CDCl$_3$) δ ppm 3.37 (s, 6 H) 3.64 (dd, J=10.68, 4.30 Hz, 2 H) 3.66 (dd, J=10.68, 5.80 Hz, 2 H) 5.35-5.41 (m, 1 H) 6.63 (dd, J=8.54, 2.14 Hz, 1 H) 6.65 (d, J=2.14 Hz, 1 H) 6.71 (s, 1 H) 7.55 (t, J=1.83 Hz, 1 H) 7.73 (d, J=1.83 Hz, 2 H) 7.81 (d, J=8.85 Hz, 1 H) 10.83 (s, 1 H). MS (ESI+) m/z 464 [M+H]$^+$.

Example 192

2-Methoxy-1-methylethyl 4-{[(3,5-dichlorophenyl)sulfonyl]amino}-2-hydroxybenzoate

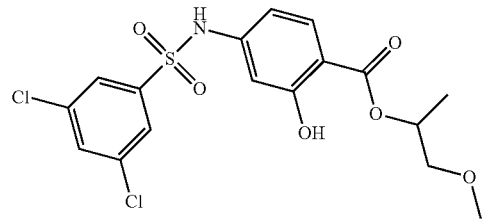 [SMILES: COCC(C)OC(=O)c1ccc(NS(=O)(=O)c2cc(Cl)cc(Cl)c2)cc1O]

The product was prepared from 4-{[(3,5-dichlorophenyl)sulfonyl]amino}-2-hydroxybenzoic acid (Intermediate 21) (0.018 g, 0.050 mmol) and 1-methoxy-2-propanol (18 mg, 0.20 mmol) according to the General Procedure 8, described in Example 60. The title compound was obtained in 82% yield (18 mg). $^1$H NMR (600 MHz, CDCl$_3$) δ ppm 1.34 (d, J=6.41 Hz, 3 H) 3.38 (s, 3 H) 3.50 (dd, J=10.68, 3.66 Hz, 1 H) 3.56 (dd, J=10.68, 6.41 Hz, 1 H) 5.29-5.38 (m, 1 H) 6.63 (d, J=8.54, 2.14 Hz, 1 H) 6.64 (d, J=2.14 Hz, 1 H) 6.71 (br. s., 1 H) 7.54 (t, J=1.98 Hz, 1 H) 7.73 (d, J=1.83 Hz, 2 H) 7.78 (d, J=8.54 Hz, 1 H) 10.94 (s, 1 H). MS (ESI+) m/z 434 [M+H]$^+$.

Example 193

1-Methyl-3-morpholin-4-ylpropyl 4-{[(4,5-dichlorothiophen-2-yl)sulfonyl]amino}-2-hydroxybenzoate) trifluoroacetate

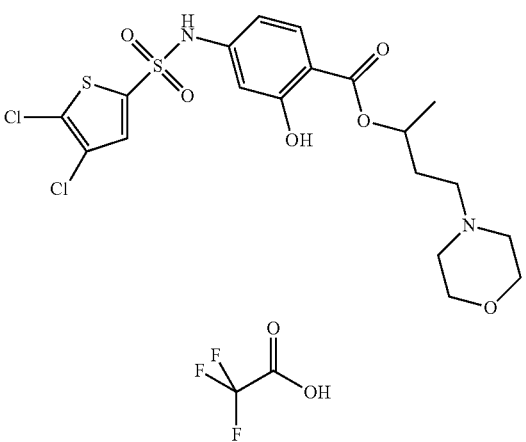

The product was prepared from 4-{[(4,5-dichlorothiophen-2-yl)sulfonyl]amino}-2-hydroxybenzoic acid (Intermediate 7) (0.018 g, 0.050 mmol) and 4-(morpholin-4-yl)butan-2-ol (16 mg, 0.10 mmol) according to the General Procedure 8, described in Example 60. The title compound was obtained in 56% yield (17 mg). $^1$H NMR (600 MHz, CDCl$_3$) δ ppm 1.41 (d, J=6.10 Hz, 3 H) 2.07-2.29 (m, 2 H) 2.73-2.92 (m, 2 H) 2.99-3.17 (m, 2 H) 3.47-3.62 (m, 2 H) 3.92-4.04 (m, 4 H) 5.16-5.22 (m, 1 H) 6.65 (dd, J=8.54, 2.14 Hz, 1 H) 6.77 (d, J=2.14 Hz, 1 H) 6.94 (br. s., 1 H) 7.43 (s, 1 H) 7.76 (d, J=8.54 Hz, 1 H) 10.80 (br. s., 1 H). MS (ESI+) m/z 509 [M+H]$^+$.

Example 194

2-Methoxy-1-methylethyl 4-{[(4,5-dichlorothiophen-2-yl)sulfonyl]amino}-2-hydroxybenzoate

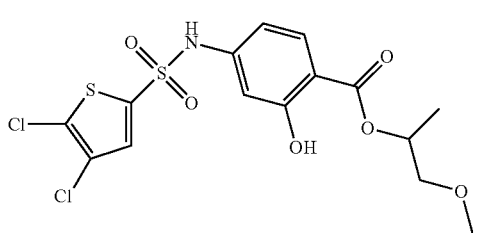 [SMILES: COCC(C)OC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (Intermediate 7) (0.018 g, 0.050 mmol) and 1-methoxy-2-propanol (18 mg, 0.20 mmol) according to the General Procedure 8, described in Example 60. The title compound was obtained in 77% yield (17 mg). $^1$H NMR (600 MHz, CDCl$_3$) δ ppm 1.36 (d, J=6.41 Hz, 3 H) 3.39 (s, 3 H) 3.51 (dd, J=10.68, 3.97 Hz, 1 H) 3.57 (dd, J=10.68, 6.41 Hz, 1H) 5.30-5.37 (m, 1 H) 6.66 (dd, J=8.70, 2.29 Hz, 1 H) 6.71 (d, J=2.14 Hz, 1 H) 6.74 (br. s., 1 H) 7.41 (s, 1 H) 7.81 (d, J=8.54 Hz, 1 H) 10.97 (s, 1 H). MS (ESI+) m/z 440 [M+H]$^+$.

Example 195

1-(Methoxymethyl)propyl 4-{[(4,5-dichlorothiophen-2-yl)sulfonyl]amino}-2-hydroxybenzoate

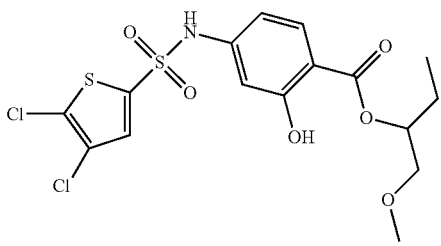 [SMILES: CCC(COC)OC(=O)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18.4 mg, 0.050 mmol) (Intermediate 7) and 1-methoxy-2-butanol (23 μL, 0.20 mmol) according to the General Procedure 8, described in Example 60. The title compound was obtained in 39% yield (8.8 mg). $^1$H NMR (600 MHz, DMSO-d$_6$: CD$_3$OD 6:1) δ ppm 0.88 (t, J=7.48 Hz, 3 H) 1.59-1.69 (m, 1 H) 1.65-1.73 (m, 1 H) 3.26 (s, 3 H) 3.49 (dd, J=10.99, 3.67 Hz, 1 H) 3.53 (dd, J=10.99, 6.54 Hz, 1 H) 5.13 (dddd, J=7.50, 6.54, 5.44, 3.67 Hz, 1 H) 6.74 (d, J=2.14 Hz, 1 H) 6.79 (dd, J=8.70, 2.14 Hz, 1 H) 7.74 (d, J=8.70 Hz, 1 H) 7.78 (s, 1 H). MS (ESI+) m/z 454 [M+H]$^+$.

Example 196

2-Methoxybutyl 4-{[(4,5-dichlorothiophen-2-yl)sulfonyl]amino}-2-hydroxybenzoate

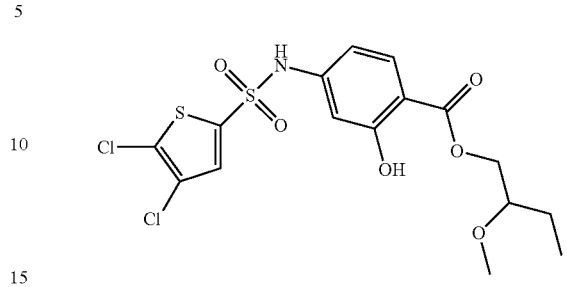

The product was prepared from 4-{[(4,5-dichlorothiophen-2-yl)sulfonyl]amino}-2-hydroxybenzoic acid (18.4 mg, 0.050 mmol) (Intermediate 7) and 2-methoxy-1-butanol (23 μL, 0.20 mmol) according to the General Procedure 8, described in Example 60. The title compound was obtained in 77% yield (17.4 mg). $^1$H NMR (600 MHz, DMSO-d$_6$: CD$_3$OD 6:1) δ ppm 0.90 (t, J=7.40 Hz, 3 H) 1.48-1.59 (m, 2 H) 3.32 (s, 3 H) 3.41 (tdd, J=6.40, 5.72, 3.66 Hz, 1 H) 4.21 (dd, J=11.67, 5.72 Hz, 1 H) 4.38 (dd, J=11.67, 3.66 Hz, 1 H) 6.75 (d, J=2.21 Hz, 1 H) 6.79 (dd, J=8.62, 2.21 Hz, 1 H) 7.74 (d, J=8.70 Hz, 1 H) 7.78 (s, 1 H). MS (ESI+) m/z 454 [M+H]$^+$.

Example 197

2-Methoxyethyl 4-{[(4-bromo-2,5-dichlorothiophen-3-yl)sulfonyl]amino}-2-hydroxybenzoate

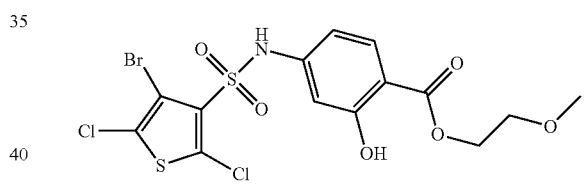

The product was prepared from 4-{[(4-bromo-2,5-dichlorothiophen-3-yl)sulfonyl]amino}-2-hydroxybenzoic acid (19.3 mg, 0.043 mmol) (Intermediate 22) and 2-methoxyethanol (14 μL, 0.172 mmol) according to the General Procedure 8, described in Example 60. The title compound was obtained in 37% yield (8.1 mg). $^1$H NMR (600 MHz, DMSO-d$_6$:CD$_3$OD 6:1) δ ppm 3.28 (s, 3 H) 3.61-3.65 (m, 2 H) 4.36-4.40 (m, 2 H) 6.67 (d, J=2.14 Hz, 1 H) 6.69 (dd, J=8.70, 2.14 Hz, 1 H) 7.71 (d, J=8.70 Hz, 1 H). MS (ESI+) m/z 504 [M+H]$^+$.

Example 198

Tetrahydrofuran-3-yl 4-{[(4-bromo-2,5-dichlorothiophen-3-yl)sulfonyl]amino}-2-hydroxybenzoate

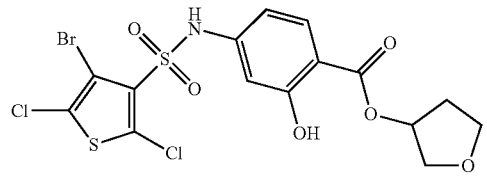 [SMILES: O=C(OC1CCOC1)c1ccc(NS(=O)(=O)c2c(Cl)sc(Cl)c2Br)cc1O]

The product was prepared from 4-{[(4-bromo-2,5-dichlorothiophen-3-yl)sulfonyl]amino}-2-hydroxybenzoic acid (19.3 mg, 0.043 mmol) (Intermediate 22) and 3-hydroxytetrahydrofuran (14 µL, 0.172 mmol) according to the General Procedure 8, described in Example 60. The title compound was obtained in 45% yield (10.1 mg). ¹H NMR (600 MHz, DMSO-d₆:CD₃OD 6:1) δ ppm 2.01-2.08 (m, 1 H) 2.17-2.25 (m, 1 H) 3.75 (td, J=8.35, 4.50 Hz, 1 H) 3.80-3.87 (m, 3 H) 5.43-5.47 (m, 1 H) 6.66 (d, J=2.14 Hz, 1 H) 6.68 (dd, J=8.54, 2.14 Hz, 1 H) 7.71 (d, J=8.54 Hz, 1 H). MS (ESI+) m/z 516 [M+H]⁺.

Example 199

3-Morpholin-4-ylpropyl 4-{[(4-bromo-2,5-dichlorothiophen-3-yl)sulfonyl]amino}-2-hydroxybenzoate trifluoroacetate

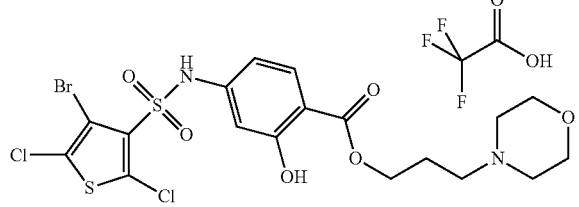

The product was prepared from 4-{[(4-bromo-2,5-dichlorothiophen-3-yl)sulfonyl]amino}-2-hydroxybenzoic acid (19.3 mg, 0.043 mmol) (Intermediate 22) and 4-(3-hydroxypropyl)morpholine (24 µL, 0.172 mmol) according to the General Procedure 8, described in Example 60 with a modified reaction time (2 days). The title compound was obtained in 41% yield (12.0 mg). ¹H NMR (600 MHz, CDCl₃) δ ppm 2.24-2.32 (m, 2 H) 2.81-2.94 (m, 2 H) 3.14-3.22 (m, 2 H) 3.54-3.65 (m, 2 H) 3.90-4.08 (m, 4 H) 4.40 (t, J=5.95 Hz, 2 H) 6.67 (dd, J=8.70, 2.29 Hz, 1 H) 6.74 (d, J=2.29 Hz, 1 H) 7.37 (s, 1 H) 7.73 (d, J=8.70 Hz, 1 H) 10.67 (br. s., 1 H) 13.54 (s, 1 H). MS (ESI+) m/z 573 [M+H]⁺.

Example 200

Methyl 4-{[(5-bromo-4-chloro-2-thienyl)sulfonyl]amino}-2-hydroxybenzoate

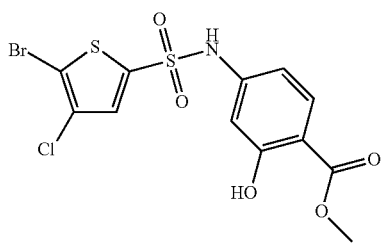 [SMILES: COC(=O)c1ccc(NS(=O)(=O)c2cc(Cl)c(Br)s2)cc1O]

The product was prepared from methyl 4-amino-salicylate (0.46 g, 2.8 mmol) and 5-bromo-4-chlorothiophene-2-sulfonyl chloride (0.68 g, 2.3 mmol) as described for Intermediate 23. The title compound was obtained in 61% yield (0.60 g). ¹H NMR (600 MHz, CDCl₃) δ ppm 3.95 (s, 3 H) 6.69 (dd, J=8.70, 2.29 Hz, 1 H) 6.74 (d, J=2.14 Hz, 1 H) 6.83 (br. s., 1 H) 7.41 (s, 1 H) 7.80 (d, J=8.54 Hz, 1 H) 10.93 (s, 1 H). MS (ESI+) m/z 426 [M+H]⁺.

Example 201

(1-Methyl-2-nitro-1H-imidazol-5-yl)methyl 4-({[5-chloro-4-(2,3-dihydro-1-benzofuran-5-yl)-2-thienyl]sulfonyl}amino)-2-hydroxybenzoate

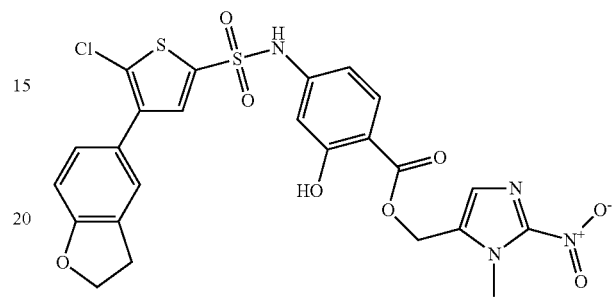

The product was prepared from 4-({[5-chloro-4-(2,3-dihydro-1-benzofuran-5-yl)thiophen-2-yl]sulfonyl}amino)-2-hydroxybenzoic acid (Intermediate 2) (0.023 g, 0.050 mmol) and (3-methyl-2-nitro-3H-imidazol-4-yl)-methanol (16 mg, 0.10 mmol) according to the General Procedure 8, described in Example 60. The title compound was obtained in 31% yield (9.2 mg). ¹H NMR (600 MHz, DMSO-d₆) δ ppm 3.21 (t, J=8.70 Hz, 2 H) 3.97 (s, 3 H) 4.57 (t, J=8.70 Hz, 2 H) 5.44 (s, 2 H) 6.76 (dd, J=8.85, 1.83 Hz, 1 H) 6.80 (d, J=1.83 Hz, 1 H) 6.84 (d, J=8.54 Hz, 1 H) 7.28 (dd, J=8.39, 1.68 Hz, 1 H) 7.33 (s, 1 H) 7.42 (s, 1 H) 7.68-7.75 (m, 2 H) 10.48 (s, 1 H) 11.20 (br. s., 1 H). MS (ESI+) m/z 591 [M+H]⁺.

Example 202

(1-Methyl-2-nitro-1H-imidazol-5-yl)methyl 4-{[(4,5-dichlorothiophen-2-yl)sulfonyl]amino}-2-hydroxybenzoate

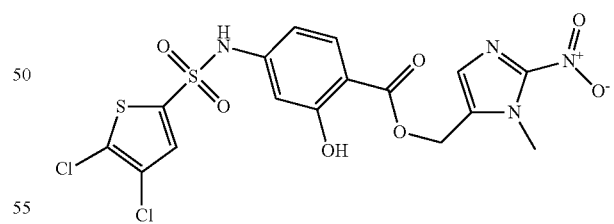

The product was prepared from 4-{[(4,5-dichlorothiophen-2-yl)sulfonyl]amino}-2-hydroxybenzoic acid (Intermediate 7) (0.018 g, 0.050 mmol) and (3-methyl-2-nitro-3H-imidazol-4-yl)-methanol (16 mg, 0.10 mmol) according to the General Procedure 8, described in Example 60. The title compound was obtained in 56% yield (14 mg). ¹H NMR (600 MHz, DMSO-d₆) δ ppm 3.98 (s, 3 H) 5.45 (s, 2 H) 6.74 (dd, J=8.85, 2.14 Hz, 1 H) 6.77 (d, J=2.14 Hz, 1 H) 7.34 (s, 1 H) 7.73 (d, J=8.85 Hz, 1 H) 7.82 (s, 1 H) 10.50 (s, 1 H) 11.31 (br. s., 1 H). MS (ESI+) m/z 507 [M+H]⁺.

Example 203

2-Phenoxyethyl 4-{[(5'-fluoro-2'-hydroxybiphenyl-3-yl)sulfonyl]amino}-2-hydroxybenzoate

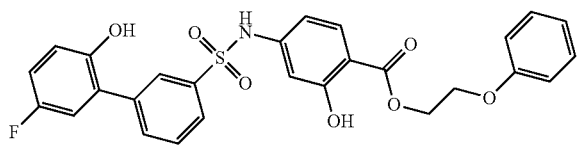 [SMILES: O=C(OCCOc1ccccc1)c1ccc(NS(=O)(=O)c2cccc(-c3cc(F)ccc3O)c2)cc1O]

The product was prepared from 4-{[(5'-fluoro-2'-hydroxybiphenyl-3-yl)sulfonyl]amino}-2-hydroxybenzoic acid (Intermediate 16) (0.020 g, 0.050 mmol) and 2-phenoxyethanol (400 µL) according to the General Procedure 12, described in Example 178 with a modified reaction time (1 day). The title compound was obtained in 59% yield (15 mg). $^1$H NMR (600 MHz, DMSO-d$_6$) δ ppm 4.25-4.33 (m, 2 H) 4.52-4.62 (m, 2 H) 6.67-6.74 (m, 2 H) 6.89-6.99 (m, 4 H) 7.03-7.09 (m, 1 H) 7.11 (dd, J=9.61, 3.20 Hz, 1 H) 7.23-7.32 (m, 2 H) 7.56-7.66 (m, 2 H) 7.77 (d, J=7.93 Hz, 1 H) 7.83 (d, J=7.63 Hz, 1 H) 8.10 (s, 1 H) 9.81 (s, 1 H) 10.52 (s, 1 H) 10.91 (s, 1 H). MS (ESI+) m/z 524 [M+H]$^+$.

Example 204

1-Benzylpyrrolidin-3-yl 2-hydroxy-4-{[(2,4,5-trichloro-3-thienyl)sulfonyl]amino}benzoate

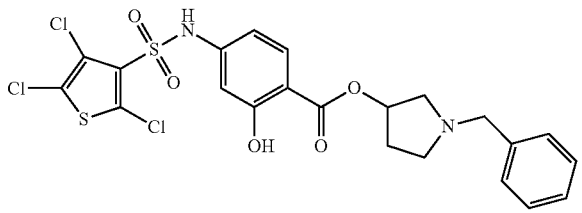 [SMILES: O=C(OC1CCN(Cc2ccccc2)C1)c1ccc(NS(=O)(=O)c2c(Cl)sc(Cl)c2Cl)cc1O]

The product was prepared from 2-hydroxy-4-{[(2,4,5-trichloro-3-thienyl)sulfonyl]amino}benzoic acid (Intermediate 18) (0.019 g, 0.048 mmol) and 1-benzylpyrrolidin-3-ol (50 mg, 0.28 mmol) according to the General Procedure 7, described in Example 59. After preparative chromatography the compound was dissolved in EtOAc and washed with Na$_2$CO$_3$ (aq. sat.). Removal of the solvents gave the title compound in 17% yield (4.7 mg). $^1$H NMR (600 MHz, CDCl$_3$) δ ppm 1.95-2.04 (m, 1 H) 2.32-2.41 (m, 1 H) 2.49-2.57 (m, 1 H) 2.73-2.80 (m, 1 H) 2.80-2.87 (m, 1 H) 2.88-2.94 (m, 1 H) 3.64 (d, J=12.21 Hz, 1 H) 3.70 (d, J=12.21 Hz, 1 H) 5.36-5.45 (m, 1 H) 6.68 (d, J=8.85 Hz, 1 H) 6.70 (s, 1 H) 7.31-7.38 (m, 5 H) 7.78 (d, J=7.63 Hz, 1 H) 10.91 (br. s., 1 H). MS (ESI+) m/z 561 [M+H]$^+$.

Example 205 tert-Butyl 3-[(2-hydroxy-4-{[(2,4,5-trichloro-3-thienyl)sulfonyl]amino}benzoyl)oxy]pyrrolidine-1-carboxylate

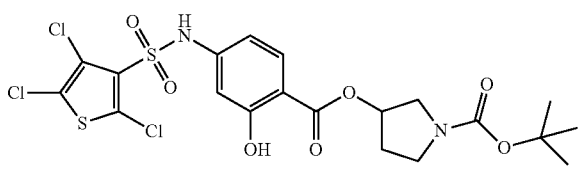 [SMILES: CC(C)(C)OC(=O)N1CCC(OC(=O)c2ccc(NS(=O)(=O)c3c(Cl)sc(Cl)c3Cl)cc2O)C1]

The product was prepared from 2-hydroxy-4-{[(2,4,5-trichloro-3-thienyl)sulfonyl]amino}benzoic acid (Intermediate 18) (0.019 g, 0.048 mmol) and tert-butyl 3-hydroxypyrrolidine-1-carboxylate (53 mg, 0.28 mmol) according to the General Procedure 7, described in Example 59. The title compound was obtained in 35% yield (10 mg). $^1$H NMR (600 MHz, CDCl$_3$) δ ppm 1.47 (s, 9 H) 2.12-2.23 (m, 2 H) 3.41-3.60 (m, 2 H) 3.60-3.68 (m, 2 H) 5.49-5.53 (m, 1 H) 6.67 (dd, J=8.70, 2.29 Hz, 1 H) 6.72 (d, J=2.29 Hz, 1 H) 7.72 (d, J=8.70 Hz, 1 H) 10.81 (s, 1 H). MS (ESI+) m/z 593 [M+Na]$^+$.

Example 206

Methyl 4-({[4-chloro-5-(2-hydroxyphenyl)thiophen-2-yl]sulfonyl}amino)-2-hydroxybenzoate

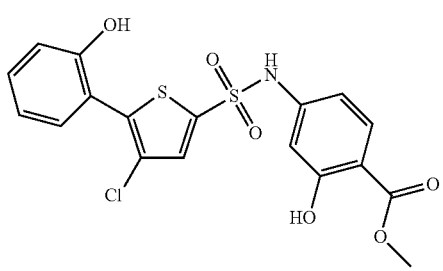 [SMILES: COC(=O)c1ccc(NS(=O)(=O)c2cc(Cl)c(-c3ccccc3O)s2)cc1O]

The product was prepared from methyl 4-{[(5-bromo-4-chloro-2-thienyl)sulfonyl]amino}-2-hydroxybenzoate (Intermediate 23) (21 mg, 0.050 mmol) and 2-hydroxybenzeneboronic acid (10 mg, 0.075 mmol) according to the General Procedure 9, described in Example 82. The title compound was obtained in 50% yield (11 mg). $^1$H NMR (600 MHz, DMSO-d$_6$) δ ppm 3.84 (s, 3 H) 6.77-6.82 (m, 2 H) 6.89 (td, J=7.55, 1.07 Hz, 1 H) 6.97 (dd, J=8.24, 0.92 Hz, 1 H) 7.27-7.32 (m, 1 H) 7.43 (dd, J=7.63, 1.53 Hz, 1 H) 7.71-7.75 (m, 2 H) 10.34 (s, 1 H) 10.63 (s, 1 H) 11.23 (s, 1 H). MS (ESI+) m/z 440 [M+H]$^+$.

Example 207

Methyl 4-({[4-chloro-5-(2-methoxyphenyl)thiophen-2-yl]sulfonyl}amino)-2-hydroxybenzoate

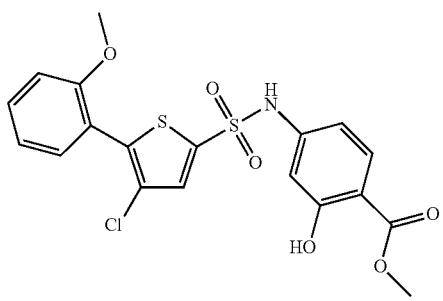 [SMILES: COC(=O)c1ccc(NS(=O)(=O)c2cc(Cl)c(-c3ccccc3OC)s2)cc1O]

The product was prepared from methyl 4-{[(5-bromo-4-chloro-2-thienyl)sulfonyl]amino}-2-hydroxybenzoate (Intermediate 23) (21 mg, 0.050 mmol) and 2-methoxyphenylboronic acid (11 mg, 0.075 mmol) according to the General Procedure 9, described in Example 82. The title compound was obtained in 42% yield (10 mg). $^1$H NMR (600 MHz, DMSO-$d_6$) δ ppm 3.79 (s, 3 H) 3.84 (s, 3 H) 6.78-6.83 (m, 2 H) 7.05 (td, J=7.55, 1.07 Hz, 1 H) 7.18 (d, J=7.93 Hz, 1 H) 7.45 (dd, J=7.63, 1.83 Hz, 1 H) 7.47-7.51 (m, 1 H) 7.69-7.75 (m, 1 H) 7.75 (s, 1 H) 10.63 (s, 1 H) 11.25 (s, 1 H). MS (ESI+) m/z 454 [M+H]$^+$.

Example 208

2-Methoxyethyl 4-({[5-chloro-4-(5-fluoro-2-hydroxyphenyl)-2-thienyl]sulfonyl}amino)-2-hydroxybenzoate

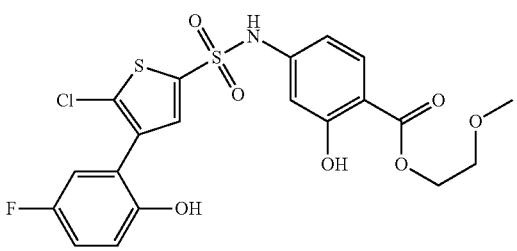 [SMILES: COCCOC(=O)c1ccc(NS(=O)(=O)c2cc(-c3cc(F)ccc3O)c(Cl)s2)cc1O]

The product was prepared from 4-({[5-chloro-4-(5-fluoro-2-hydroxyphenyl)-2-thienyl]sulfonyl}amino)-2-hydroxybenzoic acid (Intermediate 24) (22 mg, 0.050 mmol) and 2-methoxyethanol (200 μL) according to the General Procedure 12, described in Example 178 with a modified reaction temperature of 60° C. The title compound was obtained in 81% yield (20 mg). $^1$H NMR (600 MHz, DMSO-$d_6$) δ ppm 3.28 (s, 3 H) 3.60-3.66 (m, 2 H) 4.34-4.42 (m, 2 H) 6.77 (d, J=2.14 Hz, 1 H) 6.80 (dd, J=8.54, 2.14 Hz, 1 H) 6.94 (dd, J=9.00, 4.73 Hz, 1 H) 7.06-7.15 (m, 2 H) 7.68-7.75 (m, 2 H) 9.90 (s, 1 H) 10.60 (s, 1 H) 11.25 (s, 1 H). MS (ESI+) m/z 502 [M+H]$^+$.

Example 209

Tetrahydrofuran-3-yl 4-({[5-chloro-4-(5-fluoro-2-hydroxyphenyl)-2-thienyl]sulfonyl}amino)-2-hydroxybenzoate

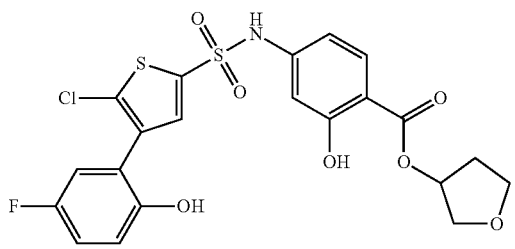 [SMILES: O=C(OC1CCOC1)c1ccc(NS(=O)(=O)c2cc(-c3cc(F)ccc3O)c(Cl)s2)cc1O]

The product was prepared from 4-({[5-chloro-4-(5-fluoro-2-hydroxyphenyl)-2-thienyl]sulfonyl}amino)-2-hydroxybenzoic acid (Intermediate 24) (22 mg, 0.050 mmol) and 3-hydroxytetrahydrofuran (200 μL) according to the General Procedure 12, described in Example 178 with a modified reaction temperature of 60° C. The title compound was obtained in 39% yield (9.9 mg). $^1$H NMR (600 MHz, DMSO-$d_6$) δ ppm 2.01-2.07 (m, 1 H) 2.18-2.25 (m, 1 H) 3.72-3.78 (m, 1 H) 3.80-3.88 (m, 3 H) 5.43-5.47 (m, 1 H) 6.74-6.77 (m, 1 H) 6.78-6.81 (m, 1 H) 6.94 (dd, J=8.85, 4.88 Hz, 1 H) 7.06-7.15 (m, 2 H) 7.71 (s, 1 H) 7.72 (d, J=8.54 Hz, 1 H) 9.91 (s, 1 H) 10.61 (s, 1 H) 11.24 (s, 1 H). MS (ESI+) m/z 514 [M+H]$^+$.

Example 210

2-Methoxybutyl 4-({[5-chloro-4-(5-fluoro-2-hydroxyphenyl)-2-thienyl]sulfonyl}amino)-2-hydroxybenzoate

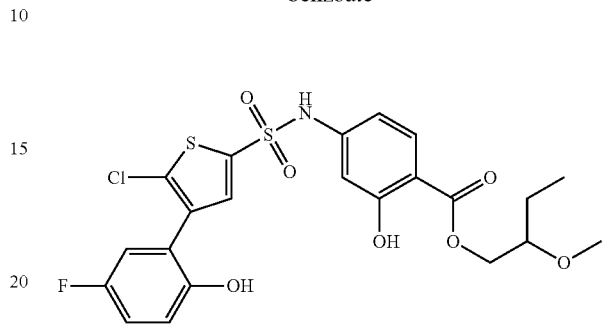

The product was prepared from 4-({[5-chloro-4-(5-fluoro-2-hydroxyphenyl)-2-thienyl]sulfonyl}amino)-2-hydroxybenzoic acid (Intermediate 24) (22 mg, 0.050 mmol) and 2-methoxy-1-butanol (200 μL) according to the General Procedure 12, described in Example 178 with a modified reaction temperature of 60° C. The title compound was obtained in 76% yield (20 mg). $^1$H NMR (600 MHz, DMSO-$d_6$) δ ppm 0.89 (t, J=7.48 Hz, 3 H) 1.50-1.57 (m, 2 H) 3.31 (s, 3 H) 4.21 (m, 1 H) 4.37 (dd, J=11.60, 3.66 Hz, 1 H) 6.78 (d, J=2.14 Hz, 1 H) 6.80 (dd, J=8.85, 2.14 Hz, 1 H) 6.94 (dd, J=8.85, 4.88 Hz, 1 H) 7.07-7.14 (m, 2 H) 7.72 (s, 1H) 7.73 (d, J=8.85 Hz, 1 H) 9.90 (s, 1 H) 10.61 (s, 1 H) 11.25 (s, 1 H). MS (ESI+) m/z 530 [M+H]$^+$.

Example 211

Ethyl 4-({[5-chloro-4-(5-fluoro-2-hydroxyphenyl)-2-thienyl]sulfonyl}amino)-2-hydroxybenzoate

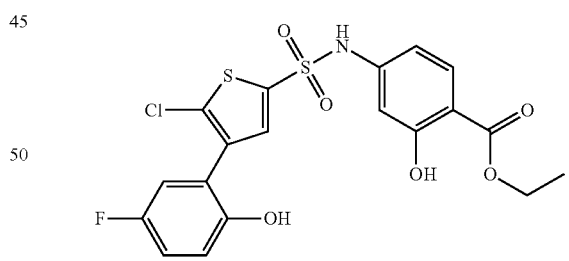

The product was prepared from 4-({[5-chloro-4-(5-fluoro-2-hydroxyphenyl)-2-thienyl]sulfonyl}amino)-2-hydroxybenzoic acid (Intermediate 24) (22 mg, 0.050 mmol) and ethanol (200 μL) according to the General Procedure 12, described in Example 178 with a modified reaction temperature of 60° C. The title compound was obtained in 92% yield (22 mg). $^1$H NMR (600 MHz, DMSO-$d_6$) δ ppm 1.30 (t, J=7.02 Hz, 3 H) 4.31 (q, J=7.02 Hz, 2 H) 6.76 (d, J=2.14 Hz, 1 H) 6.79 (dd, J=8.70, 2.29 Hz, 1 H) 6.94 (dd, J=8.85, 4.88 Hz, 1 H) 7.06-7.15 (m, 2H) 7.70 (s, 1H) 7.72 (d, J=8.85 Hz, 1H) 9.90 (s, 1H) 10.70 (s, 1H) 11.23 (s, 1H). MS (ESI+) m/z 472 [M+H]$^+$.

Example 212

General Procedure 13

3-(2,6-Dimethylmorpholin-4-yl)propyl 4-{[(5'-fluoro-2'-hydroxybiphenyl-3-yl)sulfonyl]amino}-2-hydroxybenzoate trifluoroacetate

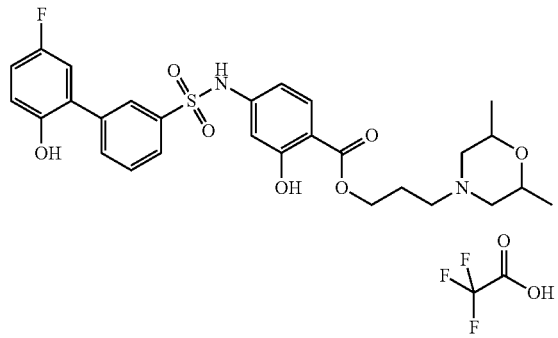

A mixture of 3-bromopropyl 4-{[(5'-fluoro-2'-hydroxybiphenyl-3-yl)sulfonyl]amino}-2-hydroxybenzoate (Intermediate 25) (14 mg, 0.027 mmol) and cis-2,6-dimethylmorpholine (23 mg, 0.20 mmol) in MeCN (0.4 mL) was heated at 60° C. overnight. The crude product was purified by preparative HPLC (acidic system). The title compound was obtained in 46% yield (8.3 mg). $^1$H NMR (600 MHz, CDCl$_3$) δ ppm 1.23 (d, J=6.41 Hz, 6H) 2.23-2.30 (m, 2H) 2.37 (t, J=10.99 Hz, 2H) 3.09-3.21 (m, 2H) 3.52 (d, J=11.29 Hz, 2H) 4.01-4.09 (m, 2H) 4.31-4.37 (m, 2H) 6.46 (d, J=2.14 Hz, 1H) 6.80 (dd, J=8.85, 4.88 Hz, 1H) 6.85-6.90 (m, 1H) 6.91 (s, 1H) 6.97-7.02 (m, 2H) 7.54-7.58 (m, 1H) 7.59-7.63 (m, 1H) 7.74 (d, J=8.85 Hz, 1H) 7.81-7.88 (m, 1H) 8.45 (t, J=1.68 Hz, 1H). MS (ESI+) m/z 559 [M+H]$^+$.

Example 213

3-Morpholin-4-ylpropyl 4-({[5-chloro-4-(5-fluoro-2-hydroxyphenyl)-2-thienyl]sulfonyl}amino)-2-hydroxybenzoate trifluoroacetate

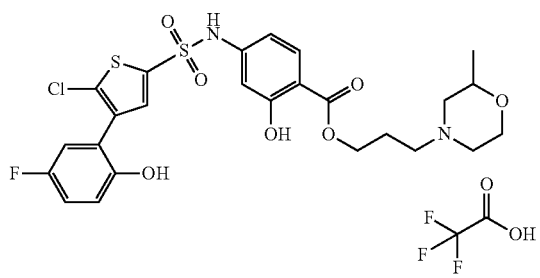

The product was prepared from 3-bromopropyl 4-({[5-chloro-4-(5-fluoro-2-hydroxyphenyl)-2-thienyl]sulfonyl}amino)-2-hydroxybenzoate (Intermediate 26) (16 mg, 0.029 mmol) and morpholine (23 mg, 0.27 mmol) according to the General Procedure 13, described in Example 212. The title compound was obtained in 74% yield (15 mg). $^1$H NMR (600 MHz, CDCl$_3$) δ ppm 2.29 (br. s., 2H) 2.90 (br. s., 2H) 3.14-3.26 (m, 2H) 3.58 (br. s., 2H) 3.99 (br. s., 2H) 4.07 (br. s., 2H) 4.33-4.44 (m, 2H) 6.58 (d, J=2.14 Hz, 1H) 6.76 (dd, J=9.16, 4.58 Hz, 1H) 6.86-6.93 (m, 3H) 7.08-7.12 (m, 1H) 7.74 (d, J=8.85 Hz, 1H) 7.85 (s, 1H). MS (ESI+) m/z 571 [M+H]$^+$.

Example 214

3-(2,6-Dimethylmorpholin-4-yl)propyl 4-({[5-chloro-4-(5-fluoro-2-hydroxyphenyl)-2-thienyl]sulfonyl}amino)-2-hydroxybenzoate trifluoroacetate

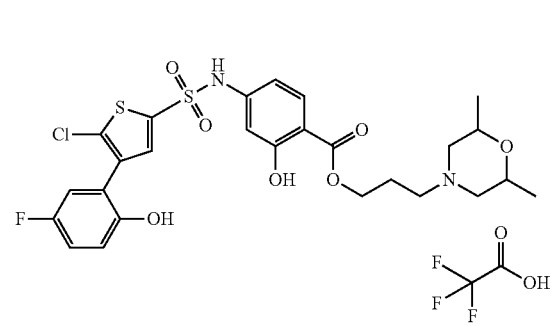

The product was prepared from 3-bromopropyl 4-({[5-chloro-4-(5-fluoro-2-hydroxyphenyl)-2-thienyl]sulfonyl}amino)-2-hydroxybenzoate (Intermediate 26) (16 mg, 0.029 mmol) and cis-2,6-dimethylmorpholine (23 mg, 0.20 mmol) according to the General Procedure 13, described in Example 212. The title compound was obtained in 77% yield (16 mg). $^1$H NMR (600 MHz, CDCl$_3$) δ ppm 1.25 (d, J=6.41 Hz, 6H) 2.24-2.33 (m, 2H) 2.39 (t, J=11.75 Hz, 2H) 3.11-3.21 (m, 2H) 3.52 (d, J=11.29 Hz, 2H) 4.05 (br. s., 2H) 4.36-4.43 (m, 2H) 6.58 (d, J=2.14 Hz, 1H) 6.75 (dd, J=9.16, 4.58 Hz, 1H) 6.84-6.93 (m, 3H) 7.11 (dd, J=8.85, 3.05 Hz, 1H) 7.74 (d, J=8.85 Hz, 1H) 7.86 (s, 1H). MS (ESI+) m/z 599 [M+H]$^+$.

Example 215

1-(Methoxymethyl)propyl 4-{[(5-chloro-4-phenyl-2-thienyl)sulfonyl]amino}-2-hydroxybenzoate

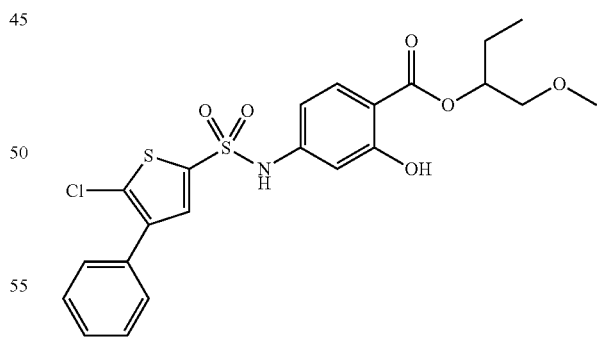

The product was prepared from 4-{[(5-chloro-4-phenyl-2-thienyl)sulfonyl]amino}-2-hydroxybenzoic acid (Intermediate 27) (16 mg, 0.040 mmol) and 1-methoxy-2-butanol (21 mg, 0.2 mmol) according to the General Procedure 8, described in Example 60. The title compound was obtained in 59% yield (12 mg). $^1$H NMR (600 MHz, CDCl$_3$) δ ppm 0.98 (t, J=7.48 Hz, 3H) 1.72-1.79 (m, 2H) 3.37 (s, 3H) 3.52-3.56 (m, 1H) 3.57-3.61 (m, 1H) 5.19-5.26 (m, 1H) 6.71 (dd, J=8.70, 2.29 Hz, 1H) 6.76 (d, J=2.14 Hz, 1H) 6.77 (s, 1H) 7.38-7.50 (m, 5H) 7.61 (s, 1H) 7.83 (d, J=8.85 Hz, 1H) 10.99 (s, 1H). MS (ESI+) m/z 496 [M+H]+.

Example 216

2-Methoxy-1-methylethyl 4-{[(5-chloro-4-phenyl-2-thienyl)sulfonyl]amino}-2-hydroxybenzoate

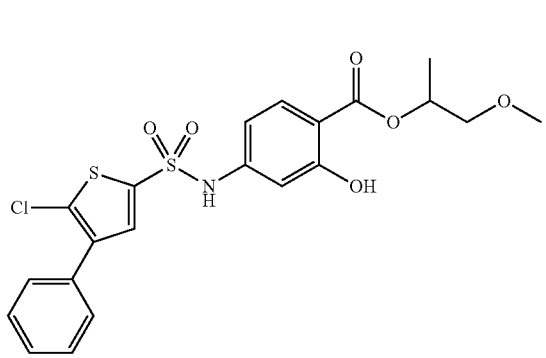 [SMILES: COCC(C)OC(=O)c1ccc(NS(=O)(=O)c2cc(-c3ccccc3)c(Cl)s2)cc1O]

The product was prepared from 4-{[(5-chloro-4-phenyl-2-thienyl)sulfonyl]amino}-2-hydroxybenzoic acid (Intermediate 27) (16 mg, 0.040 mmol) and 1-methoxy-2-propanol (18 mg, 0.2 mmol) according to the General Procedure 8, described in Example 60. The title compound was obtained in 69% yield (13 mg). $^1$H NMR (600 MHz, CDCl$_3$) δ ppm 1.36 (d, J=6.41 Hz, 3H) 3.39 (s, 3H) 3.48-3.54 (m, 1H) 3.55-3.61 (m, 1H) 5.32-5.38 (m, 1H) 6.71 (dd, J=8.55, 2.14 Hz, 1H) 6.75 (d, J=2.14 Hz, 1H) 6.77 (s, 1H) 7.37-7.51 (m, 5H) 7.60 (s, 1H) 7.82 (d, J=8.85 Hz, 1H) 10.96 (s, 1H). MS (ESI+) m/z 482 [M+H]+.

Example 217

2-Hydroxyethyl 4-{[(5-chloro-4-phenyl-2-thienyl)sulfonyl]amino}-2-hydroxybenzoate

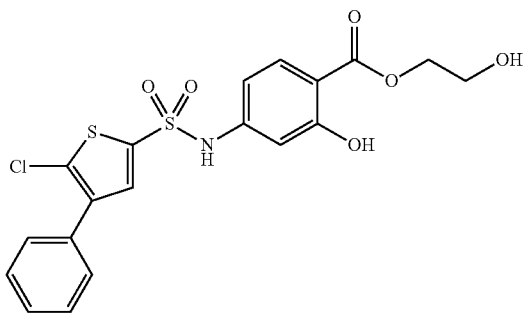 [SMILES: O=C(OCCO)c1ccc(NS(=O)(=O)c2cc(-c3ccccc3)c(Cl)s2)cc1O]

The product was prepared from 4-{[(5-chloro-4-phenyl-2-thienyl)sulfonyl]amino}-2-hydroxybenzoic acid (Intermediate 27) (16 mg, 0.040 mmol) and ethylene glycol (110 mg, 1.8 mmol) according to the General Procedure 8, described in Example 60 using preparative HPLC (basic system 2) as purification method. The title compound was obtained in 64% yield (12 mg). $^1$H NMR (600 MHz, CDCl$_3$) δ ppm 1.81 (t, J=6.10 Hz, 1H) 3.93-4.02 (m, 2H) 4.43-4.52 (m, 2H) 6.73 (dd, J=8.70, 2.29 Hz, 1H) 6.77 (d, J=2.44 Hz, 1H) 6.80 (br. s., 1H) 7.37-7.52 (m, 5H) 7.61 (s, 1H) 7.84 (d, J=8.54 Hz, 1H) 10.83 (s, 1H). MS (ESI+) m/z 454 [M+H]+.

Example 218

1-(Methoxymethyl)propyl 4-({[5-chloro-4-(3-fluorophenyl)-2-thienyl]sulfonyl}amino)-2-hydroxybenzoate

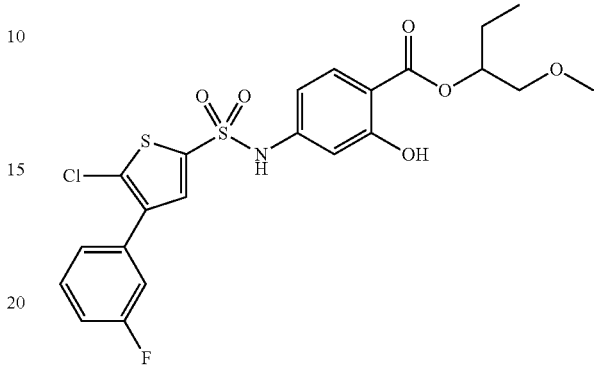

The product was prepared from 4-({[5-chloro-4-(3-fluorophenyl)-2-thienyl]sulfonyl}amino)-2-hydroxybenzoic acid (Intermediate 28) (17 mg, 0.040 mmol) and 1-methoxy-2-butanol (21 mg, 0.2 mmol) according to the General Procedure 8, described in Example 60. The title compound was obtained in 62% yield (13 mg). $^1$H NMR (600 MHz, CDCl$_3$) δ ppm 0.98 (t, J=7.48 Hz, 3H) 1.70-1.79 (m, 2H) 3.37 (s, 3H) 3.51-3.56 (m, 1H) 3.57-3.63 (m, 1H) 5.18-5.26 (m, 1H) 6.71 (dd, J=8.70, 2.29 Hz, 1H) 6.76 (d, J=2.44 Hz, 1H) 6.78 (s, 1H) 7.07-7.13 (m, 1H) 7.21 (ddd, J=9.61, 1.98, 1.83 Hz, 1H) 7.24-7.26 (m, 1H) 7.39-7.46 (m, 1H) 7.59 (s, 1H) 7.84 (d, J=8.54 Hz, 1H) 10.99 (s, 1H). MS (ESI+) m/z 514 [M+H]+.

Example 219

2-Hydroxyethyl 4-({[5-chloro-4-(3-fluorophenyl)-2-thienyl]sulfonyl}amino)-2-hydroxybenzoate

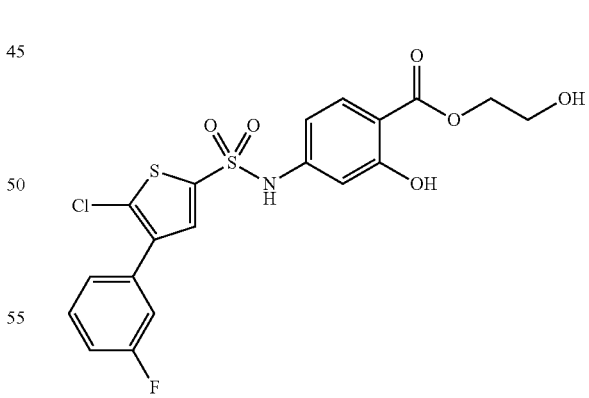

The product was prepared from 4-({[5-chloro-4-(3-fluorophenyl)-2-thienyl]sulfonyl}amino)-2-hydroxybenzoic acid (Intermediate 28) (17 mg, 0.040 mmol) and ethylene glycol (110 mg, 1.8 mmol) according to the General Procedure 8, described in Example 60, using preparative HPLC (basic system 2) as purification method. The title compound was obtained in 58% yield (11 mg). $^1$H NMR (600 MHz, CDCl$_3$) δ ppm 1.81 (t, J=5.95 Hz, 1H) 3.94-4.01 (m, 2H)

4.45-4.51 (m, 2H) 6.73 (dd, J=8.70, 2.29 Hz, 1H) 6.77 (d, J=2.14 Hz, 1H) 6.80 (br. s., 1H) 7.08-7.13 (m, 1H) 7.21 (dt, J=9.69, 2.02 Hz, 1H) 7.24-7.26 (m, 1H) 7.38-7.46 (m, 1H) 7.59 (s, 1H) 7.85 (d, J=8.55 Hz, 1H) 10.84 (s, 1H). MS (ESI+) m/z 472 [M+H]+.

Example 220

2-Methoxyethyl 4-({[5-chloro-4-(3-fluorophenyl)-2-thienyl]sulfonyl}amino)-2-hydroxybenzoate

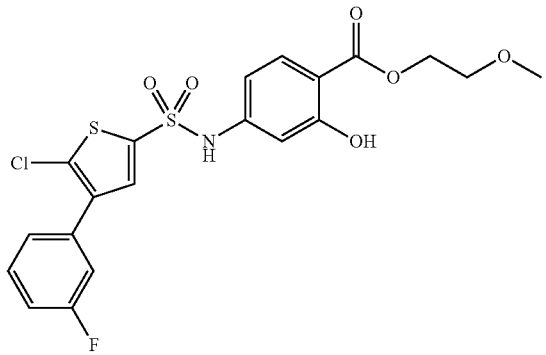 [SMILES: COCCOC(=O)c1ccc(NS(=O)(=O)c2cc(-c3cccc(F)c3)c(Cl)s2)cc1O]

The product was prepared from 4-({[5-chloro-4-(3-fluorophenyl)-2-thienyl]sulfonyl}amino)-2-hydroxybenzoic acid (Intermediate 28) (17 mg, 0.040 mmol) and 2-methoxyethanol (15 mg, 0.2 mmol) according to the General Procedure 8, described in Example 60. The title compound was obtained in 69% yield (13 mg). $^1$H NMR (600 MHz, CDCl$_3$) δ ppm 3.41 (s, 3H) 3.67-3.73 (m, 2H) 4.45-4.51 (m, 2H) 6.70 (dd, J=8.55, 2.44 Hz, 1H) 6.75 (d, J=2.44 Hz, 1H) 6.77 (s, 1H) 7.06-7.12 (m, 1H) 7.20 (dt, J=9.69, 2.02 Hz, 1H) 7.22-7.25 (m, 1H) 7.37-7.45 (m, 1H) 7.57 (s, 1H) 7.84 (d, J=8.55 Hz, 1H) 10.85 (s, 1H). MS (ESI+) m/z 486 [M+H]+.

Example 221

3-Morpholin-4-ylpropyl 4-({[5-chloro-4-(3-fluorophenyl)-2-thienyl]sulfonyl}amino)-2-hydroxybenzoate trifluoroacetate

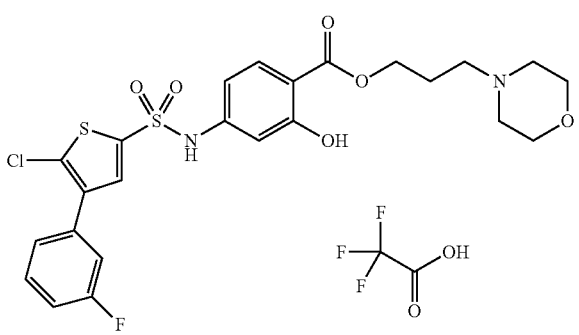 [SMILES: O=C(OCCCN1CCOCC1)c1ccc(NS(=O)(=O)c2cc(-c3cccc(F)c3)c(Cl)s2)cc1O ; O=C(O)C(F)(F)F]

The product was prepared from 4-({[5-chloro-4-(3-fluorophenyl)-2-thienyl]sulfonyl}amino)-2-hydroxybenzoic acid (Intermediate 28) (17 mg, 0.040 mmol) and 4-(3-hydroxypropyl)morpholine (29 mg, 0.2 mmol) according to the General Procedure 8, described in Example 60. The title compound was obtained in 65% yield (17 mg). $^1$H NMR (600 MHz, CDCl$_3$) δ ppm 2.30 (br. s., 2H) 2.88 (br. s., 2H) 3.14-3.21 (m, 2H) 3.59 (br. s., 2H) 4.02 (br. s., 4H) 4.41 (t, J=5.95 Hz, 2H) 6.70 (dd, J=8.70, 2.29 Hz, 1H) 6.81 (d, J=2.14 Hz, 1H) 7.07-7.14 (m, 2H) 7.20 (dt, J=9.54, 2.10 Hz, 1H) 7.24-7.27 (m, 1H) 7.42 (td, J=8.16, 6.26 Hz, 1H) 7.59 (s, 1H) 7.76 (d, J=8.55 Hz, 1H). MS (ESI+) m/z 555 [M+H]+.

Example 222

2-Methoxy-1-(methoxymethyl)ethyl 4-({[5-chloro-4-(3-fluorophenyl)-2-thienyl]sulfonyl}amino)-2-hydroxybenzoate

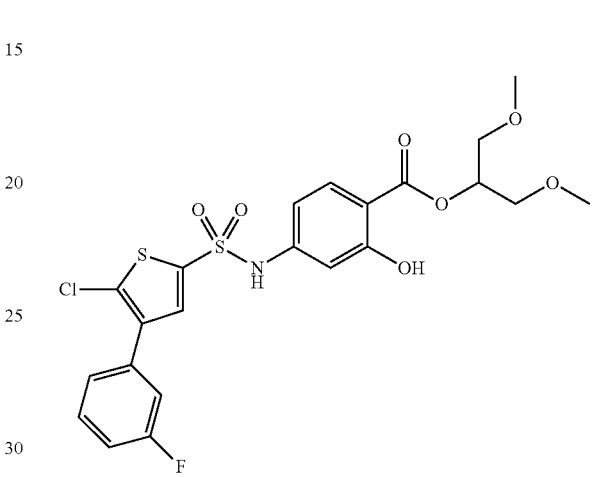

The product was prepared from 4-({[5-chloro-4-(3-fluorophenyl)-2-thienyl]sulfonyl}amino)-2-hydroxybenzoic acid (Intermediate 28) (17 mg, 0.040 mmol) and 1,3-dimethoxypropan-2-ol (24 mg, 0.2 mmol) according to the General Procedure 8, described in Example 60. The title compound was obtained in 48% yield (10 mg). $^1$H NMR (600 MHz, CDCl$_3$) δ ppm 3.39 (s, 6H) 3.61-3.71 (m, 4H) 5.36-5.44 (m, 1H) 6.71 (dd, J=8.70, 2.29 Hz, 1H) 6.76 (d, J=2.14 Hz, 1H) 6.79 (s, 1H) 7.07-7.13 (m, 1H) 7.21 (dt, J=9.54, 2.10 Hz, 1H) 7.24-7.26 (m, 1H) 7.42 (td, J=8.09, 6.10 Hz, 1H) 7.59 (s, 1H) 7.85 (d, J=8.55 Hz, 1H) 10.86 (s, 1H). MS (ESI+) m/z 530 [M+H]+.

Example 223

2-Phenoxyethyl 4-({[5-chloro-4-(3-fluorophenyl)-2-thienyl]sulfonyl}amino)-2-hydroxybenzoate

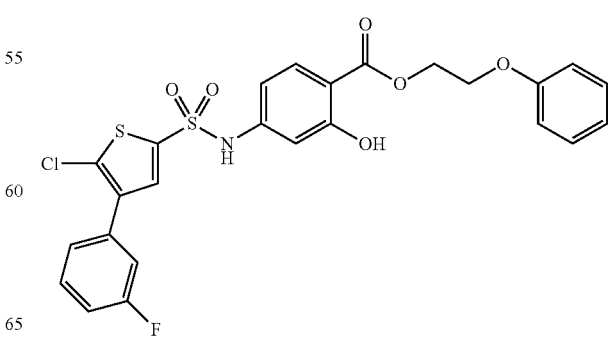

The product was prepared from 4-({[5-chloro-4-(3-fluorophenyl)-2-thienyl]sulfonyl}amino)-2-hydroxybenzoic acid (Intermediate 28) (17 mg, 0.040 mmol) and 2-phenoxyethanol (28 mg, 0.2 mmol) according to the General Procedure 8, described in Example 60. The title compound was obtained in 67% yield (15 mg). $^1$H NMR (600 MHz, CDCl$_3$) δ ppm 4.27-4.35 (m, 2H) 4.64-4.71 (m, 2H) 6.69 (dd, J=8.70, 2.29 Hz, 1H) 6.78 (d, J=2.44 Hz, 1H) 6.79 (s, 1H) 6.90-6.96 (m, 2H) 6.97-7.02 (m, 1H) 7.06-7.13 (m, 1H) 7.21 (dt, J=9.69, 2.02 Hz, 1H) 7.23-7.26 (m, 1H) 7.28-7.34 (m, 2H) 7.38-7.45 (m, 1H) 7.58 (s, 1H) 7.82 (d, J=8.55 Hz, 1H) 10.83 (s, 1H). MS (ESI+) m/z 548 [M+H]$^+$.

Example 224

Methyl 4-({[5-chloro-4-(5-fluoro-2-methoxyphenyl)-2-thienyl]sulfonyl}amino)-2-hydroxybenzoate

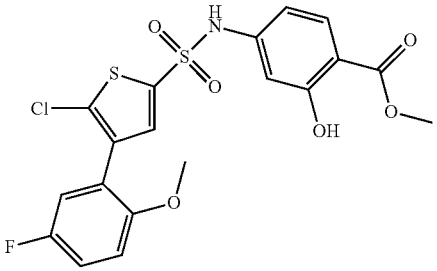 [SMILES: COC(=O)c1ccc(NS(=O)(=O)c2cc(-c3cc(F)ccc3OC)c(Cl)s2)cc1O]

The product was prepared from methyl 4-{[(4-bromo-5-chloro-2-thienyl)sulfonyl]amino}-2-hydroxybenzoate (Intermediate 3) (21 mg, 0.050 mmol) and 5-fluoro-2-methoxyphenyl boronic acid (8 mg, 0.050 mmol) according to the General Procedure 9, described in Example 82. The title compound was obtained in 50% yield (12 mg). $^1$H NMR (600 MHz, CDCl$_3$) δ ppm 3.75 (s, 3H) 3.92 (s, 3H) 6.67 (dd, J=8.70, 2.29 Hz, 1H) 6.77 (d, J=2.14 Hz, 1H) 6.80 (s, 1H) 6.89 (dd, J=8.85, 4.27 Hz, 1H) 7.02-7.09 (m, 2H) 7.63 (s, 1H) 7.78 (d, J=8.54 Hz, 1H) 10.91 (s, 1H). MS (ESI+) m/z 472 [M+H]$^+$ Example 225

2-Phenoxyethyl 4-{[(4,5-dichlorothiophen-2-yl)sulfonyl]amino}-2-hydroxybenzoate

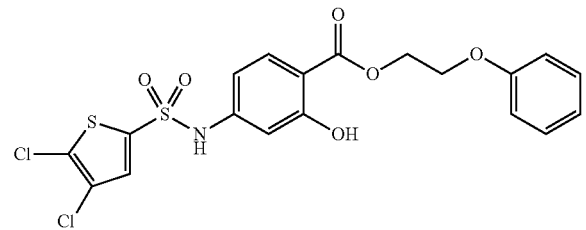 [SMILES: O=C(OCCOc1ccccc1)c1ccc(NS(=O)(=O)c2cc(Cl)c(Cl)s2)cc1O]

The product was prepared from 4-{[(4,5-dichlorothiophen-2-yl)sulfonyl]amino}-2-hydroxybenzoic acid (18 mg, 0.050 mmol) (Intermediate 7) and 1-phenoxyethanol (28 mg, 0.20 mmol) according to the General Procedure 8, described in Example 60. The title compound was obtained in 62% yield (15 mg). $^1$H NMR (600 MHz, CDCl$_3$) δ ppm 4.27-4.35 (m, 2H) 4.63-4.72 (m, 2H) 6.66 (dd, J=8.70, 2.29 Hz, 1H) 6.75 (d, J=2.14 Hz, 1H) 6.76 (br. s., 1H) 6.91-6.96 (m, 2H) 6.97-7.03 (m, 1H) 7.29-7.35 (m, 2H) 7.43 (s, 1H) 7.82 (d, J=8.55 Hz, 1H) 10.84 (s, 1H). MS (ESI+) m/z 488 [M+H]$^+$.

Example 226

2-[(6-Chloropyridin-3-yl)oxy]ethyl 4-{[(4,5-dichloro-2-thienyl)sulfonyl]amino}-2-hydroxybenzoate trifluoroacetate

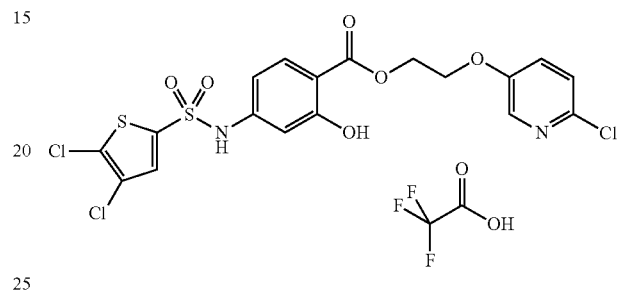

The product was prepared from 4-{[(4,5-dichlorothiophen-2-yl)sulfonyl]amino}-2-hydroxybenzoic acid (18 mg, 0.050 mmol) (Intermediate 7) and 2-[(6-chloropyridin-3-yl)oxy]ethanol (40 mg, 0.20 mmol) according to the General Procedure 8, described in Example 60. The title compound was obtained in 65% yield (17 mg). $^1$H NMR (600 MHz, DMSO-d$_6$) δ ppm 4.38-4.45 (m, 2H) 4.55-4.64 (m, 2H) 6.68-6.77 (m, 2H) 7.43 (d, J=8.55 Hz, 1H) 7.55 (dd, J=8.70, 3.20 Hz, 1H) 7.65 (d, J=9.16 Hz, 1H) 7.77 (s, 1H) 8.17 (d, J=3.05 Hz, 1H) 10.53 (s, 1H). MS (ESI+) m/z 523 [M+H]$^+$.

Example 227

2-[3-(Methoxymethyl)phenoxy]ethyl 4-{[(4,5-dichloro-2-thienyl)sulfonyl]amino}-2-hydroxybenzoate

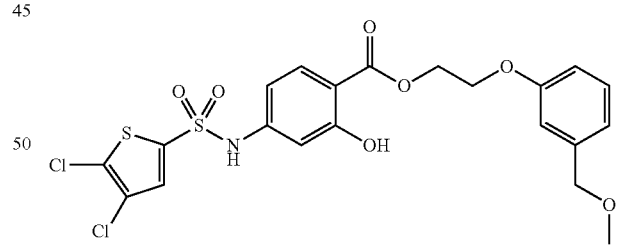

The product was prepared from 4-{[(4,5-dichlorothiophen-2-yl)sulfonyl]amino}-2-hydroxybenzoic acid (18 mg, 0.050 mmol) (Intermediate 7) and 2-[3-(methoxymethyl)phenoxy]ethanol (36 mg, 0.20 mmol) according to the General Procedure 8, described in Example 60. The title compound was obtained in 66% yield (17 mg). $^1$H NMR (600 MHz, CDCl$_3$) δ ppm 3.40 (s, 3H) 4.29-4.35 (m, 2H) 4.44 (s, 2H) 4.64-4.72 (m, 2H) 6.66 (dd, J=8.70, 2.29 Hz, 1H) 6.75 (d, J=2.14 Hz, 1H) 6.77 (br. s., 1H) 6.84-6.89 (m, 1H) 6.92-6.98 (m, 2H) 7.28 (t, J=8.24 Hz, 1H) 7.43 (s, 1H) 7.82 (d, J=8.55 Hz, 1H) 10.84 (s, 1H). MS (ESI+) m/z 549 [M+NH$_4$]$^+$.

Example 228

2-(3-Carbamoylphenoxy)ethyl 4-({[5-chloro-4-(2-fluoro-3-methoxyphenyl)-2-thienyl]sulfonyl}amino)-2-hydroxybenzoate

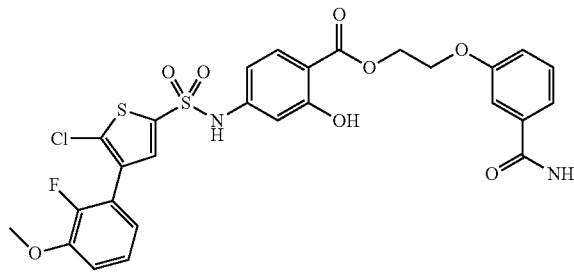

The product was prepared from 4-({[5-chloro-4-(2-fluoro-3-methoxyphenyl)-2-thienyl]sulfonyl}amino)-2-hydroxybenzoic acid (Intermediate 29) (18 mg, 0.040 mmol) and 3-(2-hydroxyethoxy)benzamide (35 mg, 0.20 mmol) according to the General Procedure 8, described in Example 60. The title compound was obtained in 53% yield (13 mg). $^1$H NMR (600 MHz, CDCl$_3$) δ ppm 3.92 (s, 3H) 4.34-4.42 (m, 2H) 4.64-4.73 (m, 2H) 6.70 (dd, J=8.70, 2.29 Hz, 1H) 6.80 (d, J=2.14 Hz, 1H) 6.93 (ddd, J=7.86, 6.18, 1.53 Hz, 1H) 7.02 (td, J=8.09, 1.22 Hz, 1H) 7.09-7.15 (m, 2H) 7.18 (br. s., 1H) 7.33-7.40 (m, 2H) 7.45-7.48 (m, 1H) 7.59 (d, J=1.53 Hz, 1H) 7.80 (d, J=8.54 Hz, 1H) 10.79 (s, 1H). MS (ESI+) m/z 621 [M+H]$^+$.

Example 229

3-Hydroxypropyl 4-({[5-chloro-4-(2-fluoro-3-methoxyphenyl)-2-thienyl]sulfonyl}amino)-2-hydroxybenzoate

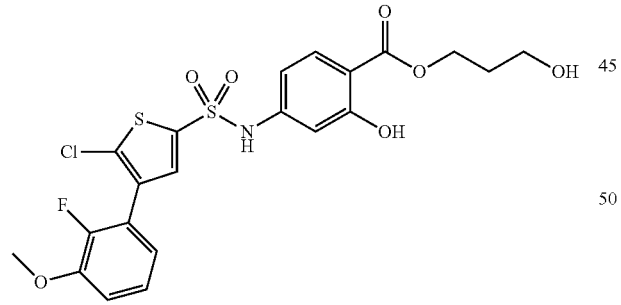

The product was prepared from 4-({[5-chloro-4-(2-fluoro-3-methoxyphenyl)-2-thienyl]sulfonyl}amino)-2-hydroxybenzoic acid (Intermediate 29) (18 mg, 0.040 mmol) and 1,3-propanediol (158 mg, 2.1 mmol) according to the General Procedure 8, described in Example 60 with a modified purification method (basic system 2). The title compound was obtained in 42% yield (8.7 mg). $^1$H NMR (600 MHz, DMSO-d$_6$) δ ppm 1.83 (quin, J=6.33 Hz, 2H) 3.53 (q, J=5.80 Hz, 2H) 3.87 (s, 3H) 4.32 (t, J=6.41 Hz, 2H) 4.60 (t, J=5.19 Hz, 1H) 6.66-6.79 (m, 2H) 6.98 (t, J=6.71 Hz, 1H) 7.19-7.30 (m, 2H) 7.61-7.75 (m, 2H) 10.65 (s, 1H). MS (ESI+) m/z 516 [M+H]$^+$.

Example 230

General Procedure 14

3-(Pyridin-3-ylamino)propyl 4-{[(5'-fluoro-2'-hydroxybiphenyl-3-yl)sulfonyl]amino}-2-hydroxybenzoate trifluoroacetate

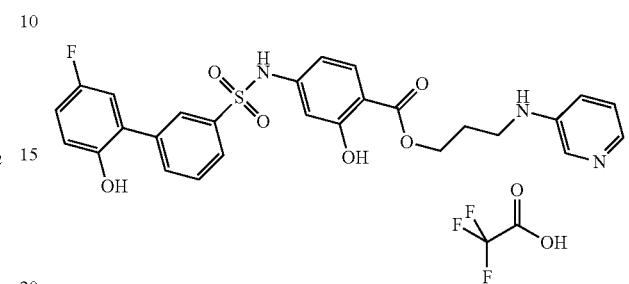

A mixture of 3-bromopropyl 4-{[(5'-fluoro-2'-hydroxybiphenyl-3-yl)sulfonyl]amino}-2-hydroxybenzoate (Intermediate 25) (16 mg, 0.031 mmol), potassium iodide (10 mg, 0.060 mmol) and 3-aminopyridine (15 mg, 0.16 mmol) in MeCN (0.4 mL) was heated at 60° C. overnight. The crude product was purified by preparative HPLC (acidic system). The title compound was obtained in 55% yield (11 mg). $^1$H NMR (600 MHz, DMSO-d$_6$) δ ppm 2.30 (dq, J=6.56, 6.36 Hz, 2H) 4.29 (t, J=5.80 Hz, 2H) 4.55 (t, J=7.17 Hz, 2H) 6.61 (br. s., 2H) 6.69-6.78 (m, 2H) 6.97 (dd, J=8.85, 4.88 Hz, 1H) 7.03-7.09 (m, 1H) 7.11 (dd, J=9.46, 3.05 Hz, 1H) 7.53 (dd, J=8.55, 1.83 Hz, 1H) 7.59 (d, J=8.55 Hz, 1H) 7.62-7.70 (m, 2H) 7.79 (d, J=8.54 Hz, 1H) 7.85 (d, J=7.63 Hz, 1H) 8.10 (d, J=7.93 Hz, 2H) 8.14 (d, J=5.80 Hz, 1H) 9.89 (s, 1H) 10.55 (s, 1H) 10.95 (s, 1H). MS (ESI+) m/z 538 [M+H]$^+$.

Example 231

3-[(1-Methyl-1H-pyrazol-5-yl)amino]propyl 4-{[(5'-fluoro-2'-hydroxybiphenyl-3-yl)sulfonyl]amino}-2-hydroxybenzoate trifluoroacetate

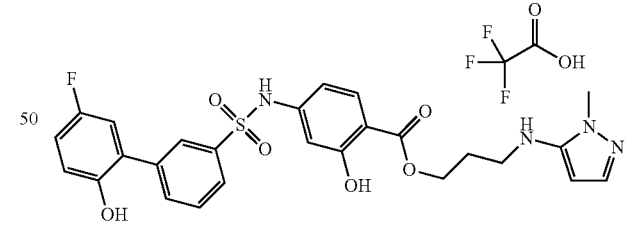

The product was prepared from 3-bromopropyl 4-{[(5'-fluoro-2'-hydroxybiphenyl-3-yl)sulfonyl]amino}-2-hydroxybenzoate (Intermediate 25) (16 mg, 0.031 mmol) and 1-methyl-1H-pyrazol-5-ylamine (15 mg, 0.15 mmol) according to the General Procedure 14, described in Example 230, but heating at 80° C. for 2 days. The title compound was obtained in 41% yield (8.0 mg). $^1$H NMR (600 MHz, DMSO-d$_6$) δ ppm 2.07-2.14 (m, 2H) 3.68 (s, 3H) 4.21 (t, J=5.95 Hz, 2H) 4.29 (t, J=6.87 Hz, 2H) 5.77 (d, J=3.36 Hz, 1H) 6.71 (d, J=2.14 Hz, 1H) 6.73 (dd, J=8.85, 2.14 Hz, 1H) 6.96 (dd, J=8.85, 4.88 Hz, 1H) 7.04-7.13 (m, 2H) 7.16 (br. s., 2H) 7.63 (t, J=7.78 Hz, 1H) 7.67 (d, J=8.85

Hz, 1H) 7.79 (d, J=8.85 Hz, 1H) 7.85 (d, J=7.63 Hz, 1H) 8.03 (d, J=3.36 Hz, 1H) 8.10 (s, 1H) 9.85 (s, 1H) 10.56 (s, 1H) 10.93 (s, 1H). MS (ESI+) m/z 541 [M+H]$^+$.

Example 232

3-[(5-Methylisoxazol-3-yl)amino]propyl 4-{[(5'-fluoro-2'-hydroxybiphenyl-3-yl)sulfonyl]amino}-2-hydroxybenzoate trifluoroacetate

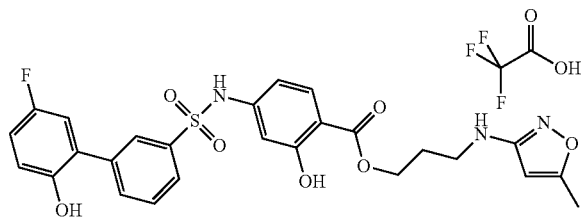

The product was prepared from 3-bromopropyl 4-{[(5'-fluoro-2'-hydroxybiphenyl-3-yl)sulfonyl]amino}-2-hydroxybenzoate (Intermediate 25) (16 mg, 0.031 mmol) and 3-amino-5-methyl-isoxazole (23 mg, 0.23 mmol) according to the General Procedure 14, described in Example 230, but heating at 80° C. for 3 days. The title compound was obtained in 44% yield (8.6 mg). $^1$H NMR (600 MHz, DMSO-d$_6$) δ ppm 2.17 (quin, J=6.26 Hz, 2H) 2.28 (s, 3H) 4.30 (t, J=5.95 Hz, 2H) 4.35 (t, J=6.56 Hz, 2H) 6.20 (s, 1H) 6.69-6.72 (m, 1H) 6.73 (dd, J=8.70, 1.98 Hz, 1H) 6.96 (dd, J=8.85, 4.88 Hz, 1H) 7.04-7.14 (m, 2H) 7.57-7.68 (m, 2H) 7.79 (d, J=8.24 Hz, 1H) 7.85 (d, J=7.93 Hz, 1H) 8.10 (s, 1H) 8.56 (br. s., 2H) 9.85 (s, 1H) 10.54 (s, 1H) 10.94 (s, 1H). MS (ESI+) m/z 542 [M+H]$^+$.

Biological Tests 6-phosphofructo-2-kinase/fructose-2,6-bisphosphatase (PFK-2/BPase-2) is a bi-functional enzyme that catalyses the formation and degradation of fructose-2,6-bisphosphate (F-2,6-P$_2$) (For reviews see e.g. Pilkis et al., (1995) Annu Rev. Biochem. 64, 799-835; and Okar et al., (2001) Trends Biochem. Sci. 26, 30-5). The relative kinase (formation) and phosphatase (degradation) activities of the bi-functional enzymes PFKFB3 and PFKFB4 control the intracellular levels of this regulator (F-2,6-P$_2$), which acts as an allosteric activator of glycolysis. Both the relative activities as well as the kinase to phosphatase ratios differ between the iso forms of the bi-functional enzymes, referred to as PFKFB1, PFKFB2, PFKFB3 and PFKFB4. Intracellular F-2,6-P$_2$ levels are consequently controlled by variable tissue expression of these isoforms, including splice variants or post-translational modifications (see e.g. Rider et al. (2007) Biochem J. 381, 561-579).

Method for Quantification of F-2,6-P$_2$ in Six Different Cancer Cell Lines

A method for quantification of F-2,6-P$_2$ has been described by Van Schaftingen et al. (1982) Eur. J. Biochem. 129, 191-5. This sensitive assay is based on the potent activation of pyrophosphate dependent phosphofructokinase-1 (PP$_i$-PFK) from potato tubers by F-2,6-P$_2$. The use of a series of coupled enzymes leads to a consumption of NADH (nicotinamide adenine dinucleotide) that can be followed spectrophotometrically (an updated protocol is available in Van Schaftingen, (1984) Methods of Enzymatic Analysis (Bergmeyer, H. U., ed.), 3rd edn., vol. 6, pp. 335-341, Verlag Chemie, Weinheim). A protocol for measurements in 96-well microtiter plate format is also available (Bruni et al., (1989) Anal. Biochem. 178, 324-6).

The levels of F-2,6-P$_2$ have been determined using the van Shaftingen assay as described in the protocol below, in six different cancer cell lines endogenously expressing varying levels of the different isoforms of PFK-2/BPase-2 (MCF-7, PANC-1, NUGC-3, SW480, SW620 and MIA PaCa-2). All reagents were purchased from commercial sources or prepared in-house.

Cell line A (MCF-7, human breast adenocarcinoma cell line): MCF-7 cells (ATCC-HTB-22), lot. no. 58469417. Growth medium: Eagle's Minimum Essential Medium (EMEM), Sigma-Aldrich #M5650, 500 ml; 10% FBS, Invitrogen, 10106-169; 5 mL 200 mM L-glutamine, Invitrogen 25030024; 5 mL 100 mM Sodium Pyruvate, Invitrogen 11360039; 0.5 mL 10 mg/ml Bovine Insulin, Sigma-Aldrich 10516. Cells were seeded at a concentration of 450 000 cells/mL in 100 µL growth medium (~45 000 cells/well).

Cell line B (PANC-1, human pancreatic carcinoma cell line): PANC-1 cells (ATCC-CRL-1469), lot. no. 58564651. Cells were seeded at a concentration of ~250 000 cells/mL in 100 µL growth medium (~25 000 cells/well).

Cell line C (NUGC-3, human gastric cancer cell line): NUGC-3 cells (JCRB0822), lot no. 04272009. Growth medium: RPMI1640, #R8758, Sigma-Aldrich; 10% FBS, Invitrogen, 10270-106 or Dulbecco's Modified Eagle's Medium, DMEM, VWR, LONZ12-604F; 10% FBS, Invitrogen, 10270-106. Cells were seeded at a concentration of ~350 000 cells/mL in 100 µL growth medium (~35 000 cells/well).

Cell line D (SW480, human colorectal adenocarcinoma): SW480 cells (ATCC-CCL-228), lot. no. 58471880. Cells were seeded at a concentration of ~350 000 cells/mL in 100 µL growth medium (~35 000 cells/well).

Cell line E (SW620, human colorectal adenocarcinoma): SW620 cells (ATCC-CCL-227), lot. no. 58483168. Cells were seeded at a concentration of ~350 000 cells/mL in 100 µL growth medium (~35 000 cells/well).

Cell line F (MIA PaCa-2, human pancreatic carcinoma): MIA PaCa-2 cells (ATCC-CRL-1420), lot. no. 59270201. Cells were seeded at a concentration of ~250 000 cells/mL in 100 µL growth medium (~25 000 cells/well).

Growth medium (cell lines B-F): Dulbecco's Modified Eagle's Medium, DMEM, VWR, LONZ12-604F; 10% FBS, Invitrogen, 10270-106.

Starvation medium (cell lines A-F): DMEM/F12 without phenol red and glucose free, SVA, 991373; 0.25% FBS, Invitrogen, 10270-106.

Induction medium (cell lines A-F): DMEM/F12 without phenol red and glucose free, SVA, 991373; 0.25% FBS, Invitrogen, 10270-106 (same as starvation medium).

Cells were seeded in 96-well Corning Costar tissue culture plates (CLS3595, Sigma-Aldrich) using the concentrations specified above for the different cell lines A-F and incubated over night at 37° C. and 5% CO$_2$. Row A in the plate was left empty and the cell lines added to rows B-H. Next day the growth medium was discarded and replaced with 100 µL starvation medium. The plates were incubated for 18 h at 37° C. and 5% CO$_2$. After 18 h of starvation the cells were induced with 100 µL compound or control solutions. Compounds were either tested in two concentrations (50 µM and 10 µM) or in dose response curves starting from 50 µM. The final DMSO concentration in assay plates was 0.5%. Also a dose response curve of a reference inhibitor was included in row H on each plate. All compounds were tested in duplicate plates. Compounds (in 96 well CLS 3365, Sigma-Aldrich plates) were serial diluted in DMSO from 10 mM compound DMSO stock solutions with Janus (automated liquid handling workstation from PerkinElmer). Five µL were transferred to a Greiner deep well plate (736-0155, VWR) with 495 µL starvation medium. The final start concentration of compounds in the dilution plate was 100 µM, 1% DMSO. For compounds tested as single points, 10 mM compound solutions were diluted five fold in DMSO to 2 mM, followed by the transfer of 5 µL to separate dilution plates with 495 µL starvation medium. The final concentrations of compounds in these dilution plates were 100 or 20 µM, respectively, and final concentration of DMSO was 1%. The plates were incubated at 37° C. and 5% $CO_2$ for 1 h, followed by the addition of 10 µL 20 mM D-glucose in starvation medium. Controls, with and without 1 mM glucose, were included in row B. The final assay volume was 210 µL per well. After 2 h of incubation at 37° C. and 5% $CO_2$, the supernatants were discarded and the cells lysed by the addition of 25 µL 250 mM NaOH. The plates were incubated at 37° C. and 5% $CO_2$ for 5 min followed by an addition of 75 µL MilliQ $dH_2O$. The supernatants were further diluted with 210 µL MilliQ $dH_2O$ to a final concentration of 20 mM NaOH. 200 µL were transferred to NUNC 96-well plates (7322661, VWR) and the plates were sealed and stored at −20° C. until analysis.

A few compounds were also tested, in parallel in NUGC-3 (9 000 cells/well) and PANC-1 (25 000 cells/well), under hypoxic conditions with oxygen $O_2$ levels set to 1%. During the addition of compounds and glucose the $O_2$ levels were ~0.6%. All additions were done manually.

The amount of F-2,6-$P_2$ was quantified based on the coupled enzymatic reaction described by Van Schaftingen. If necessary the samples were further diluted in 20 mM NaOH before quantification. Plates stored at −20° C. were thawed and the F-2,6-$P_2$ quantification was initiated by transferring 40 µL from each well of the NUNC plate to the corresponding position in a transparent 96-well SpectraPlate-MB (6005649, PerkinElmer). In order to ensure that all F-2,6-$P_2$ measured values were within the linear range of response (between 0-1 nM final concentration of F-2,6-$P_2$ as described by Van Schaftingen), the same sample volume (40 µL) of an in-house produced F-2,6-$P_2$ standard was included on each plate in row A.

The procedure described below involved consecutive additions of three solutions with the following premixed components:

Assay-mix (40 µL): Tris-acetate at pH 8.0, NADH and $Mg(OAc)_2$

Substrate-mix (80 µL): Pyrophosphate and F6P

Enzyme-mix (40 µL): Tris-acetate at pH 8.0, aldolase, triose phosphate isomerase, glycerol-3-phosphate dehydrogenase, pyrophosphate-dependent phosphofructokinase from potato tubers and bovine serum albumin (BSA)

The final concentrations of all reagents in a total assay volume of 200 µL per well were: 50 mM Tris-acetate at pH 8.0; 0.15 mM NADH; 2 mM $Mg(OAc)_2$; 1 mM F6P (acid treated and then neutralized to remove any contaminating F-2,6-$P_2$; see Van Schaftingen, 1984 in Methods of Enzymatic Analysis (Bergmeyer, H. U., ed.), 3rd edn., vol. 6, pp. 335-341, Verlag Chemie, Weinheim); 0.5 mM pyrophosphate; 0.45 U/mL aldolase; 5 U/mL triose phosphate isomerase; 1.7 U/mL glycerol-3-phosphate dehydrogenase; 0.01 U/mL pyrophosphate-dependent phosphofructokinase from potato tubers; 0.2 mg/mL BSA & Test samples containing variable concentrations of F-2,6-$P_2$ diluted in NaOH.

The coupled enzymatic reaction was allowed to proceed for 45 minutes at room temperature and the absorbance at 340 nm was continuously measured every 30 seconds (SpectraMax plate reader, Molecular Devices). The measured absorbance is proportional to the concentration of NADH, which in turn is proportional to the levels of F-2,6-$P_2$ within the linear range. This was defined by the 0 to 1.0 nM F-2,6-$P_2$ controls in row A of the SpectraPlate. The $IC_{50}$ values for test compounds were calculated using a four-parameter model (model 205) in XLfit (Excel) and in XLfit (IDBS ActivityBase).

Examples included herein have $IC_{50}$ values in the range 100 nM to 25 µM (see Table I for exemplary data) or ≥50% inhibition at 12.5-50 µM as measured using the above described assay. Examples 23, 31, 35, 36, 42, 43, 64, 65, 73, 77, 83, 98, 100, 121, 129, 130, 140, 207, 226 and 227 are representative examples with ≥50% inhibition at 12.5-50 µM in PANC-1 cells.

TABLE I $IC_{50}$ values for representative Examples in different cell lines based on quantification of F-2, 6-$P_2$

| Example | $IC_{50}$(µM) | Cell line | Example | $IC_{50}$(µM) | Cell line |
|---|---|---|---|---|---|
| 5 | 12.3 | PANC-1 | 107 | 2.8 | PANC-1 |
| 9 | 19.6 | PANC-1 | 108 | 7.7 | PANC-1 |
| 10 | 6.7 | PANC-1 | 111 | 4.6 | PANC-1 |
| 14 | 1.9 | PANC-1 | 113 | 5.4 | PANC-1 |
| 16 | 4.6 | PANC-1 | 116 | 1.7 | PANC-1 |
| 22 | 1.7 | PANC-1 | 118 | 2.0 | PANC-1 |
| 24 | 10.4 | PANC-1 | 122 | 5.9 | PANC-1 |
| 25 | 2.3 | PANC-1 | 126 | 1.4 | PANC-1 |
| 27 | 0.8 | PANC-1 | 128 | 13.3 | PANC-1 |
| 27 | 0.9 | NUGC-3 | 132 | 1.5 | PANC-1 |
| 32 | 4.8 | PANC-1 | 133 | 1.2 | PANC-1 |
| 33 | 3.6 | PANC-1 | 137 | 11.1 | PANC-1 |
| 40 | 2.1 | PANC-1 | 142 | 1.5 | PANC-1 |
| 41 | 19.0 | PANC-1 | 143 | 2.4 | PANC-1 |
| 44 | 5.8 | PANC-1 | 153 | 5.1 | NUGC-3 |
| 49 | 5.7 | PANC-1 | 155 | 4.9 | PANC-1 |
| 52 | 10.8 | PANC-1 | 156 | 2.8 | SW620 |
| 53 | 3.1 | PANC-1 | 157 | 2.0 | MIA PaCa-2 |
| 57 | 5.7 | PANC-1 | 162 | 2.8 | NUGC-3 |
| 58 | 5.6 | PANC-1 | 164 | 5.4 | SW480 |
| 61 | 0.6 | PANC-1 | 175 | 0.7 | PANC-1 |
| 63 | 4.0 | PANC-1 | 183 | 0.2 | MIA PaCa-2 |
| 66 | 5.7 | PANC-1 | 187 | 6.8 | PANC-1 |
| 67 | 5.2 | PANC-1 | 191 | 1.4 | NUGC-3 |
| 70 | 0.2 | PANC-1 | 193 | 1.2 | NUGC-3 |
| 71 | 0.8 | PANC-1 | 194 | 0.8 | SW620 |
| 76 | 0.9 | MCF-7 | 197 | 3.5 | PANC-1 |
| 82 | 1.08* | NUGC-3 | 202 | 5.6# | NUGC-3 |
| 82 | 6.2 | SW480 | 204 | 1.8 | PANC-1 |
| 87 | 1.6 | PANC-1 | 206 | 8.9 | PANC-1 |
| 89 | 6.7 | PANC-1 | 213 | 0.6 | PANC-1 |
| 91 | 4.5 | PANC-1 | 217 | 1.4 | PANC-1 |
| 95 | 1.7 | PANC-1 | 222 | 2.0 | PANC-1 |
| 99 | 2.4 | PANC-1 | 230 | 1.9 | PANC-1 |
| 101 | 8.4 | PANC-1 | 232 | 0.8 | PANC-1 |

*The cells were seeded at a concentration of 25 000 cells/well.
The experiment was carried out under hypoxia (0.6-1% $O_2$)

Method for Measurement of Inhibition of Cancer Cell Proliferation

To assess the antiproliferative response elicited by the compounds of the present invention in different tumour cell lines, total cellular protein in samples was quantified using the Sulphorhodamine B kit, TOX6, (Sigma-Aldrich). The protocol is based on quantitation of total cellular protein after indicated treatments and incubation times using the Sulphorhodamine B kit, TOX6, (Sigma-Aldrich).

Briefly, after protein precipitation using TCA according to the manufacturer's instructions, the sulphorhodamine dye (80 μL/well) was added to the air-dried wells. After 20 min incubation at room temperature, the dye was discarded and the samples were gently rinsed with 1% HOAc until clear. After air drying, bound dye was solubilised in 200 μL 10 mM Tris base, and the absorbance of dye was measured at 565 nm. To quantify growth, samples were collected also at t=0 h, and the resulting absorbance was set to 100%.

To assess the chemotherapy-potentiating, antiproliferative and anti-outgrowth effects elicited by Example 27 in combination with the standard chemotherapeutic agent cisplatin, the following protocol was applied:

The gastric cancer cell line NUGC3 was cultured at 37° C., 5% $CO_2$, in DMEM/F12 medium with 10% FBS and penicillin/streptomycin. Cells were plated at a density of 6,000 cells/well and allowed to attach overnight. Cellular protein in five or more wells was quantitated using the Sulphorhodamine B kit, in order to create a $t_0$ value from which to calculate subsequent growth. From all other samples, media supernatants were then replaced with either fresh medium, or cisplatin or Example 27 diluted in cell culture medium to indicated concentrations, and to a maximal DMSO concentration of 0.1%. Combination treatments with cisplatin and Example 27 at the indicated concentrations were also prepared. All treatments were in quadruplicate.

After 48 h, the media were removed from all samples. In one complete set of samples, the total cellular protein in each well was quantitated. In another complete set, post-treatment capacity for regrowth was assessed by allowing the cells to recuperate in fresh drug-free medium for another 48 h, after which time cellular protein was quantitated. Results (growth) are expressed as fold increase in cellular protein compared to the level at t=0.

For experiments studying the effect of the herein described compounds per se, i.e. without combination treatment with cisplatin, the above protocol was applied with the following modifications. See Table II for details for each specific cell line. Briefly, cells were plated at a density of 6,000 cells/well 96-well Corning Costar tissue culture plates (CLS3596, Sigma-Aldrich) in assay medium and allowed to attach over night at 37° C., 5% $CO_2$. Day 2 the compounds were diluted ½ in dose response curve mode in 100% DMSO, required volume was transferred to assay medium to a maximal DMSO concentration of 0.1%. The diluted compounds were added to the cells with a starting dose response concentration of 100 μM. All compounds were tested in duplicate plates. After a total of 72 h, the measured effect on cancer cell proliferation was quantified as the ratio between 72 h value and the 0 h value in percent, and this value was subsequently divided with the 72 h 0.1% DMSO control sample in percent demonstrating the growth-inhibitory effect.

After protein precipitation using TCA according to the manufacturer's instructions, the sulforhodamine B dye (50 μL/well) was added to the air-dried wells. After 20 min incubation at room temperature, the dye was discarded and the samples were gently rinsed with 1% HOAc until clear. After air drying, bound dye was solubilised in 100 μL 10 mM Tris base, and the absorbance of dye was measured at 530 nm and a background absorbance (subtract from the measurement at 530 nm) at 690 nm. To quantify growth, samples were collected also at t=0 h.

TABLE II

Experimental conditions for different cell lines used for determination of total cellular protein upon treatment with Examples of the present invention.

| Cell line | Growth medium | Assay medium | Cell density |
|---|---|---|---|
| NUGC3 | RPMI 1640 Sigma-Aldrich R8758, 10% FBS Invitrogen #10106-169 | DMEM/F12 SVA991373, 5% FBS Invitrogen #10270106, 5.5 mM glucose BDH-AnalaR B17673 | 6000 cells/well (100 μL) |
| MIA PaCa-2, PANC1, SW620 and SW480 | DMEM LONZ12-604F, 10% FBS Invitrogen #10270106 | DMEM/F12 SVA991373, 5% FBS Invitrogen #10270106, 5.5 mM glucose BDH-AnalaR B17673 | 6000 cells/well (100 μL) |

Figure 2:
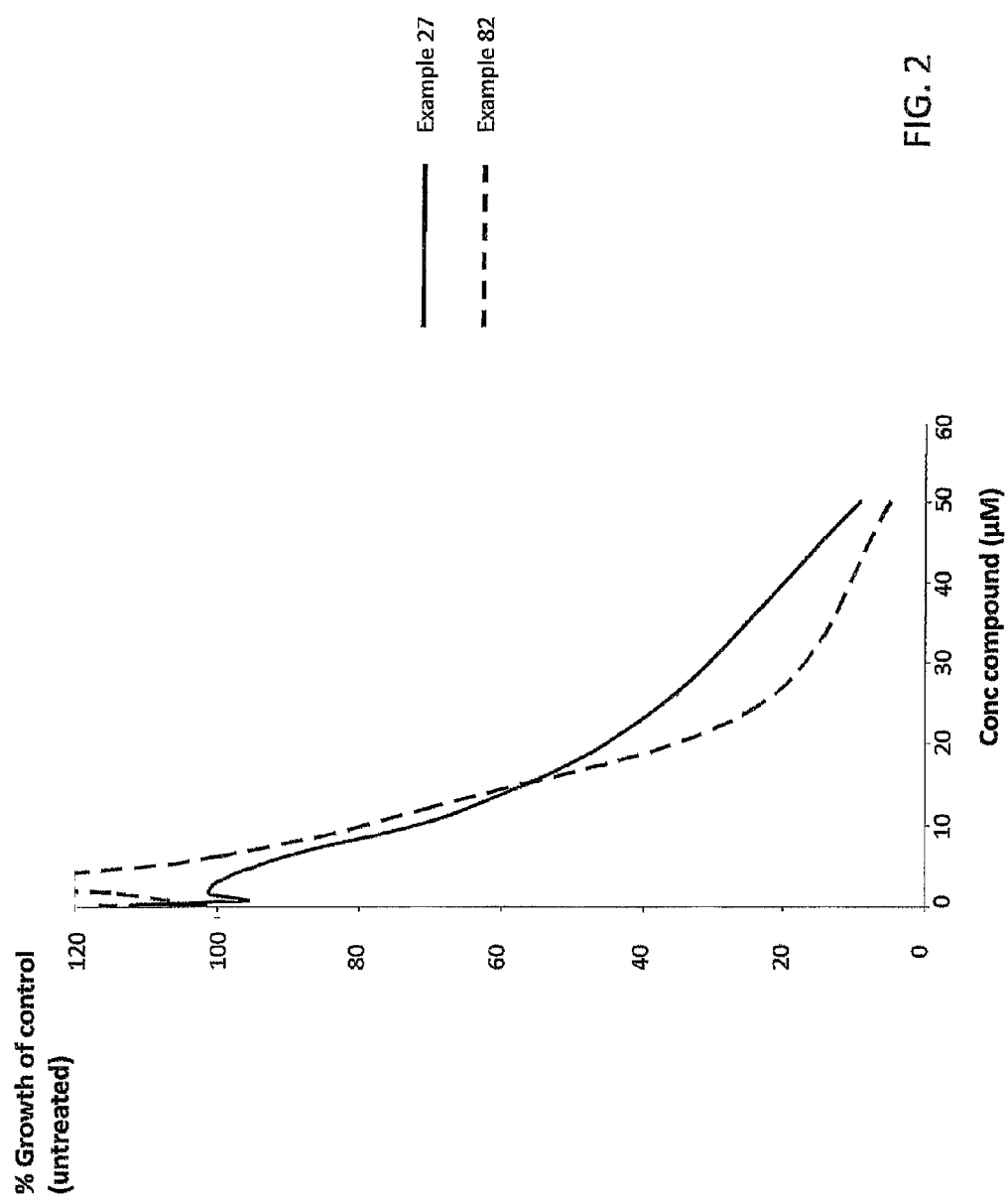
FIG. 2 is a chart representing the growth inhibitory effect of the compounds of Example 27 and Example 82, respectively, on cell proliferation in the gastric tumor cell line NUGC-3 (72 h).

Examples demonstrating the growth-inhibitory effect on different tumour cell lines are illustrated in FIGS. 1 and 2. In brief, Example 27 and cisplatin were added at the indicated concentrations (FIG. 1). After a total of 72 h, the measured effect on cancer cell proliferation was quantified as described above. FIG. 2 is a chart representing the effect of the compounds of Example 27 and Example 82 per se on cell proliferation in NUGC-3 cells.

Examples demonstrating effects on cell viability in different tumour cell lines are shown in Table III.

TABLE III $IC_{50}$ values for representative Examples in different cell lines based on quantitation of total cellular protein after treatment

| Example | $IC_{50}$ (μM) | Cell line | Example | $IC_{50}$ (μM) | Cell line |
|---|---|---|---|---|---|
| 45 | 22.5 | NUGC-3 | 172 | 15.9 | SW480 |
| 68 | 15.6 | PANC-1 | 189 | 16.4 | NUGC-3 |
| 132 | 11.8 | SW620 | 192 | 22.3 | SW480 |
| 134 | 13.0 | NUGC-3 | 195 | 20.4 | SW480 |
| 156 | 16.1 | PANC-1 | 199 | 20.6 | PANC-1 |
| 163 | 30.2 | PANC-1 | 203 | 6.8 | NUGC-3 |

Method for Measurement of Cell Toxicity

The CellTiter-Blue® Cell Viability Assay provides a homogeneous, fluorometric method for estimating the number of viable cells present in multi-well plates. It uses the indicator dye resazurin to measure the metabolic capacity of cells. Viable cells retain the ability to reduce resazurin into resorufin, which is highly fluorescent. Nonviable cells rapidly lose metabolic capacity, do not reduce the indicator dye, and thus do not generate a fluorescent signal.

Stock solutions (10 or 100 mM in DMSO) of compounds were serially diluted 1:2 in 11 concentrations. 25 nL/well (100 mM stock) or 50 nL/well (10 mM stock) were acoustically dispensed in assay plates with EDC acoustic dispenser. Final starting conc. in assay was 20 μM (0.2% DMSO) or 100 μM (0.1% DMSO) for test compounds.

Cells (MIA-PaCa-2; pancreatic carcinoma) were seeded in assay plates (384-well black/clear, Greiner #781091)

pre-dispensed with compounds, 25 µL/well, and cultured for 72 h. The cell concentration was 750 cells/well. After 72 h culture, Celltiter Blue reagent was added (5 µL/well) and the plates were incubated for 2 h. The plates were read in an Envision fluorescence reader with Ex544 nm/Em590 nm. Results were calculated as % cytotoxicity compared to background (cells treated with 0.2% DMSO).

Examples demonstrating effects on cell toxicity in different tumour cell lines are illustrated in Table IV.

TABLE IV $IC_{50}$ values for representative Examples based on cell toxicity in Mia PaCa-2 cells after treatment with compounds of the present invention.

| Example | $IC_{50}$ (µM) | Cell line |
|---|---|---|
| 75 | 25.3 | MIA PaCa-2 |
| 160 | 3.6 | MIA PaCa-2 |
| 182 | 6.3 | MIA PaCa-2 |
| 183 | 2.6 | MIA PaCa-2 |
| 205 | 17.7 | MIA PaCa-2 |

In Vitro Metabolic Stability in Human Liver Microsomes

Pooled human liver microsomes (final protein conc 0.5 mg/ml), 0.1 M phosphate buffer (pH 7.4) and NADPH (final conc 1 mM) were pre-incubated at 37° C. Example 183 (final conc 3 µM) was added to initiate the reaction. A control incubation where 0.1 M phosphate buffer (pH 7.4) was added instead of NADPH was done as a parallel experiment. After incubation for 0, 5, 10, 30 and 45 min with NADPH (for 45 min in the control incubation), MeCN containing internal standard was added to stop the reactions. The samples were centrifuged at 2500 rpm for 20 min at 4° C. before analysis using LC-MS/MS. The in vitro half life of Example 183 was found 55 min and the intrinsic clearance was 25 µL/min/mg.

In Vivo Tolerance, Plasma Exposure and Inhibition of Tumour Growth

In vivo tolerance was tested in NMRI mice using Examples 157 and 183 in 2 doses (25 and 45 mg/kg), following intraperitoneal injections daily for seven days. Macro observations during and after treatment showed no sign of abnormal behavior or health problem during and after treatment. Specific lesions consistent with toxic damage were not observed in histological examinations of adrenal gland, brain, cerebellum, heart, intestines, kidneys, liver, lungs, mesenteric lymph node, pancreas and spleen.

Figure 3:
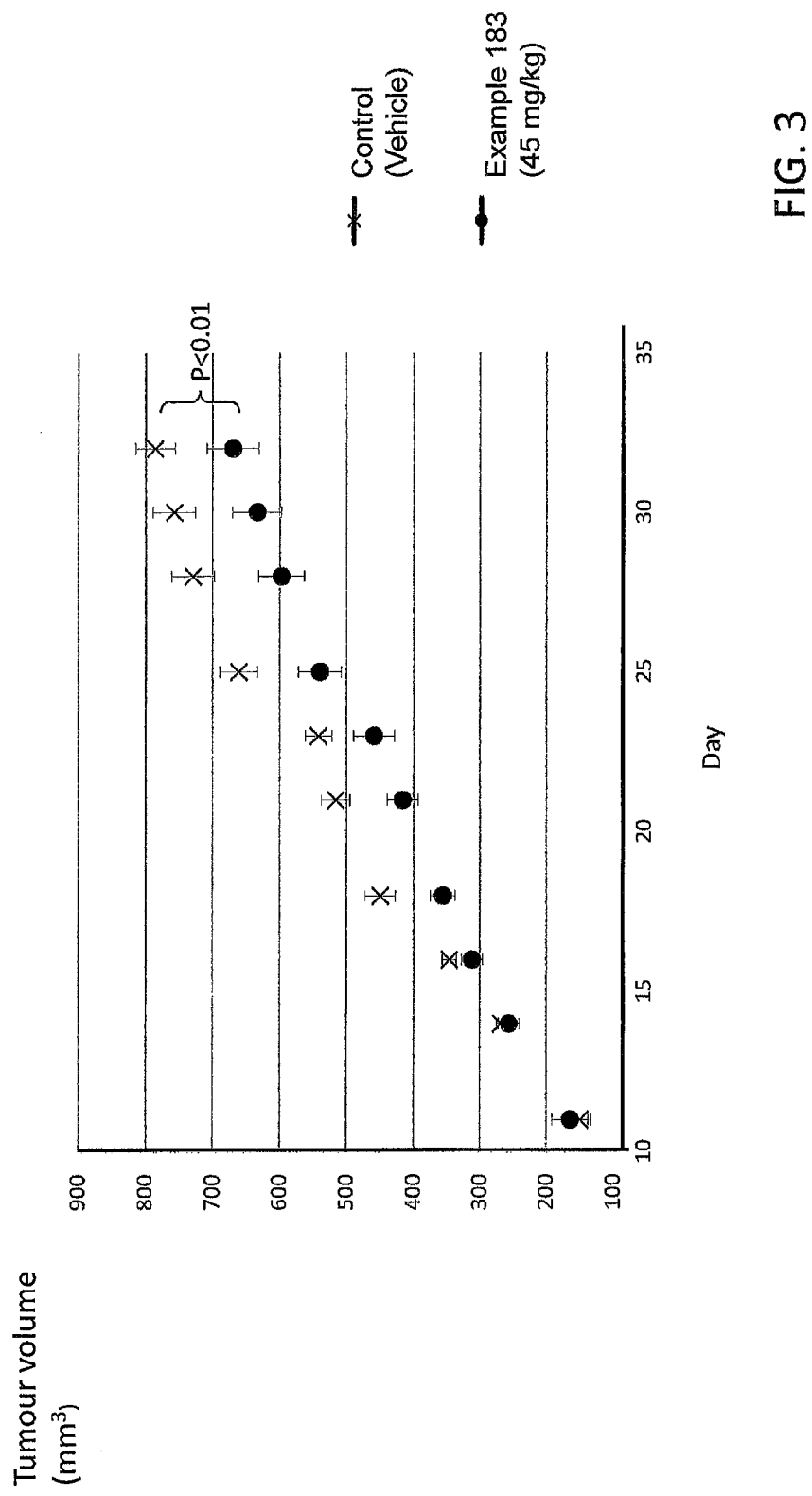
FIG. 3 is a chart representing the tumour growth inhibitory effect of the compound of Example 183 on Mia-Paca 2 xenografts in NMRI nude mice.

FIG. 3 illustrates the effects of treatment with Example 183 on the growth of established xenografts from the human pancreatic carcinoma cell line MIA PaCa-2 in NMRI nude mice. NMRI nude mice were injected subcutaneously with MIA PaCa-2 cells. At an average tumor size of around 100 mm³ mice were selected and randomized into treated (injected with substance) and control (vehicle treated) groups. Example 183 was administered at two doses, 25 mg/kg and 45 mg/kg, twice a day with 12 hours between administrations. From the day of inoculation the tumors were scored or measured three times a week using a digital caliper, and the body weights were determined at the same time points. The dose of injected substance was adjusted to the actual body weight of each animal. The dosing of the animals was in a period of 3 weeks. Treatment with Example 183 at 45 mg/kg caused a significant inhibition (p<0.01) of the tumor growth compared to a vehicle treated group.

Figure 4:
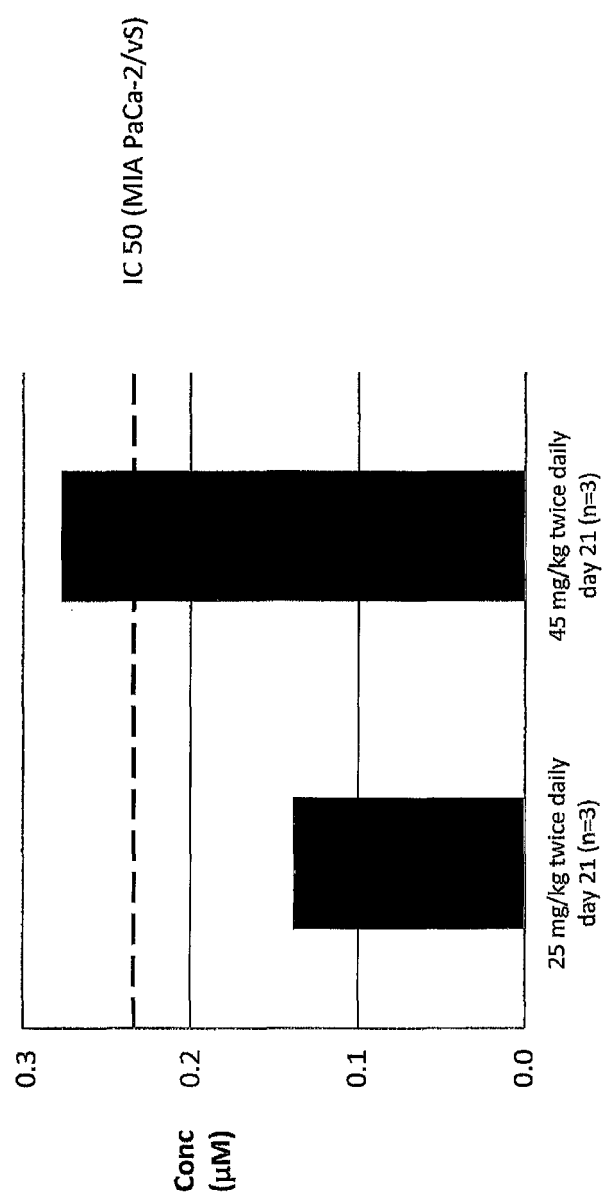
FIG. 4 is a bar chart representing the unbound plasma concentration of Example 183, 30 minutes after IP administration.

In a related study using the same dosing schedule in NMRI nude mice, blood samples were drawn 0.5 h after last injection (day 21) to determine exposure of Example 183. Plasma, prepared by centrifugation of the blood, was frozen and kept at −20° C. Thawed plasma samples were precipitated with MeCN, centrifuged and the supernatants were analyzed by LC-MSMS. Standard samples, prepared by spiking blank plasma with Example 183, were used for quantification. The exposure of unbound Example 183 exceeded the in vitro $IC_{50}$ value (MIA PaCa-2 cells) in animals dosed with 45 mg/kg (FIG. 4).

The invention claimed is:
1. A compound of formula (I)

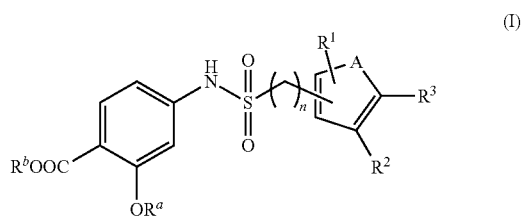

wherein
n is 0 or 1;
A is —$CR^4$=$CR^4$—;
$R^1$ is selected from H; halogen; C1-C6 alkyl, optionally substituted with at least one halogen; and C1-C6 alkoxy, optionally substituted with at least one halogen;
$R^2$ is selected from carbocyclyl-C0-C3 alkyl and heterocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$;
$R^3$ is selected from H; halogen; C1-C6 alkyl; C1-C6 alkoxy; C1-C6 alkylcarbonylamino; hydroxy-C0-C6 alkyl, C1-C6 alkylcarbonyl; C1-C6 alkoxycarbonyl; and cyano; wherein any alkyl is optionally substituted with at least one halogen;
or $R^2$ and $R^3$ form, together with the carbon atoms to which they are attached, a 5- or 6-membered carbocyclic or heterocyclic ring, which ring is optionally substituted with at least one $R^5$;
each $R^4$ is independently selected from H, halogen, and C1-C6 alkyl, wherein any alkyl is optionally substituted with at least one halogen;
each $R^5$ is independently selected from halogen; C1-C6 alkyl; C1-C6 alkoxy; phenoxy; amino; cyano; nitro; secondary or tertiary C1-C6 alkylamino; 5- or 6-membered cyclic amino, optionally containing at least one further heteroatom in the ring; C1-C6 alkylcarbonylamino; carbamoyl; secondary or tertiary C1-C6 alkylamido; 5- or 6-membered cyclic aminocarbonyl; C1-C6 alkoxycarbonylamino; hydroxy-C0-C6 alkyl; C1-C6-alkylthio; carboxy-C0-C6-alkyl; C1-C6 alkoxycarbonyl; C1-C6 alkylcarbonyl; C1-C6-alkylsulfonyl; and C1-C6 alkylsulfonylamino; wherein any alkyl is optionally substituted with at least one halogen;
$R^a$ is selected from H and C1-C6 alkylcarbonyl;
$R^b$ is selected from H, C1-C6 alkyl, C1-C6 alkyl substituted with at least one $R^6$; carbocyclyl-C0-C5 alkyl; and heterocyclyl-C0-C5 alkyl; wherein any carbocyclyl and heterocyclyl is 5- or 6-membered and is optionally substituted with at least one $R^7$ and optionally comprises at least one oxo group in the ring;
provided that $R^a$ and $R^b$ are not both H;

each R⁶ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl)amino; (C1-C6 alkylcarbonyl)(C1-C6 alkyl) amino; carbamoyl; secondary or tertiary C1-C6 alkylamido wherein any alkyl is optionally substituted by OH or $CONH_2$; 5- or 6-membered carbocyclyl- or heterocyclylcarbamoyl; 5- or 6-membered cyclic aminocarbonyl, optionally containing at least one further heteroatom in the ring, and wherein the ring is optionally substituted with at least one C1-C6 alkyl; 5-or-6-membered carbocyclylamino or heterocyclylamino; 5-or-6-membered carbocyclyloxy or heterocyclyloxy; wherein any alkyl is optionally substituted with at least one halogen and any 5- or 6-membered carbocyclyl or heterocyclyl is optionally substituted with at least one $R^8$;

each $R^7$ and $R^8$ is independently selected from C1-C6 alkyl; hydroxy-C0-C3 alkyl; C1-C6 alkoxy-C0-C3 alkyl; C1-C6 alkoxycarbonyl; carbocyclyl-C0-C4 alkyl; heterocyclyl-C0-C4alkyl; C1-C6alkylsulfinyl; amino; nitro; C1-C6 secondary or tertiary amino; halogen; carbamoyl; secondary or tertiary C1-C6 alkylamido-C0-C3 alkyl; C1-C6 alkylcarbonylamino; and 5- or 6-membered cyclic amino, optionally containing at least one further heteroatom in the ring and wherein the ring is optionally substituted with at least one C1-C6 alkyl; wherein any alkyl is optionally substituted with at least one halogen; wherein any carbocyclyl and heterocyclyl is 5- or 6-membered;

or a pharmaceutically acceptable salt thereof.

2. A compound according to claim 1, or a pharmaceutically acceptable salt thereof, wherein
$R^3$ is selected from H; halogen; and C1-C6 alkyl, wherein any alkyl is optionally substituted with at least one halogen; or $R^2$ and $R^3$ form, together with the carbon atoms to which they are attached, a 5- or 6-membered carbocyclic or heterocyclic ring, which ring is optionally substituted with at least one $R^5$.

3. A compound according to claim 1, or a pharmaceutically acceptable salt thereof, wherein n is 0.

4. A compound according to claim 1, or a pharmaceutically acceptable salt thereof, wherein $R^a$ is H.

5. A compound according to claim 1, selected from
methyl 2-hydroxy-4-{[(4-methyl-1-naphthyl)sulfonyl]amino}benzoate,
methyl 2-hydroxy-4-[(1-naphthylsulfonyl)amino]benzoate,
methyl 4-{[(4-fluoro-1-naphthyl)sulfonyl]amino}-2-hydroxybenzoate,
methyl 4-[(2,1,3-benzothiadiazol-4-ylsulfonyl)amino]-2-hydroxybenzoate,
methyl 2-hydroxy-4-[(naphthalen-2-ylsulfonyl)amino]benzoate,
methyl 4-({[5-(dimethylamino)naphthalen-1-yl]sulfonyl}amino)-2-hydroxybenzoate,
methyl 2-hydroxy-4-{[(2'-hydroxybiphenyl-3-yl)sulfonyl]amino}benzoate,
methyl 4-{[(3'-chlorobiphenyl-3-yl)sulfonyl]amino}-2-hydroxybenzoate,
methyl 4-[(biphenyl-3-ylsulfonyl)amino]-2-hydroxybenzoate,
methyl 2-hydroxy-4-{[(3-pyridin-3-ylphenyl)sulfonyl]amino}benzoate,
methyl 2-hydroxy-4-{[(3-pyridin-4-ylphenyl)sulfonyl]amino}benzoate,
methyl 4-({[3-(1-benzofuran-2-yl)phenyl]sulfonyl}amino)-2-hydroxybenzoate,
methyl 2-hydroxy-4-{[(3-quinolin-6-ylphenyl)sulfonyl]amino}benzoate,
methyl 4-{[(3'-aminobiphenyl-3-yl)sulfonyl]amino}-2-hydroxybenzoate,
methyl 4-{[(3'-acetamidobiphenyl-3-yl)sulfonyl]amino}-2-hydroxybenzoate,
methyl 2-hydroxy-4-{[(2'-nitrobiphenyl-3-yl)sulfonyl]amino}benzoate,
methyl 4-({[3-(5-acetyl-2-thienyl)phenyl]sulfonyl}amino)-2-hydroxybenzoate,
methyl 2-hydroxy-4-({[2'-(hydroxymethyl)biphenyl-3-yl]sulfonyl}amino)benzoate,
methyl 4-{[(3'-cyanobiphenyl-3-yl)sulfonyl]amino}-2-hydroxybenzoate,
methyl 2-hydroxy-4-({[4'-(methylsulfanyl)biphenyl-3-yl]sulfonyl}amino)benzoate,
methyl 2-hydroxy-4-({[4'-(trifluoromethoxy)biphenyl-3-yl]sulfonyl}amino)benzoate,
methyl 2-hydroxy-4-({[4'-(trifluoromethyl)biphenyl-3-yl]sulfonyl}amino)benzoate,
methyl 4-({[4'-(dimethylcarbamoyl)biphenyl-3-yl]sulfonyl}amino)-2-hydroxybenzoate,
methyl 4-{[(4'-carbamoylbiphenyl-3-yl)sulfonyl]amino}-2-hydroxybenzoate,
methyl 2-hydroxy-4-({[3'-(methylsulfonyl)biphenyl-3-yl]sulfonyl}amino)benzoate,
methyl 4-{[(3'-carbamoylbiphenyl-3-yl)sulfonyl]amino}-2-hydroxybenzoate,
methyl 2-hydroxy-4-({[5-(trifluoromethyl)biphenyl-3-yl]sulfonyl}amino)benzoate,
methyl 4-({[2',5'-difluoro-5-(trifluoromethyl)biphenyl-3-yl]sulfonyl}amino)-2-hydroxybenzoate,
methyl 4-({[3-(2,3-dihydro-1-benzofuran-5-yl)-5-(trifluoromethyl)phenyl]sulfonyl}amino)-2-hydroxybenzoate,
methyl 2-hydroxy-4-({[2'-hydroxy-5-(trifluoromethyl)biphenyl-3-yl]sulfonyl}amino)benzoate,
methyl 4-({[3-(2,3-dihydro-1-benzofuran-5-yl)benzyl]sulfonyl}amino)-2-hydroxybenzoate,
methyl 4-{[(3'-ethoxybiphenyl-3-yl)sulfonyl]amino}-2-hydroxybenzoate,
1-methylethyl 3'-{[3-hydroxy-4-(methoxycarbonyl)phenyl]sulfamoyl}biphenyl-3-carboxylate,
methyl 4-{[(5'-fluoro-2'-hydroxybiphenyl-3-yl)sulfonyl]amino}-2-hydroxybenzoate,
benzyl 2-acetoxy-4-[(1-naphthylsulfonyl)amino]benzoate,
2-acetoxy-4-[(1-naphthylsulfonyl)amino]benzoic acid,
methyl 2-hydroxy-4-({[3-(piperidin-1-yl)phenyl]sulfonyl}amino)benzoate,
4-(dimethylamino)butyl 2-hydroxy-4-({[3-(2-methyl-1,3-thiazol-4-yl)phenyl]sulfonyl}amino)benzoate,
methyl 4-({[5'-fluoro-2'-hydroxy-5-(trifluoromethyl)biphenyl-3-yl]sulfonyl}amino)-2-hydroxybenzoate,
methyl 4-{[(2',5'-difluorobiphenyl-3-yl)sulfonyl]amino}-2-hydroxybenzoate, methyl 4-({[3-(2,3-dihydro-1-benzofuran-5-yl)phenyl]sulfonyl}amino)-2-hydroxybenzoate,
3-morpholin-4-ylpropyl 2-hydroxy-4-{[(2'-hydroxybiphenyl-3-yl)sulfonyl]amino}benzoate,
3-morpholin-4-ylpropyl 4-{[(5'-fluoro-2'-hydroxybiphenyl-3-yl)sulfonyl]amino}-2-hydroxybenzoate,
4-morpholin-4-ylbutyl 4-{[(5'-fluoro-2'-hydroxybiphenyl-3-yl)sulfonyl]amino}-2-hydroxybenzoate,
3-morpholin-4-ylpropyl 4-{[(2',5'-difluorobiphenyl-3-yl)sulfonyl]amino}-2-hydroxybenzoate,
2-methoxyethyl 4-{[(2',5'-difluorobiphenyl-3-yl)sulfonyl]amino}-2-hydroxybenzoate,
4-morpholin-4-ylbutyl 4-{[(2',5'-difluorobiphenyl-3-yl)sulfonyl]amino}-2-hydroxybenzoate,
3-morpholin-4-ylpropyl 4-({[3-(2,3-dihydro-1-benzofuran-5-yl)phenyl]sulfonyl}amino)-2-hydroxybenzoate,
2-methoxyethyl 4-({[3-(2,3-dihydro-1-benzofuran-5-yl)phenyl]sulfonyl}amino)-2-hydroxybenzoate,
4-morpholin-4-ylbutyl 4-({[3-(2,3-dihydro-1-benzofuran-5-yl)phenyl]sulfonyl}amino)-2-hydroxybenzoate,
2-methoxy-1-methylethyl 4-{[(5'-fluoro-2'-hydroxybiphenyl-3-yl)sulfonyl]amino}-2-hydroxybenzoate,
tetrahydrofuran-3-yl 4-{[(5'-fluoro-2'-hydroxybiphenyl-3-yl)sulfonyl]amino}-2-hydroxybenzoate,
1-(methoxymethyl)propyl 4-{[(5'-fluoro-2'-hydroxybiphenyl-3-yl)sulfonyl]amino}-2-hydroxybenzoate,
2-ethoxy-1-(ethoxymethyl)ethyl 4-{[(5'-fluoro-2'-hydroxybiphenyl-3-yl)sulfonyl]amino}-2-hydroxybenzoate,
2-methoxybutyl 4-{[(5'-fluoro-2'-hydroxybiphenyl-3-yl)sulfonyl]amino}-2-hydroxybenzoate,
2-hydroxyethyl 4-{[(5'-fluoro-2'-hydroxybiphenyl-3-yl)sulfonyl]amino}-2-hydroxybenzoate,
3-hydroxypropyl 4-{[(5'-fluoro-2'-hydroxybiphenyl-3-yl)sulfonyl]amino}-2-hydroxybenzoate,
2-methoxyethyl 4-{[(5'-fluoro-2'-hydroxybiphenyl-3-yl)sulfonyl]amino}-2-hydroxybenzoate,
2-phenoxyethyl 4-{[(5'-fluoro-2'-hydroxybiphenyl-3-yl)sulfonyl]amino}-2-hydroxybenzoate,
3-(2,6-dimethylmorpholin-4-yl)propyl 4-{[(5'-fluoro-2'-hydroxybiphenyl-3-yl)sulfonyl]amino}-2-hydroxybenzoate,
3-(pyridin-3-ylamino)propyl 4-{[(5'-fluoro-2'-hydroxybiphenyl-3-yl)sulfonyl]amino}-2-hydroxybenzoate,
3-[(1-methyl-1H-pyrazol-5-yl)amino]propyl 4-{[(5'-fluoro-2'-hydroxybiphenyl-3-yl)sulfonyl]amino}-2-hydroxybenzoate,
3-[(5-methylisoxazol-3-yl)amino]propyl 4-{[(5'-fluoro-2'-hydroxybiphenyl-3-yl)sulfonyl]amino}-2-hydroxybenzoate,
or a pharmaceutically acceptable salt thereof.

6. A pharmaceutical composition comprising a compound of formula (I)

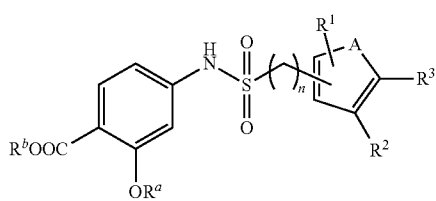

(I)

wherein
n is 0 or 1;
A is —$CR^4$=$CR^4$—;
$R^1$ is selected from H; halogen; C1-C6 alkyl, optionally substituted with at least one halogen; and C1-C6 alkoxy, optionally substituted with at least one halogen;
$R^2$ is selected from carbocyclyl-C0-C3 alkyl and heterocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$;
$R^3$ is selected from H; halogen; C1-C6 alkyl; C1-C6 alkoxy; C1-C6 alkylcarbonylamino; hydroxy-C0-C6 alkyl, C1-C6 alkylcarbonyl; C1-C6 alkoxycarbonyl; and cyano; wherein any alkyl is optionally substituted with at least one halogen;
or $R^2$ and $R^3$ form, together with the carbon atoms to which they are attached, a 5- or 6-membered carbocyclic or heterocyclic ring, which ring is optionally substituted with at least one $R^5$;
each $R^4$ is independently selected from H, halogen, and C1-C6 alkyl, wherein any alkyl is optionally substituted with at least one halogen;
each $R^5$ is independently selected from halogen; C1-C6 alkyl; C1-C6 alkoxy; phenoxy; amino; cyano; nitro; secondary or tertiary C1-C6 alkylamino; 5- or 6-membered cyclic amino, optionally containing at least one further heteroatom in the ring; C1-C6 alkylcarbonylamino; carbamoyl; secondary or tertiary C1-C6 alkylamido; 5- or 6-membered cyclic aminocarbonyl; C1-C6 alkoxycarbonylamino; hydroxy-C0-C6 alkyl; C1-C6-alkylthio; carboxy-C0-C6-alkyl; C1-C6 alkoxycarbonyl; C1-C6 alkylcarbonyl; C1-C6-alkylsulfonyl; and C1-C6 alkylsulfonylamino; wherein any alkyl is optionally substituted with at least one halogen;
$R^a$ is selected from H and C1-C6 alkylcarbonyl;
$R^b$ is selected from H, C1-C6 alkyl, C1-C6 alkyl substituted with at least one $R^6$; carbocyclyl-C0-C5 alkyl; and heterocyclyl-C0-C5 alkyl; wherein any carbocyclyl and heterocyclyl is 5- or 6-membered and is optionally substituted with at least one $R^7$ and optionally comprises at least one oxo group in the ring;
provided that $R^a$ and $R^b$ are not both H;
each $R^6$ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl)amino; (C1-C6 alkylcarbonyl)(C1-C6 alkyl)amino; carbamoyl; secondary or tertiary C1-C6 alkylamido wherein any alkyl is optionally substituted by OH or $CONH_2$, 5- or 6-membered carbocyclyl- or heterocyclylcarbamoyl; 5- or 6-membered cyclic aminocarbonyl, optionally containing at least one further heteroatom in the ring, and wherein the ring is optionally substituted with at least one C1-C6 alkyl; 5-or-6-membered carbocyclylamino or heterocyclylamino; and 5-or-6-membered carbocyclyloxy or heterocyclyloxy; wherein any alkyl is optionally substituted with at least one halogen and any 5- or 6-membered carbocyclyl or heterocyclyl is optionally substituted with at least one $R^8$;

each $R^7$ and $R^8$ is independently selected from C1-C6 alkyl; hydroxy-C0-C3 alkyl; C1-C6 alkoxy-C0-C3 alkyl; C1-C6 alkoxycarbonyl; carbocyclyl-C0-C4 alkyl; heterocyclyl-C0-C4 alkyl; C1-C6 alkylsulfinyl; amino; nitro; C1-C6 secondary or tertiary amino; halogen; carbamoyl; secondary or tertiary C1-C6 alkylamido-C0-C3 alkyl; C1-C6 alkylcarbonylamino; and 5- or 6-membered cyclic amino, optionally containing at least one further heteroatom in the ring and wherein the ring is optionally substituted with at least one C1-C6 alkyl; wherein any alkyl is optionally substituted with at least one halogen; wherein any carbocyclyl and heterocyclyl is 5- or 6-membered;

or a pharmaceutically acceptable salt thereof, provided that the compound is not ethyl 4-(4-acetamidophenylsulfonamido)-2-hydroxybenzoate, methyl 4-(4-acetamidophenylsulfonamido)-2-hydroxybenzoate, phenyl 2-hydroxy-4-(4-methylphenylsulfonamido)benzoate, or methyl 2-hydroxy-4-(4-(4-oxo-1,4-dihydropyrazolo[1,5-a][1,3,5]triazin-8-yl)phenylsulfonamido)benzoate, and optionally at least one pharmaceutically acceptable excipient.

7. A pharmaceutical composition according to claim 6, comprising a compound selected from:

methyl 2-hydroxy-4-{[(4-methyl-1-naphthyl)sulfonyl]amino}benzoate, methyl 2-hydroxy-4-[(1-naphthylsulfonyl)amino]benzoate, methyl 4-{[(4-fluoro-1-naphthyl)sulfonyl]amino}-2-hydroxybenzoate, methyl 4-[(2,1,3-benzothiadiazol-4-ylsulfonyl)amino]-2-hydroxybenzoate, methyl 2-hydroxy-4-[(naphthalen-2-ylsulfonyl)amino]benzoate, methyl 4-({[5-(dimethylamino)naphthalen-1-yl]sulfonyl}amino)-2-hydroxybenzoate, methyl 2-hydroxy-4-{[(2'-hydroxybiphenyl-3-yl)sulfonyl]amino}benzoate, methyl 4-{[(3'-chlorobiphenyl-3-yl)sulfonyl]amino}-2-hydroxybenzoate, methyl 4-[(biphenyl-3-ylsulfonyl)amino]-2-hydroxybenzoate, methyl 2-hydroxy-4-{[(3-pyridin-3-ylphenyl)sulfonyl]amino}benzoate, methyl 2-hydroxy-4-{[(3-pyridin-4-ylphenyl)sulfonyl]amino}benzoate, methyl 4-({[3-(1-benzofuran-2-yl)phenyl]sulfonyl}amino)-2-hydroxybenzoate, methyl 2-hydroxy-4-{[(3-quinolin-6-ylphenyl)sulfonyl]amino}benzoate, methyl 4-{[(3'-aminobiphenyl-3-yl)sulfonyl]amino}-2-hydroxybenzoate, methyl 4-{[(3'-acetamidobiphenyl-3-yl)sulfonyl]amino}-2-hydroxybenzoate, methyl 2-hydroxy-4-{[(2'-nitrobiphenyl-3-yl)sulfonyl]amino}benzoate, methyl 4-({[3-(5-acetyl-2-thienyl)phenyl]sulfonyl}amino)-2-hydroxybenzoate, methyl 2-hydroxy-4-({[2'-(hydroxymethyl)biphenyl-3-yl]sulfonyl}amino)benzoate, methyl 4-{[(3'-cyanobiphenyl-3-yl)sulfonyl]amino}-2-hydroxybenzoate, methyl 2-hydroxy-4-({[4'-(methylsulfanyl)biphenyl-3-yl]sulfonyl}amino)benzoate, methyl 2-hydroxy-4-({[4'-(trifluoromethoxy)biphenyl-3-yl]sulfonyl}amino)benzoate, methyl 2-hydroxy-4-({[4'-(trifluoromethyl)biphenyl-3-yl]sulfonyl}amino)benzoate, methyl 4-({[4'-(dimethylcarbamoyl)biphenyl-3-yl]sulfonyl}amino)-2-hydroxybenzoate, methyl 4-{[(4'-carbamoylbiphenyl-3-yl)sulfonyl]amino}-2-hydroxybenzoate, methyl 2-hydroxy-4-({[3'-(methylsulfonyl)biphenyl-3-yl]sulfonyl}amino)benzoate, methyl 4-{[(3'-carbamoylbiphenyl-3-yl)sulfonyl]amino}-2-hydroxybenzoate, methyl 2-hydroxy-4-({[5-(trifluoromethyl)biphenyl-3-yl]sulfonyl}amino)benzoate, methyl 4-({[2',5'-difluoro-5-(trifluoromethyl)biphenyl-3-yl]sulfonyl}amino)-2-hydroxybenzoate, methyl 4-({[3-(2,3-dihydro-1-benzofuran-5-yl)-5-(trifluoromethyl)phenyl]sulfonyl}amino)-2-hydroxybenzoate, methyl 2-hydroxy-4-({[2'-hydroxy-5-(trifluoromethyl)biphenyl-3-yl]sulfonyl}amino)benzoate, methyl 4-({[3-(2,3-dihydro-1-benzofuran-5-yl)benzyl]sulfonyl}amino)-2-hydroxybenzoate, methyl 4-{[(3'-ethoxybiphenyl-3-yl)sulfonyl]amino}-2-hydroxybenzoate, 1-methylethyl 3'-{[3-hydroxy-4-(methoxycarbonyl)phenyl]sulfamoyl}biphenyl-3-carboxylate, methyl 4-{[(5'-fluoro-2'-hydroxybiphenyl-3-yl)sulfonyl]amino}-2-hydroxybenzoate, benzyl 2-acetoxy-4-[(1-naphthylsulfonyl)amino]benzoate, 2-acetoxy-4-[(1-naphthylsulfonyl)amino]benzoic acid, methyl 2-hydroxy-4-({[3-(piperidin-1-yl)phenyl]sulfonyl}amino)benzoate, 4-(dimethylamino)butyl 2-hydroxy-4-({[3-(2-methyl-1,3-thiazol-4-yl)phenyl]sulfonyl}amino)benzoate, methyl 4-({[5'-fluoro-2'-hydroxy-5-(trifluoromethyl)biphenyl-3-yl]sulfonyl}amino)-2-hydroxybenzoate, methyl 4-{[(2',5'-difluorobiphenyl-3-yl)sulfonyl]amino}-2-hydroxybenzoate, methyl 4-({[3-(2,3-dihydro-1-benzofuran-5-yl)phenyl]sulfonyl}amino)-2-hydroxybenzoate, 3-morpholin-4-ylpropyl 2-hydroxy-4-{[(2'-hydroxybiphenyl-3-yl)sulfonyl]amino}benzoate, 3-morpholin-4-ylpropyl 4-{[(5'-fluoro-2'-hydroxybiphenyl-3-yl)sulfonyl]amino}-2-hydroxybenzoate, 4-morpholin-4-ylbutyl 4-{[(5'-fluoro-2'-hydroxybiphenyl-3-yl)sulfonyl]amino}-2-hydroxybenzoate, 3-morpholin-4-ylpropyl 4-{[(2',5'-difluorobiphenyl-3-yl)sulfonyl]amino}-2-hydroxybenzoate, 2-methoxyethyl 4-{[(2',5'-difluorobiphenyl-3-yl)sulfonyl]amino}-2-hydroxybenzoate, 4-morpholin-4-ylbutyl 4-{[(2',5'-difluorobiphenyl-3-yl)sulfonyl]amino}-2-hydroxybenzoate, 3-morpholin-4-ylpropyl 4-({[3-(2,3-dihydro-1-benzofuran-5-yl)phenyl]sulfonyl}amino)-2-hydroxybenzoate, 2-methoxyethyl 4-({[3-(2,3-dihydro-1-benzofuran-5-yl)phenyl]sulfonyl}amino)-2-hydroxybenzoate, 4-morpholin-4-ylbutyl 4-({[3-(2,3-dihydro-1-benzofuran-5-yl)phenyl]sulfonyl}amino)-2-hydroxybenzoate, 2-methoxy-1-methylethyl 4-{[(5'-fluoro-2'-hydroxybiphenyl-3-yl)sulfonyl]amino}-2-hydroxybenzoate,
tetrahydrofuran-3-yl 4-{[(5'-fluoro-2'-hydroxybiphenyl-3-yl)sulfonyl]amino}-2-hydroxybenzoate,
1-(methoxymethyl)propyl 4-{[(5'-fluoro-2'-hydroxybiphenyl-3-yl)sulfonyl]amino}-2-hydroxybenzoate,
2-ethoxy-1-(ethoxymethyl)ethyl 4-{[(5'-fluoro-2'-hydroxybiphenyl-3-yl)sulfonyl]amino}-2-hydroxybenzoate,
2-methoxybutyl 4-{[(5'-fluoro-2'-hydroxybiphenyl-3-yl)sulfonyl]amino}-2-hydroxybenzoate,
2-hydroxyethyl 4-{[(5'-fluoro-2'-hydroxybiphenyl-3-yl)sulfonyl]amino}-2-hydroxybenzoate,
3-hydroxypropyl 4-{[(5'-fluoro-2'-hydroxybiphenyl-3-yl)sulfonyl]amino}-2-hydroxybenzoate,
2-methoxyethyl 4-{[(5'-fluoro-2'-hydroxybiphenyl-3-yl)sulfonyl]amino}-2-hydroxybenzoate,
2-phenoxyethyl 4-{[(5'-fluoro-2'-hydroxybiphenyl-3-yl)sulfonyl]amino}-2-hydroxybenzoate,
3-(2,6-dimethylmorpholin-4-yl)propyl 4-{[(5'-fluoro-2'-hydroxybiphenyl-3-yl)sulfonyl]amino}-2-hydroxybenzoate,
3-(pyridin-3-ylamino)propyl 4-{[(5'-fluoro-2'-hydroxybiphenyl-3-yl)sulfony]amino}-2-hydroxybenzoate,
3-[(1-methyl-1H-pyrazol-5-yl)amino]propyl 4-{[(5'-fluoro-2'-hydroxybiphenyl-3-yl)sulfonyl]amino}-2-hydroxybenzoate,
3-[(5-methylisoxazol-3-yl)amino]propyl 4-{[(5'-fluoro-2'-hydroxybiphenyl-3-yl)sulfonyl]amino}-2-hydroxybenzoate,
or a pharmaceutically acceptable salt thereof,
and optionally at least one pharmaceutically acceptable excipient.

8. A method for the treatment of a cancer disease selected from breast, pancreatic, gastric and colorectal cancer, by administering, to a mammal in need thereof, a compound of formula (I)

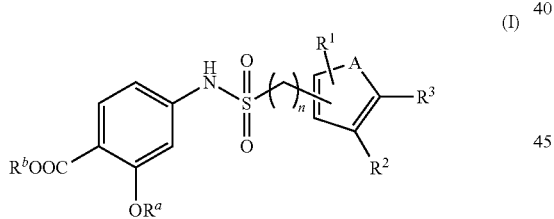

wherein
n is 0 or 1;
A is —CR$^4$=CR$^4$—;
R$^1$ is selected from H; halogen; C1-C6 alkyl, optionally substituted with at least one halogen; and C1-C6 alkoxy, optionally substituted with at least one halogen;
R$^2$ is selected from carbocyclyl-C0-C3 alkyl and heterocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one R$^5$;
R$^3$ is selected from H; halogen; C1-C6 alkyl; C1-C6 alkoxy; C1-C6 alkylcarbonylamino; hydroxy-C0-C6 alkyl, C1-C6 alkylcarbonyl; C1-C6 alkoxycarbonyl; and cyano; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one R$^5$;
or R$^2$ and R$^3$ form, together with the carbon atoms to which they are attached, a 5- or 6-membered carbocyclic or heterocyclic ring, which ring is optionally substituted with at least one R$^5$;
each R$^4$ is independently selected from H, halogen, and C1-C6 alkyl, wherein any alkyl is optionally substituted with at least one halogen; each R$^5$ is independently selected from halogen; C1-C6 alkyl; C1-C6 alkoxy; phenoxy; amino; cyano; nitro; secondary or tertiary C1-C6 alkylamino; 5- or 6-membered cyclic amino, optionally containing at least one further heteroatom in the ring; C1-C6 alkylcarbonylamino; carbamoyl; secondary or tertiary C1-C6 alkylamido; 5- or 6-membered cyclic aminocarbonyl; C1-C6 alkoxycarbonylamino; hydroxy-C0-C6 alkyl; C1-C6-alkylthio; carboxy-C0-C6-alkyl; C1-C6 alkoxycarbonyl; C1-C6 alkylcarbonyl; C1-C6-alkylsulfonyl; and C1-C6 alkylsulfonylamino; wherein any alkyl is optionally substituted with at least one halogen;
R$^a$ is selected from H and C1-C6 alkylcarbonyl;
R$^b$ is selected from H, C1-C6 alkyl, C1-C6 alkyl substituted with at least one R$^6$; carbocyclyl-C0-C5 alkyl; and heterocyclyl-C0-C5 alkyl; wherein any carbocyclyl and heterocyclyl is 5- or 6-membered and is optionally substituted with at least one R$^7$ and optionally comprises at least one oxo group in the ring;
provided that R$^a$ and R$^b$ are not both H;
each R$^6$ is independently selected from hydroxy; C1-C6 alkoxy; hydroxy-C1-C6 alkoxy; C1-C6 alkylcarbonyloxy; C1-C6 alkoxycarbonyloxy; 5- or 6-membered carbocyclylcarbonyl or heterocyclylcarbonyl; amino; secondary or tertiary C1-C6 alkylamino; secondary or tertiary hydroxy-C1-C6 alkylamino; 5- or 6-membered cyclic amino optionally containing at least one further heteroatom in the ring and wherein the ring is optionally substituted with at least one C1-C6 alkyl; C1-C6 alkylcarbonylamino; C1-C6 alkoxycarbonylamino; (C1-C6 alkoxycarbonyl)(C1-C6 alkyl)amino; (C1-C6 alkoxycarbonyl)(5- or 6-membered carbocyclyl or heterocyclyl)amino; (C1-C6 alkylcarbonyl)(C1-C6 alkyl)amino; carbamoyl; secondary or tertiary C1-C6 alkylamido wherein any alkyl is optionally substituted by OH or CONH$_2$; 5- or 6-membered carbocyclyl- or heterocyclylcarbamoyl; 5- or 6-membered cyclic aminocarbonyl, optionally containing at least one further heteroatom in the ring, and wherein the ring is optionally substituted with at least one C1-C6 alkyl; 5-or-6-membered carbocyclylamino or heterocyclylamino; and 5-or-6-membered carbocyclyloxy or heterocyclyloxy; wherein any alkyl is optionally substituted with at least one halogen and any 5- or 6-membered carbocyclyl or heterocyclyl is optionally substituted with at least one R$^8$;
each R$^7$ and R$^8$ is independently selected from C1-C6 alkyl; hydroxy-C0-C3 alkyl; C1-C6 alkoxy-C0-C3 alkyl; C1-C6 alkoxycarbonyl; carbocyclyl-C0-C4 alkyl; heterocyclyl-C0-C4 alkyl; C1-C6 alkylsulfinyl; amino; nitro; C1-C6 secondary or tertiary amino; halogen; carbamoyl; secondary or tertiary C1-C6 alkylamido-C0-C3 alkyl; C1-C6 alkylcarbonylamino; and 5- or 6-membered cyclic amino, optionally containing at least one further heteroatom in the ring and wherein the ring is optionally substituted with at least one C1-C6 alkyl; wherein any alkyl is optionally substituted with at least one halogen; wherein any carbocyclyl and heterocyclyl is 5- or 6-membered;
or a pharmaceutically acceptable salt thereof.

9. A compound according to claim 1, or a pharmaceutically acceptable salt thereof, wherein $R^2$ is selected from carbocyclyl-C0-C3 alkyl and heterocyclyl-C0-C3 alkyl; wherein any alkyl is optionally substituted with at least one halogen; any carbocyclyl or heterocyclyl is 5- or 6-membered monocyclyl or 9- or 10-membered bicyclyl; and any carbocyclyl or heterocyclyl is optionally substituted with at least one $R^5$.

10. A compound according to claim 1, or a pharmaceutically acceptable salt thereof, wherein $R^2$ is phenyl substituted with at least one $R^5$.

11. A compound according to claim 1, or a pharmaceutically acceptable salt thereof, wherein $R^2$ is phenyl substituted with 1 or 2 moieties $R^5$ selected from hydroxy, C1-C3 alkoxy and halogen.

12. A compound according to claim 1, or a pharmaceutically acceptable salt thereof, wherein $R^2$ is phenyl substituted with 2 moieties $R^5$ selected from hydroxy, C1-C3 alkoxy and halogen.

13. A compound according to claim 1, or a pharmaceutically acceptable salt thereof, wherein $R^2$ is 5-fluoro-2-hydroxyphenyl.

14. A compound according to claim 1, or a pharmaceutically acceptable salt thereof, wherein $R^3$ is H.

15. A compound according to claim 1, or a pharmaceutically acceptable salt thereof, wherein $R^1$ is H.

16. A compound according to claim 1, or a pharmaceutically acceptable salt thereof, wherein each $R^4$ is H.

17. A compound according to claim 1, of formula (ICa)

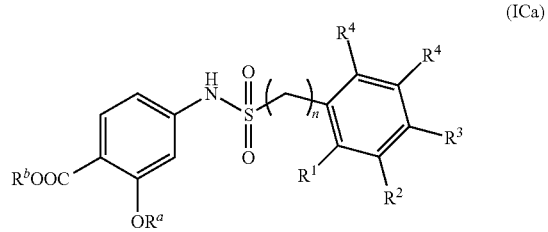

(ICa)

or a pharmaceutically acceptable salt thereof.

18. A compound according to claim 1, or a pharmaceutically acceptable salt thereof, wherein $R^b$ is C2-C4 alkyl, substituted by 1 or 2 methoxy or ethoxy groups.

19. A compound according to claim 1, or a pharmaceutically acceptable salt thereof, wherein $R^b$ is hydroxy-C2-C4 alkyl.

20. A compound according to claim 1, or a pharmaceutically acceptable salt thereof, wherein $R^b$ is tetrahydrofuryl or tetrahydrofurylmethyl.

21. The method of claim 8, wherein the cancer is pancreatic cancer.

* * * * *